United States Patent
Goletz et al.

(10) Patent No.: US 9,494,587 B2
(45) Date of Patent: Nov. 15, 2016

(54) MICROORGANISMS OR FRACTIONS THEREOF CAPABLE OF ACTIVATING CELLULAR IMMUNITY AGAINST CARBOHYDRATES

(75) Inventors: Steffen Goletz, Glienicke-Nordbahn (DE); Phillippe Ulsemer, Berlin (DE); Anja Löffler, Schorfheide (DE)

(73) Assignee: Glycotope GmbH, Berlin (DE)

( * ) Notice: Subject to any disclaimer, the term of this patent is extended or adjusted under 35 U.S.C. 154(b) by 1438 days.

(21) Appl. No.: 12/514,248

(22) PCT Filed: Nov. 12, 2007

(86) PCT No.: PCT/EP2007/009766
§ 371 (c)(1),
(2), (4) Date: Nov. 25, 2009

(87) PCT Pub. No.: WO2008/055703
PCT Pub. Date: May 15, 2008

(65) Prior Publication Data
US 2010/0158952 A1 Jun. 24, 2010

(30) Foreign Application Priority Data

Nov. 10, 2006 (EP) .................................. 06090208
Nov. 10, 2006 (EP) .................................. 06090209

(51) Int. Cl.
| | | |
|---|---|---|
| A23L 1/30 | (2006.01) | |
| G01N 33/569 | (2006.01) | |
| A61K 39/00 | (2006.01) | |
| A61K 39/02 | (2006.01) | |
| C07K 16/30 | (2006.01) | |
| C12N 1/20 | (2006.01) | |
| C12R 1/01 | (2006.01) | |
| C12R 1/19 | (2006.01) | |
| G01N 33/50 | (2006.01) | |

(52) U.S. Cl.
CPC ........ *G01N 33/56972* (2013.01); *A23L 1/3014* (2013.01); *A61K 39/0011* (2013.01); *A61K 39/02* (2013.01); *C07K 16/3092* (2013.01); *C12N 1/20* (2013.01); *C12R 1/01* (2013.01); *C12R 1/19* (2013.01); *G01N 33/5058* (2013.01); *G01N 33/56911* (2013.01); *A61K 2039/5152* (2013.01); *A61K 2039/5154* (2013.01); *A61K 2039/5158* (2013.01); *A61K 2039/52* (2013.01); *A61K 2039/521* (2013.01); *A61K 2039/522* (2013.01); *A61K 2039/54* (2013.01); *A61K 2039/542* (2013.01); *A61K 2039/57* (2013.01); *C07K 2317/73* (2013.01); *G01N 2400/00* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,931,275 A | 6/1990 | Shinitzky et al. | |
| 5,506,343 A | 4/1996 | Kufe | |
| 5,547,933 A | 8/1996 | Lin | |
| 5,683,674 A | 11/1997 | Taylor-Papadimitriou et al. | |
| 5,739,277 A | 4/1998 | Presta et al. | |
| 5,804,187 A | 9/1998 | do Couto et al. | |
| 5,948,646 A | 9/1999 | Srivastava | |
| 5,961,979 A | 10/1999 | Srivastava | |
| 6,168,793 B1 | 1/2001 | Srivastava | |
| 6,315,997 B1 | 11/2001 | do Couto et al. | |
| 6,984,384 B1 | 1/2006 | Subjeck et al. | |
| 7,268,120 B1 | 9/2007 | Horton et al. | |
| 7,595,192 B2 * | 9/2009 | Goletz et al. | 435/325 |
| 8,017,388 B2 * | 9/2011 | Goletz et al. | 435/325 |
| 8,088,357 B2 * | 1/2012 | Goletz et al. | 424/1.49 |
| 8,592,165 B2 | 11/2013 | Goletz et al. | |
| 8,609,370 B2 * | 12/2013 | Goletz et al. | 435/69.1 |
| 8,642,276 B2 * | 2/2014 | Goletz et al. | 435/7.1 |
| 8,741,365 B2 | 6/2014 | Goletz et al. | |
| 2002/0132771 A1 | 9/2002 | Madiyalakan | |
| 2004/0265998 A1 | 12/2004 | Goletz et al. | |
| 2005/0187378 A1 | 8/2005 | Kim | |
| 2005/0203010 A1 | 9/2005 | Kim | |
| 2006/0127419 A1 | 6/2006 | Goletz et al. | |
| 2006/0251668 A1 | 11/2006 | Goletz et al. | |
| 2006/0292129 A1 | 12/2006 | Goletz et al. | |
| 2007/0015239 A1 | 1/2007 | Bihoreau et al. | |
| 2007/0016704 A1 | 1/2007 | Harari et al. | |

(Continued)

FOREIGN PATENT DOCUMENTS

| | | |
|---|---|---|
| DE | 4329004 | 3/1995 |
| EP | 0 117 060 A2 | 8/1984 |

(Continued)

OTHER PUBLICATIONS

Goletz, Glycobiology, Nov. 2011, 21/11:1524 abstract only.*

(Continued)

*Primary Examiner* — Nita M Minnifield
(74) *Attorney, Agent, or Firm* — Nelson Mullins Riley & Scarborough LLP; Jane E. Remillard, Esq.; Jill Gorny Sloper, Esq.

(57) ABSTRACT

The present invention relates to the field of prevention and treatment of tumors and gastrointestinal disorders. The present invention relates to the prevention and treatment of Core-1-positive carcinomas. The invention relates to coreotics and a method of producing the same and to a method of prevention and treatment of core-1 positive disorders using the same. The invention relates to microorganisms or fractions thereof capable of activating cellular immunity against carbohydrates.

15 Claims, 20 Drawing Sheets

(56) References Cited

U.S. PATENT DOCUMENTS

Figure 2A:
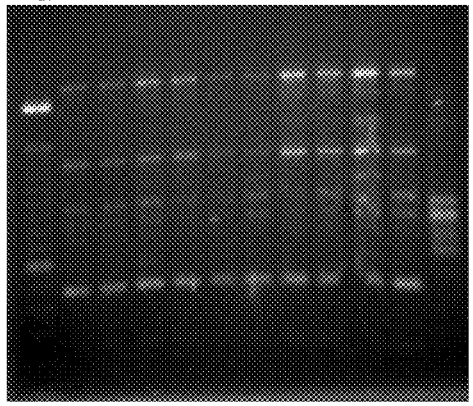

| | | | |
|---|---|---|---|
| 2008/0226681 A1 | 9/2008 | Goletz et al. | |
| 2010/0028947 A1 | 2/2010 | Goletz et al. | |
| 2010/0158952 A1* | 6/2010 | Goletz | 424/243.1 |
| 2010/0303837 A1* | 12/2010 | Goletz et al. | 424/184.1 |
| 2011/0129570 A1* | 6/2011 | Goletz | 426/61 |
| 2012/0128676 A1* | 5/2012 | Goletz et al. | 424/137.1 |
| 2012/0149877 A1* | 6/2012 | Goletz et al. | 530/387.3 |
| 2014/0302093 A1* | 10/2014 | Goletz et al. | 424/234.1 |

FOREIGN PATENT DOCUMENTS

| | | |
|---|---|---|
| EP | 1 167 537 A1 | 1/2002 |
| EP | 1920781 * | 5/2008 |
| EP | 1920781 A1 * | 5/2008 |
| WO | WO 92/15682 | 9/1992 |
| WO | WO 93/20841 | 10/1993 |
| WO | WO 94/29469 | 12/1994 |
| WO | WO 97/00957 | 1/1997 |
| WO | WO 97/30087 A1 | 8/1997 |
| WO | WO 97/40182 | 10/1997 |
| WO | WO 99/29834 | 6/1999 |
| WO | WO 00/52135 | 9/2000 |
| WO | WO 01/12217 | 2/2001 |
| WO | WO 02/44217 | 6/2002 |
| WO | WO 03/016329 | 2/2003 |
| WO | WO 03/023023 | 3/2003 |
| WO | WO 03/035636 | 5/2003 |
| WO | WO 03/044051 A1 | 5/2003 |
| WO | WO 04/009632 | 1/2004 |
| WO | WO 04/018659 | 3/2004 |
| WO | WO 04/050707 | 6/2004 |
| WO | 2005/003773 A1 | 1/2005 |
| WO | WO 2005/016962 A2 | 2/2005 |
| WO | WO 2005/017130 A2 | 2/2005 |
| WO | WO 2005/040221 A1 | 5/2005 |
| WO | WO 2005/080585 A1 | 9/2005 |
| WO | WO 2005/108423 A1 | 11/2005 |
| WO | WO 2006/012616 A2 | 2/2006 |
| WO | WO 2008/028686 A2 | 3/2008 |
| WO | WO 08/055702 | 5/2008 |
| WO | WO 2008/055703 A2 | 5/2008 |
| WO | WO 2208/055703 A2 * | 5/2008 |
| WO | WO 2013/026887 A1 * | 2/2013 |

OTHER PUBLICATIONS

Goletz et al, Glycobiology, Nov. 2011, 21/11:1525 abstract only.*
Matsumoto-Takasaki et al, BioScience Trends. 2009; 3(3):87-95.*
Ravn et al, Cancer Immunol Immunother (2007) 56:1345-1357.*
Bain et al, PLoS One, Sep. 2011, 6/9: e25007, 10 pages.*
Goletz et al, Advances in Experimental Medicine and Biology, 2003, 535:147-162.*
Henderson et al, Glycobiology vol. 21 no. 10 pp. 1277-1289, 2011.*
Irazoqui et al, Immunology and Cell Biology, 2005, 83:405-412.*
Irazoqui et al, Current Cancer Drug Targets, 2003, 3:433-443.*
Hanisch et al, Histol. Histopathol., 1997, 12:263-281.*
U.S. Appl. No. 10/524,738, filed Sep. 15, 2005, Goletz et al.
U.S. Appl. No. 10/568,098, filed Jun. 20, 2006, Goletz et al.
U.S. Appl. No. 10/536,834, filed Mar. 20, 2006, Goletz et al.
U.S. Appl. No. 10/589,447, filed Feb. 7, 2008, Goletz et al.
U.S. Appl. No. 12/440,562, filed May 14, 2009, Goletz et al.
Agrawal et al., "Cancer-associated MUC1 mucin inhibits human T-cell proliferation, which is reversible by IL-2.", Naturel. Med., 4(1):43-9 (1998).
Albert, "Dendritic cells acquire antigen form apoptotic cells and induce class I-restricted CTLs, "Nature, 392:86-89 (1998).
Allison A. et al., "The role of cytokines in the action of immunological adjuvants," Vaccine Design the Role of Cytokine Networks, Gregoriadis ed., NATO ASI Series A: Life Sciences, vol. 293, pp. 1-9, Plenum Press, NY (1997).
Anderson, "Human Gene Therapy". Science, vol. 256, pp. 808-813, (1992).
Bagshawe et al, "Antibody-Directed Enzyme Prodrug Terapy (ADEPT) for Cancer," Expert Opin Biol Ther., vol. 4, No. 11, 1777-1789 (2004).
Baumeister, "A novel expression system for production of higher active biotherapeutics with optimised glycosylation," PharmaChem, 5(4): 21-24 (2006).
Baumeister et al, "GlycoExpress: a novel expression system for the optimal glycosylation of biotherapeutics," Specialty Chemicals Magazine, (25): 46-48 (2005).
Benoist, H. et al., "Studies on the susceptibility to NK-meidated lysis and the simultaneous expression of various surface molecules in anthracyclin-treated K562 cell clones," Immunology Letters, vol. 34, Issue 1, 45-55 (1992).
Berd, "Autologous hapten-modified melanoma vaccine as postsurgical adjuvant treatment after resection of nodal metastases," J. Clin. Oncol., 15:2359-2370 (1997).
Berthier-Vergnes, "Induction of IgG Antibodies Directed to a $M_r$ 31,000 Melanoma Antigenin Patients Immunized with Vaccinia Virus Melanoma Oncolysates," Cancer Res. 54:2433-2439 (1994).
Binder, "Cutting Edge: Heat Shock Protein gp96 Induces Maturation and Migration of CD11c Cells In Vivo, "J. Immunol.; 165:6029-6035 (2000).
Boel et al., "Functional Human Monoclonal Antibodies of All Isotypes Constructed from Phage Display Library-Derived Single-Chain Fv Antibody Fragments," J. Immunological Methods, 239, 153-166 (2000).
Böhm et al., "Carbohydrate Recognition on MUC1-Expressing Targets Enhances Cytoxicity of a T cell Subpopulation", Scandinavian Journal of Immunology, vol. 46, No. 1 pp. 27-34, XP-002323076 (1997).
Bomford et al., "The control of the antibody isotype responses to recombinant human immunodeficiency virus gp 120 antigen by adjuvants," AIDS Res. Hum. Retroviruses, 8:1765 et seq. (1992).
Bonig et al. "Glycosylated vs non-glycosylated granulocyte colony-stimulating factor (G-CSF)—results of a prospective randomized monocentre study," Bone Marrow Trans. 25: 259-264 (2001).
Bourdon, "Inhibition of Tumoral Graft Growth by Pretreatment with Normal or Heat-modified Tumoral Cells," Ann. Immunology 1, 43-63 (1981).
Brechbiel et al., "Synthesis of 1-(p-isothiocyanatobenzyl) Derivatives of DTPA and EDTA. Antibody Labeling and Tumor-Imaging Studies," Inorg. Chem., 25, 2772-2781 (1986).
Brummelkamp, et al. "A System for Stable Expression of Short Interfering RNAs in Mammalian Cells". Science, vol. 296, pp. 550-553, (2002).
Burgess et al., "Possible Dissociation of the Heparin-Binding and Mitogenic Activities of the Heparin-Binding (Acidic Fibroblast) Growth Factor-1 from its Receptor Binding Activities by Site Directed Mutagenesis of a Sinale lvsine Residue," Journal of Cell Biology, vol. 111, pp. 2129-2138, 1990.
Cao, "Immunodetection of epithelial mucin (MUC1, MUC3) and mucin-associated glycoptopes (TF, Tn, and sialosyl-Tn) in benign and malignant lesions of colonic epithelium: apolar localization corresponds to malignant transformation, " Virchows Arch., 431:159-166 (1997).
Cao, Y. et al., "Expression of CD175 (Tn), CD175s (sialosyl-Tn) and CD176 (Thomsen-Friedenreich antigen) on malignant human hematopoietic cells," Intl. J. Cancer, 123: 89-99 (2008).
Carbone et al., Multistep and multifactorial carcinogenesis: when does a contributing factor become a caricnogen? Seminars in Cancer Biology vol. 14, Issue 6, Dec. 2004, pp. 399-405.
Casset et al., "A Peptide mimetic of an Anti-CD4 Monoclonal Antibody by Rational Design," Biochemical and Biophysical Research Communications, vol. 307, Issue 1, 198-205 (2003).
Cavaliere, "Selective heat sensitivity of cancer cells. Biochemical and clinical studies," Cancer 20:1351-1381 (1967).
Check, "Protection against transplanted and spontaneous lymphoma by inoculation of heat-altered syngeneic tumor cells in splenectomized mice, " Cancer, 34:197:203 (1974).
Chen et al., "Selection and Analysis of an Optimized Anti-VEGF Antibody: Crystal Structure of an Affinity-Matured FAB in Complex with an Antigen," Journal of Molecular Biology, vol. 293, Issue 4, 865-881 (1999).

(56) References Cited

OTHER PUBLICATIONS

Chen, Z. et al., "Efficient Antitumor Immunity Derived From Maturation of Dendritic Cells That had Phagocytosed Apoptotic/Necrotic Tumor Cells," International Journal of Cancer, vol. 93, No. 4, pp. 539-548 (2001).
Chothia et al., "The Predicted Structure of Immunoglobulin D1.3 and Its Comparison with the Crystal Structure," Science, 233, 755-758 (1986).
Chothia et al., "Canonical Structures for the Hypervariable Regions of Immunoglobulins," J. Mol. Biol., 196, 901-917 (1987).
Chothia et al., "Conformations of Immunoglobulin Hypervariable Regions," Nature, 342, 877-883 (1989).
Chothia et al., "Structural Repertoire of the Human VH Segments," J. Mol. Biol., 227, 799-817 (1992).
Clayman (ed.), the American Medical Association Encyclopedia of Medicine at 573-574, 576 and 1034 (1989).
Cox, J. et al., "Adjuvants—A Classification and Review of Their Modes of Action," Vaccine, vol. 15, No. 3, pp. 248-256 (1997).
Cox et al., "Development of an Influenza-ISCOM.TM. Vaccine," in Vaccine Design at pp. 33-49 (1997).
Cryz, Jr., S.J., Immunotherapy and Vaccines, edited by Stanley J. Cryz, pp. 3-11, VCH, Weinheim, Germany (1991).
Czuczman et al., Treatment of Patients With Low-Grade B-Cell Lymphoma With the Combination of Chimeric Anti -CD20 Monoclonal Antibody and CHOP Chemotherapy Journal of Clinical Oncology, vol. 17, Issue 1 (January), 1999: 268-276.
Dai et al., "Effect of Desialylation on Binding, Affinity, and Specificity of 56 Monoclonal Antibodies Against MUC1 Mucin", Tumor Biology, vol. 19, Supplemental 19, pp. 100-110, (1998).
Dall'Olio, et al., "Expression of beta-galactoside alpha 2,6-sialytransferase does not alter the susceptibility of human colon cancer cells to NK-mediated cell lysis." Glycobiology. 7:507-513 (1997).
Dermer, "Another Anniversary for the War on Cancer," Biotechnology, vol. 12, p. 320, (1994).
Dickson, "Hyperthemia in the treatment of cancer, "Lancet , 1:202-205 (1979).
Dictionary of Immunology, pp. 3, 7, 46, 87-88, 94, 97, 105, 116 (1985).
Dressel, "Heat Shock Protein 70 is Able to Prevent Heat Shock-Induced Resistance of Target Cells to CTL, "J Immunol., 164:2362-2371 (2000).
Duk et al., "Purification of Human Anti-TF (Thomesen-Friedenreich) and Anti-Tn Antibodies by Affinity Chromatography on Glycophorin A Derivatives and Characterization of the Antibodies by Mircrotiter Plate ELISA", Archivum Immunologiae et Therapiae Experimentalis, vol. 46, No. 2, pp. 69-77, XP-008045186, (1998).
Elbashir, et al. "Duplexes of 21-nucleotide RNAs mediate RNA interference in cultured mammalian Cells". Nature, vol. 411, pp. 494-498, (2001).
Euhus et al., Abstract, "Appraisal of Anti-Idiotypic Antibodies in the Treatment of Solid Tumors in Humans," Surgery, Gynecology and Obstetrics, vol. 175, No. 1, 89-96 (1992).
European Search Report for Application No. 11 17 6193, dated Apr. 16, 2012.
European Search Report for Application No. 11 17 6197, dated Apr. 12, 2012.
European Search Report for Application No. 11 17 6200, dated Apr. 12, 2012.
Feng, "Stressed apoptotic tumor cells express heat shock proteins and elicit tumor-specific immunity," Bllod, 97:3505-3512 (2001).
Ferencik, M. , Handbook of Immunochemistry, p. 115-116, Chapman & Hall (1993).
Fiebig et al., "Clonogenic Assay with Established Human Tumor Xenografts: Correlation of In Vitro to In Vivo Activity as a Basis for Anticancer Drug Discovery", European Journal of Cancer, vol. 40, pp. 802-820 (2004).
Fogolin et al. "Choice of the adequate quantification methods for recombinant human GM-CSF produced in different host systems," Electronic J. of Biotech. 5(3): 243-250 (2002).
Freshney, "Culture of Animal Cells, A Manual of Basic Technique," Alan R Liss, Inc., 1983, New York, p. 4.
Fujiwara, "Establishment of a tumor-specific immunotherapy model utilizing TNP-reactive helper T cell activitiy and its application to the autochthonous tumor system." J. Immunol., 133:509-514 (1984).
Fukuda, M. et al. "Structures of novel sialyated O-linked oligosaccharides isolated from human erythrocyte glycophorins," The Journal of Biological Chemistry, 262(25): 11952-11957 (1987).
Gallucci, "Danger signals: SOS to the immune system, "Curr. Opin. Immunol., 13:114-119 (2001).
Gallucci,"Natural adjuvants: Endogenous activators of dendritic cells, "Nat. Med., 11:1249-1255 (1999).
Giovanella, "Effects of Elevated Temperatures and Drugs on the Viability of L1210 Leukemia Cells," Cancer Res. 30:1623-1631 (1970).
Goletz et al., "Binding Patterns of 33-TD-4(MUC1) Antibodies Towards Single-Chain Fragments and Peptides Mimicking the Conformation of the MUC1 PDTRP Epitope", Tumor Biology, vol. 21, No. Supplement 1 p. 142, Sep. 2000.
Gollasch et al., "Identification of Immunogenic Peptide-Mimics for the Thomesen-Friedenreich-Glycoantigen", Annals of Hematology, Berlin, DE vol. 77, No. suppl. 2, p. S84, XP-000960533, (1998).
Gough, "Macrophages Orchestrate the Immune Response to Tumor Cell Death," Cancer Research, 61:7240-7247 (2001).
Green et al., "Activation-induced cell death in T cells," Immunological Reviews, 2003, vol. 193, pp. 70-81.
Gura, "Systems for Identifying New Drugs are Often Faulty," Science, vol. 278, pp. 1041-1042, 1997.
Herrera et al., "Efficiency of Erythropoietin's Signal Peptide for HIV MN-1 gp 120 Expression," Biochem. Biophys. Res. Com., 273, 557-559 (2000).
Hinoda et al., "Circulating Tumor-Associated Antigens Detected by Monoclonal Antibodies Against the Polypeptide Core of Mucin: Comparison of Antigen MUSE11 with CA15-3," Gastroenterologia Japonica, vol. 27, No. 3, 390-395 (1992).
Hinoda et al., Primary Structure of the variable regions of a monoclonal antibody MUSE11 recognizing the tandem repeat domain of a mucin core protein, MUC1 Journal of Clinical Laboratory Analysis, 7(2): 100-104 (1993).
Holm et al., "Functional Mapping and Single Chain Construction of the Anti-Cytokeratin 8 Monoclonal Antibody TS1," Molecular Immunology, 44 (6): 1075-1084 (2007).
Hong, Y. et al. "Lec3 Chinese Hamster Ovary Mutants Lack UPD-N-acetylglucosamine 2-EPimerase Activity Because of Mutations in the Epimerase Domain of the Gne Gene," J. Biol. Chem. 278(52): 53045-53054 (2003).
Hosse et al., "A New Generation of Protein Display Scaffolds for Molecular Recognition," Protein Science, vol. 15, pp. 14-27, 2006.
Hsieh et al., "Controlling Chemical Reactivity with Antibodies," Science, vol. 260, No. 5106, 337-339 (1993).
Huang, "Heat-induced Gene Expression as a Novel Targeted Cancer Gene Therapy Strategy," Cancer Research, 60:3435-3439 (2000).
Hufton et al., "Development and Application of Cytotoxic T Lymphocyte-Associated Antigen 4 as a Protein Scaffold for the Generation of Nevel Binding Ligands," FEBS Letters. vol. 475, Issue 3, pp. 225-231 (2000).
Ichiyama, "Induction of Non-HLA-restricted Anti-tumour Effector Cells with Strong Cytoxic Activity Using MUC1/B7 Cotransfected K562 Cells", Cell Resource Center for Biomedical Research, Institute of Development, Aging, and Cancer, Tohoku University, Sendai, Japan, vol. 51, No. 3-4, pp. 93-110, XP-001182213, (2000).
International Search Report for PCT/DE2003/003994 (WO/2004/050707 A3) dated Aug. 10, 2004.
International Search Report for PCT Application No. PCT/EP2003/009140 (WO 2004/018659) dated Feb. 9, 2004.
International Search Report for PCT/EP2004/009281 (WO2005/017130) dated Apr. 14, 2005.
International Search Report for PCT Application No. PCT/EP2005/01593 (WO 2005/080585) dated Jul. 15, 2005.

(56) References Cited

OTHER PUBLICATIONS

Isner, et al., "Clinical evidence of angiogenesis after arterial gene transfer of phVEGF165 in patient with ischaemic limb". The Lancet, vol. 348, pp. 370-374, (1996).
Jacobs, C. et al. "Substrate specificity of the sialic acid biosynthetic pathway," Biochemistry 40 (43): 12864-12874(2001).
Jager et al., "Treatment of Extranodal Marginal Zone B-cell Lymphoma of Mucosa-Associated Lymphoid Tissue Type With Cladribine: A Phase II Study," Journal of Clinical Oncology, vol. 20, Issue 18 (September), 2002: 3872-3877, 2002 American Society for Clinical Oncology.
Jensen et al., "Functional Improvement of Antibody Fragments Using a Novel Phage Coat Protein III Fusion System," Biochemical and Biophysical Research Communications, vol. 298, pp. 566-573, 2002.
Jeschke et al., "Expression of the Thomsen-Friedenreich Antigen and of its Putative Carrier Protein Muscin 1 in the Human Placenta and in Trophoblast Cells in Vitro" Histochemistry and Cell Biology, vol. 117, No. 3, 219-226 (Mar. 2002).
Jones, M. et al. "Characterization of the cellular uptake and metabolic conversion of acetylated N-acetylmannosamine (ManNAc) analogues to sialic acids," Biotechnology and Bioengineering, 85 (4): 394-405 (2004).
Kalka-Moll, W. et al., "Zwitterionic Polysaccharides Stimluate T Cells by MHC Class II-Dependent Interactions," The Journal of Immunology, vol. 169, pp. 6149-6153 (2002).
Karsten et al., "A New Monoclonal Antibody (A78-G/A7) to the Thomsen-Friedenreich Pan-Tumor Antigen," Hybridoma, vol. 14, No. 1, 37-44 (1995).
Karsten et al., "Enhanced Binding of Antibodies to the DTR Motif of MUC1 Tandem Repeat Peptide is Mediated by Site-Specific Glycosylation," Cancer Research, American Association for Cancer Research, Baltimore, MD, US, vol. 58, No. 12, pp. 2541-2549, XP-002112486 (Jun. 15, 1998).
Keppler, O. et al. "UDP-GicNac 2-Epimerase: A Regulator of Cell Surface," Science 284: 1372-1376 (1999).
Kotera Y. et al., "Comparative Analysis of Necrotic and Apoptotic Tumor Cells as a Source of Antigen(s) in Dendritic Cell-Based Immunization," Cancer Research, vol. 61 No. 22, pp. 8105-8109 (2001).
Kozak et al., "Nature of the Bifunctional Chelating Agent Used for Radioimmunotherapy with Yttrium-90 Monoclonal Antibodies: Critical Factors in Determining in vivo Survival and Organ Toxicity," Cancer Res., 49, 2639-2644 (1989).
Kunz, "Synthetic Glycopeptides for the Development of Tumour-selective Vaccines", Journal of Peptide Science: an Official Publication of the European Peptide Society, vol. 9, No. 9 pp. 563-573, XP-00845163, (Sep. 2003).
Lazar, et al., "Transforming Growth Factor Alpha: Mutation of Aspartic Acid 47 and Leucine 48 Results in Different Biological Activities," Molecular and Cellular Biology, vol. 8, pp. 1247-1252, 1988.
Leffell, Mary S., "An Overview of the Immune System: The Molecular Basis for Immune Responses", Human Immunology Handbook, 1:1-45 (1997).
Liao et al., "Design of Transgenes for Efficient Expression of Active Chimeric Proteins on Mammalian Cells," Biotechnol. Bioeng., 73, 313-323 (2001).
Libyh et al., "A Recombinant Human scFv Anti-Rh(D) Antibody with Multiple Valences Using A C-Terminal Fragment of C4-Binding Protein," Blood, 90 (10), 3978-3983 (1997).
Linardou, Abstract, "Deoxyribonuclease I (DNAse I). A Novel Approach for Targeted Cancer Therapy," Cell Biophys., vol. 24-25, 243-248 (1994).
Lozzio et al. "Human Chronic Myelogenous Leukemia Cell-Line With Positive Philadelphia Chromosome," (Blood, Mar. 1975, 45(3):321-334).
Luftig, R.B., Microbiology and Immunology, pp. 228-229, Lippincott-Raven Pub, Phila. (1998).
MacCullum et al., "Antibody-Antigen Interactions: Contact Analysis and Binding Site Topography," Journal of Molecular Biology, vol. 262, Issue 5, 732-745 (1996).
Mach, "Cytokine-secreting tumor cell vaccines, "Curr. Opin. Immunol. 12, 571-575 (2000).
Mantey, L. et al. "Efficient Biochemical Engineering of Cellular Sialic Acids Using an Unphysiological Sialic Acid Precursor in Cells Lacking UDP-N-acetylglucosamine 2-epimerase," FEBS Letters, 503, Nr-1: 80-84 (2001).
Martin et al., "Structural Families in Loops of Homologous Proteins: Automatic Classification, Modelling, and Application to Antibodies," J. Mol. Biol., 263, 800-815 (1996).
Matzinger, P., "Tolerance, Danger, and the Extended Family," Annual Review in Immunology, vol. 12, 991-1045 (1994).
Mazmanian, S. et al., "The Love-Hate Relationship Between Bacterial Polysaccharides and the Host Immune System," Nature Reviews, vol. 6, pp. 849-858 (2006).
Melcher, "Apoptosis or Necrosis for Tumor Immunotherapy: What's in a name," J. Mol. Med., 77:824-833 (1999).
Melcher, "Tumor Immunogenicity is Determined by the Mechanism of Cell Death Via Induction of Heat Shock Protein Expression," Nat. Med., 4:581-587 (1998).
Mise,"Effect of Heat Treatment on Tumor Cells and Antitumor Effector Cells, "Cancer Res., 50:6199-6202 (1990).
Mitchell, "Active Specific Immunotherapy for Melanoma: Phase I Trial of Allogeneic Lysates and a Novel Adjuvant, " Cancer Res., 48:5883-5893 (1988).
Mivechi, "Heat Sensitivity, Thermotolerance, and Profile of Heat Shock Protein Synthesis of Human Myelogeneous Leukemia," Cancer Research, Apr. 1989, 49: 1954-1958.
Mondovi, "Increased immunogenicity of Ehrlich Ascites Cells After Heat Treatment," Cancer, 30(4):885-888 (1972).
Morrison et al., "Complement Activation and Fc Receptor Binding by IgG," in: Protein Engineering of Antibody Molecules for Prophylactic and Therapeutic Applications in Man, 1993, Mike Clark, Ed., pp. 101-113.
MSNBC New Services, "Mixed Results on New Cancer Drug," Nov. 9, 2000.
Muramatsu et al., "Glycoprotein-Bound Large Carbohydrates of Early Embryonic Cells: Structural Characteristic of the Glycan Isolated from F9 Embryonal Carcinoma Cells," J. Biochem. 94:799-810 (1983).
Natali, et al., Heterogeneity in the expression of HLA and tumor-associated antigens by surgically removed and cultured breast carcinoma cells. Cancer Res 1983; 43;660-668.
Nicaise et al., "Affinity Transfer by CDR Grafting on a Nonimmunoglobulin Scaffold," Protein Science, vol. 13, pp. 1882-1891, 2004.
Novina, et al. "siRNA-directed inhibition of HIV-1 infection". Nature Medicine, vol. 8, No. 7, pp. 681-686 (2002).
Nuttall et al., "Design and Expression of Soluble CTLA-4 Variable Domain as a Scaffold for the Display of Functional Polypeptides," Proteins, 36, 217-227 (1999).
Nygren et al., "Scaffolds for Engineering Novel Binding Sites in Proteins," Curr. Opin. Struct. Biol., 7, 463-469 (1997).
Office Action (Restriction Requirement) dated Oct. 5, 2006 in U.S. Appl. No. 10/524,738.
Office Action dated Dec. 14, 2006 in U.S. Appl. No. 10/524,738.
Office Action dated Aug. 10, 2007 in U.S. Appl. No. 10/524,738.
Office Action dated Feb. 6, 2008 in U.S. Appl. No. 10/524,738.
Office Action dated Aug. 4, 2008 in U.S. Appl. No. 10/524,738.
Advisory Action dated Jan. 29, 2009 in U.S. Appl. No. 10/524,738.
Notice of Allowance dated May 19, 2009 in U.S. Appl. No. 10/524,738.
Office Action (Restriction Requirement) dated May 9, 2008 in U.S. Appl. No. 10/568,098.
Office Action dated Jan. 27, 2009 in U.S. Appl. No. 10/568,098.
Office Action dated Jul. 23, 2009 in U.S. Appl. No. 10/568,098.
Advisory Action dated Oct. 7, 2009 in U.S. Appl. No. 10/568,098.
Advisory Action dated Jan. 14, 2010 in U.S. Appl. No. 10/568,098.
Pre-Appeal Brief Conference Decision dated Feb. 25, 2010 in U.S. Appl. No. 10/568,098.
Office Action dated Sep. 29, 2010 in U.S. Appl. No. 10/568,098.

(56) References Cited

OTHER PUBLICATIONS

Examiner Interview Summary Record dated Apr. 28, 2011 in U.S. Appl. No. 10/568,098.
Examiner Interview Summary Record dated May 5, 2011 in U.S. Appl. No. 10/568,098.
Notice of Allowance dated May 12, 2011 in U.S. Appl. No. 10/568,098.
Office Action (Restriction Requirement) dated Jun. 23, 2008, in U.S. Appl. No. 10/536,834.
Office Action dated Feb. 19, 2009 in U.S. Appl. No. 10/536,834.
Office Action dated Nov. 10, 2009 in U.S. Appl. No. 10/536,834.
Office Action dated Aug. 5, 2010 in U.S. Appl. No. 10/536,834.
Office Action dated Feb. 2, 2011 in U.S. Appl. No. 10/536,834.
Notice of Allowance dated Aug. 25, 2011 in U.S. Appl. No. 10/536,684.
Office Action (Restriction Requirement) dated Nov. 30, 2011 in U.S. Appl. No. 12/514,200.
Office Action dated Oct. 13, 2011 in U.S. Appl. No. 12/440,562.
Office Action dated Oct. 28, 2010 in U.S. Appl. No. 12/440,562.
Office Action dated Feb. 3, 2011 in U.S. Appl. No. 10/589,447.
Office Action dated Aug. 26, 2011 in U.S. Appl. No. 10/589,447.
Office Action dated Apr. 9, 2012 in U.S. Appl. No. 10/589,447.
Ohyama, et al., "Dual roles of sialyl Lewis X oligosaccharides in tumor metastasis and rejection by natural killer cells". The EMBO Journal, vol. 18 No. 6, pp. 1516-1525 (1999).
Ohyma et al., "Natural Killer cells attack tumor cells expressing high levels of sialyl Lewis x oligosaccharides", PHAS, Vol. 99. No. 21, pp. 13789-13794 (2002).
Olsvik, "Magnetic Separation Techniques in Diagnostic Microbiology," vol. 7, No. 1, 43-54 (1994).
Ouagari, et al. "Glycophorin A Protects K562 Cells from Natural Killer Cell Attack". The Journal of Biological Chemistry, vol. 270 No. 45, pp. 26970-26975, (1995).
Owens, et al. "identification of two short internal ribosome entry sites selected from libraries of random oligonucleotides". PNAS, vol. 98, No. 4, pp. 1471-1476, (2001).
Paddison, et al. "Short hairpin RNAs (shRNAs) induce sequence-specific silencing in mammalian cells". Genes & Development, vol. 16, pp. 948-958, (2002).
Pahlsson, et al., "Biochemical characterization of the O-glycans on recombinant glycophorin a expressed in Chinese hamster ovary cells." Glycoconj. J., 11:43-50 (1994).
Panka et al., 'Variable Region Framework Differences Result in Decreased or Increased Affinity of Variant Anti-Digoxin Antibodies, Proc. Natl. Acad. Sci., vol. 85, No. 9, 3080-3084 (1988).
Pascalis et al., "Grafting of 'Abbreviated' Complementarity-Determining Regions Containing Specificty-Determining Residues Essential for Ligand Contact to Engineer a Less Immunogenic Humanized Monoclonal Antibody," Journal of Immunology, vol. 169, 3076-3084 (2002).
Paul, W. E. (Ed.), Fundamental Immunology, p. 1007-1009, Raven Press, NY 1989.
Peach et al., "Complementarity Determining Region 1 (CDR1)- and CDR3-analogous Regions in CTLA-4 and CD28 Determine the Binding to B7-1," Journal of Experimental Medicine, vol. 180, pp. 2049-2058, 1996.
Peters et al., "Preparation of Immuno-Therapeutic Autologous Tumor Cell Vaccines from Solid Tumors," Cancer Res., 39:1353-1360 (1979).
Phillips, T., Analytial Techniques in Immunochemistry, pp. 307-310, Marcel Dekker, NY (1992).
Price, "Effect of heat and flutaraldehyde upon the immunogenicity of Meth A sarcoma cells," Br. J. Cancer 40:663-665 (1979).
Price et al., "Summary Report on the ISOBM TD-4 Workshop: Analysis of 56 Monoclonal Antibodies Against the MUCI Mucin" Tumor Biology, Karger, Basel, CH, vol. 19, No. Suppl. 1, 1-20 (1998).
Restifo, "Building better vaccines: how apoptotic cell death can induce inflammation and activate innate and adaptive immunity," Curr. Opin. Immunol., 12:597-603 (2000).

Romani et al., "Proliferating dendritic cell prgenitors in human blood." J. Exp. Med., 180:83-93 (1994).
Rooman et al., "Amino Acid Sequence Templates Derived from Recurrent Turn Motifs in Proteins: Critical Evaluation of Their Predictive Power," Protein Eng., 3, 23-27 (1989).
Rudikoff et al., "Single Amino Acid Substitution Altering Antigen-Binding Specificity," Proc. Natl. Acad. Sci., vol. 79, No. 6, 1979-1983 (1982).
Saerens et al., "Identification of a Universal VHH Framework to Graft Non-Canonical Antigen-Binding Loops of Camel Single-Domain Antibodies," Journal of Molecular Biology, vol. 352, Issue 3, pp. 597-607, Sep. 2005.
Samali et al., "Thermotolerance and cell death are distinct cellular responses to stress: dependence on heat shock proteins," FEBS letters, Nov. 1999, 461 (3):306-310.
Santegoets et al., "In vitro priming of tumor-specific cytotoxic T lymphocytes using allogeneic dendritic cells derived from the human MUTZ-3 cell line" Cancer Immunol Immunother, 2006, vol. 55, pp. 1480-1490.
Sauter Birthe et al., "Consequences of Cell Death: Exposure to Necrotic Tumor Cells, but Not Primary Tissue Cells or Apoptotic Cells, Induces the Maturation of Immunostimulatory Dendritic Cells,"Journal of Experimental Medicine, vol. 191, No. 3 pp. 423-433 (2000).
Scheibel et al., "Contribution of N- and C-Terminal Domains to the Function of Hsp90 in *Saccharomyces Cerevisiae*," Molecular Microbiology, vol. 34, pp. 701-713, 1999.
Schild, "GP96—the immune system's swiss army knife," Nat. Immunol. 1:100-101 (2000).
Schlom, "Monoclonal Antibodies: They're More and Less Than You Think," in: Molecular Foundations of Oncology, 1991, Samuel Broder, Ed., pp. 95-134.
Schneider et al., "Thermostability of Membrane Protein Helix-Helix Interaction Elucidated by Statistical Analysis." FEBS Letters, vol. 532, No. 1-2, 231-236 (2002).
Schneider, F. et al., "Overexpression of Sialyltransferase CMP-Sialic Acid: Galbetal, 3GalNac-R Alpha6-Sialyltransferase is Related to Poor Patient Survival in Human Colorectal Carcinomas," Cancer Research, American Association of Cancer Research, vol. 61, No. 11, 4605-4611 (Jun. 1, 2001).
Selawry, "Hyperthermia in Tissue cultured Cells of Malignant Origin," Cancer Res., 17:785-791 (1957).
Sensi, "Clonal Expansion of Lymphocytes in Human Metastases after Treatment With a Hapten-modified Autologous Tumor Vaccine,"Clin. Invest. 99:710-717 (1997).
Shaif-Muthana, "Dead or Alive: Immunogenicity of human Melanoma Cells When Presented by Dendritic Cells," Cancer Res., 60:6441-6447 (2000).
Shinkawa, T. et al. "The Absence of Fucose but Not the Presence of Galactose or Bisecting N-Acetylglucosamine of Human IgG1 Complex-type Oligosaccharides Shows the Critical Rile of Enhancing Antibody-dependent Cellular Cytotoxicity," The Journal of Biological Chemistry, 278(5): 3466-3473 (2003).
Sigma-Aldrich catalog, Granulocyte Macrophage Colony—Stimulating Factor Human, dowloaded 2011.
Sivanaadham, et al. "CancerVaccines: Clinical Applications". Principles and practice of the Biologic Therapy of Cancer. Third Edition, S. Rosenberg, pp. 632-647, Lippincott Williams & Wilkins, Philadelphia, PA (2000).
Skerra, A., "Engineered Protein Scaffolds for Molecular Recognition," J. Mol. Recog., 13, 167-187 (2000).
Skerra et al., "Alternative Non-Antibody Scaffolds for Molecular Recognition," Current Opinion in Biotechnology, vol. 18, pp. 295-303, 2007.
Snippe et al., "Adjuvant Directed Immune Specificity at the Epitoope Level. Implications for Vaccine Development. A Model Study Using Semliki Forest Virus Infection of Mice,"pp. 155-166 in Vaccine Design, The Role of Cytokine Networks, Plenum Press (1997).
Somersan S. et al., "Primary Tumor Tissue Lysates Are Enriched in Heat Shock Proteins and Induce the Maturation of Human Dendritic Cells," Journal of Immunology, vol. 167, No. 9 pp. 4844-4852 (2001).

(56) References Cited

OTHER PUBLICATIONS

Springer, et al., "Immunoreactive T and Tn epitiopes in cancer diagnosis, prognosis, and immunotherapy." J. Mol. Med., 75:594-602 (1997).
Stimmel et al., "Yttrium-90 Chelation Properties of Tetraazatetraacetic Acid Macrocycles, Diethylenetriaminepentaacetic Acid Analogues, and a Novel Terpyridine Acyclic Chelator," Bioconjug. Chem., 6, 219-225 (1995).
Suzuki et al., A comparison of the genotoxicity of ethylnitrosourea and ethyl methanesulfonate in lacz transgenic mice (Muta™ Mouse) Mutation Research 1997; pp. 75-82; Abstract.
Tachibana et al; "Altered reactivity of immunoglobulin produced by human-human hybridoma cells transfected by pSV2-neo gene," (Cytotechnology, 1991, vol. 6, pp. 219-226).
Thatcher, "Anti-T Antibody in Malignant Melanoma Patients. Influence of Response and Survival Following Chemotherapy-Changes in Serum Levels Following C Parvum," BCG Immunication Cancer, vol. 46, No. 6, 1378-1382 (1980).
Todryk, "Heat Shock protein 70 induced during tumor cell killing induces Th1 cytokines and targets immature dendritic cell precursors to enhance antigen uptake, " The Journal of Immunology, 163:1398-1408 (1999).
Vajdos et al., "Comprehensive Functional Maps of the Antigen-Binding Site of an Anti-ErbB2 Antibody Obtained with Shotgun Scanning Mutagenesis," Journal of Molecular Biology, vol. 320, Issue 2, 415-428 (2002).
Van Rinsum, et al., "Specific inhibition of human natural kill cell-mediated cytotoxicity by sialic acid and sialo-oligosaccharides." Int. J. Cancer, 38:915-922 (1986).
Verma, et al. "Gene therapy-promises, problems and prospects". Nature, vol. 389, pp. 239-242, (1997).
Vermes, "A novel assay for apoptosis. Flow cytometric detection of phosphatidylserine expressionon early apopptotic cells using fluorescein labelled Annexin V," J. Immunol. Meth., 184:39-51 (1995).
Viswanatha, K. et al. "Engineering sialic acid synthetic ability into insect cells: identifying metabolic bottlenecks and devising strategies to overcome them," Biochemistry 42(51): 15215-15225 (2003).
Voshol, "Cell Surface Glycoconjugates as Possible Target Structures for Human Natural Killer Cells: Evidence Against the Involvement of Glycolipids and N-Linked Carbohydrate Chains," Glycobiology, 3:69-75 (1993).
Wang, "Second-Generation Adenovirus Vectors," Nat. Med., 2:714-716 (1996).
Wells, "Heat Shock proteins, tumor immunogenicity and antigen presentation: an integrated view,"Immunol. Today, 21:129-132 (2000).
Werkmeister, "Modulation of K562 Cells with Sodium Butyrate. Association of Impaired NK Susceptibility with Sialic Acid and Analysis of Other Parameters," Int. J. Cancer, 32:71-78 (1983).
Wu et al., "Conformation of Complementarity Determining Region L1 Loop in Murine IgG □ Light Chain Extends the Repertoire of Canonical Forms," J. Mol. Biol., 229, 597-601 (1993).
Wu, et al., "Humanization of a Murine Monoclonal Antibody by Simultaneous Optimization of Framework and CDR Residues," Journal of Molecular Biology, vol. 294, Issue 1, 151-162 (1999).
Yoshima et al., "Heat Shock Factor 1 Mediates Hemin-induced hsp70 Gene Transcription in K562 Erythroleukemia Cells," BC, Sep. 1998, 273(39): 25466-25471.
Yu, "RNA Interference by Expression of Short-Interfering RNAs and Hairpin RNAs in Mammalian Cells," PNAS, 99:6047-6052 (2002).
Zhang, "Selection of Tumor Antigens as Targets for Immune Attack Using Immunohistochemistry: II. Blood Group-Related Antigens," Intl. J. Cancer, 73, 50-56 (1997).
Springer, G.F., et al., "Origin of Anti Thomsen Friedenreich and TN Agglutinins in Man and in White Leghorn Chicks," *British Journal of Haematology*, vol. 47, No. 3, pp. 453-460 (1981).

Klaamas, K., et al., "Expression of Tumor-Associated Thomsen-Friedenreich Antigen (T AG) in Helicobacter Pylori and Modulation of T AG Specific Immune Response in Infected Individuals," *Immunological Investigations*, vol. 31, No. 3/4, pp. 191-204 (2002).
U.S. Appl. No. 12/514,200, filed May 8, 2009, Goletz et al.
Kurtenkov, O., et al., "Better Survival of Helicobacter Pylori Infected Patients With Early Gastric Cancer Is Related to a Higher Level of Thomsen-Friedenreich Antigen-Specific Antibodies," *Immunological Investigations*, vol. 32, No. 1-2, pp. 89-93 (2003).
Takahashi et al., "Antitumor Effects of the Intravesical Instillation of Heat Killed Cells of the Lactobacillus Casei Strain Shirota on the Murine Orthotopic Bladder Tumor MBT-2," Journal of Urology, vol. 166, No. 6, pp. 2506-2511 (2001).
Matsuzaki, T., et al., "Antitumor Effect of Intrapleural Administration of Lactobacillus-Casei in Mice," *Cancer Immunology Immunotherapy*, vol. 26, No. 3, pp. 209-214 (1988).
Goletz, S., et al., "Thomsen-Friedenreich Antigen: The Hidden Tumor Antigen," *Advances in Experimental Medicine and Biology*, vol. 535, pp. 147-162 (2003).
Butschak, G., et al., "Isolation and Characterization of Thomsen-Friedenreich-Specific Antibodies From Human Serum," *Tumor Biology*, vol. 23, No. 3, pp. 113-122 (2002).
Clausen, H., et al., "Monoclonal Antibodies Directed to the Blood Group A Associated Structure Galactosyl-A Specificity and Relation to the Thomsen-Friedenreich Antigen," *Molecular Immunology*, vol. 25, No. 2, pp. 199-204 (1988).
Takano, Y., et al., "Lymph Node Metastasis-Related Carbohydrate Epitopes of Gastric Cancer With Submucosal Invasion," *Surgery Today* 2000, vol. 30, No. 12, pp. 1073-1082 (2000).
Franco, A., "CTL-Based Cancer Preventive/Therapeutic Vaccines for Carcinomas: Role of Tumour-Associated Carbohydrate Antigens," *Scandinavian Journal of Immunology*, vol. 61, No. 5, pp. 391-397 (2005).
Croce, M.V., et al., "The Use of Carbohydrate Antigens for the Preparation of Vaccines for Therapy in Breast Cancer," *Drugs of Today*, vol. 38, No. 11, pp. 759-768 (2002).
MacLean, G.D., et al., "Active Immunization of Human Ovarian Cancer Patients Against a Common Carcinoma (Thomsen-Friedenreich) Determinant Using a Synthetic Carbohydrate Antigen," *Journal of Immunotherapy*, vol. 11, pp. 292-305 (1992).
Slovin, S.F., et al., "Thomsen-Friedenreich (TF) Antigen As a Target for Prostate Cancer Vaccine: Clinical Trial Results With TF cluster (c)-KLH Plus QS21 Conjugate Vaccine in Patients With Biochemically Relapsed Prostate Cancer," *Cancer Immunology Immunotherapy*, vol. 54, No. 7, pp. 694-702 (2005).
Baumeister and Goletz, "Voll Funktionsfähige Humane Dendritische Zelllinie," *Laborwelt* [online], vol. 6, 2005, url:http://www.nemod.com/downloads/nemoddc%20IN%20laborwelt%207.2.05.pdf.
Dorai, H., et al., "The Effect of Dihydrofolate Reductase-Mediated Gene Amplification on the Expression of Transfected Immunoglobulin Genes," *Journal of Immunology* (Baltimore, Md. 1950), Dec. 15, 1987, vol. 139, No. 12, pp. 4232-4241.
Kaneko, Y., et al., "Anti-Inflammatory Activity of Immunogloubulin G Resulting from FC Sialylation," *Science, American Association for the Advancement of Science*, Aug. 2006, vol. 313, No. 5787, p. 671.
Baumeister, H., "Glycoengineering-a Technology for Production of Glycoproteins," *Journal of Biotechnology*, Nov. 2004, pp. 10-11.
Kanda Yutaka, et al., "Comparison of Cell Lines for Stable Production of Fucose-Negative Antibodies with Enhanced ADCC," *Biotechnology and Bioengineering*, Jul. 2006, vol. 94, No. 4, pp. 680-688.
Goletz, S., "Turning Glycomics into Health," (2006) XP00243302.
Geneseq, "DHFR—Synuclein Fusion Protein GST—ATSalpha Seq. ID No. 81," (2005) XP002430726.
"Sequence 628 from Patent WO 2005/016962," (2005) XP002430727.
International Search Report for PCT Application No. PCT/EP2007/007877 (WO 2008/028686 A3) dated Apr. 18, 2008.
International Search Report for PCT Application No. PCT/EP2007/009766 (WO 2008/055703 A2) dated Oct. 7, 2008.

(56) References Cited

OTHER PUBLICATIONS

International Search Report for PCT Application No. PCT/EP2007/009765 (WO 2008/055702 A1) dated Apr. 15, 2008.

U.S. Appl. No. 12/991,827, filed Jan. 28, 2011, Steffen Goletz.
U.S. Appl. No. 12/514,200, filed Nov. 11, 2009, Steffen Goletz, mailed Sep. 18, 2012.

* cited by examiner

FIG. 1

```
+MU1
!
!     +Bacteroides thetaiotaomicron strain 17.4 AY319392
!     !
!     !     +Bacteroides thetaiotaomicron strain 0633 AY895186
!     !   +7
!   +11  +8 +Bacteroides thetaiotaomicron strain 8713 AY895202
!   !!   !!
!   !!  +9 +Bacteroides thetaiotaomicron BNRRR16SB M58763
!   !!  !!
!   !  +10 +Bacteroides thetaiotaomicron strain 3751 AY895192
!   !   !
+20   !     +Bacteroides thetaiotaomicron ATCC 29148 BNRRR16SAF L16489
!!   !
!!   !     +Bacteroides acidifaciens AB021156
!! +18    +2
!!!!    !+Bacteroides acidifaciens strain A1 AB021158
!!!!   +5
!!!!   !!+Bacteroides acidifaciens strain A32 AB021162
!!!!   !+4
!!!! +12 !+Bacteroides acidifaciens strain A29 AB021160
!!!!!! +3
!!!!!!    +Bacteroides acidifaciens strain A40 AB021164
!!!!!!
!!! +13 +Bacteroides caccae ATCC 43185T BC16S X83951
! +19  !
!  !  !+Bacteroides fragilis BNRRGDAM1 1656
+22  !  +6
!!  !  ! +---Bacteroides distasonis BNRRR16S M86695
!!  !  +-1
!!  !    +---------------Escherichia coli ATCC 11755T ECAT1177T X80725
!!  !
!!  !   +Bacteroides ovatus AB050108
!!  !  +14
!!  ! +15 +Bacteroides ovatus ATCC 8438T BO16S X83952
!!  !!!
!!  +17 +Bacteroides ovatus NCTC 11153 L16484 BNRRR16SAA
!!  !
!!    ! +Bacteroides ovatus strain 3941 AY895193
!!   +16
!!      +Bacteroides ovatus strain 4140 AY895197
!!
! +Bacteroideaceae bacterium Smarlab AY538687
!
! +Bacteroides sp. WH302 AY895184
23-21
! +Bacteroides sp. WH305 AY895185
!
+AG6
```

FIG. 5
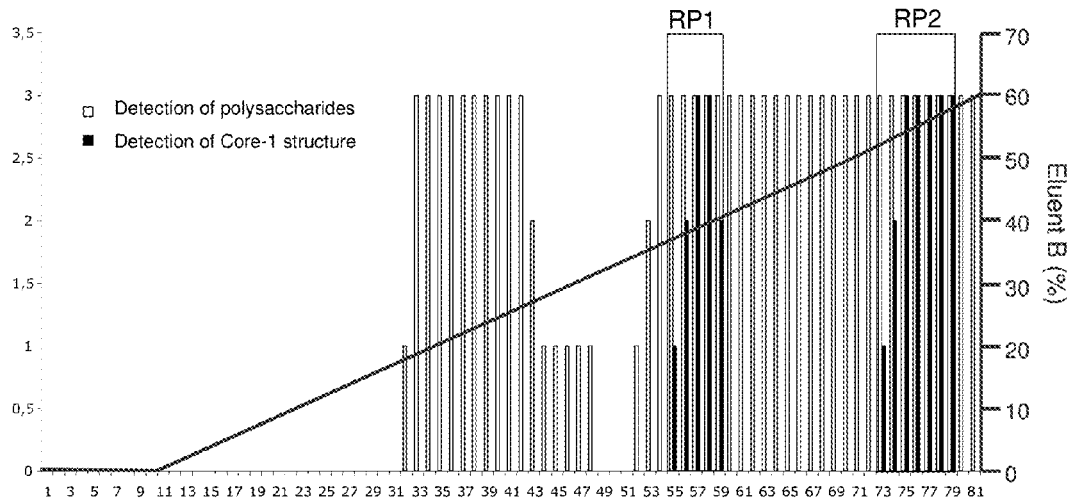
FIG. 6
-desHex-desHex-desHexM-HexNAc(HexNAc-Hex)-Hex-
FIG. 7
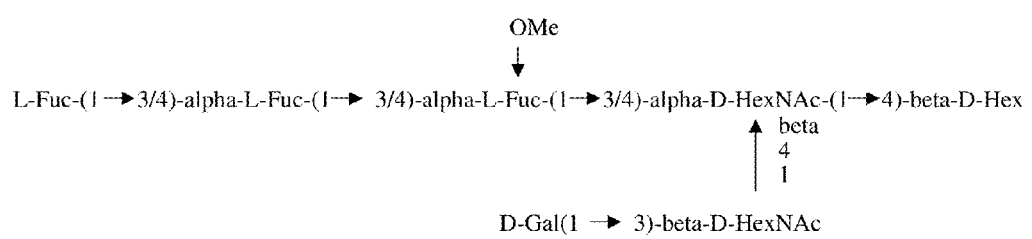

FIG. 19
1
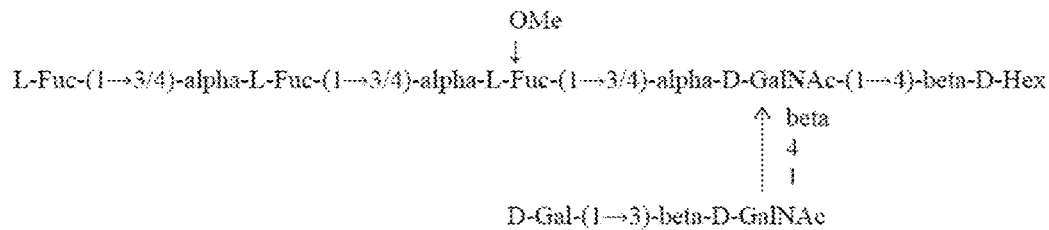
2
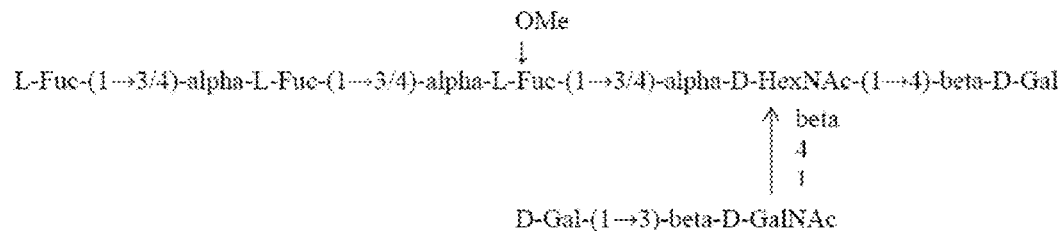
3
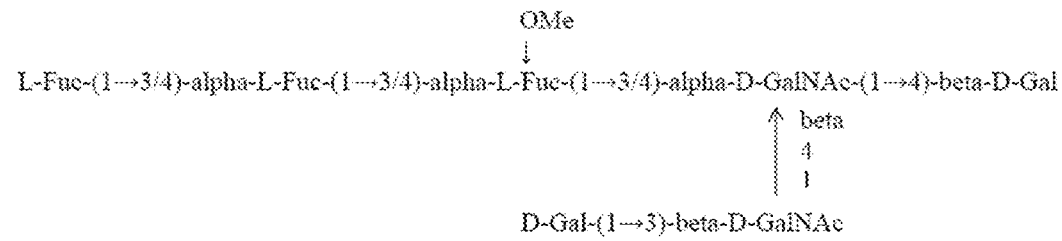
4
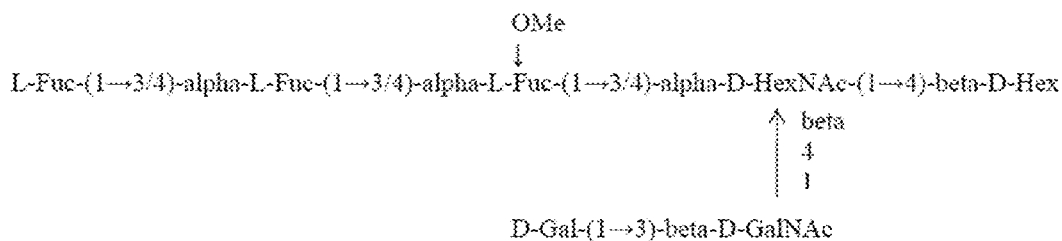
5
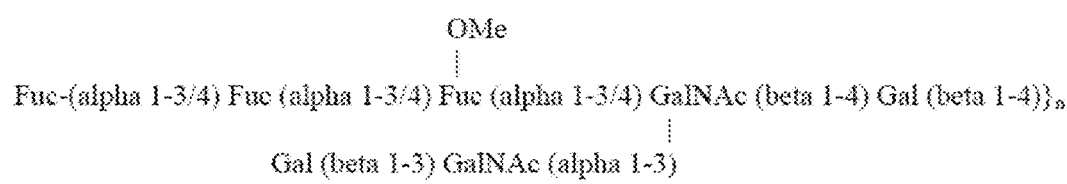

FIG. 22

Table 1

| Antibiotic/Strain | 53 | 52 | AG6 | MU1 | lac Ø | lac + | AG3 | LH2 | 32 |
|---|---|---|---|---|---|---|---|---|---|
| Species | B. ovatus | B. thetaiotaomicron | B. ovatus | B. ovatus | E. coli | E. coli | E. coli | E. coli | E. coli |
| Strain | DSMZ 1896 | DSMZ 2079 | AG6 | MU1 | lac Ø | lac + | AG3 | LH2 | DSMZ 8697 |
| Penicillin | R | R | R | MS | R | R | R | R | R |
| Mezlocillin | R | R | MS | MS | HS | S | HS | HS | S |
| Ampicillin | R | R | R | R | S | S | S | S | S |
| Ampicillin + Sulbactam | HS | HS | HS | HS | HS | HS | HS | HS | HS |
| Piperacillin + Tazobactam | S | MS | S | S | HS | HS | HS | HS | HS |
| Meropenem | HS | HS | HS | HS | HS | HS | HS | HS | HS |
| Clindamycin | HS | MS | S | R | R | R | R | R | R |
| Metronidazol | S | S | HS | HS | | | | | |

| Antibiotic/Strain | lac Ø | lac + | AG3 | LH2 | 32 | 53 | 52 | AG6 | MU1 |
|---|---|---|---|---|---|---|---|---|---|
| Species | E. coli | E. coli | E. coli | E. coli | E. coli | B. ovatus | B. thetaiotaomicron | B. ovatus | B. ovatus |
| Strain | lac Ø | lac + | AG3 | LH2 | DSMZ 8697 | DSMZ 1896 | DSMZ 2079 | AG6 | MU1 |
| Ampicillin | S | S | S | S | S | R | R | R | R |
| sulfamethoxale + trimethoprim | HS | HS | HS | HS | HS | | | | |
| Gentamycin | HS | S | S | HS | HS | | | | |
| Tobramycin | S | S | S | S | S | | | | |
| Mezloocillin | HS | HS | HS | HS | HS | R | R | MS | MS |
| Cefotiam | HS | HS | HS | HS | HS | | | | |
| Cefotaxin | HS | HS | HS | HS | HS | | | | |
| Meropenem | HS | HS | HS | HS | HS | HS | HS | HS | HS |
| Ceftriaxon | HS | HS | HS | HS | R | | | | |
| Ceufroxim | MS | MS | MS | MS | HS | | | | |
| Cefixin | HS | HS | HS | HS | HS | | | | |
| Tetracyclin | MS | MS | MS | MS | MS | | | | |
| Oxacillin | R | R | R | R | R | | | | |
| Erythromycin | R | R | R | R | R | | | | |
| Vancomycin | R | R | R | R | R | | | | |

FIG. 22 (Continued)

| | | | | | | | | |
|---|---|---|---|---|---|---|---|---|
| Ampicillin + Sulbactam | HS | HS | HS | HS | HS | HS | HS | HS |
| Linezolid | R | R | R | R | | | | |
| Piperacillin | HS | HS | HS | HS | | | | |
| Piperacillin + Tazobactam | HS | HS | HS | HS | | MS | S | |
| Amikacin | S | S | S | HS | S | | | |
| Ceftazidim | HS | HS | HS | HS | | | | |
| Imipenem | HS | HS | HS | HS | | | | |
| Rifampicin | R | R | MS | R | | | | |
| Ciprofloxacin | HS | HS | HS | HS | | | | |
| Fosfomycin | HS | S | S | HS | | | | |
| Penicillin | R | R | R | R | R | R | R | MS |
| Teicoplanin | R | R | R | R | HS | | | |
| Clindamycin | R | R | R | R | | MS | S | R |
| Bacitracin | R | R | R | R | | | | |
| Neomycin | S | S | S | S | | | | |
| Colistin | S | S | S | S | | | | |
| Fucidinsäure | R | R | R | R | S | S | | |
| Metronidazol | | | | | HS | HS | HS | HS |

S = sensitive
HS = highly sensitive
R = resistant
MS = medium sensitivity

MICROORGANISMS OR FRACTIONS THEREOF CAPABLE OF ACTIVATING CELLULAR IMMUNITY AGAINST CARBOHYDRATES

CROSS REFERENCE TO RELATED APPLICATIONS

This application is a national stage filing under 35 U.S.C. §371 of International Application No. PCT/EP2007/009766, filed on Nov. 12, 2007, and claims the benefit of priority of European Application No. 06090208.7, filed on Nov. 10, 2006, and European Application No. 06090209.5, filed on Nov. 10, 2006. All of these applications, including International Application No. PCT/EP2007/009766, are incorporated herein by reference in their entirety.

FIELD OF THE INVENTION

The present invention relates to the field of prevention and treatment of gastrointestinal disorders and cancer. More particularly, the present invention relates to the prevention and treatment of carcinomas which are Core-1-positive and thus carry the Core-1 antigen. The invention provides nutraceuticals and pharmaceutical compositions comprising Core-1 positive microorganism and fractions thereof that are suitable to induce immune responses against Core-1 and thereby also against Core-1 carrying tumor cells and Core-1 carrying molecules. By inducing or enhancing a specific immune response against Core-1 these compositions provide a shield against Core-1 positive cancer cells. Furthermore, the invention provides methods for identification, selection and isolation of Core-1 positive microorganisms which are suitable as an effective part of nutraceutical or pharmaceutical compositions inducing an immune response against Core-1 in humans or animals. The invention also provides specific humoral and cellular immune response test systems for testing Core-1 specific immune responses and it provides methods for generation of anti Core-1 antibodies and antibody compositions as well as anti Core-1 dendritic cells, activated T cells, T cell lines and clones.

BACKGROUND OF THE INVENTION

Aberrant glycosylation is a typical hallmark of cancer cells. Carbohydrate tumor antigens on glycoproteins and glycolipids are therefore targets for active and passive immunotherapy. These highly abundant antigens are de novo expressed or upregulated due to changes in the complex glycosylation apparatus of tumor cells. Various lipid or protein bound carbohydrate tumor antigens are described, e.g. GM2, GD2, GD3, fucosylated GM1, Globo H, Le$^Y$ and the mucin core structures Tn, Sialyl-Tn and the Thomson Friedenreich antigen.

Thomsen-Friedenreich antigen (TF) is a known carbohydrate structure described as a tumor antigen in a series of reports. TF exists in two forms, TF alpha and TF beta, which can be linked to proteins or glycolipids.

Core-1 is the disaccharide GalB 1-3 GalNAc, which is O-glycosidically linked in an alpha-anomeric configuration to the hydroxy amino acids serine or threonine of proteins in carcinoma cells. Core-1 corresponds to the TF alpha structure of Thomsen-Friedenreich and is linked only to proteins on tumors. Hence, the terms Core-1 and Thomsen-Friedenreich do not necessarily refer to identical structures.

Figure 20:
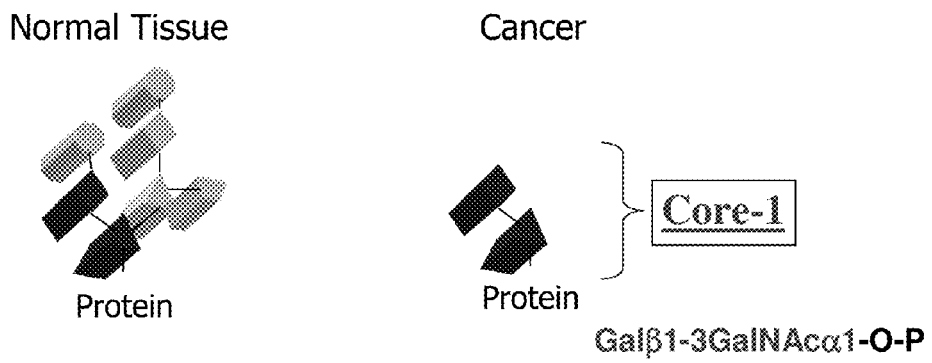

The Core-1 antigen is masked by other carbohydrate components in healthy and benign-diseased tissue but uncovered in a majority of carcinomas and in some non-epithelial malignancies. Therefore, the core-1 antigen is a specific pancarcinoma antigen (see FIG. 20 for illustration).

Core-1 is an important tumor antigen. Core-1 is expressed on over 60% of primary colon carcinomas and over 90% of liver metastases from colon cancer as well as on the majority of the carcinomas of other major indications including breast, lung, ovarian, prostate, and other gastrointestinal cancers such as gastric, and pancreatic carcinomas. Core-1 is an independent prognostic marker for patients with colon carcinomas, the mortality rate increases and the medium survival decreases in accordance with the increasing intensity of Core-1 expression. The development of liver metastases correlates with the expression of Core-1. Patients with Core-1 positive primary carcinomas develop liver metastases in nearly 60% of the cases, while the risk for liver metastasis with Core-1-negative tumours is significantly lower (less than 20%). Besides mediating metastasis into the liver Core-1 may also playa role in the metastasis via the endothelium.

The exceptionally high pan-carcinomic specificity, prognostic relevance and direct involvement in liver metastasis render Thomsen-Friedenreich and particularly Core-1 a prime target for cancer immunotherapy.

There were attempts to provide a therapy approach based on Thomsen-Friedenreich. E.g. Shigoeka et al (1999) describe the inhibition of liver metastasis from neuramidase treated Colon 26 cells by an anti-Thomsen-Friedenreich specific monoclonal antibody in a mouse model. However, due to the difficulties in generating highly specific anti-TF antibodies and because of their nature as IgM isotypes with comparably lower intrinsic affinities of single binding domains, TF-specific antibodies were not further developed so far. Further, some anti-TF-Ag antibodies are not clinically useful because they cause undesirable proliferation of tumor cells. Also WO2006/012626 describes the therapeutic use of anti-TF antigen antibodies. Binding of TF-specific Abs has been shown to inhibit the proliferation of tumour cells (Jeschke, et. al. 2006).

Furthermore, there were also attempts to develop vaccines based on Thomsen-Friedenreich. Most of them focused on the induction of antibody responses. Eg. Livingston and Lloyd (2000) used non-natural TF-conjugates, wherein synthetic TF was randomly coupled to KLH. This conjugates raised a humoral immune response against synthetic TF but not against TF on natural ligands (Adluri et al, 1995). They were thus not TF specific as they would not recognize TF on a tumor structure.

Springer and Desai used vaccination with a T/Tn vaccine composed of types 0 and MN red blood cell derived glycoproteins which resulted in improved breast cancer patient survival although only small amounts of IgM were made. However, IgM represents a less mature immune response and many previous studies relating to antibodies to TF-Ag involve IgM antibodies, therefore more pronounced highly TF specific immunoresponses would be needed and preferably an IgG response.

Few reports are known which describe microorganisms supposedly positive for TF. E.g. Springer et al. (Brit. J Haematol, 1981, 47, 453-460.Transfusion 1979, vol. 19, no. 3 pp. 233-249) report on an aerobic microorganism (Ecoli O86) which can generate a polyclonal antibody response in chickens and humans which might also recognize TF on human erythrocytes. Springer used adsorption of anti-T and hemagglutination assays with sialidase-treated T erythrocytes in order to determine roughly the specificity of the immune response. However, sialidase-treatment of human erythrocytes results in demasking of several carbohydrate epitopes, among them but not exclusively TF. Therefore, the reaction tested by Springer does not show a specificity for TF due to cross-reactivities. A respective non-specific microorganism has only a limited suitability as a vaccine due to its unspecificity as it would not raise a strong immune response which is specifically directed against TF but against similar TF-like structures and hence potentially also increasingly against non-tumor tissues or cells of the body.

Due to the complexity and species specificity of the glycosylation machinery no immunotherapy based on Core-1 is available yet to cancer patients. Even more important, there is no agent available to patients which can prevent the development of Core-1 positive tumors.

Conventional therapies usually start after tumor diagnosis, when tumors are often well established and difficult to treat. Therefore, aggressive therapies with severe side effects (chemotherapy, radiotherapy, surgery) are used to free the patients from tumor bulk. Immunotherapeutical options are mainly applied in the adjuvant setting with minimal residual disease.

The object of the present invention is to provide means for treatment or prevention of Core-1 positive tumors and gastrointestinal disorders as well as suitable tools for obtaining respective means.

DESCRIPTION OF THE INVENTION

The invention provides nutraceuticals and pharmaceutical compositions comprising a Core-1 positive microorganism or fractions thereof as well as Core-1 positive microorganisms and fractions thereof suitable to induce immune responses against Core-1 carrying tumor cells and Core-1 carrying molecules. Furthermore, it provides methods for identification, selection and isolation of Core-1 positive microorganisms which are suitable as an effective part of nutraceutical or pharmaceutical compositions inducing an immune response against Core-1 in humans or animals. It also provides specific humoral and cellular immune response test systems for testing Core-1 immune responses. It also provides methods for generation of anti Core-1 antibodies and antibody compositions as well as anti Core-1 T cell lines and clones and functional dendritic cells presenting Core-1.

Thus, the present invention provides the means for the induction or elevation of specific anti-Core-1 antibody levels in humans thereby inducing a protective immune response against tumors, especially Core-1 positive tumors. In addition, the invention provides the means for the induction of a specific cellular immune response against a carbohydrate target and especially against a tumor specific carbohydrate target such as Core-1. The invention also provides methods for identification and isolation of suitable Core-1 positive microorganisms. Another advantage of the present invention is that due to the nature of the formulation, the production is possible at very low costs. Furthermore, the formulation can be rapidly produced in large scale fermentors.

Anti-Core-1 antibodies, induced by the formulation of the present invention, serve as an immunosurveillance mechanism which may prevent the development of primary tumours and the distribution of metastases in most (unrecognised) cases, however, only if the specific immune response is sufficiently high. Therefore, the aim of the invention is to provide the means to induce a high specific anti-Core-1 titre, preferably combined with a specific cellular response, by using Core-1 positive microorganisms preferably from the intestinal flora of healthy donors as food additives in order to build a specific immune shield against tumors or prevent or reduce the incidence of Core-1 positive tumours and/or their metastases.

A) Nutraceuticals, Pharmaceutical Compositions and Immune Response Tests

According to a first aspect, the invention provides a formulation selected from the group consisting of a nutraceutical and/or a pharmaceutical composition, comprising at least one Core-1 positive microorganism and/or at least one Core-1 positive fraction or lysate thereof, wherein the Core-1 positive microorganism and/or the Core-1 positive fraction or lysate thereof is recognized by at least one Core-1 specific antibody. The invention thus provides a nutraceutical or a pharmaceutical composition comprising at least one Core-1 positive microorganism or at least one Core-1 positive fraction or lysate thereof, wherein the Core-1 positive microorganism is recognized and thus bound by at least one Core-1 specific antibody upon contact.

One important aspect of the present invention is that the Core-1 positive microorgansim and/or the Core-1 positive lysate or fraction thereof is recognized by at least one Core-1 specific antibody. Hence, the Core-1 positive microorgansim and/or the Core-1 positive lysate or fraction thereof is specifically bound by a Core-1 specific antibody when contacted with said antibody. The Core-1 structure is thus accessible for said Core-1 specific antibody in the Core-1 positive microorganism of the present invention and not "hidden" by other structures. This important characteristic which can be determined upon testing—suitable tests are described below—ensures that the Core-1 specific microorganism and/or the Core-1 positive fraction or lysate thereof carries Core-1 and is thus at least immunochemically virtually identical to Core-1 and not an epitope that is merely similar to Core-1. This feature is important to ensure that an immune response is triggered by said Core-1 positive microorganism that is sufficiently Core-1 specific. Such Core-1 specific antibodies that can be used to determine that a microorganism carries Core-1, specifically recognize the Core-1 structure in a tumor—relevant surrounding. These antibodies can thus be used to determine that the Core-1 positive microorganisms of the present invention carry Core-1 structures specifically mimicking the Core-1 antigen present on human gastrointestinal disorders and tumors. This characteristic—Core-1 specificity—delineates the Core-1 positive microorganisms of the present invention from the microorganisms known in the prior art which supposedly carry the Thomsen-Friedenreich antigen. As outlined above and will be shown in the comparative examples below, the microorganisms known in the prior art carried carbohydrate structures that were merely similar to Thomsen-Friedenreich (or Core-1) and thus cross-reacted e.g. with PNA which was used to supposedly determine TF specificity. However, PNA is not TF specific as it cross-reacts with many different carbohydrate epitopes. Hence, no differentiation occurred between TF-like (cross-reactive) and TF-identical structures. These known microorganisms are also not recognized and thus not specifically bound by Core-1 specific antibodies (see below). This demonstrates that they did not carry the Core-1 antigen and were accordingly also not able to induce a Core-1 specific immune response in a human or animal upon administration as they did not have the immunochemical/immunological characteristics of Core-1 in order to be able to elicit a respective response. Such a specific response, however, is necessary for triggering a Core-1 specific immune response and hence the therapeutic or prophylactic effect.

Due to the fact that the microorganisms of the present invention are truly Core-1 positive—what can be determined by the use of Core-1 specific antibodies—the invention provides formulations comprising Core-1 positive microorganisms which induce or enhance a specific and thus potent immune response against the Core-1 antigen. The formulation of the present invention activates the immune system in a tumor-specific manner by inducing high anti-Core-1 antibody levels which are specific for Core-1. To our knowledge, the present invention is the first antigen-specific food additive/nutraceutical or pharmaceutical which is able to activate a specific immune shield against tumors and the first food-additive which is able to induce a carbohydrate and in particular Core-1 tumor antigen-specific immune response.

The term Core-1 specific antibody, as well as preferred Core-1 specific antibodies, combinations of Core-1 specific antibodies or preferred combinations of Core-1 specific antibodies are described in detail under Definitions and elsewhere herein.

According to one embodiment, the Core-1 positive microorganism and/or the Core-1 positive lysate or fraction thereof is recognized by at least one Core-1 specific antibody which is selected from the group consisting of
Nemod—TF1
Nemod—TF2
A78-G/A7
HB-T1
HH8.

These antibodies proved to be highly Core-1 specific by showing little or no cross-reactivity to other carbohydrate structures besides Core-1. These antibodies do recognize Core-1 (either in alpha or beta anomeric form) on proteins in a tumor relevant fashion, preferably HH8, A78-G/A7, Nemod-TF2, Nemod-TF1; more preferably A78-G/A7, Nemod-TF2, Nemod-TF1. In order to enhance the specificity, one may use two or more of these antibodies in order to determine/test that a microorganism is Core-1 positive and thus a Core-1 positive microorganism according to the present invention.

That binding of the Core-1 specific antibody is specific for the carbohydrate structure and hence that the carbohydrate structure has the same binding criteria and thus the same immunochemical characteristics as human cancer associated Core-1 can be determined by analyzing whether binding of the Core-1 specific antibody is periodate sensitive. Periodate treatment destroys the outer carbohydrate ring of carbohydrate structures including Core-1 thereby destroying the Core-1 epitope. A decrease of antibody binding is usually observed after periodate oxidation. Hence, when binding of the Core-1 specific antibody is Core-1 specific, binding is reduced after periodate treatment. Surprisingly, for many organisms which were not Core-1 positive initially it was found that periodate treatment results in an increase in Ab binding. This as periodate oxidation uncovers new carbohydrate structures which are apparently TF-like. However, an increase in binding after periodate oxidation is a strong indicator that a microorganism is not originally Core-1 positive, as periodate treatment should destroy the Core-1 epitope if the Core-1 epitope is already presented accessible for the Core-1 specific antibodies on the Core-1 positive microorganism. However, such microorganisms which are not naturally Core-1 positive but may be converted to a Core-1 positive microorganism by a chemical treatment such as a periodate treatment are also comprised by the scope of the present invention and can e.g. be used after periodate treatment (uncovering Core-1) as components of the formulations of the present invention.

According to one embodiment the invention provides a nutraceutical or the pharmaceutical formulation as described above wherein at least one Core-1 positive microorganism is used that is recognized/bound by the Core-1 specific antibody NEMOD-TF1, preferably by a combination of NEMOD-TF2 or A78-G/A7 and by NEMOD-TF1 and said binding is periodate sensitive, and most preferably by NEMOD-TF2 or A78-G/A7 and NEMOD-TF1 but not by A68-B/A11. This profile is very favourable as it resembles the binding criteria of human cancer-associated Core-1 structure.

In a preferred embodiment said formulation induces or enhances an immune response against Core-1 in at least one human or animal recognizing the Core-1 antigen and/or a Core-1 positive tumor cell. Due to the fact that the microorganism is Core-1 positive, an immune response against the Core-1 antigen is induced/enhanced upon administration. Thereby an immunosurveillance mechanism is established that may e.g. eliminate or reduce the number of newly arising tumor cells carrying Core-1, thereby preventing or reducing primary tumor growth. The formulation according to the present invention induces or enhances said Core-1 specific immune response in at least one human or animal when administered, and/or which functions as a shield against Core-1 positive cancer cells by having the potential to destroy a Core-1 positive cancer cell and/or which reduces or prevents the occurrence of a Core-1 positive disease, tumor or metastasis and/or which reduces or prevents the spread or metastasis of a Core-1 positive disease or tumor and/or which strengthens the immune system and/or improves an immune response.

Therefore, the invention provides a nutraceutical comprising at least one Core-1 positive microorganism or fraction thereof which induces an immune response in humans or animals recognizing the Core-1 antigen and/or a Core-1 positive tumor cell and/or Core-1 positive disease. Conventional probiotics and prebiotics result in an overall unspecific stimulation of the immune system. There is no tumor-specific system involved in the prior art systems and especially none against Core-1.

Said Core-1 positive microorganisms, preferred Core-1 positive microorganisms, fractions of Core-1 positive microorganisms and preferred fractions of Core-1 positive microorganisms and combinations thereof are described in detail under Definitions and elsewhere herein. Said Core-1 positive microorganism is specifically recognized by at least one Core-1 specific antibody. Also described herein are methods for identifying and isolating said microorganisms or fractions thereof.

The Core-1 positive microorganism or fraction thereof represents the active ingredient which induces the specificity of the immune response against Core-1, the Core-1 antigen and/or a Core-1 positive tumor cell and/or disease due to the fact that it carries an antigen resembling Core-1.

Said Core-1 specific microorganism and/or Core-1 positive lysate or fraction thereof effectuates a specific immunisation against core 1 upon administration of said Core-1 specific microorganism. The ability to cause a Core-1 specific immunisation can be determined by at least one of the following methods:
a) said Core-1 positive microorganism is specifically recognized by at least one, preferably two Core-1 specific antibodies selected from the group consisting of
Nemod—TF1
Nemod—TF2
A78-G/A7

HH8
HB-T1
wherein binding of said antibodies is preferably periodate sensitive showing reduced binding after periodate treatment;
b) said Core-1 specific microorganism and/or Core-1 positive lysate or fraction thereof is characterised as being positive in at least one humoral immune response test as described herein;
c) said Core-1 specific microorganism and/or Core-1 positive lysate or fraction thereof is characterised as being positive in at least one cellular immune response test against Core-1 as described herein.

This ensures that the microorganism used is truly Core-1 positive and thus able to trigger the desired specific immune response against the Core-1 antigen. However, as described above, it is also within the scope of the present to use microorganisms which are converted from a Core-1 negative microorganism to a Core-1 positive microorganism by a chemical treatment such as e.g. a periodate treatment. Respectively treated microorganisms which become Core-1 positive due to a respective treatment are also within the scope of the present invention and their characteristics can be determined by the same methods/tests as those microorganisms which already carry/comprise the exposed Core-1 epitope.

In order to enhance the Core-1 specificity of the formulation one can use a microorgansim which is Core-1 positive or can be rendered Core-1 positive e.g. by periodate treatment and is specifically recognized by at least two Core-1 specific antibodies selected from the group consisting of
Nemod—TF1
Nemod—TF2
A78-G/A7
wherein binding of said antibodies is preferably periodate sensitive showing reduced binding after periodate treatment.

A Core-1 positive microorganism or fraction thereof may comprise at least one of the carbohydrate structures selected from the group comprising #1, #2, #3, #4 and/or #5 of FIG. 19 and/or repeating units thereof. As can be seen, Core-1 positive organisms may be linked on alpha- or beta anomeric configuration.

Furthermore, the inventors have surprisingly found that Core-1 positive *Bacteroides* strains such as e.g. *Bacteroides ovatus* exist. This was unknown. Hence, a Core-1 positive *Bacteroides* is provided and can also be used in the formulation according to the present invention, wherein said Core-1 positive *Bacteroides* is recognized by at least one, preferably two Core-1 specific antibodies selected from the group consisting of
Nemod—TF1
Nemod—TF2
A78-G/A7
HB-T1
HH8
Binding of said antibodies is preferably periodate sensitive showing reduced binding after periodate treatment.

Preferably, said Core-1 positive *Bacteroides* is isolated from a healthy donor. Said Core-1 positive *Bacteroides* can e.g. be or is related to *Bactertoides ovatus* such as the new strains AG6 (DSM 18726), MU1 (DSM 18728) and/or a AG6 or MU1 homolog, wherein said homolog is characterized in that it is a *Bacteroides* is recognized by at least two Core-1 specific antibodies selected from the group consisting of
Nemod—TF1
Nemod—TF2
A78-G/A7
HB-T1
HH8
wherein binding of said antibodies is preferably periodate sensitive showing reduced binding after periodate treatment. As is demonstrated in the examples, these strains elicit a very strong immune response against Core-1 and are related to *Bacteroides ovatus* They show a very strong Core1 expression and thus comprise many Core-1 epitopes and binds to Core-1 specific mAbs (TF1 and TF2), wherein binding is periodate sensitive thereby indicating that Core-1 is presented accessible on the surface. Core1 expression/detection is also unchanged after enzymatic digestion, pasteurisation and/or lyophilisation making it a suitable component for an oral pharmaceutical formulation. Furthermore, for AG6 we demonstrated a tumour-associated Core-1 structure in an alpha-anomeric configuration as a branching component within the repeating unit (see also #5 of FIG. 19). This result is very important because the exposed localization of the TF-antigen within the capsular polysaccharide might increase the induction of the humoral immune responses against Core-1 in humans by better recognition and binding of Core-1 specific antibodies.

In a preferred embodiment the invention provides a formulation selected from the group consisting of a neutraceutical and/or a pharmaceutical composition comprising at least one Core-1 positive microorganism and/or at least one Core-1 positive lysate or fraction thereof, wherein the Core-1 positive microorganism or Core-1 positive lysate or fraction is recognized by at least one Core-1 specific antibody, wherein the Core-1 specific antibody is selected from the group comprising NEMOD-TF1, NEMOD-TF2, A78-G/A7, HB-T1 and/or HHB.

In a further preferred embodiment the invention provides said formulation, wherein the Core-1 positive microorganism is bound by the Core-1 specific antibodies NEMOD-TF2 and Nemod-TF1, whereby the binding of said antibodies is periodate sensitive showing a significantly reduced binding after periodate treatment.

The formulation according to the present invention (e.g. food or drug comprising a Core-1 positive microorganism) thus can be used for prophylactic and therapeutic purposes and in supporting immunological activities. The pharmaceutical formulation of the invention contains at least one Core-1 positive microorganism—which can also be rendered Core-1 positive by a chemical treatment such as a periodate treatment—and a pharmaceutically acceptable carrier. The preparation and administration of a formulation of this invention (e.g. a drug comprising core-1 positive microorganism) is in accordance with known techniques. For example, the formulation can be combined with conventional galenic adjuvants to form a composition suitable for the desired method of application. For example, the compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaeyritol fatty acid esters, hydroxy methylcellulose, polyvinyl pyrrolidone, talc, etc. Details are described below.

Said formulation may induce or enhance a humoral and/or a cellular immune response against Core-1 in at least one human or animal recognizing the Core-1 antigen and/or a Core-1 positive tumor cell, preferably a Th1 type cellular immune response. In a preferred embodiment, the formulation induces or enhances a humoral and/or a cellular immune response against Core-1 in at least one human or animal recognizing the Core-1 antigen and/or a Core-1 positive tumor cell, preferably a cellular immune response comprising activation of CD4 positive T cells of Th1 cells and/or CD8 positive cytotoxic T cells.

The invention also provides a nutraceutical comprising at least one Core-1 positive microorganism or fraction thereof wherein the Core-1 positive microorganism is recognized/bound by at least one Core-1 specific antibody and which induces or enhances an immune response against Core-1 in at least one human or animal recognizing the Core-1 antigen and/or a Core-1 positive tumor cell.

The invention also provides a pharmaceutical composition comprising at least one Core-1 positive microorganism or fraction thereof which induces an immune response in humans or animals recognizing the Core-1 antigen and/or a Core-1 positive tumor cell and/or Core-1 positive disease.

The invention provides a pharmaceutical formulation comprising at least one Core-1 positive microorganism or fraction thereof wherein the Core-1 positive microorganism is recognized and thus bound by at least one Core-1 specific antibody if contacted with a respective antibody and which induces or enhances an immune response against Core-1 in at least one human or animal recognizing the Core-1 antigen and/or a Core-1 positive tumor cell.

The invention provides a nutraceutical or a pharmaceutical formulation comprising at least one Core-1 positive microorganism or fraction thereof wherein the Core-1 positive microorganism is recognized/bound by at least one Core-1 specific antibody and which induces or enhances a humoral and/or a cellular immune response in at least one human or animal against Core-1.

Said immune response is a humoral immune response against Core-1 and/or a cellular immune response against Core-1. Activation of cellular immunity in addition to humoral immunity strongly enhances the prophylactic and therapeutic potential of the formulation/coreotics of the present invention.

In a further embodiment the invention provides a nutraceutical or a pharmaceutical formulation comprising at least one Core-1 positive microorganism or fraction thereof which induces a humoral and a cellular immune response in humans or animals recognizing the Core-1 antigen and/or a Core-1 positive tumor cell.

In a preferred embodiment of the invention the nutraceutical or the pharmaceutical composition induces or enhances a Core-1 specific immune response in at least one human or animal functioning as a shield against Core-1 positive cancer cells by having the potential to destroy Core-1 positive cancer cells.

The nutraceutical or pharmaceutical composition comprising at least one Core-1 positive microorganism or fraction thereof can be used to build a Core-1 specific immune response which functions as a shield against Core-1 positive cancer cells by having the potential to destroy those cells as shown herein for example by the induction of the Core-1 specific antibodies, by the Core-1 specific complement dependent cytotoxicity of Core-1 antibodies against Core-1 positive tumor cells killing those effectively, or by secretion of TNFalpha and/or INFgamma by Core-1 specific T cell responses which are scientifically recognized surrogate markers by those skilled in the art for a specific cytotoxic T cell mediated tumor cell killing for those tumor cells carrying the Core-1, as shown in the examples and described herein.

In a further preferred embodiment of the invention the nutraceutical or pharmaceutical composition comprising at least one Core-1 positive microorganism or fraction thereof is used in order to build said Core-1 specific immune response which functions as a shield against Core-1 positive cancer cells which has the potential to destroy those cells as described above by orally administering the nutraceutical to (at least one) healthy individual.

In a further preferred embodiment of the invention the nutraceutical or pharmaceutical composition comprising at least one Core-1 positive microorganism or fraction thereof is used in order to reduce or even further preferred to prevent the occurrence of a Core-1 positive disease or tumor by orally administering the nutraceutical to (at least one) healthy individual.

The nutraceutical or the pharmaceutical composition of the invention is used to treat a Core-1 positive disease or tumor in at least one human or animal. In a further preferred embodiment of the invention the nutraceutical or pharmaceutical formulation comprising at least one Core-1 positive microorganism or fraction thereof is used in order to reduce or even more preferred to prevent the occurrence of a Core-1 positive disease or tumor or metastasis.

In a further embodiment the invention provides a nutraceutical or a pharmaceutical composition comprising at least one Core-1 positive microorganism or fraction thereof which reduces or prevents the spread or metastasis of a Core-1 positive disease or tumor in at least one human or animal when administered.

In a further embodiment of the invention the nutraceutical or pharmaceutical formulation comprises at least two different Core-1 positive microorganism or fractions thereof.

In a further preferred embodiment of the invention the nutraceutical or pharmaceutical formulation comprises at least one Core-1 positive microorganism or fraction thereof combined with at least one other beneficial microorganism inducing or enhancing an immune response.

In a further embodiment of the invention the nutraceutical comprising at least one Core-1 positive microorganism or fraction thereof is used in order to treat a Core-1 positive disease or tumor by orally administering the nutraceutical in patients suffering from this disease.

In a further embodiment of the invention the pharmaceutical formulation comprising at least one Core-1 positive microorganism or fraction thereof is used in order to treat a Core-1 positive disease or tumor in patients suffering from this disease.

In another embodiment of the invention the aforementioned nutraceutical or pharmaceutical composition of the invention comprise at least one Core-1 positive microorganism and at least one fraction of a Core-1 positive microorganism, preferentially from more than one Core-1 positive microorganism.

Said humoral immune response against Core-1 is an antibody response against Core-1 which can be detected by at least one of the humoral immune response tests 1, 2, 3, 4, 5 or 6 which are described in detail below.

The invention also provides a humoral immune response test (humoral immune response test 1) against Core-1 comprising testing the binding of an antibody, antibodies in serum, or antibodies gained from serum, plasma or faeces, in an ELISA to glycoproteins comprising asialoglycophorin and glycophorin or asialoglycophorin and periodate treated asialoglycophorin or asialoglycophorin and glycophorin and periodate treated asialoglycophorin whereby a positive humoral immune response against Core-1 shows a significant higher binding of the antibodies to asialoglycophorin than to glycophorin and/or periodate treated asialoglycophorin. Asialoglycophorin comprises the Core-1 structure, glycophorin does not. Hence, a positive humoral immune response triggered by a Core-1 positive microorganism of the present invention would result in a detectable binding to asialoglycophorin, but less or no binding to glycophorin. Periodate treated asialoglycophorin also loses the Core-1 epitope and is thus also a test system to determine, whether a positive humoral immune response is triggered by the Core-1 positive microorganism/formulation according to the present invention. In a more preferred embodiment, this binding is significantly higher after administration of the nutraceutical, the pharmaceutical composition, the Core-1 positive microorganism or the fraction thereof or formulations comprising those.

Said humoral immune response test 1 tests the binding of the antibodies in serum or antibodies gained from serum, plasma or faeces in an ELISA to glycoproteins comprising asialoglycophorin and glycophorin or periodate treated asialoglycophorin whereby a positive humoral immune response against Core-1 shows a significant higher binding of the antibodies to asialoglycophorin than to glycophorin and/or periodate treated asialoglycophorin. In a preferred embodiment said test comprises asialoglycophorin and glycophorin and periodate treated asialoglycophorin. In a preferred embodiment the signal to asialoglycophorin is at least 50% higher than that of glycophorin and at least 30% higher than that of periodate treated asialoglycophorin. In a preferred embodiment the signal to asialoglycophorin is at least twice that of glycophorin and/or 1.5 times that of periodate treated asialoglycophorin, and even further preferred at least 3 times that of glycophorin and/or twice that of periodate treated asialoglycophorin and even further preferred at least 5 times that of glycophorin and/or 4 times that of periodate treated asialoglycophorin. In a preferred embodiment the signal to asialoglycophorin is significantly increased after administration of a formulation according to this invention and it is at least 30% higher than that of periodate treated asialoglycophorin. In a preferred embodiment the signal to asialoglycophorin is 50% higher more preferred 80% higher and even more preferred 100% higher after administration of a formulation according to this invention and it is at least 30% higher than that to periodate treated asialoglycophorin.

A preferred embodiment of the humoral immune response test 1 is described in detail in example 11.

In another preferred embodiment the invention provides a humoral immune response test (humoral immune response test 2) against Core-1 comprising, testing the binding of an antibody, antibodies in serum, or antibodies gained from serum, plasma or faeces, in an ELISA to carbohydrate structures coupled to polyacrylamid (PAA conjugates) comprising Gal beta 1-3 GalNAc alpha1-PAA, Gal beta 1-3 GalNAc beta 1-PAA, GlcNAc beta 1-2 Gal beta 1-3 GalNAc alpha 1-PAA, and preferably periodate treated Gal beta 1-3 GalNAc alpha1-PAA, whereby a positive humoral immune response against Core-1 shows a significant higher binding of the antibody or antibodies to Gal beta 1-3 GalNAc alpha1-PAA than to periodate treated Gal beta 1-3 GalNAc alpha1-PAA and preferably also a higher binding of the antibody or antibodies to Gal beta 1-3 GalNAc alpha1-PAA than to Gal beta 1-3 GalNAc beta 1-PAA or a significant higher binding to Gal beta 1-3 GalNAc alpha1-PAA of antibodies gained from a human or an animal after immunization with a formulation according to this invention (e.g. immune sera) compared to antibodies gained from a human or an animal prior to immunization (e.g. preimmune sera). These artificial polyacrylamid structures also comprise the Core-1 structure respectively closely related structures and can thus be used to determine the specificity of the triggered humoral immune response.

Said humoral immune response test 2 tests the binding of the antibodies in serum or antibodies gained from serum, plasma or faeces in an ELISA to carbohydrate structures coupled to polyacrylamid (PAA conjugates) comprising Gal beta 1-3 GalNAc alpha1-PAA, Gal beta 1-3 GalNAc beta 1-PAA, GlcNAc beta 1-2 Gal beta 1-3 GalNAc alpha 1-PAA, and preferably periodate treated Gal beta 1-3 GalNAc alpha1-PAA whereby a positive humoral immune response against Core-1 shows a significant higher binding of the antibodies to Gal beta 1-3 GalNAc alpha1-PAA than to periodate treated Gal beta 1-3 GalNAc alpha1-PAA and preferably also to Gal beta 1-3 GalNAc beta 1-PAA. In a preferred embodiment the binding to Gal beta 1-3 GalNAc alpha1-PAA is at least twice the binding to periodate treated Gal beta 1-3 GalNAc alpha 1-PAA and to, Gal beta 1-3 GalNAc beta 1-PAA.

In a preferred embodiment the ELISA signal against Gal beta 1-3 GalNAc alpha1-PAA relative to the ELISA signal against GlcNAc beta 1-2 Gal beta 1-3 GalNAc alpha 1-PAA is 50% higher after immunization with a formulation according to this invention compared to the ELISA signal against Gal beta 1-3 GalNAc alpha1-PAA relative to the ELISA signal against GlcNAc beta 1-2 Gal beta 1-3 GalNAc alpha 1-PAA prior to immunization, more preferred at least 70% higher and even more preferred 100% higher.

In a preferred embodiment, after immunization with a formulation according to this invention, the ELISA signal against Gal beta 1-3 GalNAc alpha1-PAA is 30% higher compared to the ELISA signal against Gal beta 1-3 GlcNAc alpha 1-PAA, more preferred at least 50% higher, more preferred at least 70% and even more preferred 100% higher.

A preferred embodiment of the humoral immune response test 2 is described in detail in example 11.

In another preferred embodiment the invention provides a humoral immune response test (humoral immune response test 3) against Core-1 comprising, testing the binding of an antibody, antibodies in serum, or antibodies gained from the serum, plasma or faeces, in a flow cytometry test for its binding to cells comprising NM-D4 or NM-F9 and NM-wt or NM-H9 (or NM-H9D8 DSM ACC2806) whereby a positive humoral immune response against Core-1 shows a significant higher binding of the antibodies to NM-D4 or NM-F9 (both carrying the Core-1 antigen) than to NM-wt or NM-H9 (not carrying the Core-1 antigen) and/or a significant higher binding of the antibodies to NM-D4 or NM-F9 after administration of a formulation according to this invention.

Said humoral immune response test 3 tests the binding of the antibodies in serum or antibodies gained from the serum, plasma or faeces in a flow cytometry test for its binding to cells comprising NM-D4 or NM-F9 and NM-wt or NM-H9 whereby a positive humoral immune response against Core-1 shows a significant higher binding of the antibodies to NM-D4 or NM-F9 than to NM-wt or NM-H9. In a preferred embodiment the percentage of positive cells in NM-D4 or NM-F9 is twice that of NM-wt or NM-H9 and even further preferred 5 times.

In another preferred embodiment of the invention the flow cytometry results are calculated after the following formula:

(% positive cells to NM-D4 or NM-F9 of the immune sample−% positive cells to NM-D4 or NM-F9 of the preimmune sample)/(% positive cells to NM-wt or NM-H9 of the immune sample–% positive cells to NM-wt or NM-H9 of the preimmune sample)=X, whereby (% positive cells to NM-wt or NM-H9 of the immune sample—% positive cells to NM-wt or NM-H9 of the preimmune sample)≥1 and whereby the humoral immune response test is positive if X≥10, more preferred X>20 and even more preferred X>30.

A preferred embodiment of the humoral immune response test 3 is described in detail in example 11.

In another preferred embodiment the invention provides a humoral immune response test (humoral immune response test 4) against Core-1 comprising, testing the binding of an antibody, antibodies in serum, or antibodies gained from the serum, plasma or faeces, in an immune fluorescence test for its binding to cells comprising NM-D4 or NM-F9, and to NM-wt or NM-H9, and preferably also to periodate treated NM-D4 or NM-F9 whereby a positive humoral immune response against Core-1 shows a higher binding of a particular amount of the antibody or antibodies to NM-D4 or NM-F9 (both carrying the Core-1 antigen) than to NM-wt or NM-H9 (not carrying the Core-1 antigen) or periodate treated NM-D4 or NM-F9 (wherein the Core-1 antigen is destroyed due to the periodate treatment) and/or a significant higher binding of the antibodies to NM-D4 or NM-F9 after administration of a formulation according to this invention.

Said humoral immune response test 4 tests the binding of the antibodies in serum, plasma or faeces or antibodies gained from the serum, plasma or faeces in an immune fluorescence test for its binding to cells comprising NM-D4 or NM-F9, and to NM-wt or NM-H9, and preferably also to periodate treated NM-D4 or NM-F9 whereby a positive humoral immune response against Core-1 shows a higher binding of the antibodies to NM-D4 or NM-F9 than to NM-wt or NM-H9 or periodate treated NM-D4 or NM-F9. In a preferred embodiment the binding to NM-D4 or NM-F9 is visibly higher in fluorescence intensity and/or in the percentage of fluorescence-positive cells among NM-D4 or NM-F9 cells is higher than the percentage of fluorescence-positive cells among NM-D4 or NM-F9 after treatment with periodate. The immunofluorescence test can be made more quantitative by serial dilutions of the antisera and/or by taking photographs under identical exposure conditions.

Other suitable tests for Core-1 positivity of a humoral immune response are the use of various Core-1 positive cells, such as ZR-75-1, CAMA-1, KG-1, A-204, and Core-1—negative cell lines, such as BT-20, HT-29, in immunofluorescence or flow cytometry analyses, or other Core-1 carrying molecules such as GaI beta 1-3 GaINAc alpha1-BSA or GaI beta 1-3 GaINAc alpha1-KLH, or glycopeptides with Core-1, with or without periodate treatment of the cells or antigens, and preferably with combinations with according negative molecules without Core-1 such as BSA, or with sialylated core-1 structures, in suitable test systems, preferentially in ELISA, flow cytometry, or immune fluorescence. In principle the same carbohydrate structures coupled to polyacrylamide or carrier proteins such as glycophorin protein backbone or lipids as used in the test 1 to 4 described above can also be used when coupled to other carrier molecules such as protein backbones, or peptides or polypeptides, or lipids, or chemical structures, such as BSA, KLH or defined shorter peptides or chemical structures such as those used for column bed in chromatography. Those skilled in the art are able to identify suitable carrier molecules and to couple suitable structures to obtain the desired carbohydrate structure coupled to the carrier molecules with or without linker. Those skilled in the art are also able to select those cells or antigens, with or without periodate treatment, and to select and modify the suitable methods to test the humoral immune response for Core-1. However, the aforementioned humoral immune response tests 1 to 4 and especially the preferred combinations thereof provided by the present invention are clearly preferred and have clear advantages in respect to specificity as also seen from examples.

In another preferred embodiment the invention provides a humoral immune response test (humoral immune response test 5) against Core-1 comprising,
a.) incubating a suitable amount of ZR75-1, NM-D4, NM-F9, NM-H9, and/or NM-wt, labeled with a suitable amount of europium or chromium-51, with a suitable amount of an antibody, of antibodies in serum, or of antibodies gained from the serum, plasma or faeces, with a suitable amount of complement for a suitable time (typically between 3 to 5 hours or over night)
b.) measuring the lysis of the cells by determining the release of europium or chromium-51 after the incubation under (a) whereby a positive humoral immune response against Core-1 shows a higher lysis of NM-D4 or NM-F9 cells than of NM-wt or NM-H9 or it shows a higher lysis of NM-D4, NM-F9, or ZR-75-1, than a lysis without complement and/or than a lysis without the antibody and/or than a lysis with an antibody or antibodies which does not bind or which binds less to NM-D4, NM-F9, or ZR-75-1.

Said humoral immune response test 5 tests the Core-1 specific complement dependent cytotoxicity (CDC), an effector mechanism mediated by certain antibodies, of the induced humoral immune response or Core-1 specific antibodies in a target cell lysis test. The test comprises incubating suitable amounts of labeled Core-1 positive target cells such as ZR75-1, preferably NM-D4 or NM-F9, with suitable amounts of antibodies in serum or antibodies gained from the serum, or an isolated Core-1 antibody with suitable amounts of complement for a suitable time, typically between 3 to 5 hours. The Core-positive tumor cells are labeled with europium or chromium-51 which allows the measurement of cells which are lysed. The amount of lysed cells is determined, preferably by measuring the release of europium or chromium-51 after incubation. A suitable control can be determined by those skilled in the art such as Core-1 negative cells, preferably NM-wt and/or NM-H9, an antibody or an antibody mixture not binding to the target cell, and/or without complement. The test can be optimized in respect to suitable amounts of antibodies, numbers of labeled tumor cells, concentration of complement, and incubation time by those skilled in the art for its use in the invention and as described.

The complement-dependent cytotoxicity (CDC) of the invention is preferably determined using an Europium Release Assay. The target cells NM-D4 are incubated for 10 minutes at 4° C. in 800 µl of europium buffer (50 mM HEPES, pH 7.4, 93 mM NaCl, 5 mM KCl, 2 mM $MgCl_2$, 10 mM diethylentriaminepentaacetic acid, 2 mM europium (III) acetate), electroporated (710V, 1 pulse, 30p) in a Multiporator (Eppendorf), and subsequently incubated on ice for another 10 minutes. Thereafter, the cells are washed 5 times in RPMI/5% FCS and seeded in a 96-well round-bottom plate (Munc; $5 \times 10^3$/well). Following addition of 20 µl of antibody containing solution at varying dilutions or the corresponding controls (medium, isotype control human IgM), the samples are incubated 20 minutes at room temperature. 10 µl of 1:10 diluted complement (Baby rabbit complement) is added to correspondent wells. In the control wells 10 µl of RPMI/5% FCS are added instead of complement solution. For determination of spontaneous release target cells are incubated with media alone, and maximum release is determined by complete lysis of the target with ethanol. Following incubation at 37° C. for 4 hours, the plate is centrifuged at 500×g for 5 minutes, and 20 µl of cell-free supernatant from every well are pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined (Victor$^2$ Fluorometer, Perkin-Elmer Wallac). The specific cytotoxicity is obtained from the equation (experimental lysis–spontaneous lysis)/(maximum lysis–spontaneous lysis)×100%.

In another preferred embodiment the invention provides a humoral immune response test (humoral immune response test 6) against Core-1 comprising,
  a) incubating a suitable amount of ZR75-1, NM-D4, NM-F9, NM-H9, and/or NM-wt, labeled with a suitable amount of europium or chromium-51, with a suitable amount of an antibody, of antibodies in serum, or of antibodies gained from the serum, plasma or faeces, with a suitable amount of at least one immune effector cell or mixture of cells comprising immune effector cells or peripheral blood mononuclear cells for a suitable time, typically between 3 to 5 hours or over night and
  b) measuring the lysis of the cells by determining the release of europium or chromium-51 after the incubation under (a) whereby a positive humoral immune response against Core-1 shows a significant higher lysis of NM-D4 or NM-F9 cells than of NM-wt or NM-H9 or it shows a significant higher lysis of NM-D4, NM-F9, or ZR-75-1, than a lysis without the antibody and/or than a lysis with an antibody or antibodies which does not bind or which binds less to NM-D4, NM-F9, or ZR-75-1.

Said humoral immune response test 6 tests the Core-1 specific antibody dependent cellular cytotoxicity (ADCC), an effector mechanism mediated by certain antibodies, of the induced humoral immune response or Core-1 specific antibodies in a target cell lysis test in combination with immune effector cells. The test comprises incubating suitable amounts of labeled Core-1 positive target cells such as ZR75-1, preferably NM-D4 or NM-F9, with suitable amounts of antibodies in serum or antibodies gained from the serum, or an isolated Core-1 antibody with suitable amounts of immune effector cells such as those present in PBMC (peripheral blood mononuclear cells) for a suitable time, typically between 3 to 5 hours or over night. The Core-positive tumor cells are labeled with europium or chromium-51 which allows the measurement of cells which are lysed. The amount of lysed cells is determined, preferably by measuring the release of europium or chromium-51 after incubation. A suitable control can be determined by those skilled in the art such as Core-1 negative cells (preferably NM-wt and NM-H9), an antibody or an antibody mixture not binding to the target cell, and/or without immune effector cells (e.g. PBMC). The test can be optimized in respect to suitable amounts of antibodies, numbers of labeled tumor cells, numbers of immune effector cells, and incubation time by those skilled in the art for its use in the invention.

The antibody dependent cellular cytotoxicity (ADCC) of the invention is preferably determined using an Europium Release Assay. The target cells NM-D4 are incubated for 10 minutes at 4° C. in 800 µl of europium buffer (50 mM HEPES, pH 7.4, 93 mM NaCl, 5 mM KCl, 2 mM MgCl$_2$, 10 mM diethylentriaminepentaacetic acid, 2 mM europium (III) acetate), electroporated (710V, 1 pulse, 30p) in a Multiporator (Eppendorf), and subsequently incubated on ice for another 10 minutes. Thereafter, the cells are washed 5 times in RPMI/5% FCS and seeded in a 96-well round-bottom plate (Nunc; 5×10$^3$/well). Following addition of 20 µl of Corel-specific antibodies at varying concentrations (0.05 to 50 µg/ml final concentration in 200 µl incubation volume) or the corresponding controls (medium, isotype control IgG), PBMC (human peripheral blood mononucleare cells, 80 µl) are added as effector cells, using different effector cell/target cell ratios from 100:1 to 10:1, preferably of 50:1. To determine spontaneous release, 80 µl RPMI/5% FCS without effector cells are added. Maximum release is determined after complete lysis of the target with ethanol.

Following incubation at 37° C. for 4 hours, the plate is centrifuged at 500×g for 5 minutes, and 20 µl of cell-free supernatant from every well is pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined (Victor$^2$ Fluorometer, Perkin-Elmer Wallac). The specific cytotoxicity is obtained from the equation (experimental lysis–spontaneous lysis)/(maximum lysis–spontaneous lysis)×100%.

In a preferred embodiment said humoral immune response tests 1 to 6 further comprise prior to the test
  a. the administration of the nutraceutical, the pharmaceutical composition, the Core-1 positive microorganism or the fraction thereof or the formulations comprising those to a human or animal
  b. isolating the antibody, antibodies in serum, or antibodies gained from the serum, plasma or faeces.

In a preferred embodiment the invention provides a humoral immune response test for testing the ability of the formulation, or the Core-1 positive microorganism, or the fraction or the lysate thereof as described elsewhere herein to induce or enhance a humoral immune response against Core-1 in a human or an animal comprising,
  a) administering said formulation, said Core-1 positive microorganism or said lysate or fraction thereof, as described elsewhere herein, to a human or animal; and
  b) isolating the antibody, antibodies in serum, or antibodies gained from the serum, plasma or faeces; and
  c) testing the binding of the antibody, antibodies in serum, or antibodies gained from serum, plasma or faeces, in
    (i) an ELISA to glycoproteins comprising asialoglycophorin and glycophorin or asialoglycophorin and periodate treated asialoglycophorin or asialoglycophorin and glycophorin and periodate treated asialoglycophorin whereby a positive humoral immune response against Core-1 shows a binding of said antibody or antibodies to asialoglycophorin which is significantly higher than the binding to glycophorin and/or periodate treated asialoglycophorin, and a significantly higher binding to asialoglycophorin than an antibody or antibodies accordingly isolated from the same animal or human before administration of said formulation, said Core-1 positive microorganism or said lysate or fraction thereof; and/or
    (ii) an ELISA to carbohydrate structures coupled to polyacrylamid
    (PAA conjugates) comprising Gal beta 1-3 GalNAc alpha1-PAA, Gal beta 1-3 GalNAc beta 1-PAA, GlcNAc beta1-2 Gal beta 1-3 GalNAc alpha 1-PAA, and preferably periodate treated Gal beta 1-3 GalNAc alpha 1-PAA, whereby a positive humoral immune response against Core-1 shows a significantly higher binding of said antibody or antibodies to Gal beta 1-3 GalNAc alpha1-PAA than of an antibody or antibodies accordingly isolated from the same animal or human before administration of said formulation, said Core-1 positive microorganism or said lysate or fraction thereof; and/or (iii) a flow cytometry test for the binding to cells comprising NM-D4 or NM-F9 and NM-wt or NM-H9 whereby a positive humoral immune response against Core-1 shows a significantly higher binding of the antibodies to NM-D4 or NM-F9 than to NM-wt or NM-H9, and a significantly higher binding to NM-D4 or NM-F9 than an antibody or antibodies accordingly isolated from the same animal or human before administration of said formulation, said Core-1 positive microorganism or said lysate or fraction thereof; and/or (iv) an immune fluorescence test for its binding to cells comprising NM-D4 or NM-F9, and to NM-wt or NM-H9, and preferably also to periodate treated NM-D4 or NM-F9 whereby a positive humoral immune response against Core-1 shows a significantly higher binding of a particular amount of the antibody or antibodies to NM-D4 or NM-F9 than to NM-wt or NM-H9 or periodate treated NM-D4 or NM-F9, and a significantly higher binding to NM-D4 or NM-F9 than an antibody or antibodies accordingly isolated from the same animal or human before administration of said formulation, said Core-1 positive microorganism or said lysate or fraction thereof;

and/or d) testing the activity of the antibody, antibodies in serum, or antibodies gained from serum, plasma or faeces, comprising (i) incubating a suitable amount of ZR75-1, NM-D4, NM-F9, NM-H9, and/or NM-wt, labeled with a suitable amount of europium or chromium-51, with a suitable amount of an antibody, of antibodies in serum, or of antibodies gained from the serum, plasma or faeces, with a suitable amount of complement for a suitable time, typically between 3 to 5 hours, and measuring the lysis of the cells by determining the release of europium or chromium-51 after the incubation whereby a positive humoral immune response against Core-1 shows a significantly higher lysis of NM-D4 or NM-F9 cells than of NM-wt or NM-H9 or it shows a higher lysis of NM-D4, NM-F9, or ZR-75-1, than a lysis without complement and/or than a lysis without the antibody and/or than a lysis with an antibody or antibodies which does not bind or which binds less to NM-D4, NM-F9, or ZR-75-1, and/or than a lysis of NM-D4, NM-F9, or ZR-75-1 with an antibody or antibodies accordingly isolated from the same animal or human before administration of said formulation, said Core-1 positive microorganism or said lysate or fraction thereof; and/or (ii) incubating a suitable amount of ZR75-1, NM-D4, NM-F9, NM-H9, and/or NM-wt, labeled with a suitable amount of europium or chromium-51, with a suitable amount of an antibody, of antibodies in serum, or of antibodies gained from the serum, plasma or faeces, with a suitable amount of at least one immune effector cell or mixture of cells comprising immune effector cells or peripheral blood mononuclear cells for a suitable time, typically between 3 to 5 hours or over night, and measuring the lysis of the cells by determining the release of europium or chromium-51 after the incubation whereby a positive humoral immune response against Core-1 shows a significantly higher lysis of NM-D4 or NM-F9 cells than of NM-wt or NM-H9 or it shows a higher lysis of NM-D4, NM-F9, or ZR-75-1, than a lysis without the antibody and/or than a lysis with an antibody or antibodies which does not bind or which binds less to NM-D4, NM-F9, or ZR-75-1, and/or than a lysis of NM-D4, NM-F9, or ZR-75-1 with an antibody or antibodies accordingly isolated from the same animal or human before administration of said formulation, said Core-1 positive microorganism or said lysate or fraction thereof.

In a further preferred embodiment of the invention a nutraceutical or a pharmaceutical formulation comprising at least one Core-1 positive microorganism or fraction or lysate thereof induces a humoral immune response against Core-1 which is positive for at least two humoral immune response tests out of the humoral immune response tests 1 to 6 described above, preferably positive for humoral immune response tests 1 and 3, and more preferably for humoral immune response test 1, 2 and 3, and more preferably for humoral immune response test 1, 2, 3, and 4, and more preferably for humoral immune response test 1, 2, 3, 4, and 6, and even more preferably for humoral immune response test 1, 2, 3, 4, and 5, and most preferably positive for all 6 humoral immune response tests.

Said cellular immune response against Core-1 is a T-cell response against Core-1 which can be e.g. detected by at least one of the cellular immune response tests 1 to 5 described herein. More preferably it is a cellular immune response against Core-1 which is a cytotoxic T cell response or a helper T cell response against Core-1. Even more preferably is a cellular immune response against Core-1 which is a cytotoxic T cell response and a helper T cell response against Core-1 which can be detected by cellular immune response tests 1, 2, 3, 4 and 5 described herein. Most preferably is a cellular immune response against Core-1 which is a cytotoxic T cell response and Th1 type helper T cell response against Core-1 which can be detected by cellular immune response tests 1, 2, 3, 4 and 5.

Said cellular immune response tests comprise bringing into contact dendritic cells loaded with a Core-1 microorganism together with immune cells and cultivation for appropriate times and under appropriate conditions and subsequently adding for restimulation dendritic cells loaded with at least one Core-1 carrying molecule and cultivation for appropriate times and conditions and subsequently measuring the amount of secreted GM-CSF, TNFalpha, or INFgamma, or measuring the proliferation of T cells, or the inhibition of the secretion of GM-CSF, TNFalpha, or INF-gamma, or the proliferation by antibodies against Core-1 or measuring the presentation of Core-1 on the dendritic cells or measuring the lysis of Core-1 positive cells by activated immune cells, preferably by activated T cells.

Said dendritic cells, herein also called DC, can be any dendritic cells or a mixture of dendritic cells or a mixture of cells comprising dendritic cells or at least one dendritic cell. They can be derived from human donors which are healthy or which have a disease, such as but not limited to tumor disease or Crohns disease or Core-1 positive disease or one of the diseases listed elsewhere herein, or from animals. Said DCs can be obtained and loaded as known by those skilled in the art and are typically obtained from CD34 positive precursor cells or CD14 positive monocytic cells from human blood or bone marrow which are differentiated to immature dendritic cells (iDC) using certain combination of suitable molecules known to those skilled in the art. The iDCs are loaded with the Core-1 positive microorganism or with Core-1 carrying molecule, or appropriate controls, and are further matured using certain combination of suitable molecules known to those skilled in the art to obtain loaded dendritic cells which correspond to loaded mature dendritic cells (mDC) which are able to activate T-cells.

Said DCs can as well be originated from a dendritic cell line such as but not limited to the human dendritic cell line NEMOD-DC (obtainable from Glycotope GmbH Berlin, Germany; www.glycotope.com) or Mutz-3.

Said loading of dendritic cells means that the dendritic cells are incubated in the appropriate differentiation and maturation state with suitable amounts of a Core-1 positive microorganism, or fractions or lysates thereof or at least one Core-1 carrying-molecule for a suitable time, typically this occurs within the maturation step described above in combination with suitable molecules, typically for 24 to 48 hours, leading to loaded dendritic cells capable of activating immune cells, preferably T cells, comprising Core-1 specific T-cells.

Said immune cells can be PBMC (peripheral blood mononuclear cells) or other cell populations comprising CD4+ and/or CD8+ T-cells, preferably CD4+ and CD8+ T-cells. Those skilled in the art know how to gain those cells from a human or animal and generation of those cells can comprise preparations by ficoll gradient from human blood or from blood cells of leukapherases and can comprise in case further enrichment by T cell specific magnetic sorting technologies.

In a preferred embodiment the dendritic cells are matched in at least one MHC class molecule with the immune cells, preferably in an MHC class I molecule or MHC class II molecule, more preferable in at least one MHC class I and one MHC class II molecule, more preferably in more MHC molecules and most preferably in all MHC molecules. The latter can be achieved by obtaining the dendritic cells and the immune cells from the same individual.

Said appropriate times and conditions for cultivation of the immune cells with the loaded dendritic cells and for the subsequent adding of the loaded dendritic cells are known to those skilled in the art and can be optimized by him taking into consideration the conditions the cells are in. Typically the incubation time is 7 to 10 days for each of the two steps (primary activation and restimulation).

Said Core-1 carrying molecule in sense of the described cellular immune response tests means sufficient amounts of a cell or tumor cell carrying Core-1, a protein carrying Core-1, or a polypeptide carrying Core-1. Said cell or tumor cell carrying Core-1 can be living or dead, or a lysate from those cells or a fraction thereof, more preferred is a lysate. A protein carrying Core-1 can be any protein carrying Core-1 such as carrier proteins whereon Core-1 is bound on tumors. A polypeptide carrying Core-1 can be any polypeptide carrying Core-1, preferably those which can be presented with Core-1 on the mDC.

Said Core-1 positive microorganism in sense of the described cellular immune response tests means sufficient amounts of the particular Core-1 positive microorganism which can be living or dead, or a lysate from those cells or a fraction thereof, more preferred is a lysate or a fraction thereof.

Controls should be used to further confirm the positivity of the immune response. Those skilled in the art are able to use appropriate controls as such which are described in more detail below and in example 12. Examples are the use of controls which are loaded onto the DC as described for the Core-1 carrying molecules and used for restimulation and can comprise (i) cells which are negative for Core-1, preferably those which resemble as closely as possible the Core-1 positive cells as Core-1 carrying molecules, in the corresponding format such as living or dead, or a lysate from those cells or a fraction thereof; (ii) a protein not carrying Core-1, preferably the same protein as used as Core-1 carrying molecule but without the Core-1, preferably without any glycosylation or with a sialylated Core-1 structure, (iii) a polypeptide not carrying Core-1, preferably the same polypeptide as used as Core-1 carrying molecule but without the Core-1, preferably without any glycosylation or with a sialylated Core-1 structure or the Tn structure (GalNAcalpha1-O-Ser/Thr). Additional controls may be (iv) non-loaded mDC treated in the same way as the mDC loaded with Core-1 carrying molecules including the necessary molecules and conditions for maturation but without any additional molecule corresponding to the Core-1 carrying molecule or above mentioned controls (i-iii). The examples and the preferred embodiments describe in detail the most suitable controls, while other suitable ones might be selected by those skilled in the art.

In a preferred embodiment of the invention the dendritic cells are functional dendritic cells obtained from the leukemia cell line MUTZ-3 (DSMZ ACC295) or cells derived from MUTZ-3 such as NEMOD-DC [as described in DE10139428 A1, WO2003/023023 A1, EP01419240, US20040265998, CA2457287, 10139428.4 (DE), PCT/EP02/09260, 02758474.7 (EP), U.S. Ser. No. 10/486,966, CA2,457,287)] and obtainable from Glycotope GmbH Berlin, Germany [www.Glycotope.com]. Those dendritic cells are active dendritic cells which are fully capable to activate T cells and to process and/or present antigens on their surface including on MHC class molecules. In a further preferred embodiment of the invention the dendritic cells are functional dendritic cells obtained from MUTZ-3 or cells derived from MUTZ-3, such as NMD-200, and the immune cells are matched in MHC class I molecule such as HLA-A2 or HLA-B44, preferably HLA-A2 and HLA-B44. In a further preferred embodiment a lysate of NM-D4 or NM-F9 is used as Core-1 carrying molecule and NM-wt [which is the parental cell of NM-D4 or NM-F9 as described in WO2005/017130 A2 and EP1654353] or NM-H9 [NM-H9D8, DSM ACC2806], which differs in the potential to sialylate and hence does in contrast to NM-D4 and NM-F9 not carry Core-1 on its surface, as a control in the corresponding format such as living or dead, or a lysate from those cells or a fraction thereof, more preferred is a lysate, both loaded onto the DC and used for restimulation. In another preferred embodiment glycophorin or periodate treated asialoglycophorin as a control for asialoglycophorin each loaded onto the DC and used for restimulation. In a more preferred embodiment, a lysate of NM-D4 or NM-F9 and asialoglycophorin is used as Core-1 carrying molecule for restimulation and NM-wt [NM-H9] and glycophorin or periodate-treated asialoglycophorin and/or unloaded DC are used as negative controls.

Due to variances from experiments to experiments which is in particular typical for cellular immunological methods known to those skilled in the art, controls have to be set up in parallel to the test as known to those skilled in the art.

According to one embodiment, the invention provides an in vitro cellular immune response test against Core-1 comprising a.) Loading at least one dendritic cell with a first Core-1 positive compound, wherein said Core-1 positive compound carries Core-1;

b.) bringing into contact a suitable amount of said at least one dendritic cell loaded with said Core-1 positive compound with a suitable amount of immune cells which can be activated or inhibited by a dendritic cell;

c.) cultivation in order to allow interaction of said immune cells with said loaded dendritic cells;

d.) adding a suitable amount of antigen presenting cells (APC) loaded with a suitable amount of at least one second compound carrying Core-1, wherein said second compound is different from said first Core-1 positive compound;

e.) cultivation for restimulation of said immune cells f.) determining the amount of restimulated immune cells.

Figure 23:
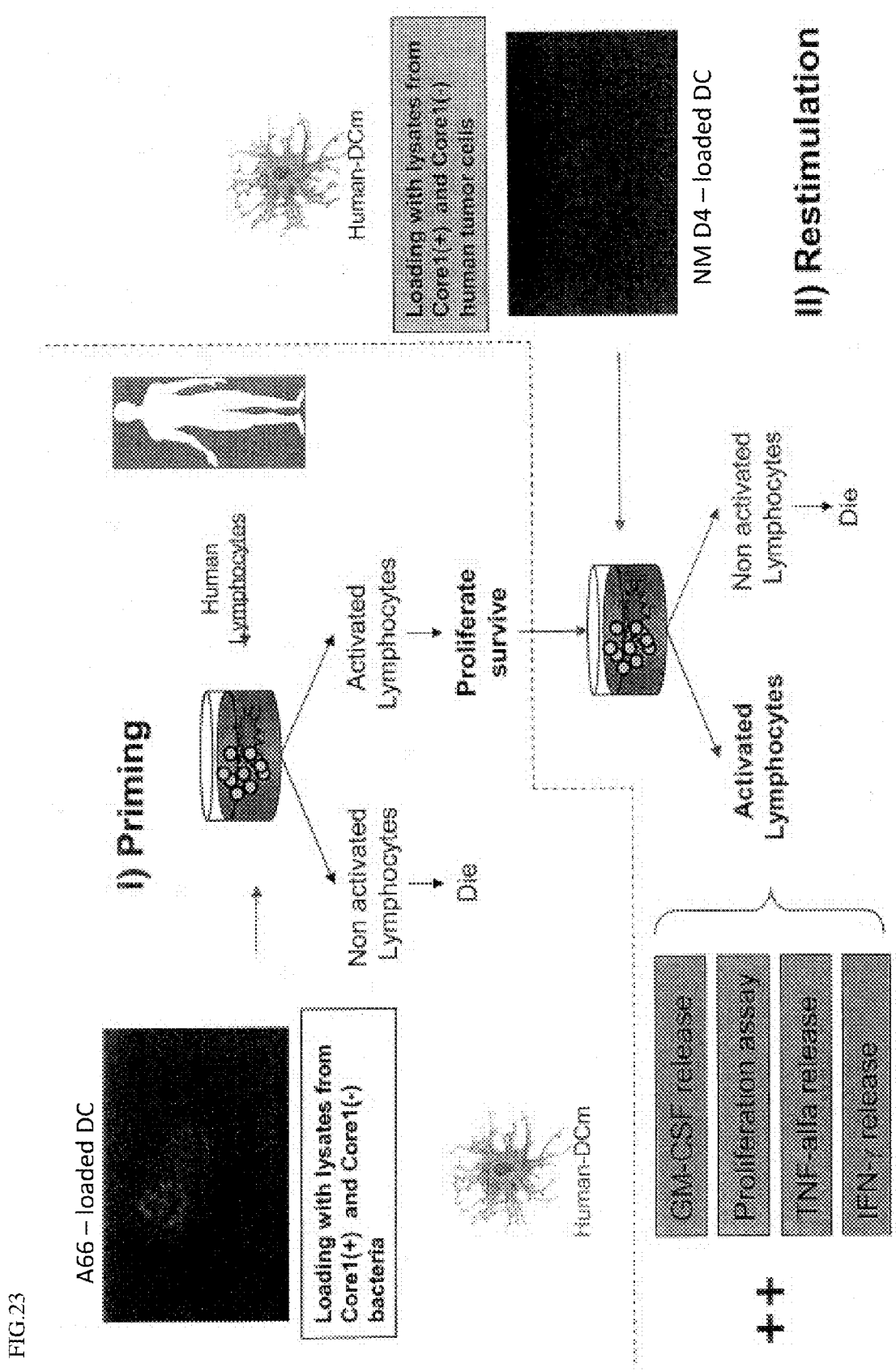

The invention provides a method for determining whether a Core-1 positive microorganism or compound in general is capable of triggering a cellular immune response. So far the prior art assumed that carbohydrates are unable to trigger a cellular immune response. However, it has now been found that certain carbohydrate epitopes are able to elicit a cellular immune response. It is thus important to provide test systems for determining whether a certain carbohydrate epitope, here Core-1, is in the presented form (e.g. by a Core-1 positive microorganism according to the present invention or a Core-1 conjugate) indeed able to trigger a respective response, thereby determining whether said Core-1 positive compound is a suitable therapeutical/nutraceutical. The invention thus uses dendritic cells as dendritic cells are able to prime and thus stimulate immune cells such as T-cells. Dendritic cells process compounds they are encountering and present the processed compounds/antigens on their surface. However, MHC cells such as dendritic cells can only present certain kinds of antigens and it is important to determine whether the Core-1 epitope—in its surrounding on the microorganism or carrier—can be presented by dendritic cells in the correct from as only then these compounds/microorganisms are able to elicit a cellular immune response. The principles of this cellular immune response test are also illustrated in FIG. 23.

Therefore, dendritic cells are loaded with the Core-1 positive compound of interest. Said compound can e.g. be a microorganism carrying Core-1 as described herein, a tumor cell or any other compound carrying Core-1. Suitable conditions for loading and suitable compounds carrying carbohydrate structures are described herein.

Said loaded dendritic cells are then contacted with immune cells, in particular lymphocytes such as T-cells. The immune cells can be obtained e.g. from human donors. Dendritic cells presenting antigens matching the receptors of the immune cells activate and thus stimulate the lymphocytes thereby allowing them to proliferate and survive. Lymphocytes which do not match the antigens presented by the dendritic cells are not activated and die.

This first round of stimulation provides activated lymphocytes which are specific for any corresponding antigen presented by said loaded dendritic cells, including Core-1 if presented. However, the aim of the present method is to identify whether the compound comprising a carbohydrate epitope/antigen of interest—here Core-1—can stimulate a cellular response specific against Core-1.

Therefore, a selection step is performed wherein the lymphocytes are restimulated in order to determine whether Core-1 stimulates the lymphocytes and thus triggers a cellular response. In said selection step antigen presenting cells such as e.g. dendritic cells are loaded with a second compound which also carries Core-1. However, said second compound is different from the first compound. E.g. the first compound is a microorganism carrying Core-1 and the second compound is a tumor cell carrying Core-1. This second compound is also processed by the APCs and the antigens are presented by said APCs. As the second compound is different from the first compound most presented antigens, preferably all antigens are—besides Core-1-different from the antigens presented in the first round. This has the effect that only those lymphocytes survive the second round of restimulation which find a matching antigen presented by said APCs, namely Core-1. In case the dendritic cells of the first round as well as the APCs of the second round both present an antigen comprising or consisting of Core-1 (or a structure immunologically mimicking Core-1), lymphocytes recognizing said antigen are stimulated and thus survive as they are also restimulated. Those lymphocytes which do not find a matching partner when contacting with said APCs loaded with said second Core-1 positive compound die due to a lack of restimulation. This selection step ensures that a cellular response against Core-1 is detected.

In the last step it is determined whether the lymphocytes were indeed restimulated. This can be done e.g. by determining secretion products of the lymphocytes which are secreted if said lymphocytes are (re)stimulated such as interferon alpha, interferon gamma or GM-CSF the proliferation of the T-cells.

Suitable tests for determining whether restimulation occurs are described herein.

The specificity of said test can be enhanced by using a carbohydrate binding structure which specifically recognizes Core-1 when presented by the dendritic cells/APCs. According to said embodiment, at least a portion of said stimulated lymphocytes according to step c) are contacted with a suitable amount of antigen presenting cells (APC) loaded with a suitable amount of at least one second Core-1 positive compound, wherein said second compound is different from said first carbohydrate positive compound, in the presence of a Core-1 binding molecule recognizing Core-1. Said Core-1 binding molecule blocks the interaction of the APCs with said lymphocytes thereby preventing restimulation and hence survival of the cells. This additional step further ensures that the carbohydrate of interest specifically stimulates lymphocytes and thus triggers a specific cellular immune response. This specificity enhancing/confirming step can be either done in parallel—by splitting the stimulated lymphocytes according to step c—or by performing said enhancing/confirming step additionally and thus afterwards. Suitable Core-1 binding molecules, preferably antibodies are described herein.

According to one embodiment the invention provides a cellular immune response test (cellular immune response test 1) against Core-1 is provided comprising a.) bringing into contact a suitable amount of dendritic cells comprising at least one dendritic cell, dendritic cells, or a mixture of cells comprising at least one dendritic cell, loaded with a suitable amount of the Core-1 positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell b.) cultivation for an appropriate time and under an appropriate condition c.) adding a suitable amount of dendritic cells comprising at least one dendritic cell, dendritic cells, or a mixture of cells comprising at least one dendritic cell, loaded with a suitable amount of at least one Core-1 carrying molecule d.) cultivation for an appropriate time and under an appropriate condition for restimulation e) measuring the amount of secreted GM-CSF e.g. by ELISA or ELISPOT, whereby a positive cellular immune response against Core-1 shows a higher GM-CSF secretion of said immune cells restimulated with said dendritic cells loaded with a Core-1 carrying molecule than the GM-CSF secretion of corresponding immune cells restimulated with corresponding unloaded dendritic cells and/or a higher GM-CSF secretion of said immune cells restimulated with said dendritic cells loaded with a Core-1 carrying molecule than the GM-CSF secretion of corresponding immune cells restimulated with corresponding dendritic cells loaded with a molecule not carrying Core-1 and/or a higher GM-CSF secretion of said immune cells restimulated with said dendritic cells loaded with asialoglycophorin than the GM-CSF secretion of corresponding immune cells restimulated with corresponding dendritic cells loaded with glycophorin or periodate treated asialoglycophorin and/or a higher GM-CSF secretion of said immune cells restimulated with said dendritic cells loaded with a lysate or fractions of NM-D4 or NM-F9 than the GM-CSF secretion of corresponding immune cells restimulated with corresponding dendritic cells loaded with a lysate of NM-wt or NM-H9.

Corresponding immune cells means that the same immune cells, which are or comprise at least one immune cell, CD4+ T cell, CD8+ T cell, a mixture of cells comprising at least one T cell, or peripheral blood mononuclear cells, or other elsewhere described cells and mixtures of cells, which can be activated or inhibited by a dendritic cell, are used for the control or comparative test with a control or test molecule, mixture of molecules, cells, cell lysates or fractions, microorganism or fractions thereof than those which are used for said immune cells in order to allow a comparison.

Corresponding dendritic cells means that the same dendritic cells, which are or comprise at least one dendritic cell, dendritic cells, or a mixture of cells comprising at least one dendritic cell or other elsewhere described cells and mixtures of cells able to active T cells, loaded with a suitable amount of at least one Core-1 carrying molecule, are used for the control or comparative test with a control or test molecule, mixture of molecules, cells, cell lysates or fractions, microorganism or fractions thereof or without any, than those which are used for said dendritic cells in order to allow a comparison.

This is known to those skilled in the art and they can be selected by those skilled in the art. This is shown in more detail in the examples. For clarification: For example, the same amount of immune cells from the same preparation are brought into contact with the same amount of dendritic cells from the same preparation loaded with the same amount of asialoglycophorin and in parallel with the same amount of glycophorin or periodate treated asialoglycophorin and used in the test in order to allow optimal comparability.

Variations are known to those skilled in the art and can be determined by those or are described in more detail in examples.

Said cellular immune response test 1 tests the activation of CD4+ and/or CD8+ T-cells to Core-1 specific CD4+ and/or CD8+ activated T-cells by a Core-1 positive microorganism by measuring the specific induced secretion of GM-CSF comprising bringing into contact dendritic cells loaded with a Core-1 microorganism, lysate or fraction thereof and immune cells and cultivation for appropriate times and conditions and subsequently adding dendritic cells loaded with Core-1 carrying molecule for restimulation and cultivation for appropriate times and conditions and subsequently measuring the amount of secreted GM-CSF in response to this restimulation. Said measuring of the amount of secreted GM-CSF is preferably done by ELISA or ELISPOT, more preferably ELISA, and is known to those skilled in the art. In the most preferred embodiment of the invention the cellular immune response test 1 comprises bringing into contact functional dendritic cells obtained from cells derived from MUTZ-3 loaded with Core-1 positive microorganism together with PBMC (peripheral blood mononuclear cells) matched at least in MHC class I (HLA-A2) and (HLA-B44) and cultivation of these cells for appropriate times and conditions, typically 7 to 10 days, and subsequently adding for restimulation functional dendritic cells obtained from cells derived from MUTZ-3 loaded with lysate of NM-D4 or NM-F9, or with asialoglycophorin and cultivation for appropriate times and conditions, typically 7 to 9 days, and subsequently measuring the amount of secreted GM-CSF in an ELISA or ELISPOT analysis. ELISA and ELISPOT analysis of GM-CSF-release is known to those skilled in the art and described in detail in examples. A positive cellular immune response against Core-1 shows a higher GM-CSF secretion of the immune cells restimulated with DC loaded with a lysate of NM-D4 or NM-F9 than the secretion of the immune cells restimulated with DC loaded with a lysate of NM-wt or NM-H9 and/or it shows a higher GM-CSF secretion of the immune cells restimulated with DC loaded with asialoglycophorin than the immune cells restimulated with DC loaded with glycophorin. In a preferred embodiment the secretion of GM-CSF induced with NM-D4 or NM-F9 is 2 times higher than that induced with NM-wt, more preferably 3 times higher. In an preferred embodiment the secretion of GM-CSF induced with asialoglycophorin is 2 times higher than that induced with glycophorin, more preferably 3 times higher. A preferred embodiment of the cellular immune response test 1 is described in detail in example 12.

In another preferred embodiment the invention provides a cellular immune response test (cellular immune response test 2) against Core-1 comprising a.) bringing into contact a suitable amount of dendritic cells comprising at least one dendritic cell, dendritic cells, or a mixture of cells comprising at least one dendritic cell, loaded with a suitable amount of the Core-1 positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell b.) cultivation for an appropriate time and under an appropriate condition c.) adding a suitable amount of dendritic cells comprising at least one dendritic cell, dendritic cells, or a mixture of cells comprising at least one dendritic cell, loaded with a suitable amount of at least one Core-1 carrying molecule d.) cultivation for an appropriate time and under an appropriate condition for restimulation e.) measuring the amount of secreted IFNgamma and/or secreted TNFalpha by ELISA or ELISPOT, whereby a positive cellular immune response against Core-1 shows a higher IFNgamma and/or TNFalpha secretion of said immune cells restimulated with said dendritic cells loaded with a Core-1 carrying molecule than the IFNgamma and/or TNFalpha secretion of corresponding immune cells restimulated with corresponding unloaded dendritic cells and/or a higher IFNgamma and/or TNFalpha secretion of said immune cells restimulated with said dendritic cells loaded with a Core-1 carrying molecule than the IFNgamma and/or TNFalpha secretion of corresponding immune cells restimulated with corresponding dendritic cells loaded with a molecule not carrying Core-1 and/or a higher IFNgamma and/or TNFalpha secretion of said immune cells restimulated with said dendritic cells loaded with asialoglycophorin than the IFNgamma and/or TNFalpha secretion of corresponding immune cells restimulated with corresponding dendritic cells loaded with glycophorin or periodate treated asialoglycophorin and/or a higher IFNgamma and/or TNFalpha secretion of said immune cells restimulated said dendritic cells loaded with a lysate or fractions of NM-D4 or NM-F9 than the IFNgamma and/or TNFalpha secretion of corresponding immune cells restimulated with corresponding dendritic cells loaded with a lysate of NM-wt or NM-H9.

Said cellular immune response test 2 tests the activation of cytotoxic T-cells such as CTL (cytotoxic T lymphocytes) and or Th1 (cytotoxic T helper cells) to Core-1 specific activated cytotoxic T-cells by a Core-1 positive microorganism by measuring the specific induced secretion of IFNgamma and/or TNFalpha comprising bringing into contact dendritic cells loaded with a Core-1 microorganism and immune cells and cultivation for appropriate times and conditions and subsequently adding dendritic cells loaded with Core-1 carrying molecule for restimulation and cultivation for appropriate times and conditions and subsequently measuring the amount of secreted IFNgamma and/or secreted TNFalpha in response to this restimulation. Said measuring of the amount of secreted IFNgamma and/or TNFalpha is preferably done by ELISA or ELISPOT, more preferably ELISPOT and is known to those skilled in the art. In the most preferred embodiment of the invention the cellular immune response test 2 comprises bringing into contact functional dendritic cells obtained from cells derived from MUTZ-3 loaded with Core-1 positive microorganism together with PBMC (peripheral blood mononuclear cells) matched at least in MHC class I (HLA-A2 and HLA-B44) and cultivation of these cells for appropriate times and conditions, typically 7 to 10 days, and subsequently adding for restimulation functional dendritic cells obtained from cells derived from MUTZ-3 loaded with lysate of NM-D4 or NM-F9, or with asialoglycophorin and cultivation for appropriate times and conditions, typically 7 to 9 days, and subsequently measuring the amount of secreted IFNgamma by ELISPOT analysis and/or secreted TNFalpha by ELISA analysis. ELISA and ELISPOT analysis of TNFalpha and IFNgamma is known to those skilled in the art and described in detail in examples. A positive cellular immune response against Core-1 shows a higher IFNgamma and/or TNFalpha secretion by the immune cells restimulated with DC loaded with a lysate of NM-D4 or NM-F9 than the secretion of the immune cells restimulated with DC loaded with a lysate of NM-wt or NM-H9 and/or it shows a higher IFNgamma and/or TNFalpha secretion of the immune cells restimulated with DC loaded with asialoglycophorin than the immune cells restimulated with DC loaded glycophorin. In a preferred embodiment the secretion of IFNgamma and/or TNFalpha induced with NM-D4 or NM-F9 is 2 times higher than that induced with NM-wt, more preferably 3 times higher. In a preferred embodiment the secretion of GM-CSF induced with asialoglycophorin is 2 times higher than that induced with glycophorin, more preferably 3 times higher. A preferred embodiment of the cellular immune response test 2 is described in detail in example 12.

In another preferred embodiment the invention provides a cellular immune response test (cellular immune response test 3) against Core-1 comprising a.) bringing into contact a suitable amount of dendritic cells comprising at least one dendritic cell, dendritic cells, or a mixture of cells comprising at least one dendritic cell, loaded with a suitable amount of the Core-1 positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell b.) cultivation for an appropriate time and under an appropriate condition c.) adding a suitable amount of dendritic cells comprising at least one dendritic cell, dendritic cells, or a mixture of cells comprising at least one dendritic cell, loaded with a suitable amount of at least one Core-1 carrying molecule d.) cultivation for an appropriate time and under an appropriate condition for restimulation and e.) measuring the proliferation and/or proliferation induction, preferably by using the WST reaction in combination with a colorimetric measurement, whereby a positive cellular immune response against Core-1 shows a higher proliferation or number of T cells after a certain time of cultivation when restimulated with said dendritic cells loaded with a Core-1 carrying molecule than when restimulated with corresponding unloaded dendritic cells and/or a higher proliferation or number of T cells after a certain time of cultivation when restimulated with said dendritic cells loaded with a Core-1 carrying molecule than when restimulated with corresponding dendritic cells loaded with a molecule not carrying Core-1 and/or a higher proliferation or number of T cells after a certain time of cultivation when restimulated with said dendritic cells loaded with asialoglycophorin than when restimulated with corresponding dendritic cells loaded with glycophorin or periodate treated asialoglycophorin and/or a higher proliferation or number of T cells after a certain time of cultivation when restimulated with said dendritic cells loaded with a lysate or fractions of NM-D4 or NM-F9 than when restimulated with corresponding dendritic cells loaded with a lysate of NM-wt or NM-H9.

Said cellular immune response test 3 tests the activation of CD4+ and CD8+ T-cells to Core-1 specific activated T-cells by a Core-1 positive microorganism by measuring the induction of the proliferation of T-cells comprising bringing into contact dendritic cells loaded with a Core-1 positive microorganism and immune cells and cultivation for appropriate times and conditions and subsequently adding dendritic cells loaded with Core-1 carrying molecule for restimulation and cultivation for appropriate times and conditions and subsequently measuring the proliferation. Said measuring of the proliferation induction is preferably done using the WST reaction in combination with a colorimetric measurement and deduction of the DC alone and the non-restimulated immune cells alone which is known to those skilled in the art and is described in example 12. In the most preferred embodiment of the invention the cellular immune response test 3 comprises bringing into contact functional dendritic cells obtained from cells derived from MUTZ-3 loaded with Core-1 positive microorganism together with PBMC (peripheral blood mononuclear cells) matched at least in MHC class I (HLA-A2 and HLA-44) and cultivation of these cells for appropriate times and conditions, typically 7 to 10 days, and subsequently adding for restimulation functional dendritic cells obtained from cells derived from MUTZ-3 loaded with lysate of NM-D4 or NM-F9, or with asialoglycophorin and cultivation for appropriate times and conditions, typically 7 to 9 days, and subsequently measuring the proliferation rate as described above and in more detail in example 12. A positive cellular immune response against Core-1 shows a higher proliferation of T cells restimulated with DC loaded with the Core-1 carrying molecule than the proliferation rate of the DC alone and the T cells put into contact with mDC unloaded or with DC loaded with the corresponding control. In a preferred embodiment the proliferation of the T-cells induced with NM-D4- or NM-F9-loaded DC is 2 times higher than that induced with NM-wt or NM-H9, more preferably 3 times higher. A preferred embodiment of the cellular immune response test 3 is described in detail in example 12.

In another preferred embodiment the invention provides a cellular immune response test (cellular immune response test 4) against Core-1 comprising bringing into contact a suitable amount of a dendritic cell, dendritic cells, or a mixture of cells comprising at least one dendritic cell, loaded with a suitable amount of the Core-1 positive microorganism, a lysate or a fraction thereof, formulations comprising those, the nutraceutical, or the pharmaceutical composition of the invention or a Core-1 carrying molecule, a mixture comprising a Core-1 carrying molecule, a cell positive for Core-1, a lysate or fraction thereof, together with a suitable amount of at least one Core-1 specific antibody, preferably Nemod-TF1, Nemod-TF2, or A78-G/A7, whereby a positive presentation of Core-1 on said dendritic cell or cells is present when the binding of the Core-1 specific antibody is higher to said dendritic cell or cells loaded with a Core-1 carrying molecule than its binding to an corresponding unloaded dendritic cell or cells or to a corresponding dendritic cell or cells loaded with a molecule not carrying Core-1 or a Core-1 carrying molecule treated with periodate and/or when the binding of the Core-1 specific antibody is higher to said dendritic cell or cells loaded with the Core-1 positive microorganism, lysate or fraction thereof, the nutraceutical, the pharmaceutical composition or formulations thereof, than to a corresponding dendritic cell or cells unloaded or than to the a corresponding dendritic cell or cells loaded with a microorganism which is not bound by a Core-1 specific antibody or than to a corresponding dendritic cell or cells loaded with the Core-1 positive microorganism after periodate treatment.

Said cellular immune response test 4 tests the ability of dendritic cells to present Core-1 on its surface after loading with a Core-1 positive microorganism showing the potential of the loaded dendritic cells to process and present the microorganism-derived Core-1 to immune cells such as T-cells comprising bringing suitable amounts of Core-1 positive microorganism and dendritic cells in a suitable differentiation and maturation state together, preferably immature DC which are then matured to mDC using an appropriate cocktail of molecules known to those skilled in the art and measure the presentation of Core-1 by the loaded DC by testing the binding of a Core-1 specific antibody of the invention to said loaded DC. Said testing of the binding is performed by appropriate methods, preferably immunocytochemistry, immunofluorescence or flow cytometry, and more preferably by immunocytochemistry which are known by those skilled in the art and are described in the examples. The test shows a positive presentation of loaded DC when the binding of the Core-1 specific antibody is higher to the DC loaded with the Core-1 positive microorganism than to DC unloaded, or more preferably to DC loaded with a microorganism which is not bound by a Core-1 specific antibody or to DC loaded with the Core-1 positive microorganism after periodate treatment. In the most preferred embodiment of the invention the cellular immune response test 4 comprises bringing into contact suitable amounts of functional immature dendritic cells obtained from cells derived from MUTZ-3 with lysates of a Core-1 positive microorganism and subsequent culturing and maturation for 24 h—48 hours using a suitable molecule cocktail such as described in example 12 and testing the presentation of Core-1 via immunofluorescence microscopy (immunocytochemistry) using the Core-1 specific antibodies Nemod-TF1 or Nemod-TF2 or A78-G/A7. In a preferred embodiment the binding of Nemod-TF1, Nemod-TF2 or A78-G/A7 is at least 2 times higher than to DC loaded with a Core-1 negative microorganism, more preferably a strong binding of Nemod-TF1, Nemod-TF2 or A78-G/A7 to DC loaded with the Core-1 positive microorganism can be detected and no binding of the antibodies above the background is obtained with unloaded DC or with DC loaded with a Core-1 negative microorganism.

A preferred embodiment of the cellular immune response test 4 is described in detail in example 12.

In another embodiment the invention provides a cellular immune response test (cellular immune response test 5) against Core-1 comprising
  a) incubating a suitable amount of target cells from the cell lines ZR-75-1, NM-D4, NM-F9, NM-H9 and/or NM-wt labelled with a suitable amount of europium or chromium-51 with at least one immune cell directed against Core-1 or a mixture of cells comprising at least one immune cell directed against Core-1 for a suitable time (typically between 3-6 hours or over night) and under suitable conditions and
  b) measuring the lysis of the target cells by determining the release of europium or chromium-51 whereby a positive cellular immune response against Core-1 shows a significant higher lysis of NM-D4 or NM-F9 cells than of NM-wt or NM-H9 or it shows a significant higher lysis of NM-D4, NM-F9, or ZR-75-1 incubated with Core-1 directed immune cells, than a lysis of NM-D4, NM-F9, or ZR-75-1 incubated with corresponding control immune cells.

Said CIRT (cellular immune response test) 5 tests the Core-1 specific cytotoxicity of immune cells directed against Core-1 such as but not limited to T cell, T cells, T cell clone, T cell line, CD4 positive T cells, CD8 positive T cells, NK cells and/or PBMCs.

The generation of Core-1 directed immune cells is described elsewhere herein.

In a preferred embodiment of the invention the Core-1 directed immune cells are obtained by the administration of the formulation of the invention, the Core-1 positive microorganism or the fraction or lysate thereof to a human or animal, more preferred by the administration of the formulation of the invention, the Core-1 positive microorganism or the fraction or lysate thereof to a human or animal and subsequent isolation of the immune cells from the human or animal by techniques known to those skilled in the art and described herein such as but not limited to Ficoll gradient separation of immune cells from whole blood or from blood cells of leukapheroses and/or separation of subpopulations of immune cells by immunomagnetic beads separation techniques.

In another preferred embodiment of the invention the Core-1 directed immune cells are restimulated at least once with dendritic cells loaded with the formulation of the invention, the Core-1 positive microorganism or the fraction or lysate thereof or a Core-1 carrying molecule or tumor cell, as described elsewhere herein, prior to their use in CIRT 5.

In a more preferred embodiment of the invention the Core-1 directed immune cells are restimulated more than once with dendritic cells loaded with the formulation of the invention, the Core-1 positive microorganism or the fraction or lysate thereof or a Core-1 carrying molecule or tumor cell prior to their use in CIRT 5, whereby Core-1 on different carriers (such as but not limited to Core-1 on or from microorganism, Core-1 carrying molecule, Core-1 carrying protein or tumor cell) is used for different rounds of restimulation.

In an even more preferred embodiment the Core-1 activated T cells are restimulated at least once with dendritic cells loaded with another molecule or cell or fraction of said cell which comprises Core-1 and which does not occur on the Core-1 microorganism, preferably a lysate from a tumour cell positive for Core-1 which is not used for measuring the amount of lysis.

In an even further preferred embodiment of the invention the activation or generation of Core-1 directed immune cells, or the restimulation of the Core-1 specific immune cells, or the lysis of the Core-1 positive tumor cells is inhibited by a suitable amount of at least one Core-1 specific antibody.

The test comprises incubating suitable amounts of labeled Core-1 positive target cells such as ZR75-1, preferably NM-D4 or NM-F9, with suitable amounts of immune cells directed against Core-1 for a suitable time, typically between 3 and 6 hours or over night. The Core-positive tumor cells are labeled with europium or chromium-51 which allows the measurement of cells which are lysed. The amount of lysed cells is determined, preferably by measuring the release of europium or chromium-51 after incubation. A suitable control can be determined by those skilled in the art such as Core-1 negative cells (preferably NM-wt or NM-H9) or corresponding control immune cells not directed against Core-1. The test can be optimized in respect to suitable numbers of labeled tumor cells, numbers of immune effector cells, and incubation time by those skilled in the art for its use in the invention.

In a preferred embodiment the CIRT 5 is performed using an Europium Release Assay. The target cells NM-D4 are incubated for 10 minutes at 4° C. in 800 µl of europium buffer (50 mM HEPES, pH 7.4, 93 mM NaCl, 5 mM KCl, 2 mM $MgCl_2$, 10 mM diethylentriaminepentaacetic acid, 2 mM europium (III) acetate), electroporated (710V, 1 pulse, 30p) in a Multiporator (Eppendorf), and subsequently incubated on ice for another 10 minutes. Thereafter, the cells are washed 5 times in RPMI/5% FCS and seeded in a 96-well round-bottom plate (Nunc; $5\times10^3$/well). Thereafter Core-1 directed immune cells or corresponding immune cells are added as effector cells (100 µl/well), using different effector cell/target cell ratios from 100:1 to 5:1, preferably effector cell/target cell ratios from 50:1 to 20:1. To determine spontaneous release, 100 µl RPMI/5% FCS without effector cells are added. Maximum release is determined after complete lysis of the target with ethanol.

Following incubation at 37° C. for 4 hours, the plate is centrifuged at 500×g for 5 minutes, and 20 µl of cell-free supernatant from every well is pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined (Victor$^2$ Fluorometer, Perkin-Elmer Wallac). The specific cytotoxicity is obtained from the equation (experimental lysis–spontaneous lysis)/(maximum lysis—spontaneous lysis)×100%.

In a preferred embodiment the invention provides a cellular immune response test against Core-1 comprising
 a.) loading a suitable amount of immature dendritic cells comprising at least one dendritic cell, dendritic cells, or a mixture of cells comprising at least one dendritic cell, with a suitable amount of the Core-1 positive microorganism, a lysate or a fraction thereof, or the formulation as described elsewhere herein
 b.) cultivation for an appropriate time and under an appropriate condition for maturation
 c.) bringing into contact a suitable amount of said loaded dendritic cells with a suitable amount of immune cells comprising at least one immune cell, T cell, CD4+ T cell, CD8+ T cell, a mixture of cells comprising at least one T cell, or peripheral blood mononuclear cells, which can be activated or inhibited by a dendritic cell
 d.) cultivation for an appropriate time and under an appropriate condition for activation or inhibition
 e.) adding a suitable amount of dendritic cells for restimulation comprising at least one dendritic cell, dendritic cells, or a mixture of cells comprising at least one dendritic cell, loaded with a suitable amount of at least one Core-1 carrying antigen or suitable control antigens
 f.) cultivation for an appropriate time and under an appropriate condition for restimulation
 g.) measuring the amount of secreted GM-CSF, IFNgamma and/or TNFalpha by ELISA or ELISPOT, whereby a positive cellular immune response against Core-1 shows a significantly higher GM-CSF, IFNgamma and/or TNFalpha secretion of said immune cells restimulated with said dendritic cells loaded with a Core-1 carrying antigen than the GM-CSF, IFNgamma and/or TNFalpha secretion of corresponding immune cells restimulated with corresponding unloaded dendritic cells and/or a significantly higher GM-CSF, IFNgamma and/or TNFalpha secretion of said immune cells restimulated with said dendritic cells loaded with a Core-1 carrying antigen than the GM-CSF, IFNgamma and/or TNFalpha secretion of corresponding immune cells restimulated with corresponding dendritic cells loaded with an antigen not carrying Core-1 and/or a significantly higher GM-CSF, IFNgamma and/or TNFalpha secretion of said immune cells restimulated with said dendritic cells loaded with asialoglycophorin than the GM-CSF, IFNgamma and/or TNFalpha secretion of corresponding immune cells restimulated with corresponding dendritic cells loaded with glycophorin or periodate-treated asialoglycophorin and/or a significantly higher GM-CSF, IFNgamma and/or TNFalpha secretion of said immune cells restimulated with said dendritic cells loaded with a lysate or fractions of NM-D4 or NM-F9 than the GM-CSF, IFNgamma and/or TNFalpha secretion of corresponding immune cells restimulated with corresponding dendritic cells loaded with a lysate of NM-wt or NM-H9.

In a further preferred embodiment of the invention a nutraceutical or a pharmaceutical composition comprising at least one Core-1 positive microorganism or lysate or fraction thereof induces a cellular immune response against Core-1 which is positive for at least two cellular immune response tests out of the cellular immune response tests 1 to 5.

In an even further preferred embodiment of the invention a nutraceutical or a pharmaceutical formulation comprising at least one Core-1 positive microorganism or lysate or fraction thereof induces a humoral and a cellular immune response against Core-1 which is positive for at least one humoral immune response test and at least one cellular immune response tests.

In an even further preferred embodiment of the invention a nutraceutical or a pharmaceutical formulation comprising at least one Core-1 positive microorganism or lysate or fraction thereof induces a humoral and a cellular immune response against Core-1 which is positive for at least two humoral immune response test and two cellular immune response tests, preferably positive for humoral immune response tests 1 and 3 and cellular immune response test 1 and 3, and more preferably for humoral immune response tests 1, 2 and 3 and cellular immune test 1, 2 and 3, and even more preferably for humoral immune response test 1, 2, 3 and 4 and cellular immune response test 1, 2, 3 and 4, and even more preferably for humoral immune response test 1, 2, 3, 4, and 6, and all 5 cellular immune response test, and even more preferably for humoral immune response test 1, 2, 3, 4, and 5, and all 5 cellular immune response test, and most preferably positive for all 6 humoral immune response tests and all 5 cellular immune response tests.

In another preferred embodiment the invention provides the cellular immune response tests 1 to 5 wherein the dendritic cell, dendritic cells or a mixture of cells comprising dendritic cell comprises at least one dendritic cell which is a mature dendritic cells when bringing into contact with said immune cells.

In another preferred embodiment the invention provides the cellular immune response tests 1 to 5 wherein the dendritic cell, dendritic cells or a mixture of cells comprise functional dendritic cells obtained from cells derived from MUTZ-3.

In another preferred embodiment the invention provides the cellular immune response tests 1 to 5 wherein said immune cells are matched with said dendritic cells at least in one MHC class I molecule.

In another preferred embodiment the invention provides the cellular immune response tests 1 to 5 wherein the Core-1 carrying molecule is a lysate or fraction of NM-D4 or NM-F9 or asialoglycophorin.

In another preferred embodiment the invention refers to the use of any of the immune response tests as described above for determining the immune response against Core-1 induced or enhanced by the nutraceutical, the pharmaceutical composition, the Core-1 positive microorganism or the fraction thereof, or formulations comprising those according to this invention in at least one human or animal.

In another preferred embodiment the invention refers to the use of any of the immune response tests as described above for testing the natural existing immune response in a human or animal without or before administration of the nutraceutical, the pharmaceutical composition, the Core-1 positive microorganism or the fraction thereof or formulations comprising those in at least one human or animal comprising.

In another preferred embodiment the invention refers to use of any of the immune response tests as described above for determining and optimizing the effective amount, maximal effective amount, dose, dose regimen, administration route, composition, formulation, carriers and other molecules used therewith of the nutraceutical, the pharmaceutical composition, the Core-1 positive microorganism or the fraction thereof, or formulations comprising those according to the invention.

Said nutraceutical of the invention can consist of at least one Core-1 positive microorganism or fraction thereof alone, such as but not limited to a microorganism that is living or dead, lyophilized, or pasteurized, or lysates, or components, or fractions thereof, or in an at least partially solubilized form in a liquid, or it can consist of additional components such as but not limited to other nutrients, nutrition additives or food or drink additives, solutions or emulsions known to those skilled in the art. Said nutraceutical can be applied orally in different forms, such as capsules, tablets, emulsions, powder, liquids. The nutraceutical can be given by itself or mixed into food or drinks. Said nutraceutical can also be any food, drink, component of a drink or food, a food additive, or a stand alone nutraceutical.

In a preferred embodiment the nutraceutical is used as a capsule or a tablet. In another preferred embodiment the nutraceutical is mixed into food or drinks such as but not limited to those listed elsewhere in that invention.

B) Methods for Testing the Potential of Core-1 Positive Microorganism to Induce Immune Responses, Methods for Isolating Core-1 Positive Microorganism, Methods for Identifying Suitable Core-1 Positive Microorganism for Nutraceuticals and Pharmaceutical Compositions The invention further provides a method for testing the potential of a Core-1 positive microorganism or fraction thereof to induce a humoral immune response against Core-1 comprising
  a.) administration of a suitable amount of the Core-1 positive microorganism or fraction thereof to at least one human or animal
  b.) testing the immune response in at least one of humoral immune response tests 1-6 against Core-1.

The invention further provides a method for testing the potential of a Core-1 positive microorganism or fraction thereof to induce a cellular immune response against Core-1 comprising
  a.) administration of a suitable amount of the Core-1 positive microorganism or fraction thereof to at least one human or animal and
  b.) testing the immune response in at least one cellular immune response test against Core-1.

In a preferred embodiment the invention provides a method for testing the potential of any of the nutraceuticals, the pharmaceutical compositions, the Core-1 positive microorganisms or the fractions thereof, or formulation comprising those, to induce an immune response and to determine which immune response is induced.

In another preferred embodiment the invention provides a method to determine the dose, the dosing regimen, the route of administration, the formulation, the carriers or other components used in or with the nutraceuticals, the pharmaceutical compositions, the Core-1 positive microorganisms or the fractions thereof, or formulation comprising those.

The invention further provides a method for testing the potential of a Core-1 positive microorganism to induce a humoral immune response comprising at least one of the humoral immune response test 1 to 6, preferably at least two, more preferably three, more preferably 4, more preferably 5, and most preferably all 6 humoral immune response tests, whereby at least one animal or human was given suitable amounts of the microorganism to be tested either orally or systemically (with or without additional adjuvants,) and the antibodies in serum or antibodies gained from the serum, plasma or faeces are tested preferably in comparison to the antibodies in serum or antibodies gained from the blood, plasma or faeces before the microorganisms were given. Those skilled in the art are able to determine suitable amounts of the microorganism and ways to gain the antibodies from blood and suitable controls. The tests are described in detail herein and/or in example 11.

The invention further provides a method for testing the potential of a Core-1 positive microorganism to induce a cellular immune response comprising at least one of the cellular immune response tests 1 to 5, preferably at least two, more preferably three, and most preferably all 5 cellular immune response tests.

The invention further provides a method for testing the potential of a Core-1 positive microorganism to induce a cytotoxic cellular immune response comprising at least the cellular immune response test 2, preferably 2 and 1, more preferably 2, 3, and, and most preferably all 5 cellular immune response tests.

In both embodiments of the invention the tests are either performed as described above in vitro or the cellular immune tests 1 to 3 or 5 were performed by giving at least one animal or human suitable amounts of the microorganism to be tested either orally or systemically (with or without additional adjuvants) and the immune cells were gained from the blood and (i) tested according to the cellular tests 1 to 3 or 5 as described above or (ii) tested according to the cellular tests 1 to 3 or 5 as described above with the difference that the immune cells are not brought into contact with dendritic cells loaded with a Core-1 microorganism and only dendritic cells loaded with Core-1 carrying molecule were added for restimulation. The (i) is preferably used to enhance the in vivo effect and to improve the read out with weaker responses and (ii) is preferably used for strong responses. Those skilled in the art are able to determine suitable amounts of the microorganism and suitable controls. The tests are described in detail in example 12.

The invention further provides in a preferred embodiment a method for testing the potential of a Core-1 positive microorganism to induce a humoral and a cellular immune response which corresponds to a combination of the above described methods, comprising at least one of the humoral immune response test 1 to 6 and at least one of the cellular immune response tests 1 to 4, preferably at least two of the humoral immune response tests 1 to 6 and at least one, more preferred at least two of the cellular immune response tests 1 to 5, more preferably at least three of the humoral immune response test 1 to 6, more preferably at least 4 of the humoral immune response tests 1 to 6 and all of the cellular immune response tests 1 to 5, more preferably at least 5 of the humoral immune response tests 1 to 6 and all of the cellular immune response tests 1 to 5, and most preferably all 6 humoral immune response tests 1 to 6 and all 5 cellular immune response tests 1 to 5.

The invention also provides methods to identify a Core-1 positive microorganism in sense of the invention and methods to isolate a Core-1 positive microorganism out of a mixture of Core-1 positive and negative microorganisms.

The invention further provides a method for isolating a Core-1 positive microorganism from a mixture of microorganism, comprising
(a) bringing a Core-1 specific antibody into contact with a mixture of microorganisms, and
(b) isolating a microorganism bound to said Core-1 specific antibody.

In a preferred embodiment the invention further provides a method for isolating a Core-1 positive microorganism from a mixture of microorganisms wherein under step (b) magnetic particles are used for separation of microorganisms bound to said Core-1 specific antibody. In a preferred embodiment the invention further provides a method for isolating a Core-1 positive microorganism from a mixture of microorganisms wherein said mixture of microorganisms is a mixture comprising microorganisms from a healthy human or patient, an animal, soil, food, or plants.

In a preferred embodiment the invention further provides a method for isolating a Core-1 positive microorganism from a mixture of microorganisms wherein said mixture of microorganisms is a mixture comprising microorganisms from the human gastrointestinal tract, human stool, human blood, human tissue, or human body fluids of healthy individuals or patients.

In a preferred embodiment the invention further provides a method for isolating a Core-1 positive microorganism from a mixture of microorganisms which is performed under anaerob conditions which allow the isolation of anaerob Core-1 positive microorganism.

Said mixture of microorganisms can be any mixture of at least two different microorganism, such as but not limited to those occurring in nature, such as but not limited to in soil, food, plants, animals, human gastrointestinal tract, human blood, human tissue, human body fluids of healthy individuals or patients, most preferred is a mixture of microorganisms from a healthy individual. The microorganisms are preferably brought into a suitable solution before bringing the mixture into contact with a Core-1 specific antibody. The Core-1 specific antibody is preferably coupled to a carrier, such as magnetic beads, which allows the separation of the microorganism bound to said carrier. And after bringing the Core-1 specific molecule together with the mixture of microorganism those microorganisms bound to the Core-1 specific antibody is separated from those not bound to the antibody. In an alternative embodiment the Core-1 specific antibody is not coupled to a carrier and the Core-1 positive microorganism is isolated together with the Core-1 specific antibody by using methods specifically isolating the antibody, such as Protein A, Protein G, Protein L or anti-IgM antibodies or anti-IgG antibodies which are itself coupled to a carrier such as a magnetic bead chromatographic bed material. In a preferred embodiment of the invention Core-1-positive microorganisms bound to the Core-1 specific antibody are thoroughly washed with a suitable buffer (such as PBS-a) and plated on selective and nonselective media such as but not limited to MRS, BSM, KF, N, S, WC, BHI, CBA and ST (for details see table 3). Resulting colonies are scraped from the plates and applied to additional rounds of affinity enrichment with Core-1-specific antibodies. Colonies are picked, re-streaked and analysed for Core-1-expression in ELISA and immunofluorescence (more details under examples 1-9). From this description and from the examples someone skilled in the art is able to adjust or optimize the methods for various bacteria from various sources.

In a preferred special embodiment the method is performed under anaerob conditions which allows the isolation of anaerob Core-1 positive microorganism, which is for example important for the majority of microorganism from the human gut. The method is described in detail in examples 1 to 9.

According to one embodiment the microorganisms are isolated from food. In an even more preferred embodiment the microorganism are isolated from a gastrointestinal system, and even more preferred from human stool. The method is described in detail in examples 1 to 9. The usage of bacteria that usually inhabit the gastrointestinal tract of humans results in a prophylactic and therapeutic agents that does not cause undesired side effects. The carbohydrate nature is responsible for the lack of relevant tolerogenicity and shows no relevant allergic reactions.

The invention further provides a method for identifying a suitable Core-1 positive microorganism for use as a component for nutraceuticals and pharmaceutical compositions of the invention comprising
a.) testing a microorganism for its binding to at least one Core-1 specific antibody and
b.) identifying this Core-1 positive microorganism which is bound by at least one Core-1 specific antibody as described herein.

Most preferably are those Core-1 positive microorganisms which are bound by the Core-1 specific antibodies NEMOD-TF1 and NEMOD-TF2 and whereby the binding is periodate sensitive showing a reduced binding of NEMOD-TF1 and NEMOD-TF2 after treatment with periodic acid.

In a preferred embodiment of the invention the testing of a microorganism for its binding to at least one Core-1 specific antibody is done by ELISA, whereby a Core-1 positive microorganism show an ELISA signal with at least one Core-1 specific antibody of at least 3 times, more preferred 5 times and even more preferred of at least 10 times of the background signal.

In another preferred embodiment of the invention the Core-1 positive microorganism shows a positive ELISA signal with the Core-1 specific antibody Nemod-TF1 when coated at a microorganism concentration of $1\times10^7$/ml more preferred of $5\times10^6$/ml, even more preferred of $1\times10^6$/ml, most preferred of $1\times10^5$/ml.

In another preferred embodiment of the invention the Core-1 positive microorganism shows a reduction of the ELISA signal with the Core-1 specific antibody after treatment with periodic acid, preferably the ELISA signal shows a reduction of at least 30%, more preferred of at least 50% and most preferred of at least 80%.

In a preferred embodiment the invention relates to a method for identifying a suitable Core-1 positive microorganism for use as a component for nutraceuticals and pharmaceutical compositions of the invention comprising
a) testing a Core-1 positive microorganism for its binding to at least one Core-1 specific antibody and
b) testing for its ability to induce an immune response in humans or animals recognizing the Core-1 antigen and/or a Core-1 positive tumor cell and
c) identifying this microorganism which is bound by at least one Core-1 specific antibody as described herein and is able to induce an immune response in humans or animals recognizing the Core-1 antigen and/or a Core-1 positive tumor cell by being positive for at least one humoral immune response test 1-6 or cellular immune response test 1-4 described herein. Preferred are those Core-1 positive microorganism which are positive for NEMOD-TF1 and NEMOD-TF2 and are periodate sensitive showing a reduced binding of NEMOD-TF1 and NEMOD-TF2 as described herein (example 9) and which induce an immune response in at least one human or animal which is positive for at least one humoral and one cellular immune response test, more preferably those which are at least positive for the cellular immune response test 2. Even more preferred are those Core-1 positive microorganism which are positive for TF1 and TF2 and are periodate sensitive showing a reduced binding of NEMOD-TF1 and NEMOD-TF2 as described somewhere herein and which are positive for the humoral immune response tests 1, 2, 3, and 4 and for the cellular immune response tests 1, 2, 3, and 4, as described herein. Most preferred are those Core-1 positive microorganism which are positive for NEMOD-TF1 and NEMOD-TF2 and are periodate sensitive showing a reduced binding of NEMOD-TF1 and NEMOD-TF2 as described somewhere herein and which are positive for at least 5 humoral immune response tests and for all 5 cellular immune response tests as described herein.

In a preferred embodiment the invention relates to a method for identifying a suitable Core-1 positive microorganism for use as a component for nutraceuticals and pharmaceutical compositions of the invention wherein the identified microorganism is bound by at least one Core-1 specific antibody which binds to TFa-PAA and less or not to TFb-PAA but not to any of the substances of #list 2# (see definitions).

In a preferred embodiment the invention relates to a method for identifying a suitable Core-1 positive microorganism for use as a component for nutraceuticals and pharmaceutical compositions of the invention wherein the identified microorganism is bound by at least one Core-1 specific antibody which binds to TFa-PAA and less or not to TFb-PAA and not to any of the X-PAA constructs listed in #list 2 # and which binds to asialoglycophorin and not to glycophorin and which binds to at least one human tumor cell line out of NM-D4 (DSM ACC2605), NM-F9 (DSM ACC2606), ZR-75-1 (ATCC CRL-1500), CAMA-1 (ATCC HTB-21), KG-1 (DSM ACC 14), or A-204 (DSM ACC 250), and whereby the binding is periodate sensitive. The NM-9 and NM-D4 cell lines have been deposited at the DSMZ by Nemod Biotherapeutics GmbH & Co. KG, Robert-Rossle-Strasse 10,13125 Berlin, Germany (i. e. the depositor) who authorise the applicant of the present application to refer to the deposited biological material described herein and give their unreserved and irrevocable consent to the applicant of the present application that the deposited biological material described herein be made available to the public in accordance with Rule 28(1)(d) of the European Patent Convention. The DSMZ is located at the Mascheroder Weg 1b, D-38124 Braunschweig, Germany. The aforementioned DSMZ deposits were made pursuant to the terms of the Budapest treaty on the international recognition of the deposit of microorganisms for purposes of patent procedure.

In a preferred embodiment the invention relates to a method for identifying a suitable Core-1 positive microorganism for use as a component for nutraceuticals and pharmaceutical compositions of the invention wherein the identified microorganism is bound by at least one antibody which binds to TFa-PAA and less or not to TFb-PAA and not to any of the X-PAA constructs listed in #list 2 # and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive, and which is bound by at least one Core-1 specific antibody with any of the above binding characteristics but which does not bind to the trisaccharide Core-2 coupled to PAA.

In a preferred embodiment the invention relates to a method for identifying a suitable Core-1 positive microorganism for use as a component for nutraceuticals and pharmaceutical compositions of the invention wherein the identified microorganism is bound by NEMOD-TF2 or A78-G/A7 or NEMOD-TF1.

In a preferred embodiment the invention relates to a method for identifying a suitable Core-1 positive microorganism for use as a component for nutraceuticals and pharmaceutical compositions of the invention wherein the identified microorganism is bound under (b) by NEMOD-TF2 or A78-G/A7 and NEMOD-TF1.

In a preferred embodiment the invention relates to a method for identifying a suitable Core-1 positive microorganism for use as a component for nutraceuticals and pharmaceutical compositions of the invention wherein the identified microorganism is bound under (b) by NEMOD-TF2 or A78-G/A7 and NEMOD-TF1 but not by A68-B/A11.

In a preferred embodiment the invention relates to a method for identifying a suitable Core-1 positive microorganism for use as a component for nutraceuticals and pharmaceutical compositions of the invention wherein the induced immune response after administration of a formulation according to the present invention in a human or an animal is an immune response positive for at least one humoral immune response test against Core-1 and at least one cellular immune response test against Core-1 as described elsewhere herein.

The methods for identifying a suitable Core-1 positive microorganism for use as a component for nutraceuticals and pharmaceutical compositions of the invention can be used to identify a suitable microorganisms from existing strains such as found at DSMZ or other collections of microorganisms or from the Core-1 positive microorganism isolated by a method for isolating a Core-1 positive microorganism from a mixture of microorganism according to the invention.

The invention relates also to a method for isolating and identifying core-1 positive bacteria comprising
a) isolating whole bacteria from faeces samples,
b) performing affinity enrichments of core-1 positive bacteria using one or more of the following monoclonal core-1 antibodies Nemod-TF1, Nemod-TF2 and A78-G/A7 under aerobic or anaerobic conditions,
c) plating the enriched bacteria on different selective media and screening of the bacteria for binding to core-1-specific antibodies or lectins.

In another preferred embodiment the invention refers to a method for isolating and identifying a Core-1 positive bacteria comprising
a.) isolating a mixture of microorganisms comprising whole bacteria from faeces samples
b.) bringing a Core-1 specific antibody into contact with a mixture of microorganisms
c.) isolating the microorganism which bind to Nemod-TF1, Nemod-TF2, or A78-G/A7 under aerobic or anaerobic conditions using magnetic particle separation,
d.) plating the enriched bacteria on at least one selective medium
e.) identifying the microorganism which is bound by at least one Core-1 specific antibody Generation also means that a Core-1 positive microorganism is generated e.g. by chemical treatment from a microorganism which comprises the Core-1 structure in a covered from. Chemical treatment such as e.g. periodate treatment may uncover the Core-1 structure thereby generating a Core-1 positive microorganism. In another preferred embodiment the invention refers to a method for isolating and identifying a Core-1 positive bacteria comprising
a.) generation of a pure bacterial strain which is bound by at least one Core-1 specific antibody; and/or
b.) testing for the ability of said pure bacterial strain to induce or enhance an immune response against Core-1 in at least one human or animal.

In another preferred embodiment, the invention provides a method for testing the potential of a Core-1 positive microorganism to induce a Core-1 specific immune response comprising the following steps:
1) identification of Core-I positive microorganisms and production in pure cultures;
2) identification of immune effective bacterial strains of the gut;
3) generation of an effective, immunologically and toxicologically tested Core-I positive preparation as a nutrition additive ready for human tests;
4) induction or enhancement of Core-1-specific immune responses in humans; and if necessary
5) isolation, identification and testing of an immune effective defined Core-1 positive fraction or component of said microorganism.

The method is also described in detail in examples 1-10.

In a preferred embodiment the invention provides a method for isolating a Core-1 positive microorganism from a mixture of microorganism, comprising
a.) bringing a Core-1 specific antibody into contact with a mixture of microorganisms selected from the group comprising microorganisms from a healthy human and/or patient, an animal, soil, food, and/or plants, and/or microorganisms from the human gastrointestinal tract, human stool, human blood, human tissue, and/or human body fluids of healthy individuals and/or patients and
b.) isolating the microorganism bound to said Core-1 specific antibody.

In another preferred embodiment the invention provides a method for isolating and identifying a Core-1 positive bacterium comprising
(a) isolating a mixture of microorganisms comprising whole bacteria from faeces samples,
(b) bringing a Core-1 specific antibody into contact with a mixture of microorganisms,
(c) isolating the microorganism which binds to the Core-1 specific antibody under aerobic or anaerobic conditions using magnetic particle separation,
(d) identifying the microorganism which is bound by Nemod-TF2 or A78-G/A7, and by Nemod-TFI, whereby the binding is periodate sensitive showing a significantly reduced binding after periodate treatment and
(e) testing for the ability to induce or enhance an immune response against Core-1 in at least one human or animal.

In another preferred embodiment the invention provides a method for identifying a suitable Core-1 positive microorganism for use as a component of the formulation of any of the preceeding claims comprising
a. testing a microorganism for its binding to at least one Core-1 specific antibody and b. testing the induction of an immune response in humans or animals recognizing the Core-1 antigen and/or a Core-1 positive tumor cell and c. identifying said microorganism which is bound by at least one Core-1 specific antibody whereby said microorganism induces or enhances an immune response against Core-1 in at least one human or animal as characterized by being positive for at least one humoral immune response test or one cellular immune response test against Core-1 as described elsewhere herein.

The invention also relates also to a method for generating Core-1 positive microorganisms comprising a.) contacting a microorganism with an agents for induction of mutations by chemical and/or physical mutagents such as but not limited to EMS, UV, methotrexat, microwave, cancerogenic substances, carcinogen, mutagen or radiation under conditions killing the majority of microorganisms and b.) cultivating surviving microorganisms under suitable conditions c.) enriching, isolating and/or identifying Core-1 positive microorganisms as described elsewhere herein d.) testing for the ability of said microorganism to induce or enhance an immune response against Core-1 in at least one human or animal.

The invention also relates also to a method for generating Core-1 positive microorganisms by genetical engineering comprising a) introduction, knock out and/or silencing of genes, part of genes, DNA, RNA, antisense RNA, oligonucleotides, oligopeptides or proteins into a microorganism thereby affecting Core-1 biosynthesis, Core-1 degradation or biosynthesis or degradation of flanking carbohydrates and b) enriching, isolating, identifying and/or testing of Core-1 positive microorganisms as described elsewhere herein.

According to one embodiment said microorganism is a Core-1 negative microorganism. In a further embodiment said microorganism is a beneficial microorganism for the intestinal tract such as but not limited to *Lactobacillus* or *Bifidobacterium*. In a further embodiment said microorganism is a microorganism used for production of conventional food such as but not limited to *Lactobacillus* or *Bifidobacterium*. In another embodiment said microorganism is already Core-1 positive and the method is used in order to increase the amount of Core-1 expressed on the cell surface.

C) Provision of Core-1 Positive Microorganism

The invention also provides a Core-1 positive microorganism wherein the Core-1 positive microorganism is recognized by at least one Core-1 specific antibody.

The invention provides a suitable Core-1 positive microorganism for use as a component for a nutraceutical or a pharmaceutical composition of the invention wherein the Core-1 positive microorganism is bound by at least one Core-1 specific antibody. The invention also provides a Core-1 positive microorganism which induces a specific immune response against Core-1, the Core-1 antigen, Core-1 positive tumor cells or Core-1 positive disease in humans or animals.

The invention also provides suitable Core-1 positive microorganisms for use as a component for a nutraceutical or a pharmaceutical composition of the invention wherein the Core-1 positive microorganism induces a specific immune response against Core-1, the Core-1 antigen or Core-1 positive tumor cells in humans or animals.

The invention also provides a Core-1 positive microorganism which represents the active ingredient of the nutraceutical or pharmaceutical composition of the invention which induces the specificity of the immune response against Core-1, the Core-1 antigen or Core-1 positive tumor cells in humans or animals.

The invention provides a Core-1 positive microorganism which induces or enhances a specific immune response against Core-1, the Core-1 antigen or Core-1 positive tumor cells in humans or animals when it is used in a nutraceutical or pharmaceutical composition of the invention In a preferred embodiment of the invention said Core-1 positive microorganism is recognized and thus bound when contacted by at least one Core-1 specific antibody of the following antibodies HB-T1, HH8, A78-G/A7, Nemod-TF1, or Nemod-TF2, more preferably by at least one antibody which binds to TFa-PAA and less or not to TFb-PAA but not to any of the substances of #list 2#; —even more preferred by at least one antibody which binds to TFa-PAA and less or not to TFb-PAA and not to any of the substances listed in #list 2 # and which binds to asialoglycophorin and not to glycophorin and this binding is periodate sensitive;

even more preferred by at least one antibody which binds to TFa-PAA and less or not to TFb-PAA and not to any of the substances listed in #list 2 # and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive (such as NEMOD-TF2 or A78-G/A7), even more preferably by at least one antibody with any of the above binding characteristics but which does not bind to the trisaccharide Core-2 coupled to PAA, even more preferably by at least one antibody which binds to TFa-PAA and less or not to TFb-PAA and not bind to the trisaccharide Core-2 coupled to PAA and not to any of the X-PAA constructs listed in #list 2# and which binds to asialoglycophorin and not to glycophorin and which binds at least to the cells NM-D4, NM-F9 and ZR-75-1, and whereby the binding is periodate sensitive (such as NEMOD-TF1);

even more preferred by at least two of the above described antibodies, even more preferred by at least one antibody which binds to TFa-PAA and less or not to TFb-PAA and not to any of the X-PAA constructs listed in #list2 # and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive, such as NEMOD-TF2 or A78-G/A7, and by at least one antibody with any of the above binding characteristics but which does not bind to the trisaccharide Core-2 coupled to PAA;

even more preferred by at least one antibody which binds to TFa-PAA and less or not to TFb-PAA and not bind to the trisaccharide Core-2 coupled to PAA and not to any of the X-PAA constructs listed in #list 2# and which binds to asialoglycophorin and not to glycophorin and which binds at least to the cells NM-D4, NM-F9 and ZR-75-1, and whereby the binding is periodate sensitive such as NEMOD-TF1;

even more preferred by NEMOD-TF2 or A78-G/A7 and NEMOD-TF1;

even more preferred by NEMOD-TF2 or A78-G/A7 and NEMOD-TF1 but not by A68-B/A11;

even more preferred by at least one antibody which binds to TFa-PAA and less or not to TFb-PAA and not to any of the X-PAA constructs listed in # list 2# and which binds to asialoglycophorin and not to glycophorin and this binding is periodate sensitive;

even more preferred by at least one antibody which binds to TFa-PAA and less or not to TFb-PAA and not to any of the X-PAA constructs listed in #list 2# and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive, such as NEMOD-TF2 or A78-G/A7, even more preferably by at least one antibody with any of the above binding characteristics but which does not bind to the trisaccharide Core-2 coupled to PAA, even more preferably by at least one antibody which binds to TFa-PAA and less or not to TFb-PAA and not bind to the trisaccharide Core-2 coupled to PAA and not to any of the X-PAA constructs listed in #list 2# and which binds to asialoglycophorin and not to glycophorin and which binds at least to the cells NM-D4, NM-F9 and ZR-75-1, and whereby the binding is periodate sensitive such as NEMOD-TF1;

even more preferred by at least two of the above described antibodies, even more preferably by at least one antibody which binds to TFa-PAA and less or not to TFb-PAA and not to any of the X-PAA constructs listed in #list 2# and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive, such as NEMOD-TF2 or A78-G/A7, and by at least one antibody with any of the above binding characteristics but which does not bind to the trisaccharide Core-2 coupled to PAA;

even more preferred by at least one antibody which binds to TFa-PAA and less or not to TFb-PAA and not to the trisaccharide Core-2 coupled to PAA and not to any of the substances listed in #list 2# and which binds to asialoglycophorin and not to glycophorin and which binds at least to the cells NM-D4, NM-F9 and ZR-75-1, and whereby the binding is periodate sensitive (such as NEMOD-TF1);

even more preferred by NEMOD-TF2 or A78-G/A7 and NEMOD-TF1;

and even more preferably by NEMOD-TF2 or A78-G/A7 and NEMOD-TF1 but not by A68-B/A11.

In a preferred embodiment the invention provides a Core-1 positive microorganism which is recognized/bound by at least two Core-1 specific antibodies.

In a preferred embodiment the invention provides a Core-1 positive microorganism which is bound by at least one antibody which binds to TFa-PAA and less or not to TFb-PAA and not to any of the substances listed in #list2 # and which binds to asialoglycophorin and not to glycophorin and which binds to a at least one human tumor cell line out of NM-D4, NM-F9, ZR-75-1, CAMA-1, KG-1, or A-204, and whereby the binding is periodate sensitive, and which is bound by at least one antibody with any of the above binding characteristics but which does not bind to the trisaccharide Core-2 coupled to PAA In a more preferred embodiment the invention provides a Core-1 positive microorganism which is recognized/bound by NEMOD-TF2 or A78-G/A7 or NEMOD-TF1.

In a preferred embodiment the invention provides a Core-1 positive microorganism that is recognized/bound by the Core-1 specific antibody Nemod-TF1 whereby the binding is tested in ELISA and the ELISA signal with the Core-1 specific antibody Nemod-TF1 is at least 3 times that of the background when coated at a microorganism concentration of $1\times10^7$/ml more preferred of $5\times10^6$/ml, even more preferred of $1\times10^6$/ml, most preferred of $1\times10^5$/ml. In another preferred embodiment the invention provides a Core-1 positive microorganism that is bound by the Core-1 specific antibody Nemod-TF2 whereby the binding is tested in ELISA and the ELISA signal with the Core-1 specific antibody Nemod-TF2 is at least 3 times that of the background when coated at a microorganism concentration of $1\times10^7$/ml more preferred of $5\times10^6$/ml, even more preferred of $1\times10^6$/ml, most preferred of $1\times10^5$/ml.

In another preferred embodiment the invention provides a Core-1 positive microorganism that is bound by the Core-1 specific antibody Nemod-TF2 whereby the binding is tested in ELISA and the ELISA signal with the Core-1 specific antibody Nemod-TF2 is at least 3 times that of the background when coated at a microorganism concentration of $1\times10^7$/ml more preferred of $5\times10^6$/ml, even more preferred of $1\times10^6$/ml, most preferred of $1\times10^5$/ml and whereby the binding is periodate sensitive showing a reduced ELISA signal after treatment with periodic acid, preferably the ELISA signal shows a reduction of at least 30%, more preferred of at least 50% and most preferred of at least 80%.

In another preferred embodiment the invention provides a Core-1 positive microorganism that is bound by the Core-1 specific antibody Nemod-TF1 whereby the binding is tested in ELISA and the ELISA signal with the Core-1 specific antibody Nemod-TF1 is at least 3 times that of the background when coated at a microorganism concentration of $1\times10^7$/ml more preferred of $5\times10^6$/ml, even more preferred of $1\times10^6$/ml, most preferred of $1\times10^5$/ml and whereby the binding is periodate sensitive showing a reduced ELISA signal after treatment with periodic acid, preferably the ELISA signal shows a reduction of at least 30%, more preferred of at least 50% and most preferred of at least 80%.

In further preferred embodiment the invention provides a Core-1 positive microorganism that is bound by the Core-1 specific antibodies Nemod-TF1 and Nemod-TF2 whereby the binding is tested in ELISA and the ELISA signal is at least 3 times that of the background when coated at a microorganism concentration of $1\times10^7$/ml more preferred of $5\times10^6$/ml, even more preferred of $1\times10^6$/ml, most preferred of $1\times10^5$/ml and whereby the binding is periodate sensitive showing a reduced ELISA signal after treatment with periodic acid, preferably the ELISA signal shows a reduction of at least 30%, more preferred of at least 50% and most preferred of at least 80%.

In a preferred embodiment the invention provides a Core-1 positive microorganism which induces or enhances a specific humoral and/or cellular immune response against Core-1, the Core-1 antigen or Core-1 positive tumor cells in humans or animals.

In a preferred embodiment of the invention said immune response is a humoral immune response against Core-1, the Core-1 antigen or Core-1 positive tumor cells or a cellular immune response against Core-1, the Core-1 antigen or Core-1 positive tumor cells.

In a further preferred embodiment of the invention said immune response is a humoral immune response against Core-1, the Core-1 antigen or Core-1 positive tumor cells and a cellular immune response against Core-1, the Core-1 antigen or Core-1 positive tumor cells.

Said Core-1 specific antibody, preferred Core-1 specific antibodies, combinations of Core-1 specific antibodies or preferred combinations of Core-1 specific antibodies are described in detail under Definitions and elsewhere herein.

Said nutraceuticals or pharmaceutical compositions and preferred embodiments thereof are described in detail elsewhere herein.

Said humoral immune response against Core-1 and said cellular immune response against Core-1 is described in detail elsewhere in the present invention as well as the humoral and cellular immune response tests which can detect the according antibody or T-cell response against Core-1, the Core-1 antigen or Core-1 positive tumor cells.

In a preferred embodiment the Core-1 positive microorganism of the invention induces or enhances a specific humoral and cellular immune response against Core-1, the Core-1 antigen or Core-1 positive tumor cells in humans or animals which can be detected by at least one humoral immune response test and at least one cellular immune response test.

In a preferred embodiment the Core-1 positive microorganism is bound by NEMOD-TF1 and NEMOD-TF2, whereby the binding is periodate sensitive and which induces or enhances a immune response in at least one human or animal which is positive in at least two of the humoral immune response tests 1, 2, and 3 and in at least one of the cellular immune response tests 1, 2, and 3.

In a further preferred embodiment of the invention said immune response is a humoral immune response against Core-1 which is positive for at least two humoral immune response tests out of the humoral immune response test 1 to 6, preferably positive for humoral immune response tests 1 and 3, and more preferably for humoral immune response test 1, 2 and 3, and more preferably for humoral immune response test 1, 2, 3, and 4, and more preferably for humoral immune response test 1, 2, 3, 4, and 6, and more preferably for humoral immune response test 1, 2, 3, 4, and 5, and most preferably positive for all 5 humoral immune response tests.

In a further preferred embodiment of the invention said immune response is a cellular immune response against Core-1 which is positive for at least two cellular immune response tests out of the cellular immune response tests 1 to 5.

In an even further preferred embodiment of the invention said immune response is a humoral and a cellular immune response against Core-1 which is positive for at least one humoral immune response test and at least one cellular immune response tests.

In an even further preferred embodiment of the invention said immune response is a humoral and a cellular immune response against Core-1 which is positive for at least two humoral immune response test and two cellular immune response tests, preferably positive for humoral immune response tests 1 and 3 and cellular immune response test 1 and 3, and more preferably for humoral immune response tests 1, 2 and 3 and cellular immune test 1, 2 and 3, and even more preferably for humoral immune response test 1, 2, 3 and 4 and cellular immune test 1, 2, 3 and 4, and more preferably for humoral immune response test 1, 2, 3, 4 and 6 and all 5 cellular immune tests, and even more preferably for humoral immune response test 1, 2, 3, 4 and 5, and all 5 cellular immune response tests, and most preferably positive for all 6 humoral immune response tests and all 5 cellular immune response tests.

In a further preferred embodiment the invention provides a Core-1 positive microorganism which can be used to build a Core-1 specific immune response which functions as a shield against Core-1 positive cancer cells by having the potential to destroy those cells as shown herein for example by the induction of the Core-1 specific antibodies, by the Core-1 specific complement dependent cytotoxicity of Core-1 antibodies against Core-1 positive tumor cells killing those effectively, and/or by secretion of TNFalpha and/or INFgamma by Core-1 specific T cell responses which are scientifically recognized surrogate markers by those skilled in the art for a specific cytotoxic T cell mediated tumor cell killing for those tumor cells carrying the Core-1, when used as a nutraceutical or a pharmaceutical composition of the invention.

In a further preferred embodiment the invention provides a Core-1 positive microorganism which can be used to build said Core-1 specific immune response which functions as a shield against Core-1 positive cancer cells which has the potential to destroy those cells as described elsewhere herein by orally administering the nutraceutical in (at least one) healthy individuals.

In a further preferred embodiment the invention provides a Core-1 positive microorganism which can be used to reduce or even further preferred to prevent the occurrence of a Core-1 positive disease or tumor by orally administering it as a component of the nutraceutical of the invention to (at least one) healthy individuals.

In a further preferred embodiment the invention provides a Core-1 positive microorganism which can be used to reduce or even more preferred to prevent the occurrence of a Core-1 positive disease or tumor when administered as a component of a pharmaceutical formulation of the invention in (at least one) individual.

In another preferred embodiment the invention provides a Core-1 positive microorganism which is used as the active ingredient of a nutraceutical to treat a Core-1 positive disease or tumor by orally administering the nutraceutical in patients suffering from this disease.

In a preferred embodiment the invention provides a Core-1 positive microorganism which is used as the active ingredient of a pharmaceutical composition to treat a Core-1 positive disease or tumor in patients suffering from this disease by administering the pharmaceutical composition as described elsewhere herein.

In a more preferred embodiment the present invention provides a Core-1 positive microorganism which is a suitable component of a nutraceutical formulation that preferentially shows the induction of an immune response in humans recognizing the Core-1 antigen and/or a Core-1 positive tumor cell by being positive after oral administration of the Core-1 positive microorganism for at least one humoral or cellular immune test described herein and preferred embodiments as described above.

In the most preferred embodiment said Core-1 positive microorganism is positive for binding to the Core-1-specific antibodies NEMOD-TF1 and NEMOD-TF2, whereby the binding of said antibodies is periodate sensitive showing a reduced binding of NEMOD-TF1 and NEMOD-TF2 after treatment with periodic acid as described somewhere herein and which induces an immune response in at least one human or animal which is positive for the humoral immune response tests 1, 2, and 3 and for the cellular immune response tests 1, 2, and 3, and even more preferred for at least 5 humoral immune response tests and for all 5 cellular immune response tests, and even more preferred for all 6 humoral immune response tests and for all 5 cellular immune response tests as described herein.

In a preferred embodiment the invention provides or uses the
(i) Core-1 positive microorganism of the invention, or
(ii) the nutraceutical or the pharmaceutical formulation or food additive comprising a Core-1 positive microorganism
which is selected from the group consisting of enterobacterioceae, *Escherichia coli, Streptococcus, Bacteroides, Rhuminococcus, Lactobacillus, Bifidobacterium, Peptostreptococcus, Fusobacterium, Johnsonella, Atopobium, Staphylococcus, Eubacterium, Finegoldia, Clostridium, Eggerthella, Butyribacterium, Citrobacter, Helicobacter, Propionibacterium* and *Corynebacterium, Bacteroides ovatus, Bacteroides thetaiotaomicron, Bacteroides acidophilus, Bacteroides caccae*, AG6 (DSM 18726) and/or MU 1 (DSM 18728) wherein said microorganism selected from said group is Core-1 positive and is specifically recognized by at least one Core-1 specific antibody.

As these microorganisms are not per se Core-1 positive, it is important to select a microorganism/strain which is able to trigger a Core-1 specific immune response. Therefore, it is important that said microorganism is specifically recognized by at least one Core-1 specific antibody and is thus bound by said antibody if contacted therewith. The ability to trigger a Core-1 specific immune response can also be determined by the humoral and cellular test systems described herein. That this specificity selection is important also becomes apparent when comparing the microorganisms according to the present invention with the prior art.

E.g. G. F. Springer et al. describe the induction of T-antigen after feeding of *E. coli* from a strain of the serotype O86. In these experiments, for evaluation of anti-T antibodies an agglutination test with sialidase-treated erythrocytes was used. Sialidase-treatment of erythrocytes results in demasking of Core-1 epitope but many further epitopes are demasked as well. Therefore, this assay is not Core-1 specific. No specific anti-Core-1 antibodies were used. In order to find out whether these strains are Core-1 positive according to the invention we included several *E. coli* strains in our screening procedure, among them 7 established *E. coli* strains from culture collections and especially *E. coli* strain DSMZ 8697 (strain 32), which is of seroytope O86 and thus strongly related to the *E. coli* strain used by Springer; the original strain was impossible to be obtained. Furthermore, we tested 12 *E. coli* strains obtained from fecal samples of 3 healthy human subjects after affinity enrichment with TF-specific antibodies. However, none of these strains showed the desired reduction of the binding of TF-specific antibodies Nemod-TF-1 and Nemod-TF2 after periodate treatment. For the *E. coli* strain of seroytope O86 (strain 32) binding with Nemod-TF1, Nemod-TF2 and B/A11 was shown only after treatment with periodate (destroying sugar structures). This indicates a cryptic Core-1 expression, meaning that the Core-1 epitope is not accessible and thus not available for triggering a Core-1 specific immune response. To confirm that, the *E. coli* strain of serotyope O86 (=32) was also tested in the humoral immune response tests after immunization of mice. Surprisingly, while we found anti-AGP antibodies in the serum of these mice in HIRT 1 (which is less specific), there were no positive results in the specific tests HIRT 2 and HIRT 3. These results demonstrate that there is no Core-1 specific immune response induced by said *E. coli* strain that is recognizing Core-1 on PAA or human tumor cells (for details see examples). Hence, the *E. coli* strain of serotyope O86 which was allegedly TF positive is in fact unsuitable for solving the problem as it—in contrast to the Core-1 positive microorganisms of the present invention—is not able to trigger a Core-1 specific immune response. Hence, it is important to select an *E. coli* strain which is Core-1 positive and is specifically recognized by at least one Core-1 specific antibody and thus bound by said antibody if contacted therewith. As outlined above, respective microorganisms which comprise Core-1 in a hidden form may be converted to Core-1 positive microorganisms by chemical treatment such as periodate treatment. Suitable test methods for determining that the microorganism is after said treatment a Core-1 positive microorganism are described above.

A similar result was also found with *Heliobacter*. Klaamas et al. (Immunological Investigations vol. 31, Nos 3&4, pp. 191-204, 2002) describe *Helicobacter pylori* strain NCTC 11637 as being positive for binding with T antigen specific antibodies. We used *Helicobacter pylori* strain NCTC 11637 in parallel in our ELISA experiments with about $5-10 \times 10^6$ bacteria per well, which results in a strong binding of Nemod-TF1 and Nemod-TF2 antibodies for the Core-1 positive strains AG6 and MU1. However, we could not detect binding of Nemod-TF1 and Nemod-TF2 antibodies to *Helicobacter pylori* strain NCTC 11637. Only after treatment with periodic acid, *Helicobacter pylori* strain NCTC 11637 was bound by Nemod-TF1 antibody, but not by Nemod-TF2 antibody. This also indicates a cryptic expression of Core-1 on *Helicobacter pylori* that is only detected after periodate treatment. In the experiments of Klaamas et al. Core-1 the results might be due to lesser specificity of the used antibodies or due to the use of a very high amount of bacteria ($10^8$/tube) which might contain to some extent degradation products containing Core-1. Furthermore, the use of *Heliobacter* in a neutraceutical or pharmaceutical is difficult.

*Helicobacter pylori* colonization of the human stomach induces chronic infections and plays an important role in the pathogenesis of gastroduodenal ulcer disease and is associated with the development of B cell lymphomas of the gastric mucosa. Therefore, application of *H. pylori* in the prophylaxis or treatment of humans is difficult. Therefore, *H. pylori* is preferably not used according to the present invention.

More preferably said Core-1 positive microorganism is selected from the group comprising *Escherichia coli, Bacteroides*, such as *Bacteroides ovatus, Bacteroides thetaiotaomicron, Bacteroides acidophilus* and *Bacteroides caccae* and even more preferred selected from the group comprising the new strain *Bacteroides* AG6 (DSM 18726), the new strain *Bacteroides* MU1 (DSM 18728) deposited at the "DSMZ-Deutsche Sammlung von Mikroorganismen and Zellkulturen GmbH" in Braunschweig (Germany), by Glycotope GmbH, Robert-Rossle-Str. 10, 13125 Berlin (Germany) at the Oct. 20, 2006.

In another preferred embodiment provides the formulation of the invention, wherein the Core-1 positive microorganism is selected from the group comprising *Escherichia coli, Streptococcus, Bacteroides, Rhuminococcus, Lactobacillus, Bifidobacterium, Peptostreptococcus, Fusobacterium, Johnsonella, Atopobium, Staphylococcus, Eubacterium, Finegoldia, Clostridium, Eggerthella, Butyribacterium, Citrobacter, Helicobacter, Propionibacterium* and *Corynebacterium, Bacteroides ovatus, Bacteroides thetaiotaomicron, Bacteroides acidophilus, Bacteroides caccae*, AG6 (DSM 18726), MU1 (DSM 18728).

In a preferred embodiment the bacterial strain is selected from the group comprising AG6 (DSM 18726), MU1 (DSM 18728).

In a further preferred embodiment of the invention the Core-1 positive microorganism (active component) of the nutraceutical or the pharmaceutical formulation is a combination of Core-1 positive microorganisms of different strains.

In a further preferred embodiment said active component is a combination of Core-1 positive microorganisms of different strains selected from the strains AG6 and MU1.

In a further preferred embodiment the nutraceutical or pharmaceutical composition (formulation) of the invention comprises at least one Core-1 positive microorganism combined with at least one other beneficial microorganism, such as but not limited to a *lactobacillus* and/or *bifidobacterium*, even more preferred a combination of Core-positive microorganisms of different strains combined with other beneficial microorganisms.

In a preferred embodiment of the invention the Core-1 microorganism is a non-pathogenic microorganism. In a further preferred embodiment of the invention the Core-1 microorganism is isolated from a healthy donor. In a further preferred embodiment of the invention the Core-1 microorganism can be isolated from a healthy donor.

In a further preferred embodiment of the invention the Core-1 positive microorganism and/or a fraction thereof is used for the manufacturing of a medicament and/or nutraceutical for therapy or prophylaxis of a tumor, by techniques known to those skilled in the art.

In another preferred embodiment of the invention the Core-1 microorganism used in the nutraceutical or pharmaceutical composition is dead.

In an even further preferred embodiment of the invention the Core-1 microorganism used in the nutraceutical or pharmaceutical composition is pasteurized.

In an even more preferred embodiment of the invention the Core-1 microorganism is used in the nutraceutical or pharmaceutical composition as a living organism and was isolated from a healthy human donor and can colonize the human gut and is antibiotic sensitive.

In an even more preferred embodiment of the invention the Core-1 microorganism is used in the nutraceutical in a pasteurized form and was isolated from the gut of a healthy human donor and which is antibiotic sensitive.

In another preferred embodiment of the invention the Core-1 microorganism used in the pharmaceutical composition is dead or lysed.

In a further preferred embodiment of the invention the Core-1 microorganism used in the nutraceutical or pharmaceutical composition is lyophilized.

Selected Core-1 positive strains as well as strains that were not Core-1 positive were characterized by their sensitivity against different antibiotics (see table 1—FIG. 22) and by their binding to Core-1 specific antibodies (see table 2).

TABLE 2

| Code | Species | Binding to NEMOD-TF1 | Periodate sensitivity of binding to NEMOD-TF1 | Binding to NEMOD-TF2 | Periodate sensitivity of binding to NEMOD-TF2 | Binding to A68-B/A11 | Periodate sensitivity of binding to A68-B/A11 |
|---|---|---|---|---|---|---|---|
| AG6 | *Bacteroides ovatus* | positive | Signal reduction | positive | Signal reduction | negative | No signal reduction |
| MU1 | *Bacteroides ovatus* | positive | Signal reduction | positive | Signal reduction | negative | No signal reduction |
| LH2 (DSM 18727), | *E. coli* | negative | No signal reduction | negative | No signal reduction | positive | Signal reduction |
| 32 | *E. coli* | negative | No signal reduction | negative | No signal reduction | negative | No signal reduction |
| 52 | *Bacteroides thetaiotaomicron* | negative | No signal reduction | negative | No signal reduction | negative | No signal reduction |
| 53 | *Bacteroides ovatus* | negative | No signal reduction | negative | No signal reduction | positive | Signal reduction |
| AG3 | *E. coli* | negative | No signal reduction | negative | No signal reduction | negative | No signal reduction |

In a further preferred embodiment of the invention the Core-1 positive microorganism and/or a fraction thereof is used in vivo or in vitro for inducing or enhancing a Core-1 specific immune response and/or for generating functional dendritic cells or activated T cells, T cell lines or T cell clones or antibodies against Core-1.

In a further preferred embodiment of the invention the Core-1 microorganism is used in the nutraceutical or pharmaceutical composition as a living organism.

In a further preferred embodiment of the invention the Core-1 microorganism is used as a living organism and is administered orally.

In a further preferred embodiment of the invention the Core-1 microorganism used in the nutraceutical or pharmaceutical composition is sensitive to at least one antibiotic.

In a further preferred embodiment of the invention the Core-1 microorganism used in the nutraceutical can colonize the gut.

D) Provision of Fractions of the Core-1 Positive Microorganism

The invention provides a fraction of the Core-1 positive microorganism of the invention wherein the Core-1 positive microorganism is recognized/bound by at least one Core-1 specific antibody.

The invention provides a suitable fraction of the Core-1 positive microorganism of the invention for use as a component for a nutraceutical or a pharmaceutical composition of the invention wherein the Core-1 positive microorganism is recognized/bound by at least one Core-1 specific antibody.

The invention provides a fraction of the Core-1 positive microorganism of the invention which induces a specific immune response against Core-1, the Core-1 antigen or Core-1 positive tumor cells in humans or animals.

The invention provides a suitable fraction of the Core-1 positive microorganism for use as a component for a nutraceutical or a pharmaceutical composition of the invention wherein the fraction of the Core-1 positive microorganism induces a specific immune response against Core-1, the Core-1 antigen or Core-1 positive tumor cells in humans or animals.

The invention provides a fraction of the Core-1 positive microorganism which represents the active ingredient of the nutraceutical or pharmaceutical composition of the invention and which induces the specificity of the immune response against Core-1, the Core-1 antigen or Core-1 positive tumor cells in humans or animals.

The invention provides a fraction of the Core-1 positive microorganism which induces or enhances a specific immune response against Core-1, the Core-1 antigen or Core-1 positive tumor cells in humans or animals when it is used in a nutraceutical or pharmaceutical composition of the invention.

Said Core-1 specific antibody, preferred Core-1 specific antibodies, combinations of Core-1 specific antibodies or preferred combinations of Core-1 specific antibodies are described in detail under Definitions and elsewhere herein.

Said nutraceuticals or pharmaceutical compositions and preferred embodiments thereof are described in detail elsewhere herein.

Said fraction of a core-1-positive microorganism means preparations or purifications of smaller parts of said microorganisms such as cell wall preparation, envelope preparation, lysates, lipopolysaccharide preparation, preparation of capsules, or capsule polysaccharide preparation, which are described in the examples (example 10) or someone skilled in the art is able to optimize and select one suitable method or a combination of suitable methods. They preferably comprise at least one Core-1 positive component of said Core-1 positive microorganism. They can be obtained by preparations or purifications from at least one Core-1 positive microorganism. Said preparations and purifications can be obtained by methods known to those skilled in the art such as those described above or single or sequential cell fractionation, phenol water extractions, ether extractions, lysozyme digestions or chromatographic methods. The Core-1 positive component or the fraction containing the Core-1 positive component is detected by binding of the fraction to at least one Core-1 specific antibody in test systems such as but not limited to ELISA or Dot blots which are known to those skilled in the art. In a preferred embodiment of the invention the fraction comprising a Core-1 positive component is obtained by affinity chromatography using at least one Core-1 specific antibody.

In a preferred embodiment a single preparation or purification step is used. In another preferred embodiment a combination of at least preparation and purification steps are used.

In a further preferred embodiment the Core-1 positive component is enriched in said fraction when compared to the whole microorganism as can be determined by an increased binding of at least one Core-1 specific antibody to the fraction in comparison to the microorganism, for example by ELISA, and preferably then when the weight of the contained biological material in the same volume is equal.

Said Core-1 positive component means any component of a Core-1 positive microorganism which is bound by at least one Core-1 specific antibody. Said Core-1 positive component comprises at least one Core-1 carbohydrate structure or Core-1 mimicking structure which can be available in form of its natural molecule where it is part of on the microorganism, such as a peptide, oligopeptide, polypeptide, lipid, ceramide, carbohydrate, lipoprotein, polysaccharide, oligosaccharide, polysaccharide, proteoglycan, lipopolysaccharide or glycoprotein, or as a part of said natural molecule, or alone. Said Core-1 positive component can also be obtained from components which carry Core-1 in disguised from, e.g. by a chemical treatment such as a periodate treatment releasing Core-1. The Core-1 positive component can be used in sense of the invention as a fraction of the Core-1 positive microorganism as such or coupled to other non-natural carrier structures such as proteins, lipids, chemical molecules such as polyacrylamide. Preferably it is used in its natural form. The Core-1 positive component can comprise a single Core-1-carbohydrate structure or Core-1 mimicking structure or repeating units of said structures and can contain additional carbohydrate structures or units or other biomolecule structures. Said Core-1 mimicking structure is a structure which is bound by at least one Core-1 specific antibody and/or induces an immune response against Core-1, preferentially a humoral immune response against Core-1 or a cellular immune response against Core-1, and more preferentially a humoral immune response against Core-1 and a cellular immune response against Core-1.

In a preferred embodiment of the invention said immune response is a humoral immune response against Core-1, the Core-1 antigen or Core-1 positive tumor cells or a cellular immune response against Core-1, the Core-1 antigen or Core-1 positive tumor cells.

In a further preferred embodiment of the invention said immune response is a humoral immune response against Core-1, the Core-1 antigen or Core-1 positive tumor cells and a cellular immune response against Core-1, the Core-1 antigen or Core-1 positive tumor cells.

Said humoral immune response against Core-1 and said cellular immune response against Core-1 are described in detail elsewhere in the present invention as well as the humoral and cellular immune response tests which can detect the according antibody or T-cell response against Core-1, the Core-1 antigen or Core-1 positive tumor cells.

In a further preferred embodiment of the invention said immune response is a humoral immune response against Core-1 which is positive for at least two humoral immune response tests out of the humoral immune response test 1 to 6, preferably positive for humoral immune response tests 1 and 3, and more preferably for humoral immune response test 1, 2 and 3, and more preferably for humoral immune response test 1, 2, 3, and 4, and more preferably for humoral immune response test 1, 2, 3, 4 and 6, and more preferably for humoral immune response test 1, 2, 3, 4 and 5, and most preferably positive for all 6 humoral immune response tests.

In a further preferred embodiment of the invention said immune response is a cellular immune response against Core-1 which is positive for at least two cellular immune response tests out of the cellular immune response tests 1 to 5.

In an even further preferred embodiment of the invention said immune response is a humoral and a cellular immune response against Core-1 which is positive for at least one humoral immune response test and at least one cellular immune response tests.

In an even further preferred embodiment of the invention said immune response is a humoral and a cellular immune response against Core-1 which is positive for at least two humoral immune response tests and two cellular immune response tests, preferably positive for humoral immune response tests 1 and 3 and cellular immune response test 1 and 3, and more preferably for humoral immune response test 1, 2 and 3 and cellular immune test 1, 2 and 3, and even more preferably for humoral immune response test 1, 2, 3 and 4 and cellular immune test 1, 2, 3 and 4, and even more preferably for humoral immune response test 1, 2, 3, 4 and 6 and all 5 cellular immune tests, and even more preferably for humoral immune response test 1, 2, 3, 4 and 5 and all 5 cellular immune tests, and most preferably positive for all 6 humoral immune response tests and all 5 cellular immune response tests.

In a further preferred embodiment the invention provides a fraction of the Core-1 positive microorganism which can be used to build a Core-1 specific immune response which functions as a shield against Core-1 positive cancer cells by having the potential to destroy those cells as shown herein for example by the induction of the Core-1 specific antibodies, by the Core-1 specific complement dependent cytotoxicity of Core-1 antibodies against Core-1 positive tumor cells killing those effectively, and/or by secretion of TNFalpha and/or INFgamma by Core-1 specific T cell responses which are scientifically recognized surrogate markers by those skilled in the art for a specific cytotoxic T cell mediated tumor cell killing for those tumor cells carrying the Core-1, when used as a nutraceutical or a pharmaceutical composition of the invention.

In a further preferred embodiment the invention provides a fraction of the Core-1 positive microorganism which can be used to build said Core-1 specific immune response which functions as a shield against Core-1 positive cancer cells which has the potential to destroy those cells as described above by orally administering the nutraceutical in (at least one) healthy individuals.

In a further preferred embodiment the invention provides a fraction of the Core-1 positive microorganism which can be used to reduce or even further preferred to prevent the occurrence of a Core-1 positive disease or tumor by orally administering it as a component of the nutraceutical of the invention to (at least one) healthy individuals.

In a further preferred embodiment the invention provides a fraction of the Core-1 positive microorganism which can be used to reduce or even more preferred to prevent the occurrence of a Core-1 positive disease or tumor when administered as a component of a pharmaceutical formulation of the invention to (at least one) individual.

In another preferred embodiment the invention provides a fraction of the Core-1 positive microorganism which is used as the active ingredient of a nutraceutical to treat a Core-1 positive disease or tumor by orally administering the nutraceutical in patients suffering from this disease.

In a preferred embodiment the invention provides a fraction of the Core-1 positive microorganism which is used as the active ingredient of a pharmaceutical composition to treat a Core-1 positive disease or tumor in patients suffering from this disease by administering the pharmaceutical composition as described elsewhere herein.

In a more preferred embodiment the present invention provides a fraction of the Core-1 positive microorganism which is a suitable component of a nutraceutical formulation that preferentially shows the induction of an immune response in humans recognizing the Core-1 antigen and/or a Core-1 positive tumor cell by being positive after oral administration of the fraction of the Core-1 positive microorganism for at least one humoral or cellular immune test described herein and preferred embodiments as described above.

In the most preferred embodiment said fraction of the Core-1 positive microorganism is positive for binding to the Core-1-specific antibodies NEMOD-TF1 and NEMOD-TF2, whereby the binding of said antibodies is periodate sensitive showing a reduced binding of NEMOD-TF1 and NEMOD-TF2 after treatment with periodic acid as described somewhere herein and which induces an immune response which is positive for the humoral immune response tests 1, 2, and 3 and for the cellular immune response tests 1, 2, and 3, and even more preferred for all 6 humoral immune response tests and for all 5 cellular immune response tests as described herein.

In another preferred embodiment of the invention the Core-1 positive component is not part of the bacterial lipopolysaccharide.

In a preferred embodiment the invention provides or uses the fraction of the Core-1 positive microorganism of the invention, or the nutraceutical or the pharmaceutical formulation or food additive comprising at least one fraction of at least one Core-1 positive microorganism, whereby the Core-1 positive microorganism is selected from the group consisting of enterobacterioceae, *Escherichia coli*, *Streptococcus*, *Bacteroides*, *Rhuminococcus*, *Lactobacillus*, *Bifidobacterium*, *Peptostreptococcus*, *Fusobacterium*, *Johnsonella*, *Atopobium*, *Staphylococcus*, *Eubacterium*, *Finegoldia*, *Clostridium*, *Eggerthella*, *Butyribacterium*, *Citrobacter*, *Helicobacter*, *Propionibacterium* and *Corynebacterium*, *Bacteroides ovatus*, *Bacteroides thetaiotaomicron*, *Bacteroides acidophilus*, *Bacteroides caccae*, AG6 (DSM 18726) and/or MU1 (DSM 18728) wherein said microorganism selected from said group is Core-1 positive and is specifically recognized by at least one Core-1 specific antibody. As *Heliobacter* is a pathogen, said Core-1 positive microorganism is preferably not *Heliobacter* as *Heliobacter* can—due to its pathogenic nature—not be used alive without risks.

More preferably said Core-1 positive microorganism is selected from the group comprising *Escherichia coli*, *Bacteroides* such as *Bacteroides ovatus*, *Bacteroides thetaiotaomicron*, *Bacteroides acidophilus* and *Bacteroides caccae* and even more preferred selected from the group comprising the new strain AG6(DSM 18726), MU1(DSM 18728) deposited at the "DSMZ-Deutsche Sammlung von Mikroorganismen and Zellkulturen GmbH" in Braunschweig (Germany), by Glycotope GmbH, Robert-Rossle-Str. 10, 13125 Berlin (Germany) at the Oct. 20, 2006.

In a further preferred embodiment of the invention the fraction of the Core-1 positive microorganism (active component) of the nutraceutical or the pharmaceutical formulation comprises a combination of fractions from one Core-1 positive microorganism or preferentially from different Core-1 positive microorganisms of different strains. The fractions can be of the same or a different preparation or purification type, preferably is a combination of Core-1 positive components which have different molecular carrier or mimikry structures such as but not limited to a peptide, oligopeptide, polypeptide, lipid, ceramide, carbohydrate, lipoprotein, polysaccharide, oligosaccharide, polysaccharide, proteoglycan or glycoprotein, or as a part of another natural or synthetic molecule.

In a further preferred embodiment said fraction of the Core-1 positive microorganism (active component) comprises a combination of Core-1 positive components of Core-1 positive microorganisms of at least two different strains, preferably the new strains AG6(DSM 18726) and MU1(DSM 18728).

In a further preferred embodiment said fraction of the Core-1 positive microorganism (active component) comprises the Core-1 positive components of Core-1 positive microorganisms of strain AG6.

In another preferred embodiment of the invention said fraction of the Core-1 positive microorganism comprises carbohydrates structures selected from the group comprising #1, #2, #3, #4 and/or #5 of FIG. 19.

In another preferred embodiment of the invention said fraction of the Core-1 positive microorganism comprises repeating units of the carbohydrates structures selected from the group comprising #1, #2, #3, #4 and/or #5 of FIG. 19.

In another preferred embodiment of the invention, said fraction comprises at least one of the carbohydrate structures selected from the group comprising #1, #2, #3, #4 and/or #5 of FIG. 19 and/or repeating units thereof.

In another preferred embodiment of the invention said carbohydrate structure or said repeating units thereof are obtained by enrichment and/or purification and/or isolation from a Core-1 positive microorganism.

In a further preferred embodiment of the invention said carbohydrate structure or said repeating units thereof are obtained by enrichment and/or purification and or isolation from strain AG6.

Details are shown in example 10.

In a further preferred embodiment of the invention said carbohydrate structure or said repeating units thereof are obtained by chemical synthesis.

Figure 8:
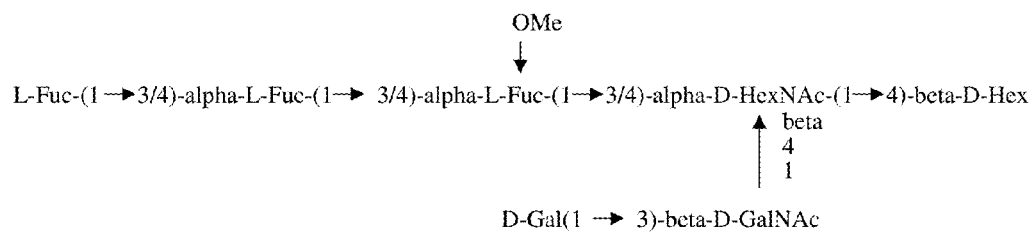

Those skilled in the art are able to determine suitable conditions and methods for chemically synthesizing carbohydrate structure according to FIG. 8 or repeating units thereof.

In a further preferred embodiment said fraction of the Core-1 positive microorganism (active component) comprises the Core-1 positive components of Core-1 positive microorganisms of strain MU1.

In another preferred embodiment the nutraceutical or pharmaceutical composition of the invention comprises at least one fraction of the Core-1 positive microorganism and at least one Core-1 positive microorganism.

In a further preferred embodiment the nutraceutical or pharmaceutical composition of the invention comprises at least one fraction of the Core-1 positive microorganism combined with at least one other beneficial microorganism, such as but not limited to a *lactobacillus* and/or *bifidobacterium*, even more preferred a combination fractions of Core-1 positive microorganisms of different strains combined with other beneficial microorganisms.

In another preferred embodiment the nutraceutical or pharmaceutical composition of the invention comprises at least one fraction of the Core-1 positive microorganism and at least one Core-1 positive microorganism combined with at least one other beneficial microorganism, such as but not limited to a *lactobacillus* and/or *bifidobacterium*.

In another preferred embodiment the invention provides a Core-1 positive microorganism or fraction thereof which induces or enhances a humoral and/or cellular immune response against Core-1, the core-1 antigen or a Core-1 positive tumor cell in at least one human or animal when administered in a suitable composition or formulation.

In another preferred embodiment the invention provides a Core-1 positive microorganism or fraction thereof which induces or enhances a Core-1 specific immune response in at least one human or animal functioning as a shield against Core-1 positive cancer cells by having the potential to destroy Core-1 positive cancer cells when administered in a suitable composition or formulation.

In another preferred embodiment the invention provides a Core-1 positive microorganism or fraction thereof which reduces or prevents the occurrence of a Core-1 positive disease, tumor or metastasis in at least one human or animal when administered in a suitable composition or formulation.

In another preferred embodiment the invention provides a Core-1 positive microorganism or fraction thereof which reduces or prevents the spread or metastasis of a Core-1 positive disease or tumor in at least one human or animal when administered in a suitable composition or formulation.

In another preferred embodiment the invention provides a Core-1 positive microorganism or fraction thereof which is used to treat a Core-1 positive disease or tumor in at least one human or animal when administered in a suitable composition.

In another preferred embodiment the invention provides a Core-1 positive microorganism or fraction thereof which is used as the active ingredient of a nutraceutical to prevent, reduce risk of developing of, or reduce the occurrence of a Core-1 positive tumor by orally administering the nutraceutical in a healthy individual.

In another preferred embodiment the invention provides a Core-1 positive microorganism or fraction thereof which is used as the active ingredient of a nutraceutical to prevent or reduce the spread of the tumor or metastasis or the spread of metastasis or time to relapse of a Core-1 positive tumor or tumor cells, to improve quality of life or median survival or rate of time to relapse, or to treat a tumor patient which has or had Core-1 positive tumor cells by orally administering the nutraceutical in patients suffering from this disease.

In another preferred embodiment the invention provides a Core-1 positive microorganism or fraction thereof which is used as the active ingredient of a pharmaceutical composition to prevent, reduce the risk of developing of, or reduce the occurrence of a Core-1 positive tumor by administering the pharmaceutical composition in a healthy individual.

In another preferred embodiment the invention provides a Core-1 positive microorganism or fraction thereof which is used as the active ingredient of a pharmaceutical composition to prevent or reduce spread of the tumor or metastasis or spread of metastasis or time to relapse of a Core-1 positive tumor or tumor cells, to improve quality of life or median survival or rate of time to relapse, or to treat a tumor patient which has or had Core-1 positive tumor cells by administering the pharmaceutical composition in patients suffering from this disease.

E) Methods for Inducing an Immune Shield Against Core-1 Positive Cancer Cells, for Preventing and/or Treating Core-1 Positive Tumors and for Treating or Preventing a Core-1 Positive Disease.

The invention provides a method for inducing or enhancing a specific humoral and/or cellular immune response against Core-1, the Core-1 antigen or Core-1 positive tumor cells comprising administering in a human or an animal an effective amount of the nutraceutical, or the pharmaceutical composition, or the Core-1 positive microorganism, or the fraction thereof which are described elsewhere herein, or formulations comprising those.

In another preferred embodiment, the invention provides a method for inducing or enhancing a specific humoral and/or cellular immune response against Core-1, the Core-1 antigen or Core-1 positive tumor cells comprising administering in a human or an animal an effective amount of the formulation, or the Core-1 positive microorganism, or the fraction or lysate thereof as described elsewhere herein.

In a preferred embodiment the invention provides the above mentioned method wherein said nutraceutical, or said pharmaceutical formulation, or said Core-1 positive microorganism, or said fraction thereof, or said formulations comprising those comprising at least one microorganism, lysate or fraction from a Core-1 positive microorganism recognized/bound by Nemod-TF1 or A78-G/A7 and Nemod-TF2.

The invention provides a method for inducing or enhancing a Core-1 specific immune response which functions as a shield against Core-1 positive cancer cells by having the potential to destroy at least one Core-1 positive cancer cell.

In a preferred embodiment the invention provides a method for inducing a Core-1 specific immune response which functions as a shield against Core-1 positive cancer cells by having the potential to destroy those cells as shown herein, for example by the induction of the Core-1 specific antibodies, by the Core-1 specific complement dependent cytotoxicity of Core-1 antibodies against Core-1 positive tumor cells killing those effectively, and/or by secretion of TNFalpha and/or INFgamma by Core-1 specific T cell responses which are scientifically recognized surrogate markers by those skilled in the art for a specific cytotoxic T cell mediated tumor cell killing for those tumor cells carrying the Core-1, as shown in the examples and described herein, comprising administering in a human or an animal an effective amount of the nutraceutical, or the pharmaceutical formulation, or the Core-1 positive microorganism, or the fraction thereof which are described elsewhere herein, or formulations comprising those.

The invention further provides a method for reducing or even further preferred for preventing the occurrence of a tumor, preferably a Core-1 positive tumor, comprising administering to a human or an animal an effective amount of the nutraceutical, or the pharmaceutical formulation, or the Core-1 positive microorganism, or the fraction thereof which are described elsewhere herein, or formulations comprising those, preferably in a healthy individual.

The invention further provides a method for reducing or even further preferred for preventing the spread or metastasis of a tumor, preferably of a Core-1 positive tumor, comprising administering in a human or an animal an effective amount of the nutraceutical, or the pharmaceutical formulation, or the Core-1 positive microorganism, or the fraction thereof which are described elsewhere herein, or formulations comprising those.

The invention provides a method to treat a tumor, preferably a Core-1 positive tumor, comprising administering in a human or an animal an effective amount of the nutraceutical, or the pharmaceutical formulation, or the Core-1 positive microorganism, or the fraction thereof which are described elsewhere herein, or formulations comprising those.

The invention provides a method for reducing or even further preferred for preventing the occurrence of a Core-1 positive disease comprising administering in a human or an animal an effective amount of the nutraceutical, or the pharmaceutical formulation, or the Core-1 positive microorganism, or the fraction thereof which are described elsewhere herein, or formulations comprising those, preferably in a healthy individual.

In another preferred embodiment the present invention provides a method for the vaccination or immunization of a human or an animal against Core-1 comprising
  i) administration to a human or an animal of an effective amount of functional dendritic cells or a mixture of cells comprising at least one functional dendritic cell directed against Core-1 at least once and induction of an immune response by said functional dendritic cells in the human or animal and
  ii) boostering of the immune response by the administration of an effective amount of a pharmaceutical composition comprising at least one Core-1 positive microorganism and/or a fraction and/or a lysate thereof at least once.

In another preferred embodiment the present invention provides a method for the vaccination of a human or an animal against a carbohydrate epitope present on a molecule from a human or animal cell comprising
  i) administration to a human or an animal an effective amount of activated T cells, T cell clone, T cell line or a mixture of cells comprising at least one activated T cell directed against Core-1 a least once and induction of an immune response by said activated T cells in the human or animal and
  ii) boostering of the immune response by the administration of an effective amount of a pharmaceutical composition comprising Core-1 positive microorganism and/or a fraction and/or a lysate thereof at least once.

The generation of functional dendritic cells, activated T cells, T cell lines and T cell clones is described elsewhere herein.

In a preferred embodiment of the invention the administration according to the previous methods under (i) is performed once. In another preferred embodiment of the invention the administration according to the previous methods under (i) is performed twice. In another preferred embodiment of the invention the administration according to the previous methods under (i) is performed at least three to five times.

In a preferred embodiment of the invention the boostering of the immune response by the administration of an effective amount of a pharmaceutical composition according to (ii) of the previous methods is performed once, in another preferred embodiment of the invention the boostering is performed 2-10 times, more preferably more than 10 times, more preferably up to 20 times, most preferably boostering is performed continually at regular time intervals over a period of several month to several years.

In a preferred embodiment of the invention the boostering of the immune response is done 1-5 times close to the priming and thereafter at intervals from 3 month to 1 year or 1 year to 10 years.

The generation of functional dendritic cells, activated T cells, T cell lines and T cell clones is described elsewhere herein.

The invention provides a method for reducing or even further preferred for preventing the spread of a Core-1 positive disease comprising administering in a human or an animal an effective amount of the nutraceutical, or the pharmaceutical formulation, or the Core-1 positive microorganism, or the fraction thereof which are described elsewhere herein, or formulations comprising those.

The invention provides a method to treat a Core-1 positive disease comprising administering in a human or an animal an effective amount of the nutraceutical, or the pharmaceutical formulation, or the Core-1 positive microorganism, or the fraction thereof which are described elsewhere herein, or formulations comprising those.

The invention provides a method to strengthen the immune system or to improve an immune response comprising administering in a human or an animal an effective amount of the nutraceutical, or the pharmaceutical formulation, or the Core-1 positive microorganism, or the fraction thereof which are described elsewhere herein, or formulations comprising those. This can be for example but is not limited to a general improvement of the condition of the immune system for example against infectious diseases or tumors, an improvement of the activity of other immune stimulatory agents or probiotics or prebiotics, or an action as an adjuvant.

In a preferred embodiment of the invention the nutraceutical, or the pharmaceutical formulation, or the Core-1 positive microorganism, or the fraction thereof which are described elsewhere herein, or formulations comprising those of above described methods comprises at least one microorganism, lysate or fraction from a Core-1 positive microorganism recognized/bound by Nemod-TF1 and/or A78-G/A7 and Nemod-TF2.

In a preferred embodiment the nutraceutical, or the pharmaceutical formulation, or the Core-1 positive microorganism, or the fraction thereof which are described elsewhere herein, or formulations comprising those of above described methods comprises at least one microorganism, lysate or fraction from the strain AG6(DSM 18726) and/or MU1 (DSM 18728).

The term formulation means any substance or composition of substances in a suitable form for administration comprising at least one of the nutraceutical, the pharmaceutical composition, the Core-1 positive microorganism or the fraction thereof which can comprise a pharmaceutically acceptable carrier or a carrier acceptable for food additives and/or nutraceutical or the nutraceutical, the pharmaceutical composition, the Core-1 positive microorganism or the fraction thereof alone.

The term preventing the occurrence refers to using the nutraceutical, the pharmaceutical composition, the Core-1 positive microorganism or the fraction thereof or formulations comprising those to a subject with the purpose to reduce the risk or the rate or the probability of developing a Core-1 positive cancer or Core-1 positive disease.

The term reducing or preventing the spread of a tumor or Core-1 positive disease or metastasis of a tumor refers to using the nutraceutical, the pharmaceutical composition, the Core-1 positive microorganism or the fraction thereof or formulations comprising those to a subject with the purpose to reduce the risk or the rate or the probability of metastasis or spread of the disease to other organs or other sites in the body or other individuals.

The term treating refers to using the nutraceutical, the pharmaceutical composition, the Core-1 positive microorganism or the fraction thereof or formulations comprising those to an individual or subject with the purpose to cure, heal, alleviate, relieve, alter, remedy, ameliorate, improve, or affect cancer, the symptoms of cancer, the predisposition toward cancer, time of survival, or time to progression.

Said Core-1 positive disease is any disease which is associated with a virus, microorganism or other biological material which can be bound by at least one of the Core-1 specific antibodies or which is associated with a component of the body or occurring in the body of a human or animal such as but not limited to a cell, microorganism, virus or particle which is bound by at least one of the Core-1 specific antibodies.

The "effective amount" of any of the nutraceutical, pharmaceutical composition, the Core-1 positive microorganism or the fraction thereof or formulations comprising those comprises living or dead microorganism, or lysates or fractions of these microorganisms which correspond to or are derived from about $1 \times 10^6$ to about $1 \times 10^{14}$ cfu per person per day (cfu/person/day) whereby cfu is a colony forming unit as a measure for one microorganism as such known to and can be determined by those skilled in the art;

In another embodiment of the invention the effective amount is the amount of the nutraceutical, the pharmaceutical composition, the Core-1 positive microorganism or the fraction thereof or formulations comprising those which induces a humoral or cellular immune response against Core-1 in at least one individual, preferably a humoral and a cellular immune response against Core-1, detectable by at least one of the immune response tests against Core-1 described elsewhere herein.

In another embodiment of the invention the effective amount is the amount of the nutraceutical, the pharmaceutical composition, the Core-1 positive microorganism or the fraction thereof or formulations comprising those which is required to confer an immune shield against Core-1 positive tumor cells, to have a prophylactic effect against cancer or to have a therapeutic effect against cancer, or to have a prophylactic or therapeutic effect against another Core-1 positive disease, each in at least one individual.

The effective amount for an individual or a group of individuals can be determined and/or optimized by those skilled in the art, preferably using at least one immune response test against Core-1 described elsewhere herein and preferably those combinations of immune response tests against Core-1 which are described elsewhere herein as preferred embodiments and/or clinical response tests known to those skilled in the art or described elsewhere herein.

These effective amounts can vary from above described amounts or dosages or preferred amounts or dosages described elsewhere herein for a person depending for example on the subject, on the number and time schedule of dosages, on the format or formulation of the nutraceutical, the pharmaceutical composition, the Core-1 positive microorganism or fraction thereof, on the route and time scheme of administration, on the purpose it is used for such as prophylaxis or treatment, on the state of a Core-1 positive disease or cancer, and they can vary depending on the species, races and between an individual animal or individual human receiving the nutraceutical, the pharmaceutical composition, the Core-1 positive microorganism or the fraction thereof or formulations comprising those. Those skilled in the art are able to determine the suitable and/or the optimal dosage, administration route and time scheme for an individual or for a group of individuals preferably by using the description and an embodiment of the invention described herein.

Preferred are those effective amounts and dosages of the nutraceutical, the pharmaceutical composition, the Core-1 positive microorganism or the fraction thereof or formulations comprising those which induce or enhance said immune response against Core-1 in more than one individual, more preferably in a significant number of individuals, more preferably in at least 10%, more preferably in at least 20%, more preferably in at least 30%, more preferably in at least 40%, more preferably in at least 50%, and most preferably in the majority of individuals.

In a preferred embodiment the effective amount is the amount of said nutraceutical, said pharmaceutical composition, said Core-1 positive microorganism or said fraction thereof or said formulations comprising those which induces an immune response against Core-1 in at least one individual.

In a preferred embodiment said induced or enhanced immune response is a humoral and a cellular immune response against Core-1, detectable by at least one of the humoral immune response tests 1 to 6 and one of the cellular immune response tests 1 to 5. In a preferred embodiment the effective amount is the amount of the nutraceutical, the pharmaceutical composition, the Core-1 positive microorganism or the fraction thereof or formulations comprising those which induces an immune response which is positive in at least two of the herein described immune response tests against Core-1, more preferably positive for humoral immune response tests 1 and 3, more preferably for humoral immune response test 1, 2 and 3, more preferably for humoral immune response test 1, 2, 3, and 4, more preferably for humoral immune response test 1, 2, 3, 4, and 6, even more preferably for humoral immune response test 1, 2, 3, 4, and 5, and more preferably positive for all 6 humoral immune response tests, even more preferably positive for at least two cellular immune response tests out of the cellular immune response tests 1 to 5, even more preferably for at least one humoral immune response test and at least one cellular immune response tests, even more preferably positive for at least two humoral immune response test and two cellular immune response tests, preferably positive for humoral immune response tests 1 and 3 and cellular immune response test 1 and 3, and more preferably for humoral immune response test 1, 2 and 3 and cellular immune test 1, 2 and 3, even more preferably for humoral immune response test 1, 2, 3 and 4 and cellular immune test 1, 2, 3 and 4, even more preferably for humoral immune response test 1, 2, 3, 4, and 6, and all 5 cellular immune response test, even more preferably for humoral immune response test 1, 2, 3, 4, and 5, and all 5 cellular immune response test, and most preferably positive for all 6 humoral immune response tests and all 5 cellular immune response tests.

In a preferred embodiment, the effective amount is the amount of said nutraceutical, said pharmaceutical composition, said Core-1 positive microorganism or said fraction thereof or said formulations comprising those which is required to confer an immune shield against Core-1 positive tumor cells, to have a prophylactic effect against cancer or to have a therapeutic effect against cancer, or to have a prophylactic or therapeutic effect against another Core-1 positive disease, each in at least one individual.

In another preferred embodiment, the effective amount is the amount of said nutraceutical, said pharmaceutical composition, said Core-1 positive microorganism or said fraction thereof or said formulations comprising those which induces the maximal or near to maximal immune response against Core-1 in at least one individual.

In an even more preferred embodiment the preferred effective amount is the amount of the nutraceutical, the pharmaceutical composition, the Core-1 positive microorganism or the fraction thereof or formulations comprising those which induces the maximal or near to maximal immune responses against Core-1 as detected in the immune response tests against Core-1 by those skilled in the art, whereby this maximal immune response does not have to be such which is positive in all immune response tests but preferably such which gives the highest antibody responses or antibody titers against Core-1 and/or the highest T cell response against Core-1 and more preferably against Core-1 positive tumor cells, more preferably both, and most preferably those which show at least in the humoral immune response tests 1 and 3 against Core-1 the highest antibody titres and/or at least in the cellular immune response test 1 or 2 or 3 against Core-1 the highest T cell responses against Core-1.

In preferred embodiment, the effective amount of said nutraceutical, said pharmaceutical composition, said Core-1 positive microorganism or said fraction thereof or said formulations comprising living or dead microorganism, or lysates or fractions of these microorganisms which correspond to or are derived from about $1\times10^6$ to about $1\times10^{14}$ cfu per individual per dose.

In a more preferred embodiment the effective amount of the nutraceutical, the pharmaceutical composition, the Core-1 positive microorganism or the fraction thereof or formulations comprising those comprises living or dead microorganism, lysates or fractions of these microorganisms which correspond to or are derived from $1\times10^7$ to $1\times10^{13}$ cfu/person/day, more preferably to $2\times10^8$ to $1\times10^{12}$, and more preferrably $1\times10^9$-$1\times10^{11}$ cfu/person/day.

The effective amounts or effective doses can also vary, as recognized by those skilled in the art, depending on the route of administration, excipient usage, and the possibility of co-usage with other agents, such as those for immune enhancement, for inducing an immune response, or building an immune shield, or preventing or treating cancer.

The effective amounts or effective doses can also vary, as recognized by those skilled in the art, depending on the format of use such as use as the nutraceutical, as the pharmaceutical composition, as the Core-1 positive microorganism or as the fraction thereof or as the formulations comprising those as well as if they comprise living, dead lysates or fractions thereof, as well as on the amounts of doses as well as on the time intervals between doses. Those can be determined and optimized by those skilled in the art preferably by using the provided invention, tests and methods of the invention.

In a preferred embodiment, the nutraceutical is administered orally from more than one dose daily, to one dose daily, weekly, or monthly from a short term interval to a year long use, preferably daily or weekly use over 4 weeks to 2 years.

In another preferred embodiment, a single dose is administered to an individual. In another preferred embodiment multiple doses are administered to an individual. In another preferred embodiment, the effective amount corresponds to a single dose. In another preferred embodiment, the effective amount corresponds to multiple doses.

In a preferred embodiment, the pharmaceutical composition can be administered systemically for as little as only one dosage to many dosages, preferably weekly to monthly to 3 monthly or 6 monthly or a staggered combination thereof, and can be combined with a 6 monthly to yearly, to 5 yearly to ten yearly refreshment of the immunization.

In another preferred embodiment of the invention the effective dosage of the nutraceutical formulation comprising at least one Core-1 positive microorganism or lysate or fraction thereof in humans is 0.1 mg/m$^2$-10 g/m$^2$, more preferred 10 mg/m$^2$-10 g/m$^2$, even more preferred 0.1 g/m$^2$-10 g/m$^2$.

In another preferred embodiment the formulation is administered first systemically with subsequent oral refreshments of the immunization.

The term administration means bringing into contact a human or an animal with an effective amount of the nutraceutical, the pharmaceutical composition, the Core-1 positive microorganism or the fraction thereof or formulations comprising those for which additional carriers can be used. The routes of administration include any way to bring the human or animal into contact with the nutraceutical, the pharmaceutical composition, the Core-1 positive microorganism or the fraction thereof or formulations comprising those. Preferred are those routes of administration, such as but not limited to oral administration, systemic administration, administration via inhalation or via bringing into contact with skin or another epidermis, which lead to an immune response against Core-1, a immune shield against Core-1 or Core-1 positive tumor cells, prophylactic effect against cancer or a therapeutic effect against cancer, which can be determined in its preferred forms as described above or elsewhere herein. Those skilled in the art can select the most suitable route of administration.

Examples for and preferred routes of administration and formulations are described in the following:

The nutraceuticals are preferably administered orally for example as either as capsules, tablets, emulsions, powder, liquids, in form of any food or drink, or as a component of a food or a drink such as a food additive. The nutraceutical can be given by itself or mixed with at least one other ingredient. The nutraceutical by itself or its mixture with at least one other ingredient can be given by itself or mixed into a food or a drink.

A formulation for oral administration of the nutraceutical, but also the pharmaceutical composition, the Core-1 positive microorganism or the fraction thereof or formulations comprising those can be any orally acceptable dosage form or effective amount of the nutraceutical, the pharmaceutical composition, the Core-1 positive microorganism or the fraction thereof or formulations comprising those including, but not limited to, tablets, capsules, nanoparticles, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A formulation for oral administration can be any orally acceptable dosage form or effective amount of the nutraceutical, the pharmaceutical composition, the Core-1 positive microorganism or the fraction thereof or formulations comprising those including, but not limited to, tablets, capsules, nanoparticles, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The formulation of the present invention may be administered orally or parenterally. The parenteral administration includes injections such as drop infusion, hypodermic, intravenous or intramuscular injections, transdermal application with ointment or transdermal drug, and rectal application with suppository. Where the composition is administered orally, it may be prepared in the form of hard capsule, soft capsule, granule, powder, fine granule, pill, troche tablet, system of gradual active-ingredient delivery, liquid, and suspension. The preparation can be easily carried out by conventional methods in the pharmaceutical field.

The mode of administration and dosage forms will of course affect the therapeutic amounts of the compounds or compositions which are desirable and efficacious for the given treatment application. Where the formulation of the present invention is prepared in the form of oral administration, the composition may be prepared using conventional pharmaceutical ingredients in a normal medicine such as filler, extender, binder, disintegrator, surfactant, diluents such as lubricant and excipient. Particular examples of the conventional ingredients include recipients such as milk sugar, white sugar, sodium chloride, glucose, urea, starch, calcium carbonate, kaolin, crystal cellulose and silicic acid; binders such as water, ethanol, simple syrup, glucose liquid, starch liquid, gelatin solution, carboxymethyl cellulose, shellac, methyl cellulose, potassium phosphate and polyvinyl pyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic acid monoglyceride, starch, and milk sugar; decay inhibitors such as white sugar, stearic acid, cacao butter and hydrogenated oil; absorbefacients such as quaternary ammonium salt and sodium lauryl sulfate; moisturizing agents such as glycerin and starch; absorbents such as starch, milk sugar, kaolin, bentonite and colloidal silicic acid; and lubricants such as purified talc and stearate. If necessary, the preparation further includes colorant, preservative, perfume, flavor agent and sweetening agent.

Suitable pharmaceutically acceptable salts are well known to those skilled in the art and in-dude basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of the present invention may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

In a preferred embodiment, the route of administration of the pharmaceutical composition is selected from the group consisting of intravenous injection, intraperitoneal injection, intra-muscular injection, intracranial injection, intratumoral injection, intraepithelial injection, transcutaneous delivery, per oesophageal administration, intraabdominal administration, in-traapendicular administration, intraarterial administration, intraarticular administration, intrabronchial administration, intrabuccal administration, intracapsular administration, intracardial administration, intracartilaginous administration, intracavitary administration, intracephalic administration, intracolic administration, intracutaneous administration, intracystic administration, intradermal administration, intraductal administration, intraduodenal administration, intrafascicular administration, intrafat administration, intrafilar administration, intrafissural administration, intragastric administration, intraglandular administration, intrahepatic administration, intraintestinal administration, intralamellar administration, intralesional administration, intraligamentous administration, intralingual administration, intramammary administration, intramedullary administration, intrameningeal administration, intramyocardial administration, intranasal administration, intraocular administration, intraoperative administration, intraoral administration, intraosseous administration, intraovarian administration, intrapancreatic administration, intraparietal administration, intrapelvic administration, intrapericardial administration, intraperineal administration, intraperitoneal administration, intraplacental administration, intrapleural administration, intrapontine administration, intraprostatic administration, intrapulmonary administration, intrarachidian administration, intrarectal administration, intrarenal administration, intrascleral administration, intrascrotal administration, intrasegmental administration, intrasellar administration, intraspinal administration, intrasplenic administration, intrasternal administration, intrastromal administration, intrasynovial administration, intratarsal administration, intratesticular administration, intrathoracic administration, intratonsillar administration, intratracheal administration, intratubal administration, intratympanic administration, intraureteral administration, intraurethral administration, intrauterine administration, intravaginal administration, intravascular administration, intraventricular administration, intravertebral administration, intravesical administration, and intravitreous administration.

In a more preferred embodiment of the invention examples of routes of administration (=contacting) include parenteral, e.g., intravenous, intradermal, subcutaneous, oral, transdermal (topical), transmucosal, intraperitoneal, intranasal, rectal enteral and oral administration.

A formulation of the present invention can include pharmaceutically acceptable salts of the components therein. Pharmaceutically acceptable salts include the acid addition salts that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamino, 2-ethylamino ethanol, histidine, procaine and the like. Physiologically tolerable carriers are well known in the art. Exemplary of liquid carriers are sterile aqueous Solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium Chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. A formulation contains a Core-1 positive microorganism, lysate or fraction thereof of the present invention, typically an amount of at least 0.1 weight percent of a Core-1 positive microorganism, lysate or fraction thereof per weight of total composition. A weight percent is a ratio by weight of a Core-1 positive microorganism, lysate or fraction thereof to total composition. Thus, for example, 0.1 weight percent is 0.1 grams of a Core-1 positive microorganism Core-1 positive microorganism, lysate or fraction thereof per 100 grams of total composition.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

The formulation comprising as the active ingredient Core-1 positive microorganism, lysate or fraction thereof) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and U.S. Pat. No. 4,265,874, to form osmotic therapeutic tablets for control release. A formulation according to the present invention may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antinflammatories (e.g., ibuprofen and indomethacin), anthelmintics, antidepressants, antidotes, antiemetics, antihistamines, antihypertensives, antimalarials, antimicrotubule agents (e.g., colchicine or *vinca* alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

Formulations for oral use may also be presented as hard gelatin capsules where in the active ingredient is mixed with an inert solid diluent, for example calcium carbonate, calciumphosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or Saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous Suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The formulation of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agent. The pharmaceutical compositions may be in the form of a sterile injectable aqueous or oleagenous Suspension. This Suspension may be formulated according to the known art using those suitable dispersing or wetting agents and suspending agents which have been mentioned above. The sterile injectable preparation may also be in a sterile injectable solution or Suspension in a non-toxic parenterally-acceptable diluent or solvent, for example as absolution in 1,3-butane diol. Among the acceptable vehicles and solvents that may be employed are water, Ringer's solution and isotonic sodium Chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables. Dosage levels of the order of from about 0.01 mg to about 140 mg per kilogram of body weight per: day are useful in the treatment of the above-indicated conditions (about 2.5 mg to about 7 g per patient per day). For example, a Core-1 positive tumor may be effectively treated by the administration of from about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 10 g of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds are preferably being used in the form of pharmaceutical compositions or nutraceuticals.

Formulation of pharmaceutically-acceptable excipients and carrier Solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

A. Oral Delivery

In certain applications, the formulations disclosed herein may be delivered via oral administration to a human or an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or Saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient (s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount/effective dose to a composition that may include water, binders, abrasives, flavoring agents, foaming agents, and humectants. Alternatively the compositions may be fashioned into a tablet or solution form that may be placed under the tongue or otherwise dissolved in the mouth.

B. Injectable Delivery

In certain circumstances it will be desirable to deliver the formulations disclosed herein parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous Solutions or dispersions and sterile powders for the extemporaneous preparation of sterile injectable Solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium Chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous Solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some Variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity Standards as required by national or regional Offices of biologics Standards.

Sterile injectable Solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable Solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, Solutions will be administered in a manner compatible with the dosage formulation and in such amount as is therapeutically effective. The formulations are easily administered in a variety of dosage forms such as injectable Solutions, drug-release capsules, and the like.

As used herein, "carrier" includes any and all solvents, dispersion media, vehicles, coatings, diluents, antibacterial and antifungal agents, isotonic and absorption delaying agents, buffers, carrier Solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid Solutions or suspensions; solid forms suitable for solution in, or Suspension in, liquid prior to injection can also be prepared. The preparation can also be emulsified.

In a preferred embodiment of the invention the nutraceutical or formulations thereof comprising at least one Core-1 positive microorganism or fraction thereof are applied to humans as a medical food.

The invention relates also to the nutraceutical or a formulation thereof which comprise at least one Core-1 positive microorganism or fraction thereof as a food-additive or as food or as a component thereof. Food in the context of invention is any substance consumed by living organisms, including liquid drinks. Food is the main source of energy and of nutrition for animals/humans, and is usually of animal or plant origin. The food is preferred vegan food which is generally all types of food that are free of animal products, like meat, milk or eggs. The food in the context of the invention is also preferred non-vegan food containing animal products. Food in the context of the invention is:

(i) any substance or product, whether processed, partially processed or unprocessed, intended to be, or reasonably expected to be ingested by humans whether of nutritional value or not;
(ii) water and other drinks;
(iii) chewing gum or candy products; and/or
(iv) articles and substances used as an ingredient or component in the preparation of food. Food in the context of the invention is traditionally obtained through farming, ranching, and fishing, with hunting, foraging and other methods of subsistence locally important for some populations, but minor for others. In the modern era, in developed nations, food supply is increasingly dependent upon agriculture, industrial farming, aquaculture and fish farming techniques which aim to maximise the amount of food produced, whilst minimising the cost. These include a reliance on mechanised tools which have been developed, from the threshing machine, seed drill, through to the tractor and combine, etc. These have been combined with the use of pesticides to promote high crop yields and combat those insects or mammals which reduce yield. More recently, there has been a growing trend towards more sustainable agricultural practices. This approach—which is partly fuelled by consumer demand—encourages biodiversity, local self-reliance and organic farming methods.

Types of manufactured food (food which contains at least one Core-1 positive microorganism or fraction thereof) in the context of the invention are:

drinks: beer, juice, soft drink, squash, wine, drinks containing milk, milk products or other alcoholic or non-alcoholic beverages, e.g. water, including just carbonated water, fruit juices and vegetable juices, soft drinks, aguas frescas, lemonade, cola, ginger ale, irn bru, root beer, sarsaparilla, cream soda, dandelion and burdock, squash, a fruit-flavoured syrup diluted with water, sports drinks, infusions, coffee, tea, dairy drinks, for example milk, yogurt drink, chocolate milk, milkshake, egg nog, almond milk, horchata, alcoholic beverages, cocktails—mixed drinks, hot beverages, for example hot chocolate, hot cider, cappuccino or pearl milk tea bread is a staple food for many nations, being made of risen dough of wheat or other cereal e.g. rye-wheat, toastbread (white bread), whole-grain, wheat-rye, white bread, multi-grain, rye, sunflower seed, pumpkin seed, pizza, chapatis, tortillas, baguettes, pitas, lavash, biscuits, pretzels, naan, bagels, purls, cake, pumpernickel, wholemeal bread, wheatgerm bread, wholegrain, granary bread and many other variations cakes and cookies, e.g. angelfood cake, apple cake, babka, buccellato, bundt cake, butter cake, butterfly cake, carrot cake, cheesecake, chocolate cake, christmas cake, chiffon cake, croquembouche, cupcake, devil's food cake, eccles cake, fairy cake, fruit cake, german chocolate cake, génoise cake, gingerbread, gob, gooey butter cake, hot milk cake, ice cream cake, jaffa cakes, leavened cake, mooncake, panettone, pineapple cake, pound cake, Queen Elisabeth cake, red bean cake, red velvet cake, sachertorte, simnel cake, spice cake, sponge cake, suncake, teacake, tarte tatin, vanilla slice or wedding cake cheese is a curdled milk product, of which many varieties exist e.g. sardo cheese, testouri cheese, bokmakiri cheese, kwaito cheese, wookie cheese, ackawi cheese, basket cheese, labneh, jibneh arabieh cheese, kenafa cheese, naboulsi cheese, paneer, affineur, bergkase, brimsen, dachsteiner, tyrolean grey cheese, luneberg, beauvoorde cheese, brussels' cheese, herve cheese, limburger cheese, maredsous cheese, passendale cheese, plateau de herve cheese, postel cheese, remedou cheese, danish blue cheese, danish tilsit or tilsit havarti, allgau emmental cheese, cambozola cheese, harzer cheese, limburger cheese, spundekas cheese, feta cheese, halloumi cheese or mozzarella cheese dessert is a course, usually sweet, and generally served after the main course, e.g. ice cream e.g. biscuits or cookies, cakes, crumbles, custards, fruit, gelatin desserts, ice creams, meringues, pastries, pies or tarts, puddings, sorbets, souffles or trifles french fries, chips e.g. potato chips or "crisps", tortilla chips or corn chips functional food (functional foods are called nutraceuticals, a portmanteau of nutrition and pharmaceutical, and can include food that has been genetically modified; the general category includes processed food made from functional food ingredients, or fortified with health-promoting additives, like "vitamin-enriched" products, and also, fresh foods (e g vegetables) that have specific claims attached)

jam and Jelly e.g. gooseberries-, redcurrants-, blackcurrants-, citrus fruits-, apples-, raspberries-, strawberries- and ripe blackberries-jam or royal jelly pasta e.g. shaped pasta, campanelle, casarecci, cavatelli, conchiglie, conchiglioni, farfalle, fiori, fusilli, fusilli bucati, gemelli, gigli, gramigna, lumache, lumaconi, maltagliati, orecchiette, pipe, quadrefiore, radiatori, ricciolini, rotelle, rotini, spiralini, strozzapreti, torchio or trofie pie e.g. bacon and egg pie, chicken and mushroom pie, corned beef pie, cornish pasty, fish pie, kalakukko, kulebjaka, pizza pie, pork pie, pot pie, scotch pie, shepherd's pie, stargazy pie, steak pie, steak and kidney pie, apple pie, banana cream pie, blackberry pie, blueberry pie, boston cream pie, bumbleberry pie, cherry pie, chocolate cream pie, coconut cream pie, custard pie, dutch apple pie, grape pie, key lime pie, lemon meringue pie, lemon pie, mixed berry pie, orange pie, peach pie, rhubarb pie, strawberry-rhubarb pie, strawberry pie or vinegar pie pizza e.g. the classic types and their respective toppings include: marinara or napoletana: tomato, olive oil, oregano, and garlic; margherita: tomato, olive oil, fresh basil leaves, and fior-di-latte (mozzarella made from cow's milk) or mozzarella di bufala; formaggio e pomodoro: tomato, olive oil, and grated parmesan cheese, basil leaves are optional; ripieno or calzone: fior-di-latte or mozzarella di bufala, sometimes also ricotta cheese, olive oil, and salami, other meats, vegetables, etc or stromboli: mozzarella, meat, vegetables, etc.

processed meats e.g. meat form amphibians, toad, artificial meat, imitation meat, in vitro meat, beef (bovines), buffalo, cattle, steak, veal (calves), yak, poultry (birds), chicken, duck, game birds, turkey, canids, seafood, fish, shark, crustaceans, crab, rabbit, mutton (sheep), lamb, pork (pigs), ham (haunch), bacon (cured strips of meat) or insects sandwiches e.g. aram sandwich, filled baguette, bacon butty, bun, burger, burrito, chip butty, club sandwich, grilled cheese, doner kebab, georgia hots, melt sandwich: tuna melt, etc., panini, steak sandwich, taco, tea sandwich, toasted sandwich, torta or wrap salad e.g. caesar salad, chef salad, cobb salad, greek salad, italian salad, mesclun salad, niçoise salad, bean salads like green bean salad, seven bean salad, chicken salad, egg salad, fruit salad (sliced, peeled fruits served in their own juices or with a dressing), larb, pasta salad, potato salad, somen salad, som tam, tabouli, waldorf salad or watergate salad sauce e.g. white sauces, mushroom sauce, sauce allemande, sauce américaine, sauce suprême, elouté brown sauces, bordelaise sauce, bourguignonne sauce, chateaubriand sauce, sauce africaine, sauce robert, béchamel sauce, mornay sauce, emulsified sauces, béarnaise sauce, hollandaise sauce, mayonnaise, tartar sauce, salad cream, butter sauces, beurre blanc, café de paris, sweet sauces, fish sauce, sambal, barbecue sauce, mole, tomato sauce or tzatziki sausage e.g. andouille, black pudding, blood sausage, boerewors, bratwurst, breakfast sausage, butifarra, chorizo, cumberland sausage, falukorv, fuet, haggis, kieska, kielbasa, kishka, kishke, knackwurst, kovbasa, landjager, linguiça, liver sausage, lukanka, mettwurst, mincemeat, mortadella, salami, soujouk, thvringer, weißwurst or white pudding snack food: confectionery, potato chips, chocolate, hardtack, candy bars, junk food e.g. boiled peanuts, candy bars, cheetos, chex mix, cookies, crackers, combos, fudge rounds, hula hoops, ice cream, moon pies, pirate's booty, popcorn, pork rinds, potato chips, pretzels, smart puffs, soft drinks, snow balls, student food, swiss cake rolls, tings, twinkies, veggie booty or zebra cakes soup e.g. dessert soups (ginataan, filipino soup made from coconut milk, milk, fruits and tapioca pearls); oshiruko, a Japanese azuki bean soup or fruit soups, winter melon soup, miso soup, pho, ramen, saimin, romanian potato soup, avgolemono, borscht, bouillabaisse, callaloo, cock-a-leekie, fanesca, gazpacho, lentil soup, minestrone, mulligatawny soup, scotch broth, snert, solyanka, tarator or waterzooi.

sugar or sugar products e.g. golden syrup, candies or chocolates.

yoghurt, curds, sour cream, whipped cream e.g. lassi, kefir, ayran, doogh or tarator.

drink powders or tablets e.g. vitamin drinks or mineral drinks capsules or tablets therapeutic foods (therapeutic foods are food designed for specific, usually nutritional, therapeutic purposes), functional food, medical food, enteral food, parenteral food, food of specified health use. Examples are Ensure, a fortified milkshake drink designed primarily for the elderly, and Plumpy'nut, a peanut based food designed for emergency feeding of severely malnourished children.

In another preferred embodiment the formulation of the invention is manufactured as an over the counter drug.

In another preferred embodiment the invention provides a method to induce or enhance a Core-1 specific immune response and/or to prevent or treat a Core-1 positive disease wherein said nutraceutical, said pharmaceutical composition, said Core-1 positive microorganism or said fraction thereof or said formulations comprising those is administered to a healthy individual.

In another preferred embodiment the invention provides a method to induce or enhance a Core-1 specific immune response and/or to prevent or treat a Core-1 positive disease wherein said nutraceutical, said pharmaceutical composition, said Core-1 positive microorganism or said fraction thereof or formulations comprising those is administered to an individual with a cancer, a tumor, at least one tumor or cancer cell, or at least one metastasis.

In particular, the nutraceutical, the pharmaceutical composition, the Core-1 positive microorganism or the fraction thereof or formulations comprising those can be used to induce an immune response against a cancer, tumor, cancer cell, or cancer cells or the metastasis derived therefrom, to induce an immune response which functions as an immune shield against tumor cells, a cancer, tumor, cancer cell, or cancer cells or the metastasis derived therefrom, to treat a tumor or cancer, metastases and/or metastasis, and/or to reduce or to prevent the occurance, spread or metastasis of a cancer, tumor, cancer cell, or cancer cells or the metastasis derived therefrom in healthy individuals or patients, respectively, each preferably comprising at least one Core-1 positive tumor cell, selected from a cancers, tumor or cancerous or tumorous diseases as described below or elsewhere herein. For example, the treatment is directed against primary tumors or cancers, minimal residual tumor or cancer diseases, relapses and/or metastases or parts thereof. The treatment of the tumors or cancers can also be effected as an adjuvant treatment. The nutraceutical, the pharmaceutical composition, the Core-1 positive microorganism or the fraction thereof or formulations comprising those can also be used in the prophylaxis of Core 1-positive tumor diseases, tumors or tumor cells. For example, prophylactic use is directed to the prophylaxis of tumors and metastases. These anti-tumor agents are administered in a suitable form according to well-known methods or as described elsewhere herein. A preferred variant is injection or administration of these anti-tumor agents or drugs orally, intravenously, locally in body cavities, e.g. intraperitoneal, intrarectal, intragastrointestinal routes, locally, e.g. directly in a tumor, in organs or lymphatic vessels (intranodal), but also subcutaneously, intradermally or on the skin, and intramuscularly. In a preferred fashion, types of administration can also be combined, in which case administration can be effected on different days of treatment or on one day of treatment as described in detail elsewhere herein. According to the invention, it is also possible to combine two or more of the inventive nutraceuticals, pharmaceutical compositions, Core-1 positive microorganisms or the fractions thereof or formulations comprising those as well as combine one or a combination of those with one or more drugs or tumor treatments, such as antibody therapies, chemotherapies or radiotherapies, suitably administered or applied at the same time or separately in time.

The cancer, tumor, tumor cells, cancer cells or the metastasis derived therefrom is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the cancer, tumor, tumor cells, cancer cells or the metastasis derived therefrom may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia, and/or metastases derived from anyone of these.

In a preferred embodiment the cancer, tumor, tumor cells, cancer cells or the metastasis derived therefrom is selected from the group of cancerous diseases or tumor diseases comprising at least one cell or preferably a significant number of cells or more preferably a majority of tumor cells which are positive for Core-1 in the definition according to the invention, selected from the group of: tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs, comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarian carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancies such as Kaposi sarcoma, AIDS-associated lymphomas, AIDS-associated lymphomas of the central nervous system, AIDS-associated Hodgkin disease, and AIDS-associated anogenital tumors, transplantation-related malignancy, metastasized tumors comprising brain metastases, lung metastases, liver cancer, liver metastases, bone metastases, pleural and pericardial metastases, and malignant ascites, and/or metastases derived from anyone of these.

In another preferred embodiment the cancer, tumor, tumor cells, cancer cells or the metastasis derived therefrom is selected from the group comprising cancerous diseases or tumor diseases such as mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In a further preferred embodiment the cancer, tumor, tumor cells, cancer cells or the metastasis derived therefrom is selected from the group of cancerous diseases or tumor diseases comprising at least one cell, preferably a significant number of cells, or more preferably a majority of tumor cells, which are positive for Core-1 in the definition according to the invention, selected from the group of mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In another preferred embodiment the invention provides a method to induce or enhance a Core-1 specific immune response and/or to prevent or treat a Core-1 positive disease, the cancer, a tumor, at least one tumor or cancer cell, or at least one metastasis comprise at least one cell which is Core-1 positive.

In further preferred embodiment the invention provides a method to induce or enhance a Core-1 specific immune response and/or to prevent or treat a Core-1 positive disease wherein the individual has a cancer, a tumor, at least one tumor or cancer cell, or at least one metastasis selected from the group of cancerous diseases or tumor diseases comprising mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In a study with healthy human volunteers serum antibody titers against Core-1 are determined by using at least one of the humoral immune response tests 1 to 6 determining the existing antibody response against Core-1 before first application of the nutraceutical and preferably volunteers with no or lower anti-Core-1 antibody levels are selected for the human trial. In those volunteers the nutraceutical comprising AG6 or MU1 or a placebo are orally given over a period of 3 to 30 weeks. Oral application of at least two different dosages is performed. Immune responses are followed by determination of the antibody and/or T cell response against Core-1 by using at least one of the humoral response tests 1 to 6 and/or cellular immune response tests 1 to 5 prior to and in suitably intervals after start of oral administration of the nutraceutical. There is a significant elevation of the antibody response against Core-1 and/or T cell response against Core-1 observed in a significant number of volunteers in the volunteer group that receives the nutraceutical in comparison to the titer before the study as positively tested by being positive in at least one of the humoral immune response tests 1 to 6 or in at least one of the cellular immune response tests 1 to 5. In the placebo group elevation of antibody or T-cell response against Core-1 is less frequently observed or to a lesser extent.

This shows the effectiveness of the nutraceutical in humans for building an immune response against Core-1 which functions as a shield against Core-1 positive cancer cells for the prevention, reduction or spread of Core-1 positive tumors or metastasis or its treatment.

In a study with human immuno competent cancer patients with Core-1 positive tumors serum antibody titers against Core-1 are determined by using at least one of the humoral immune response tests 1 to 6 determining the existing antibody response against Core-1 before first application of the pharmaceutical composition. The pharmaceutical composition comprising AG6 or MU1 or a placebo are administered several times orally, intra peritoneally or intra venously over a period of 3 to 70 weeks. Administration of at least two different suitable dosages is performed. Immune responses are followed by determination of the antibody and/or T cell response against Core-1 by using at least one of the humoral response tests 1 to 6 and/or cellular immune response tests 1 to 5 and/or the clinical response are followed by determination of time to progression, tumor free survival and/or tumor volumes and/or sites, each prior to and in suitably intervals after start of the administration of the pharmaceutical composition. There is a significant elevation of the antibody response against Core-1 or of the T cell response against Core-1 observed in a significant number of volunteers in the group that receives the formulation of the invention in comparison to the titer before the study as positively tested by being positive in at least one of the humoral immune response tests 1 to 6 or in at least one of the cellular immune response tests 1 to 5 and/or a partial or complete clinical response or a elongated time to progression or time of survival in a significant number of the patients receiving the formulation. In the placebo group elevation of antibody or T-cell response against Core-1 is less frequently observed or to a lesser extend and/or no or a significantly lower clinical response is observed.

This shows the effectiveness of the pharmaceutical composition in humans for building an immune response against Core-1 which functions as a shield against Core-1 positive cancer cells for the prevention, reduction or spread of the occurrence of Core-1 positive tumors or metastasis or its treatment.

The contacting of the Core-1 positive microorganism or fraction thereof within the body of the living organism (human/animal) initiates the production of antibodies binding Core-1, the Core-1 antigen, or Core-1 positive tumor cells. Surprisingly, antibodies against Core-1 function as an immunosurveillance mechanism against newly arising cancer cells.

F) Methods for Treating or Preventing a Gastrointestinal Disorder

In another preferred embodiment the invention provides a method for reducing or preventing the occurrence or spread of a gastrointestinal disorder or disease comprising administering in a human or an animal an effective amount of the nutraceutical, or the pharmaceutical formulation, or the Core-1 positive microorganism, or the fraction thereof, or formulations comprising those.

Effective amounts of the nutraceutical, or the pharmaceutical formulation, or the Core-1 positive microorganism, or the fraction thereof, or formulations comprising those are describes elsewhere herein.

In another preferred embodiment the invention provides a method for reducing or preventing the occurrence or spread of a gastrointestinal disorder or disease wherein said nutraceutical, or said pharmaceutical formulation, or said Core-1 positive microorganism, or said fraction thereof which are described elsewhere herein, or said formulations is or comprises at least one microorganism, lysate or fraction from a Core-1 positive microorganism recognized/bound by Nemod-TF1 or A78-G/A7 and Nemod-TF2.

In another preferred embodiment the invention provides a method for reducing or preventing the occurrence or spread of a gastrointestinal disorder or disease wherein said nutraceutical, or said pharmaceutical formulation, or said Core-1 positive microorganism, or said fraction thereof which are described elsewhere herein, or said formulations is or comprises at least one microorganism, lysate or fraction from the strain AG6(DSM 18726), MU1(DSM 18728) and LH2 (DSM 18727), more preferably from the strains AG6 or MU1, most preferably from the strain AG6.

In another preferred embodiment the invention provides a method to treat a gastrointestinal disorder or disease comprising administering in a human or an animal an effective amount of the nutraceutical, or the pharmaceutical formulation, or the Core-1 positive microorganism, or the fraction thereof, or formulations comprising those.

In another preferred embodiment the invention provides a method to treat a gastrointestinal disorder or disease wherein the gastrointestinal disease is an inflammatory bowl disease or a functional bowl disorder.

The invention provides a method for reducing or preferably for preventing the occurrence of a gastrointestinal disorder or disease, preferably an inflammatory bowl disease or a functional bowl disorders, comprising administering in a human or an animal an effective amount of the nutraceutical, or the pharmaceutical formulation, or the Core-1 positive microorganism, or the fraction thereof which are described elsewhere herein, or formulations comprising those, preferably in a healthy individual.

The invention provides a method for reducing or even further preferred for preventing the spread of a gastrointestinal disorder or disease, preferably an inflammatory bowl disease or a functional bowl disorders, comprising administering in a human or an animal an effective amount of the nutraceutical, or the pharmaceutical formulation, or the Core-1 positive microorganism, or the fraction thereof which are described elsewhere herein, or formulations comprising those.

The invention provides a method to treat a gastrointestinal disorder or disease, preferably an inflammatory bowl disease or a functional bowl disorders, comprising administering in a human or an animal an effective amount of the nutraceutical, or the pharmaceutical formulation, or the Core-1 positive microorganism, or the fraction thereof which are described elsewhere herein, or formulations comprising those.

In a preferred embodiment of the invention the nutraceutical, or the pharmaceutical formulation, or the Core-1 positive microorganism, or the fraction thereof which are described elsewhere herein, or formulations comprising those of above described methods comprise at least one microorganism, lysate or fraction from a Core-1 positive microorganism recognized/bound by Nemod-TF1 or A78-G/A7 and Nemod-TF2.

In a preferred embodiment the nutraceutical, or the pharmaceutical formulation, or the Core-1 positive microorganism, or the fraction thereof which are described elsewhere herein, or formulations comprising those of above described methods comprises at least one microorganism, lysate or fraction from the strain AG6 (DSM 18726), the strain MU1 (DSM 18728), and more preferably from the strain AG6.

Routes of administration, effective dosages, formulations are such as described elsewhere herein, preferably those as described within the methods for treating or preventing Core-1 positive diseases or tumors. In a preferred embodiment two doses per day comprising $10^9$ to $10^{12}$ Core-1 positive microorganism are administered over at least two weeks.

The gastrointestinal disorders are preferably selected from the group comprising functional bowel disorders and inflammatory bowel diseases; whereby the inflammatory bowel diseases are selected form the group comprising Crohn's disease, ileitis, and/or ulcerative colitis and the functional bowel disorders are selected form the group comprising gastro-esophageal reflux, dyspepsia, irritable bowel syndrome and/or functional abdominal pain. The gastrointestinal tract in the context of the invention consists of the following components: mouth (buccal cavity; includes salivary glands, mucosa, teeth and tongue), pharynx, esophagus and cardia, stomach, which includes the antrum and pylorus, bowel or intestine: small intestine, which has three parts: duodenum, jejunum, ileum; large intestine, which has three parts: cecum (the vermiform appendix is attached to the cecum); colon (ascending colon, transverse colon, descending colon and sigmoid flexure); rectum and/or anus.

In a study with human patients with Irritable Bowel Syndrome, Crohn's disease (CD), ileitis, or ulcerative colitis the nutraceutical or the pharmaceutical composition comprising AG6 or MU1 are administered orally or a placebo over a period of 3 to 30 weeks. Administration of at least two different suitable dosages is performed. Clinical responses such as reduction of bloating or flatulence, maintaining the remission in CD, improvement of quality of life, reduction of the time to or severity of a flare, decrease of diarrhea, maintenance of remission of pouchitis, induction or maintenance of the remission of active ulceratice colitis, are followed, respectively prior to and in suitably intervals after start of the administration of the nutraceutical or the pharmaceutical composition. There is a significant improvement of at least one of above symptoms or clinical responses observed in a significant number of patients that receives the nutraceutical or the pharmaceutical composition than those in the placebo group.

This shows the effectiveness of the nutraceutical or pharmaceutical composition in humans for the prevention, reduction, spread or treatment of gastrointestinal disorders.

G) Methods for Antibody Generation

The invention provides a method for generation of an anti Core-1 antibody or antibody composition or polyclonal serum comprising
 (a) bringing into contact the nutraceutical, the pharmaceutical composition, the Core-1 positive microorganism or fraction thereof with a human or an animal
 (b) inducing or enhancing a humoral immune response recognizing the Core-1 antigen and/or Core-1 positive tumor cell
 (c) isolating said anti Core-1 antibody or antibody composition.

In another preferred embodiment, the invention provides a method for generating a cell producing an anti Core-1 antibody or antibody composition comprising
 (a) bringing into contact the formulation, the Core-1 positive microorganism or fraction thereof of any of the preceeding claims with a human or animal
 (b) inducing or enhancing a humoral immune response against Core-1 (b) generating at least one cell producing said anti Core-1 antibody or antibody composition.

In another embodiment the invention provides a method for generating a cell producing an anti Core-1 antibody or antibody composition comprising
 (a) bringing into contact the nutraceutical, the pharmaceutical composition, the Core-1 positive microorganism or fraction thereof according to the invention with a human or animal
 (b) inducing or enhancing a humoral immune response against Core-1
 (c) generating at least one cell producing said anti Core-1 antibody or antibody composition.

Said final step (c) can be done by various methods such as
 (i) by immortalization of at least one cell producing the anti Core-1 antibody, preferably by fusion with an immortal cell line as performed in the hybridoma technology, or preferably by infection with a suitable virus such as Epstein Barr Virus (EBV), or by recombinant transfection with at least one gene which causes immortalization of the cell such as E1 from EBV; or (ii) by analysis of the peptide sequence of at least the variable regions of the anti Core-1 antibody or at least the binding region of the anti Core-1 antibody responsible for the specificity of the antibody and transformation of cells with DNA encoding the anti-Core 1 antibody as a whole antibody of any isotype or a fragment thereof or a fusion protein of a fragment of the anti-Core-1 antibody or the whole antibody with at least one other amino acid or polypeptide sequence.

Preferred are cells which are able to stably produce the antibodies meaning that the cells can be passaged over a suitable amount of cycles for production of the antibodies such as but not limited to hybridoma cells and otherwise immortalised cells or by recombinantly stably transformed cells such as but not limited to CHO, NS0, SP2, Y0, PerC.6, Hec293. However, also transient expression such as the expression in COS or Hec293 cells or B cells are an embodiment of the invention.

In another embodiment the invention provides a method for generation of an anti Core-1 monoclonal antibody further comprising
 (a) growing at least one cell of said cell producing the anti Core-1 antibody or antibody composition under suitable conditions
 (b) isolating said anti Core-1 antibody or antibody composition.

In a preferred embodiment of the invention said anti-Core-1 monoclonal antibody is isolated from the culture supernatant.

In a preferred embodiment of the invention said cell producing an anti-Core-1 monoclonal antibody is obtained by single cell cloning.

In another embodiment the invention provides a method for generation of a DNA sequence encoding the anti Core-1 antibody monoclonal antibody or fragment thereof comprising
 (a) bringing into contact the nutraceutical, the pharmaceutical composition, the Core-1 positive microorganism or fraction thereof with a human or animal
 (b) inducing or enhancing a humoral immune response against Core-1
 (c) isolating a cell or cell clone producing the anti Core-1 antibody
 (d) analysing the genetic material encoding the anti Core-1 antibody or fragment thereof or analysing the peptide sequences of the anti Core-1 antibody or fragments thereof.

In a preferred embodiment the invention provides the nucleic acid encoding the anti Core-1 antibody monoclonal antibody or a fragment thereof.

In another embodiment the invention provides the DNA sequence encoding the anti Core-1 monoclonal antibody or fragment thereof.

In a preferred embodiment the invention provides an anti Core-1 antibody or antibody composition or polyclonal serum, the anti Core-1 monoclonal antibody or at least one fragment thereof.

In another embodiment the invention provides an anti Core-1 monoclonal antibody or fragments thereof.

In another embodiment the invention provides a cell producing an anti Core-1 antibody or antibody composition or at least one fragment thereof.

In a further preferred embodiment the invention provides an anti Core-1 monoclonal antibody or the fragment thereof which is a humanized antibody or a human antibody from a transgenic mouse.

In a preferred embodiment the invention provides the cell producing an anti Core-1 antibody or antibody composition, the anti Core-1 monoclonal antibody or at least one fragment thereof as described above.

Said anti-core-1 antibody in sense of the invention can be any inducible antibody in a human or an animal recognizing the Core-1 antigen and/or a Core-1 positive tumor cell, preferably those antibodies which are Core-1 specific antibodies with the binding or specificity criteria described under definitions or elsewhere herein, more preferred herein are those antibodies which bind to TFa-PAA and less or not to TFb-PAA and bind to the trisaccharide Core-2 coupled to PAA and not to any of the X-PAA constructs listed in #list 2# and which binds to asialoglycophorin and not to glycophorin and which binds at least one tumor cell such as NM-D4, NM-F9 or ZR-75-1, and whereby the binding is periodate sensitive, and even more preferred is such an antibody which binds to TFa-PAA and less or not to TFb-PAA and not bind to the trisaccharide Core-2 coupled to PAA and not to any of the X-PAA constructs listed in #list 2 # and which binds to asialoglycophorin and not to glycophorin and which binds at least to the cells NM-D4, NM-F9 and ZR-75-1, and whereby the binding is periodate sensitive.

Said anti Core-1 antibody composition in sense of the invention can be any inducible mixture of antibodies in a human or an animal recognizing the Core-1 antigen and/or a core-1 positive tumor cell. Said anti Core-1 antibody or antibody composition in sense of the invention can be a single antibody or a mixture of antibodies, such as but not limited to a monoclonal antibody, a mixture of monoclonal antibodies, a polyclonal antibody mixture such as an antibody serum or a fraction thereof, or a mixture of at least one monoclonal antibody with a polyclonal antibody mixture. Said anti Core-1 antibody or antibody composition can be or comprise any inducible antibody format such as IgG, IgM, IgA, IgE, IgD or any fragment derived therefrom by technologies known to those skilled in the art such as but not limited to Fab, F(ab)2, single chain antibodies, single domain antibodies, multibodies, antibody fusion proteins, bispecific antibodies or antibody, and humanized or chimerized antibodies.

The anti-core-1 antibodies or antibody compositions generated by the methods of the invention have advantages over currently available Core-1 specific antibodies or Core-1 specific antibodies in antibody compositions which are at least one of the following features:

Anti Core-1 antibodies can be obtained which
 (i) have an antibody format different from IgM
 (ii) can be generated or isolated more quickly
 (iii) can be generated in higher amounts
 (iv) recognize more tumor cases
 (v) have a higher affinity
 (vi) show higher binding signals in immune tests, such as ELISA, Western Blot, flowcytometry, immune histochemistry or immunocytochemistry
 (vii) have a ADCC activity against at least one Core-1 positive tumor cell
 (viii) inhibit cell growth or proliferation in at least one Core-1 positive tumor cells when incubated with suitable amounts of the antibody
 (ix) induce cell death such as apoptosis in at least one Core-1 positive tumor cells incubated with suitable amounts of the antibody
 (x) are IgG.

Anti Core-1 antibody compositions can be obtained which
(i) comprise antibodies against Core-1 with an antibody format different from IgM
(ii) comprise IgG antibodies against Core-1
(iii) comprise IgG antibodies as a major anti Core-1 fraction of the antibodies
(iv) comprise higher amounts of antibodies recognizing the Core-1 antigen or a Core-positive tumor cell
(v) comprise higher titers of anti Core-1 antibodies
(vi) show higher binding signals in immune tests, such as ELISA, Western Blot, flow cytometry, immune histochemistry, immunocytochemistry or immunofluorescence
(vii) have a higher affinity
(viii) have a ADCC activity against at least one Core-1 positive tumor cell
(ix) inhibit cell growth or proliferation in at least one Core-1 positive tumor cells when incubated with suitable amounts of the antibody
(x) induce cell death such as apoptosis in at least one Core-1 positive tumor cells incubated with suitable amounts of the antibody Preferred are those anti Core-1 antibodies or antibody compositions which show at least two, more preferred those which show at least three, more preferred those which show at least four, more preferred those which show at least five, more preferred those which show at least six, more preferred those which show at least seven, more preferred those which show at least eight, more preferred those which show at least nine, more preferred those which show all of the above features.

In a preferred embodiment the anti Core-1 antibody is a monoclonal antibody.

In a preferred embodiment the anti Core-1 antibody mixture is a polyclonal antiserum.

Any animal or human can be brought into contact with the nutraceutical, the pharmaceutical composition, the Core-1 positive microorganism and/or fraction thereof, preferred are humans and mice, rats, rabbits, goats, camels, chicken, hamster, guinea pig or monkeys, even further preferred are animals which are known to those skilled in the art to be particularly suitable for generating an antibody response such as but not limited to rabbits, goats, rats, humans, chimpanzees and mice for polyclonal antibody sera and those which are known to those skilled in the art to be particularly suitable for generating monoclonal antibodies such as but not limited to mice, rats, human, further preferred are transgenic mice which carry at least parts of the human antibody genes and humans.

Bringing into contact means any method or route of administration described elsewhere herein for administering the nutraceutical, the pharmaceutical composition, the Core-1 positive microorganism and/or fraction thereof, which is able to induce a humoral response against Core-1. Additional adjuvants may be used for increasing the immunogenicity which are known to those skilled in the art. Preferred is the oral and the systemic administration and within the latter the intra veneous, the intra dermally, or the subcutaneous and even more the intra peritoneal administration.

The induction of the humoral immune response against Core-1 can be tested in the humoral immune response tests of the invention and at least one of the humoral immune response tests 1 to 6 has to be positive as described elsewhere herein, whereby in a preferred embodiment said antibodies gained from the serum, plasma or faeces also include those which are gained from cells producing antibodies against Core-1, such as B-cells, or immortalized B-cells, or cells recombinantly expressing Core-1 antibodies. These antibodies can be gained in a variety of ways known to those skilled in the art, in a preferred embodiment sera from blood, or fractions of a sera, or a serum or a fraction of a serum which was preabsorbed against suitable antigens such as microbial antigens negative for Core-1, preferably microorganism negative for Core-1, or antibodies from an antibody producing cell such as those described above in form of whole or fractionated cell supernatants or purified antibodies are used as said antibodies gained from the serum, plasma or faeces in at least one of the humoral immune test 1 to 6.

In a preferred embodiment the invention provides an anti Core-1 antibody or antibody composition or polyclonal serum, the anti Core-1 monoclonal antibody or at least one fragment thereof which is positive in at least five humoral immune response tests out of the humoral immune response test 1 to 6.

In a further preferred embodiment the invention provides an anti Core-1 antibody or antibody composition or polyclonal serum, the anti Core-1 monoclonal antibody or at least one fragment thereof which is preferably positive for humoral immune response tests 1 and 3, and more preferably for humoral immune response test 1, 2 and 3, and more preferably for humoral immune response test 1, 2, 3, and 4, and more preferably positive for humoral immune test 5 and most preferably positive for humoral immune test 6.

In a further preferred embodiment the invention provides an anti Core-1 antibody or antibody composition or polyclonal serum, the anti Core-1 monoclonal antibody or at least one fragment thereof which binds to TFa-PAA and less or not to TFb-PAA and not to any of the substances listed in #list 2# and which binds to asialoglycophorin and not to glycophorin and which binds at least to the cells NM-D4, NM-F9 and ZR-75-1, and whereby the binding is periodate sensitive, and which is or which originates from an IgG.

In a preferred embodiment the anti-Core-1 antibody is a monoclonal antibody or a fragment thereof which is Core-1 specifically binding to TFa-PAA and less or not to TFb-PAA and not to any of the substances listed in #list 2# and which binds to asialoglycophorin and not to glycophorin and which binds at least to the cells NM-D4, NM-F9 and ZR-75-1, and whereby the binding is periodate sensitive, and which is or originates from an IgG, more preferably the monoclonal antibody is a humanized antibody or a human antibody from a transgenic mouse or a human, most preferably the antibody shows an ADCC activity against Core-1 positive tumor cells.

Those skilled in the art are able to use the described methods for its purpose and are able to select and adopt suitable conditions to achieve the described purposes. Those skilled in the art are for example able to select suitable animals or humans and immunization conditions, to select suitable cells and to immortalize cells, to analyse the peptide sequence or DNA encoding the peptide sequence of an antibody or fragment or part thereof, to select suitable antibody formats or fragments and to generate suitable vectors for recombinant transfection of cells, to select and stably or transiently transform suitable cells for antibody production, to select and grow the cells or cell clone and isolate and purify antibodies or fragments thereof.

In another embodiment of the invention anti-Core-1 antibodies can be generated by using at least one of the Core-1 positive microorganisms or fragments thereof to isolate an anti Core-1 antibody or antibody mixture from an antibody library using technologies such as phage display or ribosomal display.

In another embodiment the invention refers to a method for generation of an anti Core-1 antibody or antibody composition comprising,
a.) bringing into contact the nutraceutical, the pharmaceutical composition, the Core-1 positive microorganism or fraction thereof with an antibody phage library (for example phagemid or phage vector based libraries) or antibody ribosomal display library derived from human or animal or chimaeric antibody
b.) isolating said anti Core-1 antibody or antibody composition by its binding to said nutraceutical, the pharmaceutical composition, the Core-1 positive microorganism or fraction thereof.

In a preferred embodiment the synthetic antibody libraries of human, humanized, chimaeric, or animal antibody genes is used. In a more preferred embodiment the libraries are constructed from the repertoire of at least one animal and/or a human which was immunized by the nutraceutical, the pharmaceutical composition, the Core-1 positive microorganism and/or fraction. Those skilled in the art know how to construct these libraries and to use those libraries for generating or selecting specific antibodies.

Preferred embodiments of the invention are described in the examples.

H) Generation of Core-1 Specific Dendritic Cells, T Cells, T Cell Clones and T Cell Lines Surprisingly, the provided Core-1 positive microorganisms of the invention were also capable of activating human T cells in a Core-1 specific manner when presented by human dendritic cells (in vitro). There are no reports documenting a cellular immune response and especially a cytotoxic cellular immune response against a carbohydrate tumor antigen and especially a small non-charged carbohydrate such as Core-1. There are also no reports of presentation of human tumor carbohydrate antigens on human dendritic cells, the key regulators of the immune system, and especially not of human carbohydrate structures originating from microorganism. In contrast, the general scientific opinion is that humans do not develop a carbohydrate specific cellular immune response and especially not against carbohydrate tumor antigens. The Core-1 positive microorganisms of this invention were processed and presented by human dendritic cells and those respectively-loaded dendritic cells could be used to activate primary human T cells specifically against Core-1. Those T cells generated by sensitization with lysates from Core-1 positive bacteria of the present invention showed strong immune responses after restimulation with Core-1 positive human tumor cell lysates as documented by secretion of cytokines which document the specific T cell response and especially the cytotoxic T cell response.

It is surprising that it is possible to load human dendritic cells with a Core-1 positive microorganism according to the present invention or with Core-1 carrying molecules in general and achieve a Core-1 specific activation of human T cells. It is even more surprising that immune cells activated by human dendritic cells loaded with said Core-1 positive microorganisms can be further activated or restimulated using human dendritic cells loaded with the Core-1 carrying molecules such as lysates from NM-D4 or NM-F9 or asialoglycophorin showing that (i) Core-1 specific T cells can be activated by Core-1 positive microorganism, and that (ii) this immune responses comprises Core-1 specific T cells which can be further activated or restimulated by DC loaded with Core-1 carrying molecules. It is further surprising that the Core-1 structure can be detected by Core-specific antibodies on DC loaded with Core-1 positive microorganism as well as on DC loaded with asialoglycophorin. It is further surprising that not only the secretion of GM-CSF and the proliferation of T-cells can be potently induced using Core-1 positive microorganism of the invention but also the secretion of INFgamma (interferon gamma) and even more surprising TNFalpha (tumor necrosis factor alpha) showing the activation of Core-1 specific cytotoxic T-cells. It is further surprising that the Core-1 specific T-cells can be restimulated, preferably for at least 4 times in vitro which indicates a strong and specific cellular immune response against the tumor antigen and tumor mediated by the T-cells. These immune responses are a proof to those skilled in the art that the Core-1 positive microorganism provided by the present invention is able to induce a potent anti-Core-1 cellular immune response in humans.

The invention accordingly also provides a method for generation of a functional dendritic cell against Core-1 comprising bringing into contact a suitable amount of a dendritic cell or a mixture of dendritic cells or a mixture of cells comprising at least one dendritic cell with a suitable amount of at least one Core-1 positive microorganism, lysate, or fraction thereof, as described elsewhere herein, or a Core-1 carrying molecule or Core-1 positive tumor cell, lysate or fraction thereof, for a suitable time under suitable conditions to generate at least one functional dendritic cell against Core-1.

The invention provides a method for generation of a functional dendritic cell against Core-1 comprising bringing into contact a suitable amount of a dendritic cell or a mixture of dendritic cells or a mixture of cells comprising at least one dendritic cell with a suitable amount of at least one Core-1 positive microorganism, lysate, or fraction thereof, as described elsewhere herein for a suitable time under suitable conditions to generate at least one functional dendritic cell loaded with Core-1.

The invention provides a method for generation of a functional dendritic cell against Core-1 comprising bringing into contact a suitable amount of a dendritic cell or a mixture of dendritic cells or a mixture of cells comprising at least one dendritic cell with a suitable amount of at least one Core-1 carrying molecule or Core-1 positive tumor cell, lysate or fraction thereof, as described elsewhere herein, for a suitable time under suitable conditions to generate at least one functional dendritic cell loaded with Core-1.

Said functional dendritic cell against Core-1 is a dendritic cell or a mixture of dendritic cells which activates at least one T cell against Core-1 which can preferentially be tested by a cellular immune response test of the invention and is positive against Core-1 in at least one of the cellular immune response tests described elsewhere herein. In a preferred embodiment the functional dendritic cell is presenting the Core-1 on its surface and can be detected by a Core-1 specific antibody as described for example in the cellular immune response test 4. In a preferred embodiment of the invention the functional dendritic cell against Core-1 was obtained by bringing into contact an immature dendritic cell or a mixture of immature dendritic cells or a mixture of dendritic cells comprising at least one immature dendritic cell with a suitable amount of at least one Core-1 positive microorganism, lysate, or fraction thereof, as described elsewhere herein for a suitable time and under suitable conditions to mature said dendritic cell using suitable conditions as described elsewhere herein and as known to those skilled in the art, comprising for example the molecules TNFalpha (tumor necrosis factor alpha), LPS (Lipopolysaccharide) or BCG (Bacille Calmette Guerin), INFgamma (interferon gamma), dexamethasone, and/or TGFbeta (transforming growth factor beta), to a functional dendritic cell loaded with Core-1. In a preferred embodiment of the invention the dendritic cell is derived from MUTZ-3 or NemodDC (obtainable from Glycotope GmbH Berlin, Germamy; www.glycotope.com), and further preferred immature dendritic cells were generated from MUTZ-3 cells or NemodDC under suitable conditions comprising using IL-4 and GM-CSF typically for about one week, the resulting immature dendritic cells or iNMDC are brought into contact with said suitable amount of at least one Core-1 positive microorganism, lysate, or fraction thereof, the cells are matured using a suitable conditions comprising for example TNFalpha, LPS, BCG, INFgamma, dexamethasone, or TGFbeta, preferably TNFalpha, typically for about one to two days resulting in mature dendritic cells loaded with Core-1 corresponding to said functional dendritic cell against Core-1.

Preferred Embodiments of the Invention are Described in the Examples.

The invention provides a method for generation of an activated T cell or T cells against Core-1 comprising
- (a) bringing into contact a suitable amount of functional dendritic cells or a mixture of cells containing at least one functional dendritic cell, loaded with suitable amounts of the Core-1 positive microorganism, lysate or fraction thereof with at least one T cell or T cells
- (b) cultivation of said T cell or T cells together with said loaded functional dendritic cells for a suitable time under suitable conditions to activate or prime a T cell or T cells against Core-1.

The invention provides a method for generation of an activated T cell or T cells against Core-1
- (a) bringing into contact a suitable amount of functional dendritic cells or a mixture of cells containing at least one functional dendritic cell loaded with suitable amounts of a Core-1 carrying molecule or Core-1 positive tumor cell, lysate or fraction thereof with a T cell or T cells or a mixture of cells containing at least one T cell
- (b) cultivation of said T cell or T cells or mixture of cells containing at least one T cell together with said loaded functional dendritic cells for a suitable time under suitable conditions to activate or prime a T cell or T cells against Core-1.

In a preferred embodiment the invention provides a method for generation of an activated T cell or T cells against Core-1 comprising
- a) bringing into contact suitable amounts of functional dendritic cells loaded with suitable amounts of the Core-1 positive microorganism, lysate or fraction thereof with a T cell or T cells
- (b) cultivation of said T cell or T cells together with said loaded functional dendritic cells for a suitable time under suitable conditions to activate or prime a T cell or T cells against Core-1
- (c) adding functional dendritic cells loaded with a Core-1 carrying molecule or Core-1 positive tumor cell, lysate or fraction thereof for restimulation
- (d) cultivation for appropriate times and conditions.

In a preferred embodiment the invention provides a method for generation of an activated T cell or T cells against Core-1 comprising
- a) bringing into contact a suitable amount of at least one functional dendritic cell loaded with a suitable amount of at least one Core-1 positive microorganism, lysate or fraction thereof with a suitable amount of at least one T cell or a mixture of T cells or a mixture of cells comprising at least one T cell
- b) cultivating said T cell or mixture of T cells or mixture of cells comprising at least one T cell with said loaded functional dendritic cells for a suitable time under suitable conditions to activate or prime a T cell or T cells against Core-1.

In a preferred embodiment the invention provides a method for generation of an activated T cell or T cells against Core-1 comprising
- a) bringing into contact a suitable amount of at least one functional dendritic cell loaded with a suitable amount of at least one Core-1 carrying molecule or Core-1 positive tumor cell, lysate or fraction thereof with a suitable amount of at least one T cell or a mixture of T cells or a mixture of cells comprising at least one T cell
- b) cultivating said T cell or mixture of T cells or mixture of cells comprising at least one T cell with said loaded functional dendritic cells for a suitable time under suitable conditions to activate or prime a T cell or T cells against Core-1.

In another preferred embodiment the invention provides a method for generation of an activated T cell or T cells against Core-1 comprising the steps (a) and (b) of the preceeding methods and subsequently comprising,
- (c) adding a suitable amount of at least one functional dendritic cell loaded with a suitable amount of at least one Core-1 carrying molecule or Core-1 positive tumor cell, lysate or fraction thereof for restimulation;
- or adding a suitable amount of at least one functional dendritic cell loaded with a suitable amount of at least one Core-1 positive microorganism, lysate or fraction thereof for restimulation; and
- (d) cultivation for an appropriate time and under an appropriate condition In another preferred embodiment the invention provides a method for generation of a T cell line against Core-1 comprising the steps (a), (b), (c) and (d) of the preceeding method and subsequently comprising at least one further round of restimulation whereby one round of restimulation comprises either steps (e) and (f) or steps (g) and (h), with
- (e) adding a suitable amount of at least one functional dendritic cell loaded with a suitable amount of at least one Core-1 carrying molecule or Core-1 positive tumor cell, lysate or fraction thereof for restimulation;
- (f) cultivation for an appropriate time and under an appropriate condition and
- (g) adding a suitable amount of at least one functional dendritic cell loaded with a suitable amount of at least one Core-1 positive microorganism, lysate or fraction thereof for restimulation
- (h) cultivation for an appropriate time and under an appropriate condition In a further preferred embodiment the invention provides a method for generation of a T cell line against Core-1 additionally comprising two further rounds of said round of restimulation. In a more preferred embodiment the invention provides a method for generation of a T cell line against Core-1 comprising three further rounds of said round of restimulation. In an even more preferred embodiment the invention provides a method for generation of a T cell line against Core-1 comprising five further rounds of said round of restimulation.

In a further preferred embodiment the invention provides a method for generation of a T cell clone against Core-1 wherein an additional step of cloning the cells at least before one round of said rounds of restimulation is performed.

In a preferred embodiment the activated T cell or T cells is a T cell line against Core-1, whereby preferably (c) and (d) which correspond to one round of restimulation is performed two times, more preferably three times, more preferably 4 times, and most preferably a T cell line for which more than 4 rounds of restimulation are performed.

In a preferred embodiment the activated T cell or T cells is a T cell clone against Core-1, whereby preferably (c) and (d) which correspond to one round of restimulation is performed two times, more preferably three times, more preferably 4 times, and most preferably a T cell line for which more than 4 rounds of restimulation are performed, and the cells are at least once cloned, for example by single cell dilution, before restimulation.

In a further preferred embodiment the invention provides a method for generation of a T cell clone against Core-1 wherein said functional dendritic cell is a mature dendritic cell.

In a further preferred embodiment the invention provides a method for generation of a T cell clone against Core-1 wherein said functional dendritic cell and the T cell or T cells are human cells.

In a further preferred embodiment the invention provides a method for generation of an activated T cell, T cell line or T cell clone against Core-1 wherein said functional dendritic cell is derived from MUTZ-3 [patent applications 10139428.4 (DE), PCT/EP02/09260, 02758474.7 (EP), U.S. Ser. No. 10/486,966, CA2,457,287, DE10139428A1, WO2003/023023A1, EP01419240, US20040265998, CA2457287] such as Nemod-DC (obtainable from Glycotope GmbH Berlin, Germany, www.glycotope.com).

In a further preferred embodiment the invention provides a method for generation of an activated T cell, T cell line or T cell clone against Core-1 wherein said functional dendritic cell and the T cell or T cells are matched in at least one MHC class molecule.

In a preferred embodiment the invention provides a method for generation of an activated T cell, T cells, T cell clone or T cell line against Core-1 comprising
  a. bringing into contact a suitable amount of at least one functional dendritic cell against Core-1 as described elsewhere herein with a suitable amount of at least one T cell or a mixture of T cells or a mixture of cells comprising at least one T cell; and
  b. cultivation of said T cell or mixture of T cells together with said loaded functional dendritic cells for a suitable time under a suitable condition to activate or prime a T cell or T cells against Core-1.

In a preferred embodiment the invention provides a method for generation of an activated T cell, T cells, T cell clone or T cell line against Core-1, comprising either
  a) bringing into contact a suitable amount of at least one functional dendritic cell against Core-1 loaded with said Core-1 positive microorganism, lysate, or fraction thereof, with a suitable amount of at least one T cell or a mixture of T cells or a mixture of cells comprising at least one T cell; and
  b) cultivation of said T cell or mixture of T cells together with said loaded functional dendritic cells for a suitable time under a suitable condition to activate or prime a T cell or T cells against Core-1; and
  c) adding a suitable amount of at least one functional dendritic cell loaded with said Core-1 carrying molecule or Core-1 positive tumor cell, lysate or fraction thereof for restimulation; and
  d) cultivation for an appropriate time and under an appropriate condition;
or
  a) bringing into contact a suitable amount of at least one functional dendritic cell against Core-1 loaded with said Core-1 carrying molecule or Core-1 positive tumor cell, lysate or fraction thereof with a suitable amount of at least one T cell or a mixture of T cells or a mixture of cells comprising at least one T cell; and
  b) cultivation of said T cell or mixture of T cells together with said loaded functional dendritic cells for a suitable time under a suitable condition to activate or prime a T cell or T cells against Core-1; and
  c) adding a suitable amount of at least one functional dendritic cell loaded with said Core-1 positive microorganism, lysate or fraction thereof of any of the preceeding claims for restimulation; and
  d) cultivation for an appropriate time and under an appropriate condition.

Preferred Embodiments of the Invention are Described in the Examples.

In a further preferred embodiment the invention provides the activated T cell or T cells against Core-1, the cell composition comprising T cells against Core-1, the T cell line against Core-1, or the T cell clone against Core-1 as described above.

In a further preferred embodiment the invention provides the activated T cell or T cells against Core-1, the cell composition comprising T cells against Core-1, the T cell line against Core-1, or the T cell clone against Core-1 as described above comprising at least one CD4+ helper cell against Core-1

In a further preferred embodiment the invention provides the activated T cell or T cells against Core-1, the cell composition comprising T cells against Core-1, the T cell line against Core-1, or the T cell clone against Core-1 as described above comprising at least one cytotoxic T cell against Core-1.

In a further preferred embodiment the invention provides the activated T cell or T cells against Core-1, the cell composition comprising at least one T cell against Core-1, the T cell line against Core-1, or the T cell clone against Core-1 as described above which kills at least one Core-1 positive tumor cell or secretes molecules which mediate the killing of at least one tumor cell.

The activated T cell or T cells against Core-1, the cell composition comprising T cells against Core-1, the T cell line against Core-1, or the T cell clone against Core-1 of the invention which kill at least one Core-1 positive tumor cell or secrete molecules which mediate the killing of at least one tumor cell means that said cytotoxic T cell or cells against Core-1 kill a Core-1 positive tumor cell which can be determined either by using the according cellular immune response test described elsewhere herein measuring the secretion of INFgamma or TNFalpha or by a cytotoxicity test (such as cellular immune response test 5) wherein at least one labelled Core-1 positive tumor cell is lysed by said T cells principally known to those skilled in the art by using the T cells of the invention, for example CTL or Th1 response or by inducing a specific CD4 T helper response which mediates the activation of according humoral and cellular immune responses which result in the killing of at least one Core-1 positive tumor cell.

In a preferred embodiment the invention provides a method to treat a cancer patient comprising the administration of any of the activated T cell or T cells against Core-1, the cell composition comprising at least one T cell against Core-1, the T cell line against Core-1, or the T cell clone against Core-1 as described above or a composition comprising those.

In a preferred embodiment the invention provides a method to treat a cancer patient comprising the administration of a suitable amount of at least one of the functional dendritic cells against Core-1 as described above or a composition comprising those.

In a preferred embodiment the invention provides a method to treat a cancer patient wherein the patient has or had a cancer cell positive for Core-1.

In a more preferred embodiment the invention provides a method to treat a cancer patient wherein the functional dendritic cell is autologous. In another preferred embodiment the invention provides a method to treat a cancer patient wherein the functional dendritic cell is allogeneic origination from a donor.

In a preferred embodiment the invention provides a method to treat a cancer patient wherein the functional dendritic cell is derived from MUTZ-3.

In a preferred embodiment the invention provides a method to treat a cancer patient wherein the functional dendritic cell shares at least one MHC class molecule with the said patient.

The invention further provides a method to treat a cancer patient comprising the administration of any of the activated T cell or T cells against Core-1, the cell composition comprising at least one T cell against Core-1, the T cell line against Core-1, or the T cell clone against Core-1 described elsewhere herein or a composition comprising at least one those.

The invention further provides a method to treat a cancer patient comprising the administration of a suitable amount of at least one of the functional dendritic cells against Core-1 described elsewhere herein or a composition comprising those.

In a preferred embodiment of the invention at least one of said methods are used for a patient which has or had a cancer cell positive for Core-1 which is detectable by at least one Core-1 specific antibody and in its preferred embodiment described elsewhere herein. Further preferred are said methods wherein the functional dendritic cell is autologous, further preferred wherein the functional dendritic cell is allogeneic, further preferred when the functional dendritic cell originates from a donor, even more preferred when the functional dendritic cell is derived from MUTZ-3, even more preferred when any of the described functional dendritic cells shares at least one MHC class molecule with the individual it is administered to.

Those skilled in the art are able to perform the described task by using the herein disclosed methods and material. They can determine the best conditions to obtain those functional dendritic cells or T cells, the best route of administration, and/or suitable compositions comprising those and/or and are further described in preferred embodiments for generation and use in patent applications DE10139428A1, WO2003/023023A1, EP01419240, US20040265998, CA2457287.

Said activated T cell or T cells against Core-1 means that the generated T cell, T cells or cell composition comprising T cells is positive for at least one of the cellular immune tests of the invention, preferably for two, more preferably for three and most preferably for all 4. Preferably they comprise at least one CD4+ helper cell, and even more preferably at least one cytotoxic T cell able to kill at least one Core-1 positive tumor cell.

Said T cell or T cells used for bringing into contact is either at least one CD4+ and/or CD8+ T-cell which was isolated or enriched before by standard methods or is a cell composition which comprises at least one CD4+ and/or CD8+ T-cells.

Said lysate can be any lysate from a Core-1 positive microorganism or from a Core-1 positive tumor cell, respectively, such as but not limited to a lysate generated by repetitive freeze-thawing, by sonication, by mechanical force or by temperature induction.

For details on generation of Core-1 specific T cells see example 12.

A functional dendritic cell is a cell which can activate a T cell. Activation of a T cell means stimulation of proliferation and/or the conversion from a naïve to an active T cell. An active T cell secretes molecules which induce or help an immune response against the target Core-1 or tumor cells carrying Core-1, preferably those cytotoxic T cells which mediate the killing of a Core-1 positive tumor cell.

In a preferred embodiment said functional dendritic cell is a mature dendritic cell. More preferred the dendritic cell precursor from which the mature cell is derived from is obtained from a human, more preferably from a human from which the T cell or T cells were also obtained or which are matched in at least one MHC class molecule. In a more preferred embodiment the functional dendritic cell is derived from MUTZ-3, and even further preferred the MUTZ-3 cells or cells derived therefrom were differentiated using Il-4 and GM-CSF, loaded with appropriate amounts of the Core-1 positive microorganism, lysate or fraction thereof or the Core-1 carrying molecule or Core-1 positive tumor cell, lysate or fraction thereof, and further matured using for example suitable amounts of TNF-alpha to mature dendritic cells which correspond to the functional dendritic cells of the invention. In an even more preferred embodiment loaded functional dendritic cells are used together with PBMC (peripheral blood mononuclear cells) matched at least in MHC class I (HLA-A2) and (HLA-B44).

Those skilled in the art are able to determine the suitable conditions for generating functional dendritic cells loaded with the Core-1 positive microorganism, lysate or fraction thereof or the Core-1 carrying molecule or Core-1 positive tumor cell, lysate or fraction thereof, as well as suitable amounts and enrichment or purification procedures of a T cell or T cells and suitable conditions for culturing both cells together, such as comprising times, media, culture conditions and additional factors needed. Functional dendritic cells are typically differentiated from precursor cells within 6-10 days and loaded and matured for another 1 to 2 days. Cultivation of said T cell or T cells together with said loaded functional dendritic cells is typically for 7 to 10 days, and the addition and cultivation of loaded functional dendritic cells for restimulation typically for 7 to 9 days for each round of restimulation. Further details are shown in the example 12.

In another preferred embodiment different dendritic cells or functional dendritic cells from different sources, such as MUTZ-3 derived and donor derived dendritic cells from a human, are used for the different steps of priming and restimulation. Those skilled in the art are able to select the best combination.

The successful generation of a T cell, T cells or cell compositions comprising a T cell, T cells, CD4+ and/or CD8+ T cells against Core-1 can be tested by using at least one cellular immune response test of the invention. Further details are described elsewhere herein. Preferably at least two cellular immune response tests are positive, more preferably three, more preferably four and most preferably all five.

Description used here for the dendritic cells, their usage and suitable conditions and molecules for its use is also valid for the cellular immune response tests described elsewhere herein and vice versa and will be valid for all other parts of the invention.

In another embodiment the invention provides an activated T cell against Core-1.

In another embodiment the invention provides T cells comprising at least one activated T cell against Core-1.

In another embodiment the invention provides a T cell line against Core-1. In another embodiment the invention provides a T cell clone against Core-1.

In a preferred embodiment the T cell line or T cell clone was generated using MUTZ-3 derived functional dendritic cells loaded with the Core-1 positive microorganism, lysate or fraction thereof in combination with at least one round of restimulation with MUTZ-3 derived functional dendritic cells loaded with at least one Core-1 carrying molecule or Core-1 positive tumor cell, lysate or fraction thereof from a donor, and even more preferred from a tumor patient, and even more preferred from a tumor patient whose tumor is positive for binding with a Core-1 specific antibody.

The invention further provides a method for generating at least one activated T cell for use as a tumor therapy comprising administering the activated T cells against Core-1 positive tumor cells into a patient.

In a preferred embodiment the invention provides the functional dendritic cell against Core-1, the activated T cell or T cells against Core-1, the cell composition comprising T cells against Core-1, the T cell line against Core-1, or the T cell clone against Core-1 produced by a method as described above which induces a humoral and/or a cellular immune response against Core-1 positive cells and/or diseases.

In another preferred embodiment the formulation and/or of the functional dendritic cell and/or of the activated T cell, T cells, T cell clone or T cell line as described above is used for manufacturing a medicament and/or a nutraceutical for prophylaxis or therapy of a tumor by techniques known to those skilled in the art.

Preferred Embodiments of the Invention are Described in the Examples.

I) Kits

The invention relates also to a kit for inducing a specific humoral and/or cellular immune response in a human or animal against Core-1, the Core-1 antigen or Core-1 positive tumor cells, as described elsewhere herein, comprising the nutraceutical, or the pharmaceutical formulation, or the Core-1 positive microorganism, or the fraction thereof or or formulations comprising those, which are described elsewhere herein, and an information about the use of the kit.

In a more preferred embodiment said Core-1 specific immune response functions as a shield against Core-1 positive cancer cells.

The invention relates also to a kit for reducing or preventing the occurrence of a Core-1 positive disease or a tumor, preferably a Core-1 positive tumor, comprising the nutraceutical, or the pharmaceutical formulation, or the Core-1 positive microorganism, or the fraction thereof or formulations thereof which are described elsewhere herein, or formulations comprising those, and an information about the use of the kit.

The invention relates also to a kit for reducing or preventing the spread of a Core-1 positive disease or metastasis of a tumor, preferably of a Core-1 positive tumor, comprising the nutraceutical, or the pharmaceutical formulation, or the Core-1 positive microorganism, or the fraction thereof or formulations thereof which are described elsewhere herein, or formulations comprising those, and an information about the use of the kit.

The invention relates also to a kit to treat a Core-1 positive disease or a tumor, preferably a Core-1 positive tumor, comprising the nutraceutical, or the pharmaceutical formulation, or the Core-1 positive microorganism, or the fraction thereof or formulations thereof which are described elsewhere herein, or formulations comprising those, and an information about the use of the kit.

The invention relates also to a kit for the prevention and treatment of gastrointestinal disorders comprising the nutraceutical, or the pharmaceutical formulation, or the Core-1 positive microorganism, or the fraction thereof or formulations thereof which are described elsewhere herein, or formulations comprising those, and an information about the use of the kit.

The invention relates also to a kit to strengthen the immune system or to improve an immune response as described elsewhere herein comprising the nutraceutical, or the pharmaceutical formulation, or the Core-1 positive microorganism, or the fraction thereof or formulations thereof which are described elsewhere herein, or formulations comprising those, and an information about the use of the kit.

In a preferred embodiment of the invention the nutraceutical, or the pharmaceutical formulation, or the Core-1 positive microorganism, or the fraction thereof or formulations comprised in above described kits comprises at least one microorganism, lysate or fraction from a Core-1 positive microorganism bound by Nemod-TF1 and/or A78-G/A7 and Nemod-TF2, preferably from the strain AG6 (DSM 18726), the strain MU1 (DSM 18728), and/or the strain LH2 (DSM 18727), and more preferably from the strains AG6 and/or MU1, most preferably from strain AG6.

The kit may include information (instruction leaflet, internet address) explaining how to combine the components of the kit. Said information can also be related to a therapeutic scheme.

The invention relates also to a kit for the determination of the immune response against Core-1 comprising at least one of the herein described immune response tests against Core-1, preferably at least two, and more preferably at least one humoral and one cellular immune response test, comprising at least one of the material described under the according immune response test and an information about the use of the kit. In a preferred embodiment the kit additionally comprises according controls, and more preferably at least one of the nutraceutical, or the pharmaceutical formulation, or the Core-1 positive microorganism, or the fraction thereof or formulations thereof which are described elsewhere herein, or formulations comprising those.

The invention relates also to a kit for generating an anti Core-1 antibody or antibody composition as described elsewhere herein, comprising the nutraceutical, or the pharmaceutical formulation, or the Core-1 positive microorganism, or the fraction thereof or formulations thereof which are described elsewhere herein, or formulations comprising those, and an information about the use of the kit.

The invention relates also to a kit for generating at least one functional dendritic cell against Core-1, comprising the nutraceutical, or the pharmaceutical formulation, or the Core-1 positive microorganism, or the fraction thereof or formulations comprising those, and an information about the use of the kit.

In preferred embodiment the kit for generating at least one functional dendritic cell against Core-1 further comprises immature dendritic cells derived from a dendritic cell line such as but not limited to MUTZ-3 or Nemod-DC.

The invention relates also to a kit for generating at least one activated T cell, T cells, T cell clone or T cell line against Core-1, comprising the nutraceutical, or the pharmaceutical formulation, or the Core-1 positive microorganism, or the fraction thereof or formulations thereof, or formulations comprising those, and an information about the use of the kit.

The invention relates also to a kit for isolating a Core-1 positive microorganism or a fraction of a microorganism comprising at least one Core-1 molecule or structure, comprising at least one Core-1 specific antibody or an anti Core-1 antibody or antibody composition and an information about the use of the kit.

The invention relates also to a kit for identifying a Core-1 positive microorganism or a fraction of a microorganism comprising at least one Core-1 molecule or structure, comprising at least one Core-1 specific antibody or an anti Core-1 antibody or antibody composition and an information about the use of the kit.

The invention relates also to a kit for identifying or isolating a Core-1 positive microorganism or a fraction of a microorganism comprising at least one Core-1 molecule or structure or for identifying a suitable Core-1 positive microorganism for use as a component for nutraceuticals and pharmaceutical compositions of the invention comprising at least one Core-1 specific antibody or an anti Core-1 antibody or antibody composition and an information about the use of the kit.

In preferred embodiments of the invention the preferred Core-1 specific antibodies as described elsewhere herein are used, most preferably Nemod-TF1, Nemod-TF2 and/or A78-G/A7.

In a preferred embodiment the kit comprises at least one Core-1 positive microorganism, lysate or fraction thereof as a positive control.

Preferred Embodiments of the Invention are Described in the Examples

DEFINITIONS

In accordance with the present invention the term "nutraceutical" means any nutrient, composition of nutrients or formulation which can be taken orally by a human or animal such as but not limited to nutrients, nutrition additives, food additives, dietary supplements, medical food, clinical food, parenteral food, enteral food, food for special dietary use, food of specified health use or functional food that can be applied orally in different forms, such as but not limited to capsules, tablets, emulsions, powder, liquids, as well as in form of any food or drink or as a part of it. In special cases the nutraceutical can be given parenterally (parenteral food). The nutraceutical can be given by itself or mixed with at least one other ingredient. The nutraceutical by itself or its mixture with at least one other ingredient can be given by itself or mixed into a food or a drink. The term nutraceutical also means any food, beverage, capsule, tablet, emulsion, powder, or liquid.

In accordance with the present invention the term "pharmaceutical composition" means any composition which can be used as a drug, or a pharmaceutical, or a biological, or is a component of a drug or a pharmaceutical or a biological.

In accordance with the present invention the term "Core-1" means the carbohydrate structure galactose beta 1-3 linked to N-Acetyl-galactosamine alpha 1-linked (Gal beta1-3GalNAc alpha 1; TF alpha, TFa). On the protein or polypeptide Core-1 is covalently linked via an O-glycosidic linkage to serine or threonine amino acids (Gal beta1-3GalNAc alpha 1-O-Ser/Thr). Core-1 can also be linked via various linkers and various densities to natural or synthetic carriers, such as polyacrylamide (herein also called PAA), or other molecules such as chromatographic bed materials (e.g. sepharose), biotin or proteins, such as bovine serum albumin (BSA), ovalbumin (Ova), human serum albumin (HSA) or Keyhole limpet hemocyanin (KLH), toxins, toxoids, beads or nanoparticles. In the sense of this invention the term Core-1 means also Core-1 mimickry structures such as polypeptides, peptides, lipids or carbohydrates or combinations thereof having a chemical structure different from Core-1 but which have a conformational structure which can be recognized by Core-1 specific antibodies of the invention and are thus immunochemically identical to Core-1. The term Core-1 thus also comprises Core-1 in a beta anomeric configuration (see also FIG. 19).

In accordance with the present invention the term "Core-1 specific antibody" particularly means any antibody which specifically binds to Gal beta1-3GalNAc alpha1-PAA (TFa-PAA, TFalpha-PAA, Core-1-PAA) but not to any of the substances of #list 1#.

list1#

GlcNAcβ1-2Galβ1-3GalNAcalpha-PAA (GlcNAcβ1-2' TF)

Fucalpha1-2 Galβ1-3GalNAcalpha-PAA (H type 3)

GalNAcalpha1-3-Galβ3-PAA ($A_{di}$)

Galalpha1-3-GalNAcβ-PAA ($T_{alpha\beta}$)

which were obtained from Lectinity holdings, Inc.

Alternatively all structures can be generated by one skilled in the art, who also can select another suitable polyacrylamide for conjugation or another suitable carrier molecule as well as the suitable conjugation methods for coupling of the according carbohydrate structures and the synthesis of the necessary intermediates.

A Core-1 specific antibody is e.g.

an antibody which binds to asialoglycophorin (carrying Core-1) but not glycophorin (not carrying Core-1), and this binding is periodate sensitive, more preferably any antibody which binds to TFa-PAA and less or not to TFb-PAA (Gal beta1-3GalNAc beta1-PAA) but not to any of the substances of #list 2#:

proteins:

Glycophorin

BSA (bovine serum albumin)

PAA-Conjugates:

Aminoglucitol

β-N-acetylneuraminic acid (beta-N-acetylneuraminic acid)

alpha-D-glucose (alpha-D-glucose)

β-D-glucose (beta-D-glucose)

alpha-D-galactose (alpha-D-galactose)

β-D-galactose (beta-D-galactose)

alpha-D-mannose (alpha-D-mannose)

alpha-D-mannose-6-phosphate (alpha-D-mannose-6-phosphate)

alpha-L-fucose (alpha-L-fucose)

β-N-acetyl-D-glucosamine (beta-N-acetyl-D-glucosamine)

alpha-N-acetyl-D-galactosamine (alpha-N-acetyl-D-galactosamine, Tn, $T_n$)

β-D-galactose-3-sulfate (beta-D-galactose-3-sulfate)
alpha-N-acetylneuraminic-acid (alpha-N-acetylneuraminic-acid)
β-N-acetyl-D-glucosamine-6-sulfate (beta-N-acetyl-D-glucosamine-6-sulfate) Lac-di-NAc (GalNAcβ1-4GlcNAcβ-, GalNAcbeta1-4GlcNAcbeta-)
GlcNAcβ3Gal (GlcNAcβ1-3Galβ-, GlcNAcbeta1-3Galbeta-)
Gala4GlcNAc (Galα1-4GlcNAcβ-, Galalpha1-4GlcNAcbeta)
Maltose
Galβ3Gal (Galβ1-3Galβ-, Galbeta1-3Galbeta)
Le$^c$(Galβ1-3GlcNAcβ-, Galbeta1-3GlcNAcbeta-)
Lac (Galβ1-4Glcβ3-, Galbeta1-4Glcbeta)
LacNAc (Galβ1-4GlcNAcβ-, Galbeta1-4GlcNAcbeta-)
Fuca3GlcNAc (Fucα1-3GlcNAcβ-, Fucalpha1-3GlcNAcbeta-)
Fuca4GlcNAc, (Fucα1-4GlcNAcβ-, Fucalpha1-4GlcNAcbeta-)
Fs-2 (GalNAcα1-3GalNAcβ-, GalNAcalpha1-3GalNAcbeta)
Core 5 (GalNAcα1-3GalNAcα-, GalNAcalpha1-3GalNAcalpha-)
Talphaalph3Galα1-3GalNAcα-, Galalpha1-3GalNAcalpha-, Talpha alpha)
Galalpha2Gal (Galα1-2Galβ-, Galalpha1-2Galbeta-, Gala2Gal)
SiaTn (Neu5Acα2-6GalNAcα-; Neu5Acalpha2-6GalNAcalpha sTn)
3'-su-LacNAc (3'-O-su-LacNAcβ-, 3'-O-su-LacNAcbeta-)
3'-su-Le$^c$(3'-O-su-Galβ1-3GlcNAcβ-, 3'-O-su-Galbeta1-3GlcNAcbeta)
melibiose (Galα1-6Glcβ-, Galalpha1-6Glcbeta-)
(Sia)$_2$ (Neu5Acα2-8Neu5Aca-, Neu5Acalpha2-8Neu5Acalpha)
GalβGal (Galβ1-2Galβ-, Galbeta1-2Galbeta-, Galbeta2Gal-)
6-O-su-LacNAc (Galβ1-4(6-O-su)GlcNAcβ-, Galbeta1-4(6-O-su)GlcNAcbeta-)
A$_{di}$, (GalNAcα1-3Galβ-, GalNAcalpha1-3Galbeta-)
B$_{di}$ (Galα1-3Galβ-, Galalpha1-3Galbeta)
6'-O-su-LacNAc (6'-su-LacNAcβ-, 6'-su-LacNAcbeta-)
H$_{di}$ (Fucα1-2Galβ-, Fucalpha1-2Galbeta)
3'-O-su-TF (3'-O-su-Galβ1-3GalNAcα-, 3'-O-su-Galbeta1-3GalNAcalpha-)
di-GalNAcβ (GalNAcβ1-3GalNAcβ-, GalNAcbeta1-3GalNAcbeta)
core 3 (GlcNAcβi-3GalNAcα-, GlcNAcbeta1-3GalNAcalpha)
core 6 (GlcNAcβ1-6GalNAcα-, GlcNAcbeta1-6GalNAcalpha)
GA1, GgOse3 (GalNAcβ1-4Galβ1-4Glcβ3-, GalNAcbeta1-4Galbeta1-4Glcbeta)
Galα-3'Lac (Galα1-3Galβ1-4Glcβ-, Galalpha1-3Galbeta1-4Glcbeta)
GlcNAcβ1-2' TF (GlcNAcbeta1-2Galbeta1-3GalNAcalpha-)
Man$_3$ (Manα1-6 Manα-Manα1-3)
3'SLN (Neu5Acalpha2-3Galbeta1-4GlcNAcbeta-)
Pk (Gb3, GbOse3,Galα1-4Galβ1-4Glcβ-)
Le$^a$ (Fucα1-4 GlcNAcβ-Galβ1-3)
Le$^d$ (H type 1, Fucα1-2Galβ1-3GlcNAcβ-)
Le$^x$ (Fucα1-3 GlcNAcβ-Galβ1-4)
3'-SiaLe$^c$ (Neu5Acα2-3Galβ1-3GlcNAcβ-)
H type 3 (Fucα1-2Galβ1-3GalNAcα-)
3'-SL (Neu5Acα2-3Galβ1-4Glcβ-)

6'-SL (Neu5Acα2-6Galβ1-4Glcβ-)
3'-O-su-Le$^a$ (Fucα1-4 GlcNAcβ-O-su-3Galβ1-3)
3'-O-su-Lex (Fucα1-3 GlcNAcβ-O-su-3Galβ1-4)
Gala 1-3'LacNAc (Galα1-3Galβ1-4GlcNAcβ-)
(Sia)$_3$ (Neu5Acα2-8Neu5Acα2-8Neu5Acα2-)
GlcNAcβ1-3'TF (GlcNAcβ1-3Galβ1-3GalNAcα-)
A$_{tri}$ (Fucα1-2 Galβ-GalNAcα1-3 which were obtained from Lectinity holdings, Inc.

Alternatively all structures can be generated by one skilled in the art, who also can select another suitable polyacrylamide for conjugation or another suitable carrier molecule as well as the suitable conjugation methods for coupling of the according carbohydrate structures and the synthesis of the necessary intermediates.

even more preferably an antibody selected from the following antibodies: HB-T1 (IgM) [obtainable from DakoCytomation GmbH, Hamburg; Giuffré G, Vitarelli E, Tuccari G, Ponz de Leon M, Barresi G: Detection of Tn, sialosyl-Tn and T antigens in hereditary nonpolyposis colorectal cancer. Virchows Arch 429:345-352 (1996)], HH8 (IgM) [Clausen H, Stroud M, Parker J, Springer G, Hakomori S: Monoclonal antibodies directed to the blood group A associated structure, galactosyl-A: specificity and relation to the Thomsen-Friedenreich antigen. Mol Immunol 25:199-204 (1988)], A78-G/A7 [Glycotope GmbH, Berlin; Karsten U, Butschak G, Cao Y, Goletz S, Hanisch FG. A new monoclonal antibody (A78-G/A7) to the Thomsen-Friedenreich pan-tumor antigen. Hybridoma 1995 February; 14(1):37-44], Nemod-TF1 [Glycotope GmbH, Berlin; Goletz S, Cao Y, Danielczyk A, Ravn P, Schoeber U, Karsten U. Thomsen-Friedenreich antigen: the "hidden" tumor antigen. Adv Exp Med Biol. 2003; 535:147-62], or Nemod-TF2 [Glycotope GmbH, Berlin; Goletz S, Cao Y, Danielczyk A, Ravn P, Schoeber U, Karsten U. Thomsen-Friedenreich antigen: the "hidden" tumor antigen. Adv Exp Med Biol. 2003; 535:147-62], even more preferably an antibody which binds to TFa-PAA and less or not to TFb-PAA and not to any of the proteins and X-PAA constructs listed in #list2 # and which binds to asialoglycophorin and not to glycophorin and this binding is periodate sensitive, even more preferably any antibody which binds to TFa-PAA and less or not to TFb-PAA and not to any of the proteins and X-PAA constructs listed in #list 2 # and which binds to asialoglycophorin and not to glycophorin and which binds to at least one human tumor cell line out of NM-D4 [DSM ACC2605], NM-F9 [DSM ACC2606], ZR-75-1, CAMA-1, KG-1, or A-204, and whereby the binding is periodate sensitive, such as NEMOD-TF2 or A78-G/A7, more preferably is any antibody with any of the above binding characteristics but which does not bind to the trisaccharide Core-2 coupled to PAA, such as e.g. NEMOD-TF1, most preferably any antibody which binds to TFa-PAA and less or not to TFb-PAA and not bind to the trisaccharide Core-2 coupled to PAA and not to any of the proteins and X-PAA constructs listed in #list 2 # and which binds to asialoglycophorin and not to glycophorin and which binds at least to the cells NM-D4, NM-F9 [DSM ACC2606] and ZR-75-1, and whereby the binding is periodate sensitive, such as NEMOD-TF1.

Said Core-1 specific antibody can be a whole antibody from any animal or human such as murine, rat, human, camel, humanized or chimaeric antibody of different antibody classes such as but not limited to IgM, IgG, IgG1, IgG2, IgG3, IgG4, IgA, IgE, IgD or any fragment of an antibody as long as it comprises the binding specificity against Core-1, such as Fab, F(ab)2, single chain Fv, or single domain antibodies. Those antibodies can also contain at least one additional amino acid or mutations or polypeptide sequences, such as tags, linkers or multimerization domains and they can also originate from other sources than animals, such plants and such as selection from synthetic antibody libraries using for example phage display or ribosome display or by recombinant construction.

The periodate treatment to test the periodate sensitivity of the binding of a Core-1 specific antibody towards TFa-PAA; TFb-PAA (TFβ-PAA, TF beta-PAA) or other PAA-constructs (X-PAA), asialoglycophorin, or tumor cells are according to Woodward et al. [Woodward M P et al., (1985) J. Immunol. Methods 78: 143-153] and are described in detail in the examples. Those skilled in the art may adopt the technology and optimise the conditions to alternative methods described elsewhere herein.

In accordance with the present invention the term "periodate sensitivity" means that the binding of an antibody to an antigen or cell is less when this antigen or cell was treated with periodate than its binding to the same antigen or cell which was treated without periodate as is e.g. described in detail under periodate treatment in example 9. To determine the periodate sensitivity of an antibody for its Core-1 specificity the periodate sensitivity of its binding is preferably tested with TFa-PAA, TFb-PAA, asialoglycophorin, NM-D4 [03018576.3 (EP), PCT/EP2004/009281, WO2005/017130 A2, EP1654353]) and/or other tumor cells. Preferably the reduced binding after periodate treatment of the antigen or cell is less than 50% of the non-periodate treated counterpart, and even more preferred less than 20% of the binding to the same antigen or cell which was treated without periodate.

Preferred Core-1 specific antibodies according to the invention are NEMOD-TF1, NEMOD-TF2, A78-G/A7, HB-T1, HH8 preferred antibodies are NEMOD-TF1, NEMOD-TF2, A78-G/A7, and HH8, more preferred are NEMOD-TF1, NEMOD-TF2, and A78-G/A7, even more preferred NEMOD-TF1 and NEMOD-TF2, and most preferred NEMOD-TF1. NEMOD-TF1 and NEMOD-TF2 are also described in DE 10256900.2, PCT/DE2003/003994, EP 03788853.4, U.S. Ser. No. 10/536,834. NEMOD-TF1, NEMOD-TF2, A78-G/A7 and also A68 B/A11 can also be acquired by purchase and are e.g. obtainable from Glycotope GmbH Berlin, Germany.

The binding of an antibody to Gal beta 1-3 GalNAc alpha1-PAA, Gal beta 1-3 GalNAc beta 1-PAA, GlcNAc beta1-2 Gal beta 1-3 GalNAc alpha 1-PAA, asioaloglycophorin, and glycophorin is preferably determined in ELISA, and the binding to the tumor cells is preferably determined in flow cytometry analyses or immunofluorescence analyses which are described in detail in examples. Those skilled in the art may use and adopt alternative methods to test the binding of such antibodies such as but not limited to scatchard analyses for cell binding, BIACORE analysis, Western blot analysis, or Dot blot analysis for antigen binding. Those skilled in the art may also use other Core-1 carrying molecules for testing a Core-1 binding such as (Gal beta1-3 GalNAc alpha1-) coupled with or without a suitable linker to KLH, biotin or BSA, however, the above described preferred embodiments are preferred in sense of the invention.

In accordance with the present invention the term "Core-1 positive microorganism" means any microorganism which is bound by at least one Core-1 specific antibody, if said microorgansim is contacted with said antibody. For determining that a microorganism is Core-1 positive, it is thus decisive that said microorgansim is recognized by a Core-1 specific antibody. Thereby it is ensured that the microorganism carries an epitope that is Core-1 or which structure specifically resembles Core-1 (Core-1 mimickry structures) and is thus capable of eliciting a Core-1 specific immune response. This also comprises microorganisms wherein Core-1 is coupled in the beta form (see also FIG. 19). A microorganism may be naturally Core-1 positive or can be rendered Core-1 positive by treating the microorganism with a chemical exposing Core-1 such as e.g. a periodate treatment in some embodiments. In case a respective treatment results in Core-1 positive microorganism that is specifically bound by at least one Core-1 specific antibody, if said microorgansim is contacted with said antibody it is a Core-1 positive microorganism according to the present invention. However, the alternative wherein the microorganism is already Core-1 positive is preferred.

There are also other structures besides antibodies which recognize and thus bind Core-1 upon contact. A lectin is e.g. a carbohydrate binding molecule which is no antibody molecule, which is capable of binding to Core-1. E.g. peanut agglutinin (PNA) has been for years the classical Thomsen-Friedenreich reagent. It is, however, not Thomsen-Friedenreich specific as it also binds to other glycans with terminal Galbeta structures and also shows a rather broad reactivity with normal tissue (Cao et al, 1996). According to one embodiment said Core-1 positive microorganism is characterised in that it is recognized/bound by at least one Core-1-specific antibody and at least one non-antibody Core-1-binding protein (lectin) such as (but not limited to) *Arachis hypogaea* (peanut) agglutinin (PNA), *Amaranthus caudatus* agglutinin (ACA), *Artocarpus integrifolia* lectin (Jacalin), *Bauhinia purpurea* lectin (BPL), or *Agaricus bisporus* agglutinin (ABA) [The lectins are available from Vector Labs., Burlingame, Calif., USA, Sigma-Aldrich, St. Louis, Missouri, USA, or other sources]. In a preferred embodiment said Core-1 positive microorganism is characterised in that it is recognized/bound by at least two Core-1 specific antibodies. In a more preferred embodiment said Core-1 positive microorganism is characterised in that it is recognized/bound by at least two Core-1 specific antibodies and the binding is periodate sensitive. In a further preferred embodiment, the Core-1 positive microorganism is characterised in that it is bound/recognized by the Core-1 specific antibodies NEMOD-TF1, NEMOD-TF2 or A78-G/A7 wherein the binding is periodate sensitive. In the most preferred embodiment said Core-1 positive microorganism is recognized/bound by NEMOD-TF1 and NEMOD-TF2 or NEMOD-TF1 and A78-G/A7 and the binding is periodate sensitive. These antibodies are also very suitable for generating Core-positive microorganisms with a sufficient Core-1 specificity in one of the selection/identification processes described herein.

Suitable methods for testing if a Core-1 specific antibody binds to a micoorgansim in this invention are ELISA and immunofluorescence (see examples), but those skilled in the art might use other test systems such as flow cytometry or several adsorption technique in order to identify Core-1 positive microorganisms.

The periodate treatment to test the periodate sensitivity of the binding of a Core-1 specific antibody towards a microorganism is described in detail in example 9.

In accordance with the present invention the term "Core-1 periodate sensitivity of a microorganism" means that the binding of a Core-1 specific antibody to said microorganism is altered (e.g. less or higher) when said microorganism was treated with periodate than its binding to the same microorganism which was treated without periodate as is e.g. described in detail in the examples. In a preferred embodiment said binding of a Core-1 specific antibody to said microorganism is less and thus reduced when said microorganism was treated with periodate than its binding to the same microorganism which was not treated with periodate. As outlined above, periodate destroys the specific structure of the Core-1 antigen. In a more preferred embodiment said reduced binding of the Core-1 specific antibody to said microorganism after periodate treatment of the microorganism is less than 80% of the non-periodate treated counterpart, and even more preferred less than 50% and most preferred less than 30%.

A Core-1 positive microorganism can be any microorganism such as but not limited to bacteria, cyanobacteria, eubacteria, algae, fungi (mushrooms, yeasts, smuts, molds etc.), viruses and protozoa. Preferred are bacterial microorganisms such as but not limited to microorganisms isolated from the soil, from plants, animals, humans or other higher living organisms such as cats, dogs, pigs, cows, goat, rabbit, mice, chimpanzees. In a preferred embodiment the Core-1 positive microorganism is a microorganism which originates from the human gastrointestinal system.

In accordance with the present invention the term "fraction of a core-1-positive microorganism" means preparations or purifications of smaller parts of said microorganisms such as e.g. a cell wall preparation, envelope preparation, lysates, lipopolysaccharid preparation, preparation of capsules, or capsule polysaccharide preparation or Core-1 positive components of said core-1 positive microorganism. They should comprise or consist of at least one Core-1 positive component of said Core-1 positive microorganism in order to be able to elicit the desired immune response. They can be obtained by preparations or purifications from at least one Core-1 positive microorganism. Said preparations and purifications can be obtained by methods known to those skilled in the art such as those described above or single or sequential cell fractionation(s), phenol water extractions, ether extractions, lysozyme digestions or chromatographic methods. Furthermore, the term fraction of a core-1-positive microorganism also comprises artifically produced Core-1 positive components which are also found on Core-1 positive microorganisms of the present invention. FIG. 19 e.g. shows some Core-1 positive components and thus fractions of a Core-1 positive microorganism (here: AG6). These Core-1 positive components/fractions of the Core-1 positive microorganism AG6 could also be produced chemically. The Core-1 positive component or the fraction containing the Core-1 positive component can be detected by binding of the fraction to at least one Core-1 specific antibody in test systems such as but not limited to ELISA or Dot blots which are known to those skilled in the art. In a preferred embodiment of the invention the fraction comprising a Core-1 positive component is obtained by affinity chromatography using at least one Core-1 specific antibody. In a preferred embodiment a single preparation or purification step is used. In another preferred embodiment a combination of at least two preparation or purification steps are used.

In accordance with the present invention the term "Core-1 positive component" means any component of a Core-1 positive microorganism which is bound by at least one Core-1 specific antibody. Said Core-1 positive component comprises at least one Core-1 carbohydrate structure or Core-1 mimicking structure which can be available in form of its natural molecule where it is part of on the microorganism, such as a peptide, oligopeptide, polypeptide, lipid, ceramide, carbohydrate, lipoprotein, polysaccharide, oligosaccharide, polysaccharide, proteoglycan or glycoprotein, or as a part of said natural molecule, or alone. The Core-1 positive component can be used in sense of the invention as a fraction of the Core-1 positive microorganism as such or coupled to other non-natural carrier structures such as proteins, lipids, chemical molecules such as polyacrylamide. Preferably it is used in its natural form. The Core-1 positive component can comprise a single Core-1-carbohydrate structure or Core-1 mimicking structure or repeating units of said structures and can contain additional carbohydrate structures or units or other biomolecule structures. Said Core-1 mimicking structure is a structure which can be bound by at least one Core-1 specific antibody and/or can induce an immune response against Core-1, preferentially a humoral immune response against Core-1 or a cellular immune response against Core-1, and more preferentially a humoral immune response against Core-1 and a cellular immune response against Core-1.

In accordance with the present invention the term Coreotic™ means a nutraceutical or nutraceutical formulation comprising at least one Core-1-positive microorganism or fraction thereof.

In accordance with the present invention the term "Core-1 positive disease" means any disease which is associated with a virus, microorganism, eukaryotic cell, tumor cell or other biological material which is charactrised by the occurrence of the Core-1 antigen which is recognized and can thus be bound by at least one of the Core-1 specific antibodies or which is associated with a component of the body or occurring in the body of a human or animal such as but not limited to a cell, tumor cell, microorganism, virus or particle which is charactrised by the occurrence of the Core-1 antigen which is recognized and can thus be bound by at least one of the Core-1 specific antibodies.

The term "therapeutic agent", as used herein, comprises at least one Core-1 positive microorganism or fraction thereof and can further comprise other components or elements or preferred a carrier of a pharmaceutical composition, drug and medicament known-to-those skilled in the art.

A carrier is a substance that may be associated with an active compound prior to administration to a human or a patient, generally for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and poly-saccharides such as aminodextran and polyamidoamines. Carriers also include solid support materials such as beads and microparticles comprising, for example, polylactate polyglyco-late, poly(lactide-co-glycolide), polyacrylate, latex, starch, cellulose or dextran. A carrier may bear the compounds in a variety of ways, including covalent bonding either directly or via a linker group, noncovalent interaction or admixture.

The induction of an immune response against Core-1 as described elsewhere herein does also mean in the sense of the invention the enhancement of an already existing immune response against Core-1

Without intending to be limiting, the invention will be explained in more detail with reference to the following examples.

101

FIGURE LEGENDS

FIG. 1
Unrooted tree based on the unambiguously aligned sequences (1248 base pairs) of the isolates AG6, MU1, their closest relatives and the *E. coli* type strain obtained with the Neighbor-Joining method (7).

FIG. 2A
LH *E. coli* strain PCR products obtained after amplification with the primer OPL07—lane 1-1 kb ladder; lanes 2-11—LH strains 2-5, 8, 13-16, 18; lane 12—strain 32 *E. coli* DSMZ 8697

Figure 2B:
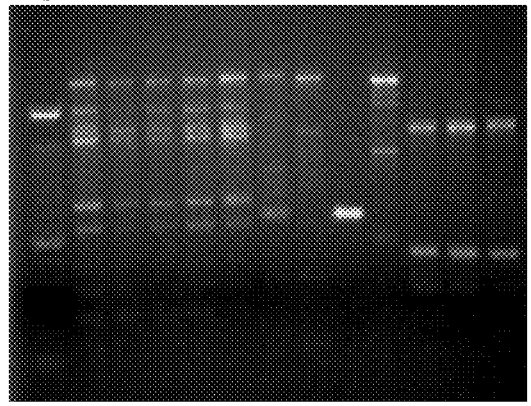

FIG. 2B
MU strains and AG6 obtained after amplification with the primer OPA18—lane 1—1 kb ladder; lanes 2-5—MU strains 1, 3-5; lane 6—AB12; lane 7—*B. thetaiotaomicron* DSMZ 2079; lane 8—*B. ovatus* DSMZ 1896; lane 9—*B. vulgatus* DSMZ 1447; lane 10—*B. acidifaciens* DSMZ 15896; lanes 11-13-AG6

Figure 3A:
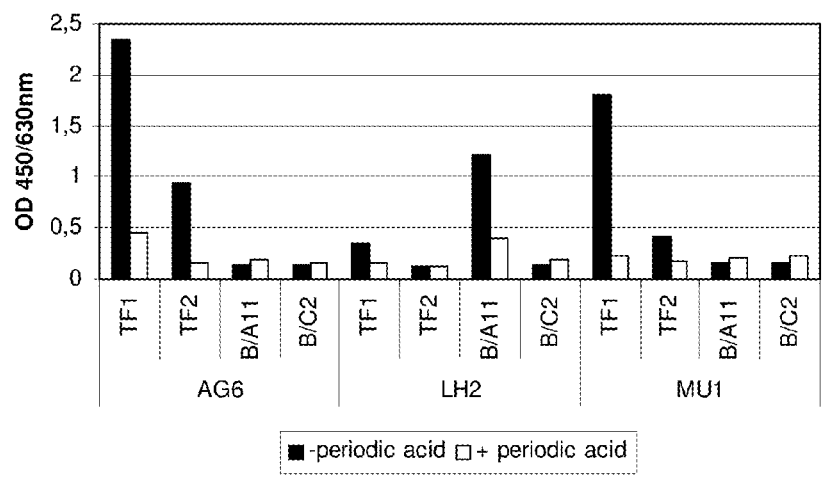

FIG. 3A
ELISA with coated bacterial strains AG6, LH2 and MU1 ($5 \times 10^6$ bacteria/ml) and the Core-1 specific monoclonal antibodies Nemod-TF1, Nemod-TF2 and less specific A68-B/A11 and control antibody A63-B/C2.

Figure 3B:
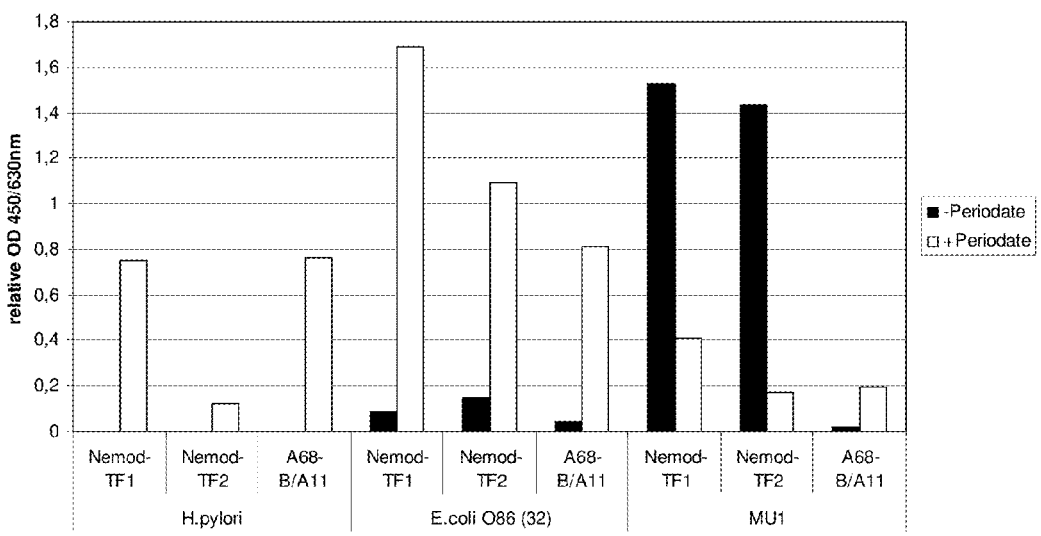

FIG. 3B
ELISA with coated bacterial strains *Helicobacter pylori* NCTC 11637, *E. coli* strain DSMZ 8697(strain 32) and *Bacteroides ovatus* strain MU1 (each at a density corresponding to $10 \times OD_{650nm}$ 0.1) and the monoclonal antibodies Nemod-TF1 Nemod-TF2 and A68-BA11 ($OD_{450/630nm}$ minus $OD_{450/630\ nm}$ of control antibody A63-B/C2).

Figure 4:
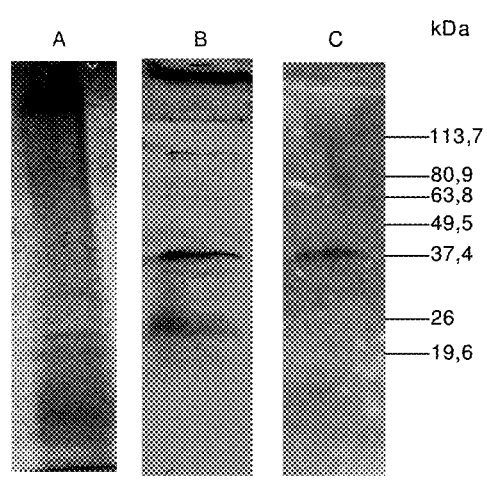

FIG. 4
SDS-PAGE and western blot analyses of capsule preparation of strain AG6
A) Alcian blue dye of SDS-polyacrylamide gel
B) DIG-glycan staining of western blot
C) staining of western blot with Nemod-TF2

FIG. 5
Enrichment of core-1-positive polysaccharides by reversed phase chromatography FIG. 6
Sequence of repeating units of core-1-positive capsular polysaccharide of *B. ovatus* strain AG6

FIG. 7
Structure of repeating units of core-1-positive capsular polysaccharide of *B. ovatus* AG6 (L-Fuc: L-fucose, D-Gal: D-galactose, HexNAc: N-acetylhexosamin, D-Hex: D-hexose, OMe: O-methyl group)

FIG. 8
Structure of repeating units of core-1-positive capsular polysacharid of *B. ovatus* AG6 (L-Fuc: L-fucose, D-Gal: D-galactose, HexNAc: N-acetylhexosamin, D-Hex: D-hexose, OMe: O-methyl group)

Figure 9:
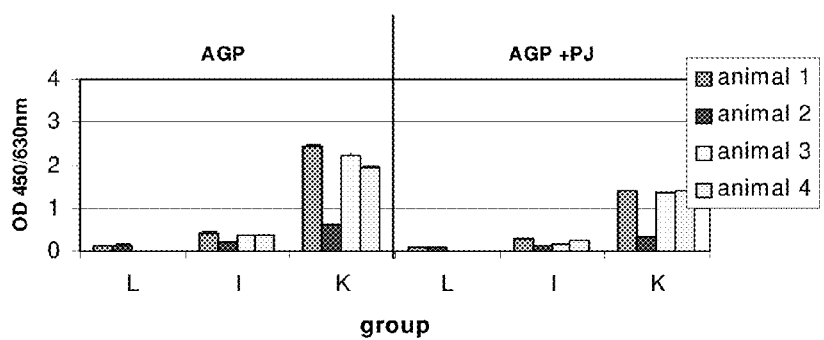

FIG. 9
Analysis of mouse sera by humoral immune response test 1
IgM antibodies against AGP and periodic acid treated AGP were determined by ELISA in sera from mice immunized with PBS (group L), Core-1 negative bacteria (group I) and Core-1 positive bacteria (group K)
Serum dilution 1:200, day 21

Figure 10A:
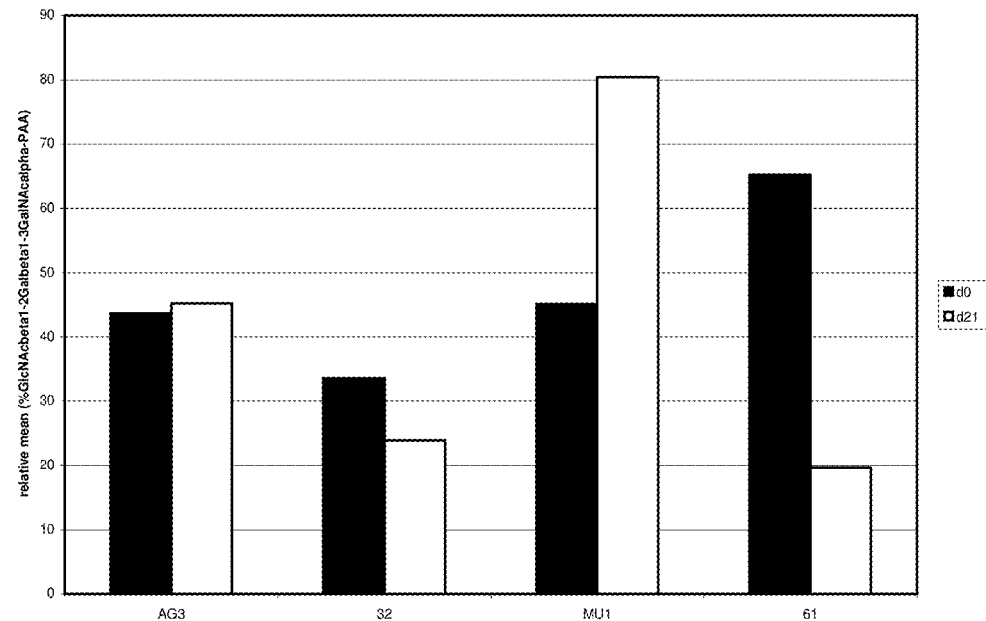
Figure 10B:
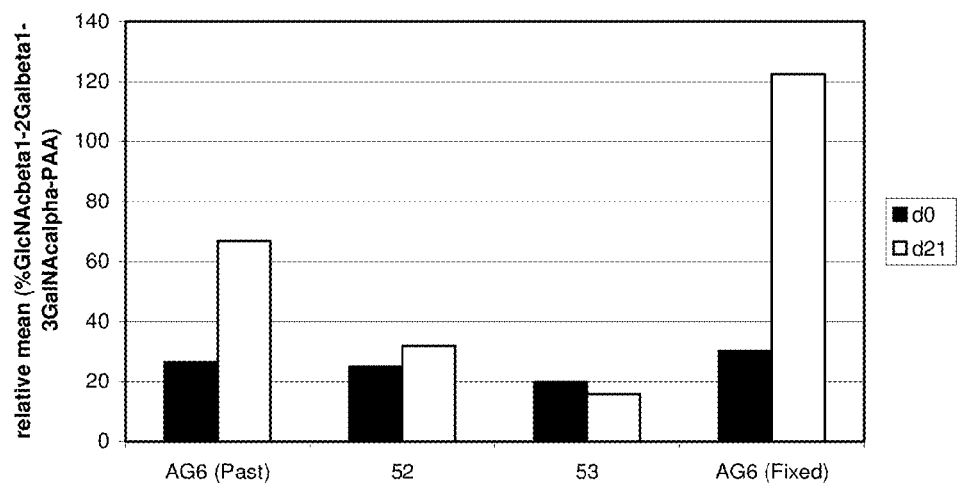

FIG. 10A-B
ELISA signals of immune sera on carbohydrate-PAA conjugates mean value of ELISA signals from 4 C3H mice against the PAA conjugate Gal beta1-3GalNAc alpha1-PAA relative to the ELISA signal against GlcNAcβ1-2Galβ1-3GalNAcalpha-PAA (dilution of sera 1:100)

102

Figure 11A:
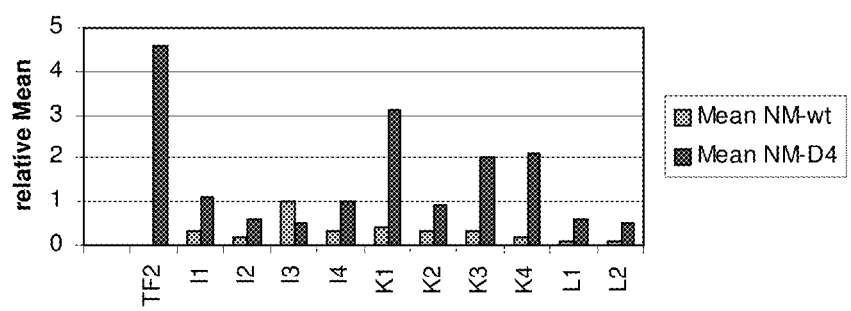
Figure 11B:
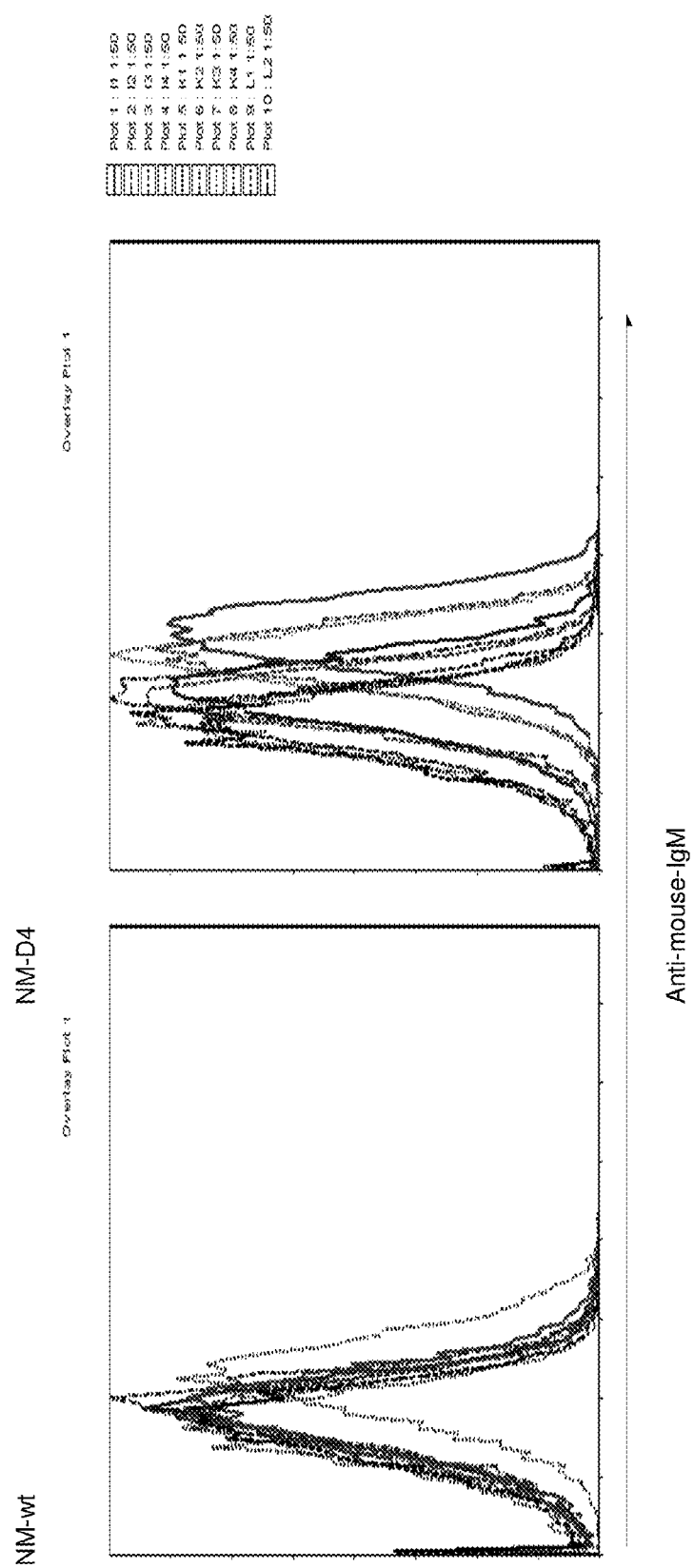
Figure 11C:
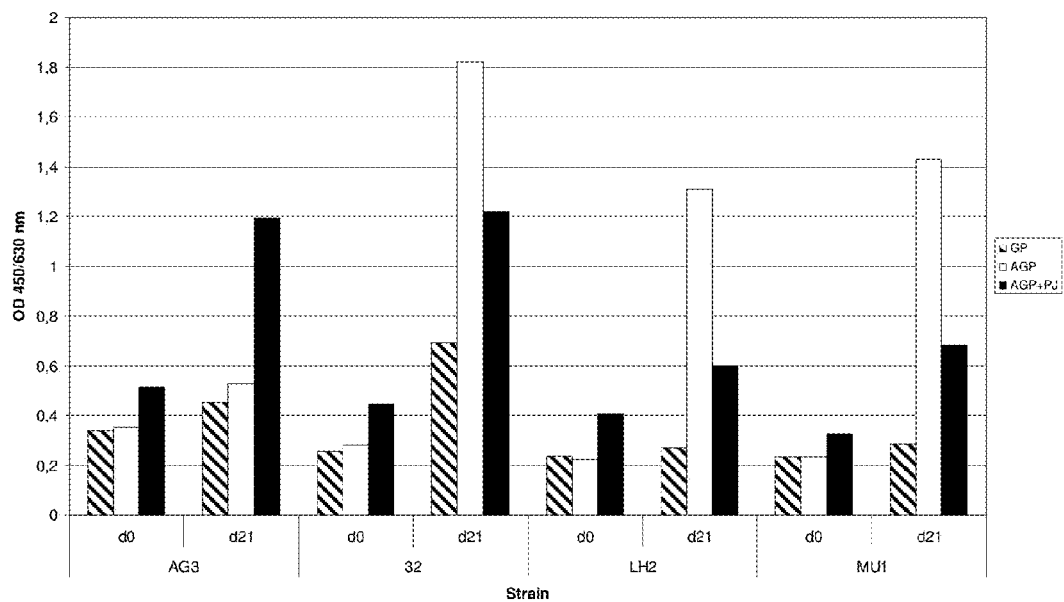

FIG. 11 A-E
FACS analysis of mouse sera from mice immunized with PBS (group L), Core-1 negative bacteria (group I) and Core-1 positive bacteria (AG6, group K) at day 21
FIG. 11A shows the mean fluorescence intensity of FACS analysis
FIG. 11B shows a histogram overlay (black:group L, blue: group I, red: group K)
FIG. 11Ce shows the results of the humoral immune response test 1 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).
FIG. 11D shows the results of the humoral immune response test 2 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).
FIG. 11E e shows the results of the humoral immune response test 3 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).

Figure 12:
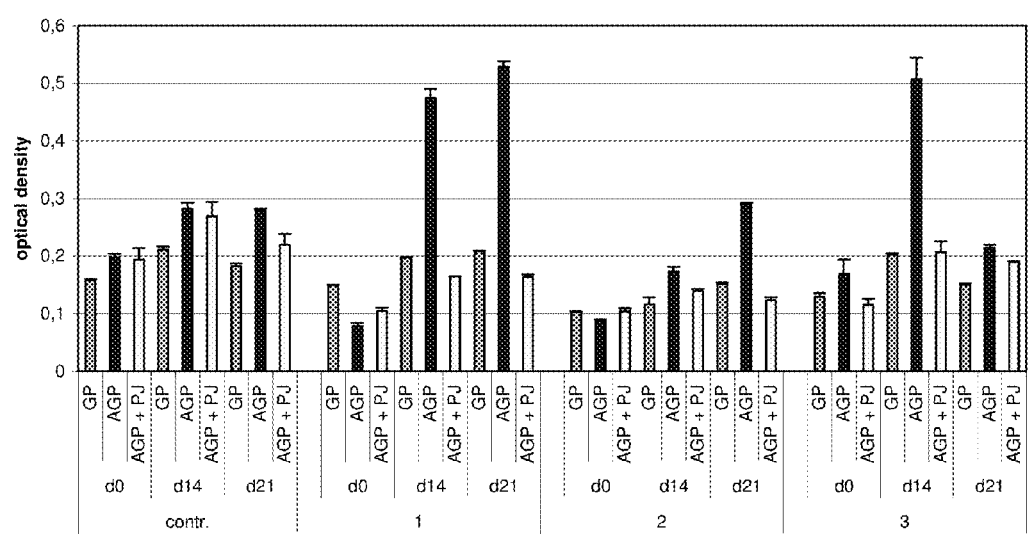

FIG. 12
Humoral immune response test 1 of sera from germ free mice (control mouse and 3 different mice immunized with bacteria strain AG6)

Figure 13A:
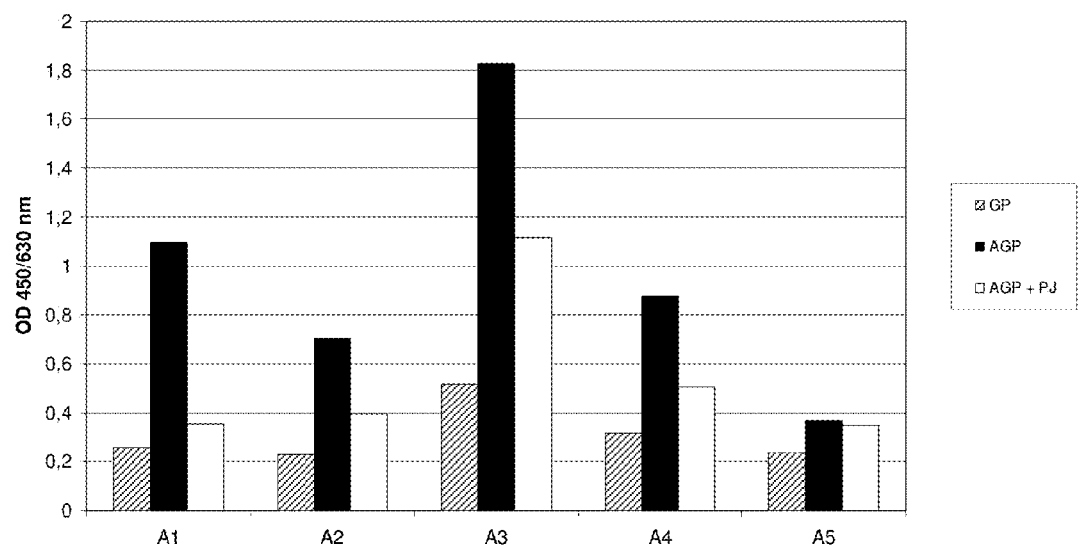
Figure 13B:
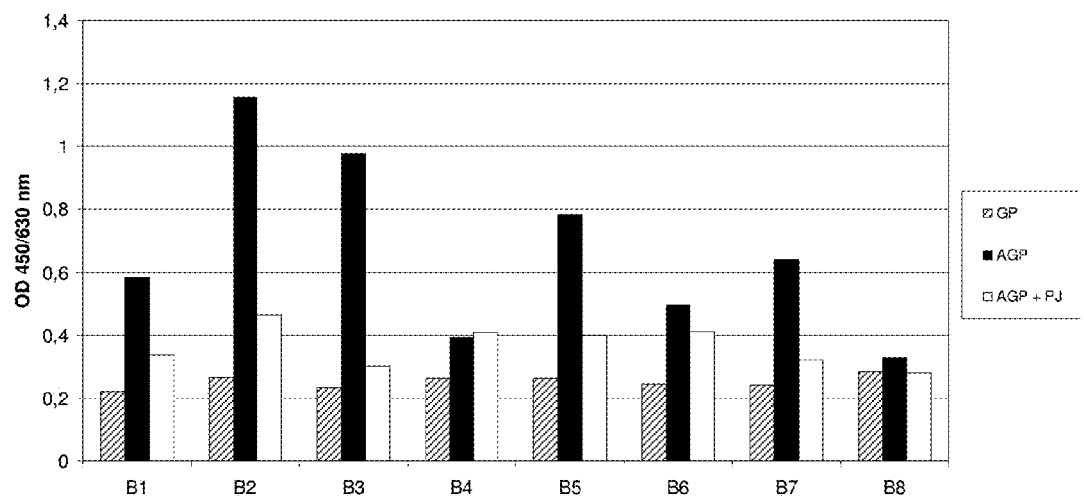

FIG. 13A-B
Humoral immune response test 1 of sera from C3H mice orally immunized with A) $2 \times 10^{11}$ (group A) or B) $2 \times 10^{10}$ (group B) pasteurized bacteria of strain AG6 daily at days 0 to 28. ELISA signals at day 21 against glycophorin (GP), asialoglycophorin (AGP) and periodate-treated AGP (AGP+ PJ) of individual mice are shown FIG. 14
Humoral immune response test 3 of sera from C3H mice orally immunized with pasteurized Core-1 positive bacteria (strain AG6). Sera from day 0 and day 28 were diluted 1:300 and analysed in flow cytometry for binding on the cell lines NM-wt and NM-D4.

Figure 15A:
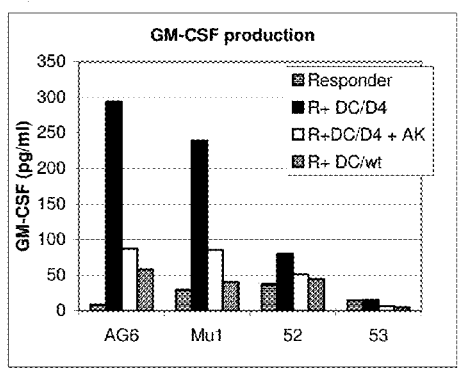
Figure 15B:
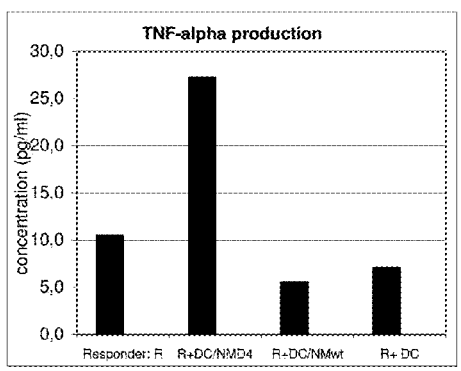

FIG. 15 A-B
Cytokine production by T cells generated to Core1-positive bacteria lysates (AG6 and MU1) after restimulation with DC loaded with Core1-positive MN-D4 (DC/D4) or -negative NMwt (DC/wt) cell-lysates from human tumor cell lines. Inhibition of the cytokine production through pre-incubation of the lysate-loaded NM-DC with Core1-specific antibody (DC/D4+Ak).
FIG. 15A GM-CSF production by T cells (CIRT 1)
FIG. 15B TNF alpha production by T cells (CIRT 2)

Figure 16:
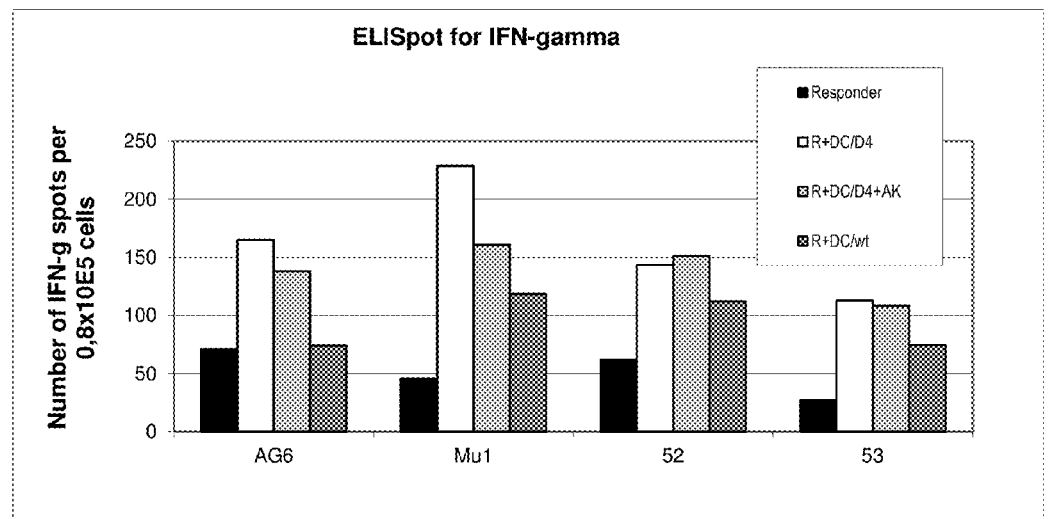

FIG. 16
Cellular immune response test 2: Results of ELISpot assay for IFN-gamma production by responder T cells after restimulation with DC loaded with Core1-positive (DC/D4) or -negative (DC/wt) cell-lysates from human tumor cell lines and inhibition of the cytokine production through pre-incubation of the lysate-loaded NM-DC with Core1-specific antibody (DC/D4+Ak).

Figure 17:
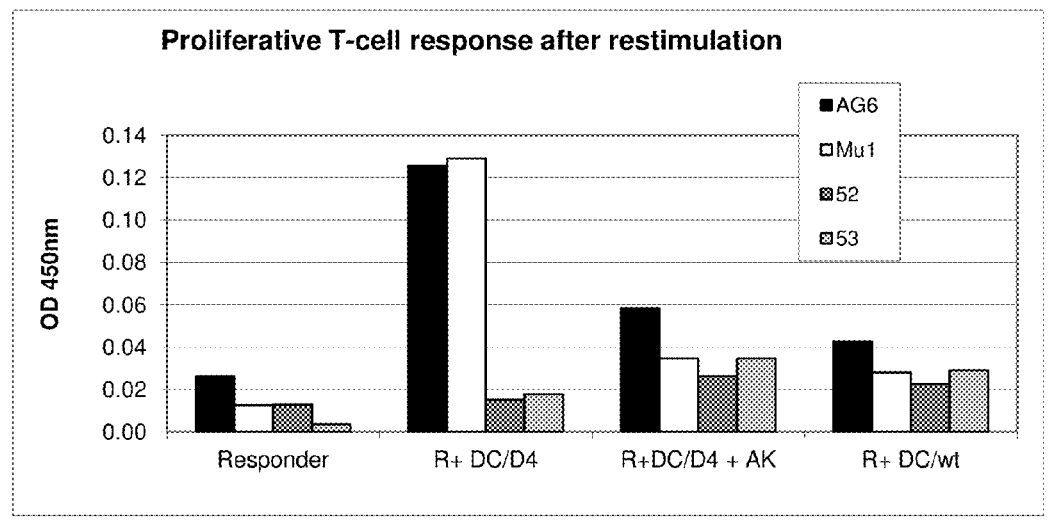

FIG. 17
Cellular immune response test 3: T cell proliferation assay (WST) on responder cells (R) after restimulation with DC loaded with Core1-positive (DC/D4) or-negative (DC/wt) cell-lysates from human tumor cell lines and inhibition of the proliferation through pre-incubation of the lysate-loaded NM-DC with Core1-specific antibody (DC/D4+Ak).

FIG. 18

Cellular immune response test 4: immunofluorescence analysis of mNM-DC loaded with Core-1 negative (AG3) or Core-1 positive (AG6) bacteria or Core-1 negative (NM-wt) or Core-1 positive (NM-D4) human cell line.

FIG. 19

Carbohydrate structures of Core-1 positive components
L-Fuc: L-fucose, D-GalNAc: N-acetylgalactosamin, D-Gal: D-galactosamin, Hex: hexose, HexNAc: N-acetylhexosamin, OMe: O-methylation Such structures are e.g. found on AG6.

FIG. 20

The hidden and exposed Core-1 antigen.

FIG. 21 shows the ELISA signals against the PAA conjugate Galβ1-3 GalNAca-PAA and the PAA conjugate Galβ1-3 GlcNAc a-PAA at day 21. Sera were considered as positive if the signal on PAA 48 was at least 30% higher then the signals on PAA 43. Considering this criteria, 5 (A1, A2, A3, B1 and B5) from the 6 mice developed a core-1 specific humoral immune response.

FIG. 22 shows table 1, wherein selected Core-1 positive strains as well as strains that were not Core-1 positive were characterized by their sensitivity against different antibiotics.

FIG. 23

Overview over a cellular response test according to the present invention.

EXAMPLES

Example 1

Anaerobic Culture Techniques and Media

Anaerobic techniques employed in the cultivation of bacteria were based on methods previously described which have been summarised by Breznak and Costilow. Media prepared with cysteine. HCl as a reducing agent were dispensed into anaerobic culture tubes (Ochs, Bovenden, Germany) or glass serum bottles, leaving approximately half to a third of the total vessel volume as gas head space, and sealed with butyl rubber stoppers. Solutions prepared without reducing agents (e.g. PBS-a) were boiled prior to dispensing. Before autoclaving, the gas phase was replaced with $N_2/CO_2$ (80/20, v/v). To achieve this, needles were thrust through the butyl rubber-stoppered bottles and the bottles were evacuated by means of a vacuum pump (Vacuubrand, Wertheim, Germany). Following evacuation, bottles, which were repeatedly shaken during the entire process, were gassed with $N_2/CO_2$ (80/20, v/v). This evacuation and gassing procedure was carried out three times in total. Prior to entering the vessels, the gas mixture was passed over a hot palladium catalyst to remove residual traces of oxygen present in the gas mixture. Resazurin (1 mg $l^{-1}$) was used as a redox indicator.

Media for plating were poured under a laminar flow hood and stored under anoxic conditions for at least 24 h before use. This was achieved in either pressurised ($1.5 \times 10^5$ Pa) anaerobic jars with a 3.5 l AnaeroGen (Oxoid, Basingstoke, England) or with a repeatedly flushed $N_2/CO_2/H_2$ (80/10/10, v/v/v) anaerobic chamber airlock (Don Whitley Scientific, Shipley, England). Manipulation of samples was carried out in an anaerobic chamber (MACS variable atmosphere workstation, Don Whitley Scientific, Shipley, England or Coy Laboratory Products, Grass Lake, USA).

Non-sterile solutions and materials were sterilised by autoclaving (121 C, $1.2 \times 10^5$ Pa, 15 min). Heat-labile compounds were made as concentrated stock solutions in milli-Q water, sterile-filtered (0.22 μm, mixed cellulose ester, Roth, Karlsruhe, Germany) and added to media at the concentrations required.

Example 2

Affinity Enrichment of Core-1 Positive Microorganisms 2.1 Preparation of TF1 and TF2 Coated Dynabeads®

A volume of 100 μl Dynabeads® (M-450 Rat Anti-Mouse IgM, Dynal Biotech ASA, Oslo, Norway) each was placed in 2 ml Safe-Lock Eppendorf tubes (Eppendorf, Hamburg, Germany), washed twice with 2 ml phosphate buffered saline a (PBS-a: 8.1 g $l^{-1}$ NaCl, 0.16 g $l^{-1}$ $NaH_2PO_4.H_2O$, 0.98 g $l^{-1}$ $Na_2HPO_4.2H_2O$, 1 g $l^{-1}$ BSA, pH 7.4) using the Dynal Magnetic Particle Concentrator®-S (MPC®-S, Dynal Biotech, Oslo, Norway) and suspended in 25 μl of PBS-a. Lyophilised TF1 or TF2 cell culture supernatants were dissolved in 1 ml milli-Q synthesis grade water (Millipore, Billerica, Mass., USA). Dissolved TF1 or TF2 cell culture supernatants (1 ml) were added to the tubes with Dynabeads® and incubated for 30 min at 4 C on a test tube rotator (model 34528, Snijders Scientific, Netherlands). Tubes were placed in the MPC®-S and left to stand for 3 min before removing the fluid with a pipette. The Dynabeads® were re-suspended in 2 ml PBS-a, placed in the MPC®-S and the fluid removed by pipetting. This washing step was performed three times. Washed Dynabeads® were suspended in their original volume of 100 μl PBS-a. Dynabeads® prepared in this manner were either used immediately or within two weeks of preparation after a repeated three-fold wash step with 2 ml PBS-a.

2.2 Collection and Processing of Fecal Samples for Dynabeads® Enrichment

Fecal samples of eight volunteers (Table 3) were collected in perforated plastic tubes, maintained under anoxic conditions using an AnaeroGen Compact (Oxoid, Basingstoke, England) and stored at 4° C. for a maximum of 4 h before processing. Volunteers were healthy adults who had not taken antibiotics for at least 3 months prior to the sampling date and consumed their usual diets.

TABLE 3

| Individual parameters at the time of faecal sample collections | | |
| --- | --- | --- |
| Subject number | Age | Gender |
| 1 - GH | 24 | female |
| 2 - RM | 26 | female |
| 3 - TC | 25 | male |
| 4 - AG | 27 | female |
| 5 - AB | 37 | female |
| 6 - MU | 36 | female |
| 7 - LH | 24 | female |
| 8 - CA | 50 | male |

A tenfold (w/v) dilution of the fecal samples was prepared in PBS-b (PBS-b: 8.5 g $l^{-1}$ NaCl, 0.3 g $l^{-1}$ $KH_2PO_4$, 0.6 g $l^{-1}$ $Na_2HPO_4$, pH 7.0 containing 0.1 g $l^{-1}$ peptone and 0.25 g $l^{-1}$ cysteine.HCl). Six sterile 3 mm diameter glass beads were added and the diluted samples were homogenised by low speed vortexing. The homogenised sample was centrifuged (300×g, 1 min, 21 C) to sediment debris. A 200 μl portion of the resulting supernatant was added to 1.8 ml PBS-b resulting in an approximately 100-fold dilution of the original fecal sample. These dilutions were washed once with 2 ml PBS-b (8000×g, 5 min, 21 C) and the pellets suspended in 2 ml PBS-b.

2.3 Dynabeads® Enrichment Procedure

A volume of 20 µl from the 100-fold dilution was added to a 2 ml tube containing 180 µl of PBS-a and 5 µl of either TF1 or TF2 antibody coated Dynabeads®. The tubes were incubated for 30 min at 4 C on a test tube rotator. Tubes were placed in the MPC®-S and left to stand for 3 min before removing as much of the supernatant as possible by aspiration with a syringe and needle. The samples were washed three times with 2 ml PBS-a, again removing as much of the supernatant as possible.

2.4 Plating on Selective and Non-Selective Media

Washed samples were suspended in 1 ml PBS-b and 100 µl aliquots were spread-plated on various selective and non-selective media (Table 4) and incubated for 48h at 37° C. in an anaerobic chamber.

TABLE 4

Media employed for spread-plating

| Media | Manufacturer | Selective for | Abbreviation |
|---|---|---|---|
| de Man, Rogosa and Sharpe | Merck, Darmstadt, Germany | lactobacilli, lactic acid bacteria | MRS |
| Bifidus Selective Medium | Fluka, St. Gallen, Switzerland | bifidobacteria | BSM |
| K-F Streptococcus Agar | Oxoid | streptococci | KF |
| Nutrient Agar | Oxoid | non-selective | N |
| Schaedler Anaerobe Agar | Oxoid | non-selective | S |
| Wilkins Chalgren Anaerobe Agar | Oxoid | non-selective | WC |
| Brain Heart Infusion Agar | Biomérieux, Marcy l'Etoile, France | non-selective | BHI |
| Columbia Agar with 5% sheep blood | Biomérieux | non-selective | CBA |
| Stamm Agar | | non-selective | ST |

Solid media were prepared according to the manufacturers' instructions. The composition of ST agar was as follows: 1 g $l^{-1}$ proteose peptone, 9 g $l^{-1}$ peptone from meat, 3 g $l^{-1}$ NaCl, 2 g $l^{-1}$ Na2HPO$_4$.2H$_2$O, 3 g $l^{-1}$ meat extract, 4 g $l^{-1}$ yeast extract, 6 g $l^{-1}$ D (+)-glucose, 0.5 ml $l^{-1}$ Tween 80, 0.25 g $l^{-1}$ cysteine.HCl, 1 mg $l^{-1}$ resazurin, 0.1 g $l^{-1}$ MgSO$_4$.7H$_2$O, 5 mg $l^{-1}$ FeSO$_4$.7H$_2$O, 0.5 g $l^{-1}$, 3.4 mg $l^{-1}$ MnSO$_4$.2H$_2$O, 1.5 g $l^{-1}$ bacteriological agar, pH 7.0.

For subjects 1 to 4, colonies from one enrichment procedure were selected for ELISA-based screening. For subjects 5 to 8, the Dynabeads® enrichment procedure was repeated twice as follows: Following 48 h incubation, colonies were scraped from the plates, suspended in PBS-b within the range of McFarland turbidity standards 3 to 5 (prepared as in (13)). As before, a 20 µl aliquot of this suspension was added to 180 µl of PBS-a. The enrichment and plating procedure was performed three times in total, as previously described.

The fecal samples of a further four subjects (5 AB, 6 MU, 7 LH and 8 CA) were enriched for Core 1 positive bacteria. The enrichment procedure was modified slightly in that the enrichment was carried out three times in total. I.e. colonies obtained after the initial isolation were scraped from the plates and subjected to a further enrichment. Sixty new isolates were obtained in this manner.

Example 3

Identification of Isolates 3.1 Biochemical

Bacteria were identified with the VITEK system (Biomérieux, Marcy l'Etoile, France). Bacteria were prepared according to the manufacturer's instructions and the identification cards used were as follows: ANI cards for anaerobic isolates and faculatively anaerobic Gram-positive rods able to grow in MRS broth (suspected lactobacilli), GPI cards for Gram-positive isolates and GN1+ cards for Gram negative aerobic isolates.

The biochemical identity of the isolates obtained using the VITEK system (Biomerieux, Marcy l'Etoile, France) is summarised in Table 5. The anaerobic isolates AG6, MU (1, 3-5) and AB12 all belong to the *Bacteroides fragilis* group, whereas the aerobic isolates are all members of the Enterobacteriaceae; both are Gram-negative.

TABLE 5

Identification of the isolated strains based upon biochemical characteristics (VITEK)

| Strain | Identification | Probability |
|---|---|---|
| AG6 | *Bacteroides ovatus* | 82-95% |
| MU (1, 3-5) | | |
| AB12 | | |
| AG3 | *Escherichia coli* | 89-99% |
| LH (2-5, 8, 13-16, 18) | | |

3.2 Molecular (Sequencing)

DNA was extracted with the Invisorb Genomic DNA Kit III (Invitek, Berlin, Germany) following manufacturer's instructions for protocol III B with washed cell pellets obtained from liquid cultures suspended in 1 ml of lysis buffer D. Primers 27f (5' AGA GTT TGA TCC TGG CTC AG) and 1492r (5' TAC CTT GTT ACG ACT T) (10) were used to amplify the bacterial 16S ribosomal RNA gene.

Each PCR was performed in triplicate and the reaction mixture (50 µl) contained: 50 mM KCl, 20 mM Tris-HCl, 1 mM MgCl$_2$, 0.25 mM each dNTP, 1 µM each primer, 2.5 units Taq DNA polymerase (Invitrogen, Karlsruhe, Germany) and 1 µl of the template DNA. The PCR program was: 94° C. for 5 min, 30 cycles of 94° C. for 1 min, 55° C. for 1 min and 72° C. for 1 min, and finally 72° C. for 10 min. PCR products were purified with the High Pure PCR Product Purification Kit (Roche, Indianapolis, USA) following manufacturer's instructions. The products were analyzed by electrophoresis on a 1% agarose gel (w/v) in Tris-Acetate-EDTA buffer (4.84 g $l^{-1}$ Tris, 1.142 ml $l^{-1}$ glacial acetic acid 0.372 g $l^{-1}$ EDTA, pH 8.0). The DNA concentration was estimated using the Low DNA Mass Ladder (Invitrogen, Carlsbad, USA).

For sequencing, we used either primer 27f, 338f (5' GCT GCC TCC CGT AGG AGT) (2), 338r (5' ACT CCT ACG GGA GGC AGC), 968f (5' AAC GCG AAG AAC CTT AC) (14), or 1492r. Sequencing reactions were performed with the DYEnamic™ ET Dye Terminator Cycle Sequencing Kit (Amersham Biosciences, Little Chalfont, England) following manufacturer's instructions. Sequencing products were analyzed with the MegaBACE 1000 System (Molecular Dynamics, Sunnyvale, USA). Sequences were assembled and manually adjusted using the ContigExpress function of the Vector NTI Suite 9.0.0 (Invitrogen, Carlsbad, USA). They were subsequently aligned with highly similar sequences (92% similarity or more) obtained with the BLAST function of the National Center for Biotechnology Information (NCBI) (1). Percentages of similarity were calculated from unambiguously aligned sequences using the Sequence Identity Matrix function of the Bioedit software version 5.0.9 or the Similarity Matrix version 1.1 of the Ribosomal Database Project. Sequencing results were confirmed by comparison with sequences obtained from a 16S rRNA gene sequencing service provider (AMODIA, Braunschweig, Germany).

The identity of the isolates is depicted in Table 6 and an unrooted phylogenetic tree based on the sequences of the isolates AG6, MU1, their closest relatives and the *E. coli* ATCC 11755 type strain is depicted in FIG. 1.

TABLE 6

Identification of the isolated strains based upon the unambiguously aligned sequences of the 16S rRNA genes using the similarity matrix function version 1.1 of the Ribosomal Database Project (5)

| Strain | Identity | Similarity (%) | to strain | Accession number |
|---|---|---|---|---|
| AG6 | *Bacteroides ovatus* | 98.2 | ATCC 8483T | X83952 |
|  | *Bacteroides thetaiotaomicron* | 97.1 | ATCC 29148T | L16489 |
| MU1 | *Bacteroides ovatus* | 98.0 | ATCC 8483T | X83952 |
|  | *Bacteroides thetaiotaomicron* | 97.1 | ATCC 29148T | L16489 |
| AG3 | *Escherichia coli* | 99.5 | k12 MG1655 | AE000460 |
| GH1 | *Lactobacillus paracasei* sp. *paracasei* | 99.4 | JCM 8130T | D79212 |
|  | *L. paracasei* sp. *tolerans* | 99.4 | JCM 1171T | D16550 |
| 96 | *Staphylococcus warneri* | 99.2 | ATCC 27836T | L37603 |
|  | *Staphylococcus pasteuri* | 99.0 | ATCC 51129T | AF041361 |
| TC7 | *Lactobacillus rhamnosus* | 99.6 | JCM 1136T | D16552 |
|  | *Lactobacillus zeae* | 98.7 | ATCC 15820 | D86516 |

3.3 Random Amplified Polymorphic DNA (RAPD)

Some Core 1 positive isolates obtained with the repeated Dynabead® enrichment procedure appeared very similar in their cell and colony morphology, despite having being isolated from different media. The strains were also very similar with regard to their biochemical profiles obtained with the VITEK system. The question arose, whether the isolated bacteria are identical strains. RAPD is a method that does not require sequence information, which can be applied to distinguish strains. Briefly, total genomic DNA is PCR amplified with a 10 base pair primer at low stringency so that random sequences of DNA are amplified based on homologous sequences to the primer being present in the target DNA. The resulting PCR products can be separated by agarose gel electrophoresis and the resulting pattern can be compared between strains. The resulting band patterns for alt LH strains were analogous for the five RAPD primers (OPL07, M13, OPX14, OPA16, OPA18) employed. The pattern clearly differs from that of *E. coli* strain DSMZ 8697 (FIG. 2*a*), a strain that has been reported to have blood group B activity. The MU strains also appear very similar (FIG. 2*b*); however their band pattern clearly differs from that of other *Bacteroides* strains, including AG6. It would appear that one Core 1 positive strain was repeatedly enriched from each positive donor during the isolation process. The strains isolated differed between individuals.

Example 4

Growth and Fixation of Bacteria for the ELISA-Based Screening

Well separated colonies were randomly picked from selective and non-selective agar plates and re-streaked three times on non-selective media. Single colonies were picked and inoculated into ST (as above, omitting the agar), WC or MRS broth, depending on which afforded best growth, and grown overnight at 37° C. These cultures were inoculated (1%) into 300 ml fresh ST, WC or MRS broth and grown overnight at 37° C. Cells were pelleted (8000×g, 15 min, 4 C) and re-suspended in 10 ml PBS-c (8 g $l^{-1}$ NaCl, 0.2 g $l^{-1}$ KCl, 1.44 g $l^{-1}$ Na$_2$HPO$_4$, 0.24 g $l^{-1}$ KH$_2$PO$_4$) (12). This suspension was fixed 3 for to 4 h at 4 C by the addition of 30 ml of 4% paraformaldehyde (PFA) solution (prepared according to (8)) in PBS-c. Next, samples were washed with 40 ml PBS-c (8000×g, 15 min, 4 C) and the pellets suspended in 15 ml PBS-c, followed by addition of an equal volume of 96% ice-cold ethanol. Samples were stored at −20 C until analysis.

The purity of cultures was checked by comparing cell morphology, as well as Gram staining behaviour. Cultures were plated aerobically on CBA to determine their ability to grow in the presence of oxygen and to check for the absence of aerobic contaminants.

Example 5

Maintenance of Isolates

Cryo-stocks were maintained in Microbank tubes (MAST Diagnostica, Reinfeld, Germany) according to the manufacturer's instructions and stored at −80° C. Working stocks were maintained in WC, ST or MRS broth. These were sub-cultured every 14 days. The purity of the cultures was ascertained by observation of Gram-staining behaviour, cell morphology and periodic comparison of colony morphologies on CBA streak plates under both aerobic and anaerobic conditions.

Example 6

Growth, Fixation and Lyophilisation of Bacteria for Animal Experiments

For use in animal experiments the bacteria were grown and fixed as described in section 3 with the following modifications: The initial culture volume amounted to approximately 4 I. Before fixation, bacteria were washed once with 100 ml PBS-b (8000×g, 15 min, 4 C) and re-suspended in the minimal possible volume of PBS-b. This suspension was split into two equal portions, one for fixation (7.1), the other for lyophilisation (7.2).

6.1 Fixation

The portion for fixation was washed (8000×g, 15 min, 4 C) and re-suspended in 30 ml PBS-c. This suspension was added to 90 ml of the 4% PFA solution in PBS-c and fixed for 3 to 4 h at 4 C. To improve the removal of PFA, samples were washed three times with 120 ml PBS-c (8000×g, 15 min, 4 C). Cell pellets were suspended in 45 ml PBS-c, followed by addition of an equal volume of 96% ice-cold ethanol. Samples were stored at −20° C.

Before administration to the animals, fixed bacteria were lyophilised under sterile conditions in $Lid_{Bac}$ tubes (Eppendorf, Hamburg, Germany) to evaporate the ethanol. To ensure non-viability of the fixed bacteria, they were inoculated (1%) into WC broth and plated on CBA and monitored for absence of growth for the period of one week.

6.2 Pasteurization

Bacterial suspensions were washed twice in PBS and resuspended in a small volume of PBS. Bacterial suspensions were incubated at 72° C. for 30 min. As a control for successful inactivation bacteria were incubated in a suitable culture medium as described in example 4.

6.3 Lyophilisation

The portion for lyophilisation was added to an equal volume of 24% sterile-filtered sucrose and aliquoted in 300 μl portions into 2 ml $Lid_{Bac}$ tubes. These aliquots were snap-frozen in liquid nitrogen for 1 h and lyophilized (Alpha 2-4, Christ, Osterode, Germany) after placing them into racks pre-cooled to −80° C. Following lyophilisation, the lids of the tubes were closed and they were stored at 4° C. using the Anaerocult® C mini gas generator system (Merck, Darmstadt, Germany) with the addition of silica gel orange (Roth, Karlsruhe, Germany) as a desiccant.

6.4 Enumeration of bacteria preparations

Total cell numbers of fixed and lyophilised bacteria preparations were determined with a 0.01 mm depth Thomachamber (LO-Laboroptik, Friedrichsdorf, Germany). For lyophilised bacteria, the colony-forming units (CFU) were determined by plating 10-fold serial dilutions on WC agar of the overnight cultures and immediately before and after lyophilisation. For this purpose, the lyophilate was dissolved in 300 μl WC broth, left to stand for 15 min, re-suspended by low speed vortexing and serially diluted. The CFU of lyophilised preparations were enumerated before and after use in animal experiments to ensure viability. The purity of the preparations was checked as described in section 4.

Example 7

Serum Samples

Blood was collected with the S-monvette system (Sarstedt, Nümbrecht, Germany) and serum was prepared according to the manufacturer's instructions. Serum samples were stored in aliquots at −80° C. prior to analysis Example 8

Fecal IgA Extraction

Fecal samples were collected, stored at −80° C. Faeces were lyophilised and net dry weights recorded. All manipulations were carried out on ice. Fecal IgA was extracted according to Grewal (6) with some modifications. Lyophilised samples (~30 mg) were suspended at a ratio of 15 μl/mg dry weight in IgA extraction buffer (PBS-Dulbecco (Biochrom, Berlin, Germany) with 1 g $l^{-1}$ BSA) with protease inhibitors (5 μg $ml^{-1}$ leupeptin (Calbiochem, Merck), 48 μg $ml^{-1}$ 4-(2-aminoethyl)benzenesulfonylfluoride (Merck), 1 μg $ml^{-1}$ aprotinin, 2 μg $ml^{-1}$ bestatin (Sigma, Steinheim, Germany) and homogenised. The samples were mixed by vortexing every 10 min. Following a 1 h incubation period, the samples were centrifuged (16000×g, 10 min, 4° C.) and the supernatant was collected in a new tube. The remaining pellet was suspended at a ratio of 10 μl/mg dry weight in IgA extraction buffer and homogenised. The extraction procedure was repeated and the resulting supernatant combined with the supernatant from the first extraction step. These supernatants were centrifuged (16000×g, 10 min, 4° C.) and the resulting supernatant was dispensed into new tubes, snap-frozen in liquid nitrogen and stored at −80° C. until analysis.

Example 9

Screening of Bacterial Strains by Enzyme-Linked Immunosorbent Assay

Fixed bacteria were diluted in PBS, cell numbers were adjusted to $1×10^5$, $1×10^6$, $5×10^6$, $1×10^7$, $1×10^8$ or $5×10^8$ cells/ml.

50 μl of bacterial solution were coated per well of a 96 well microtiterplate over night at 37° C. Plates were washed 3 times with PBS/0.02% Tween 20 (Identical washing steps were performed after each incubation step). After blocking of plates with PBS/2% BSA, ELISA plates were incubated with hybridoma culture supernatants containing different Core-1 recognizing monoclonal antibodies (Nemod-TF1, Nemod-TF2 or less specific A68/BA11,) or control antibody (A63-B/C2) in different dilutions. As secondary antibody served a peroxidase-conjugated polyclonal goat-anti-mouse immunoglobulin (Dako P0260). The assay was developed with TMB as substrate, reaction was stopped by addition of 2.5 N $H_2SO_4$ and extinction was measured at 450/630 nm. For determination of periodate sensitivity of the antibody binding, coated ELISA plated were incubated with sodium periodate prior to the incubation with antibodies. Therefore, plates were washed with sodium acetate buffer (50 mM, pH 4.5) for 5 min and afterwards incubated with 10 mM periodic acid in sodium acetate buffer for 1 h in the dark. Plates were washed with sodium acetate buffer (5 min) and the reaction was stopped by addition of 50 mM sodium borohydrid in PBS (30 min).

Example of such ELISA results is shown in FIGS. 3 and 3a.

Example 10

Preparation of Core-1-Containing Components of Bacteria 10.1. Analysis of Crude Capsule Preparations by SDS-PAGE and Western Blot Analyses Crude capsule preparations of strain AG6 were performed according to Pantosti et al. (1991, Infect. Immun. 59, 2075-2082).

Capsule preparation was analysed by SDS-PAGE and polysaccharide in the preparation were detected by alcian blue staining after Karlyshev et al. (2001, J. Clin. Microbiol. 39, 279-284) showing a variety of carbohydrate containing bands and high percentage of high molecular weight carbohydrates within the preparation (FIG. 4A). After Western blot, polysaccharides were detected by the DIG-Glycan Detection Kit (LaRoche Diagnostics). Showing strong bands at 37 and 26 kDa. (FIG. 4B). Detection of core-1-containing polysaccharige on the western blot was performed using the core-1-specific antibody NEMOD-TF2 (culture supernatant) showing a core-1-positive band at 37 kDa (FIG. 4C).

10.2. Chromatographic Enrichment of Core-1 Positive Polysaccharides

Within the capsule preparation of strain AG6 there were still contaminants of lipopolysaccharides as shown by the measurement or KDO content of 11.2 pmol/µg after Haraet al. 1989, Anal. Biochem. 179, 162-166) and by SDS-PAGE.

Therefore capsule polysaccharides and lipopolysaccharides were separated by reversed phase chromatography on a C18 column using a propanol/methanol-gradient (see FIG. 5) according to Hashimoto et al. (2001, Eur. J. Biochem. 268, 3139-3144). Polysaccharides were eluted by a gradient of eluent B (72% propanol/8% methanol in 0.1M ammonium acetate pH 4.5). Detection of polysaccharides within the fractions was performed by dot blot and DIG-Glycan-Kit. Detection of core-1 was performed using the core-1 specific antibodies Nemod-TF1 and Nemod-TF2. Polysaccharides were eluted at propanol concentrations of 14-19% and 25-43%. Core-1 specific carbohydrate were only detected at 29-29.4% propanol (RP1) and 39-42% propanol (RP2), see FIG. 5 snowing strong enrichment of core-1 positive polysaccharide by this method.

Core-1 positive fractions were used for additional chromatographic separations by mild acid hydrolysis followed by DEAE-chromatography using a 0-0.5M NaCl gradient according to Tzianabos et al. (1992, J. Biol. Chem. 267, 18230-18235). By this method the Core-1-positive polysaccharides were separated into three fractions eluted at 0 M NaCl (D1), 0.04 M NaCl (D2) and 0.9-0.17 M NaCl (D3), resulting in a further enrichment of core-1-positive polysaccharides.

In the process according to the instant invention, capsular polysaccharides of B. ovatus AG6 are purified and the structure is analysed by mass spectrometry. Preferable, the capsular polysaccharidee of B. ovatus AG6 are accumulated by the phenol water extraction followed by ether extraction as already described by Pantosti et al. 1991. Thereafter, the core-1-positive polysaccharide is accumulated from rough capsular preparation (CPS) by reverse phase chromatography (C18 Synergi 4☐ Fusion-RP 80i, 250 mm×10 mm, Phenomenex). The monosaccharide contents of rough capsular polysaccharide extract and purified core-1-positive polysaccharide are determined by HPAEC-PAD analyses (high pH anion exchange chromatography, pulsed amperometric detection). Finally the structure of the core-1-positive capsular polysaccharide is analysed by mass spectrometry.

10.3 Monosaccharide Analyses of Rough Capsular Preparation Extract and Purified Capsular Extract of B. Ovatus AG6

In the first step, the core-1-positive polysaccharide of the rough capsular preparation of B. ovatus AG6 was accumulated by reverse phase chromatography as already described before. Thereafter, the yield of purification as well as the monosaccharide content of accumulated core-1-positive polysaccharide was determined by HPAEC-PAD analyses.

Before monosaccharide analyses occurred, polysaccharide extracts was completely hydrolysed by 2 N trifluoroacetic acid (TFA) at 100° C. for 4 h. During the TFA hydrolyses the acetyl groups were lost. Therefore the monosaccharides glucosamin and galactosamin (GlcNH$_2$ and GalNH$_2$) could not distinguish from N-acetylglucosamin and N-acetylgalactosamin (GlcNAc and GalNAc). Monosaccharides were separated by high pH anion exchange chromatography and detected by pulsed amperometry as already described before. To identify the monosaccharides and to determine their concentrations, external and internal monosaccharide standards were used.

The proportional monosaccharide content of rough CPS extract, which was determined for LPS and CPS comparison (mentioned before), obviously vary from the proportional monosaccharide content of rough CPS extract determined for this comparison. Both rough CPS extracts were prepared from different cultures of B. ovatus AG6, which might be an explication for the mentioned variety of monosaccharide contents.

The yield of core-1-positive polysaccharides accumulated by reverse phase chromatography was 30%. Comparison of proportional monosaccharide contents of rough and purified capsular extracts revealed an increased amount of fucose, GalNAc/GalNH2, galactose and glucose, whereas glucose might be a contamination (table 7). The proportional content of rhamnose, GlcNH2/GlcNAc and mannose could be reduced by reverse phase chromatography (table 7). Galacturonic acid and glucuronic acid, which are characteristics components of capsular polysaccharides, could not be identified in the purified core-1-positive polysaccharide extract. These might indicate that B. ovatus AG6 have more than one capsular polysaccharide. Both capsular polysaccharides might be separated from each other by reverse phase chromatography. Tzianabos et al. (1992) also described, that the capsule of B. fragilis consists of two different polysaccharides.

TABLE 7

Monosacchride analyses of rough capsular polysaccharide extract (CPS) and core-1-positive polysaccharide extract purified by reverse phase chromatography.

| Monosaccharides | Rough CPS-extract (%) | Purified CPS-extract (%) |
|---|---|---|
| Fucose | 9.5 | 11.4 |
| Rhamnose | 17.7 | 3.1 |
| GalNH2/GalNAc | 5.2 | 14.9 |
| GlcNH2/GlcNAc | 14 | 3.5 |
| Galaktose | 4.6 | 6.9 |
| Glucose | 44.2 | 50 |
| Mannose | 18.2 | 6.9 |
| Galacturonic acid | 10 | 0 |
| Glucuronic acid | 0.5 | 0 |
| n.d. | 3 | 2 |

The proportional monosaccharide content is related to the total amount of monosaccharides.

The accumulation of fucose, GalNH2/GalNAc and galactose might be an indication, that these monosaccharides are components of the repeating units of the core-1-positive polysaccharide. Whereas the strongly reduced monosaccharides could be low contaminations.

10.4 Structure Analyses of the Core-1-Positive Polysaccharide by Mass Spectrometry The structure of core-1-positive polysaccharide was analysed by matrix-assisted laser time-off flight mass spectrometry (MALDI-TOF-MS) as already described above and by electrospray-Ion-Trap-mass spectrometry (ESI-Ion-Trap-MS).

For ESI-Ion-Trap mass spectrometry the accumulated core-1-positive polysaccharide was fragmented either by hydrolysis with 1% acidic acid (1.5h, at 100° C.) or enzymatic digestion with chondroitinase ABC (cleavage of beta1-4GalNAc/GlcNAc bounds) or with beta1-3 galactosidase. Furthermore, fragmentation by dobble digestion with chondroitinase ABC/alpha1-3,4 fucosidase or 1% acidic acid/beta1-3 galactosidase occurred (all enzymes were received from Glyko GmbH). All enzymatic digestions were incubated at 37° C. overnight. Mass spectrometric analyses (MS as well as MS/MS) were carried out in the positive and in the negative mode. Before analyses occurred, all samples were desalted by Carbograph SPE (Aalltech Associates Inc.) as described by manufactures manual and diluted in 2.5 mM NH3/40% acetonitril.

The structure of core-1-positive glycan fragments, which was already identified by MALDI-MS analyses, could be verified by ESI-Ion-Trap determination. Additional fragments could also be identified by ESI-Ion-Trap mass spectrometry (table 8).

In both eluats of double digested sample galactose (first eluat) and GalNAc (second eluat) could by identified by monosaccharide analyses. While in the eluat of negative control, which was only digested with the exoglycosidase HexNAcase, neither galactose nor GalNAc could be identified. This is a strong indication for the branching core-1-structure, Galbeta1-3GalNAc.

Dot-Blot analyses of double digested retentat and HexNAcase digested sample using the DIG-Glykan detection Kit revealed similar polysaccharide concentrations, which was applied on the nitrocellulose membrane. The core-1-structure could not detected in the dobble digested sample

TABLE 8 structure analyses by ESI-Ion-Trap mass spectrometry (positive mode).

| MS | | MS/MS | |
| --- | --- | --- | --- |
| Determined masses $(M + H^+/M + NH_4^+)$ | Identified sequence | Determined masses $(M + Na^+)$ | Identified sequence |
| 425/442 | HexNAc-HexNAc | | |
| 573/590 | HexNAc(HexNAc)-Hex | 390 | HexNAc-Hex |
| 749/766 | HexNAc(HexNAc-Hex)-Hex | 595 | HexNAc-HexNAc-Hex |
| 529/545 | DesHex-desHexM-HexNAc | | |
| 690/706 | DesHex-desHexM-HexNAc-Hex | | |
| 733/750 | DesHex-HexNAc(HexNAc)-Hex | | |
| 674/591 | DesHex-desHex-desHexM-HexNAc | 493 | DesHex-desHex-desHexM |
| 633/650 | Hex-desHex-desHex-desHexM | | |

The purified core-1-positive polysaccharide was fragmentated by hydrolyses with 1% acidic acid for 1.5 h at 100° C.
HexNAc: N-acetylhexosamin, Hex: hexose, desHex: desoxyhexose, M: methyl-group The sequence of repeating units of core-1-positive capsular polysaccharide was determined by overlapping fragments (FIG. 6).

Mass spectrometric analyses of enzymatically digested core-1-positive polysaccharides gave indications of glycosidic bounds between the monosaccharides. Furthermore galactose (successful cleavage by beta1-3 galactosidase) and fucose (successful cleavage by alpha1-3,4 fucosidase) could be identified (FIG. 7).

This result is in accordance with the monosaccharide analyses mentioned before, which revealed an accumulation of fucose, galactose and GalNAc.

10.5 Verification of core-1-structure as branching disaccharide of repeating unit of capsular polysaccharide The branching core-1-structure, Galbeta1-3GalNAc, in the repeating unit should be identified by double digestion with the exoglycosidases beta1-3 galactosidase and HexNAcase (beta1-2,3,4,6 GalNAc/GlcNAc cleavage) followed by monosaccharide analyses as described above.

Two samples containing equal amounts of core-1-positive polysaccharide were filtrated to purify them from free monosaccharides. Afterwards one of both samples was digested with beta1-3 galactosidase at 37° C. overnight. Both samples were filtrated once again to separate free galactose from the digested sample, whereas the undigested sample were used as negative control. Subsequently, the retentats were collected and digested with HexNAcase. Finally both samples were filtrated again. All eluates were analysed by HPAEC-PAD.

To control, if the core-1-structure was removed by double digestion but was untouched by HexNAcase digestion (negative control), the retentates were analysed by dot-blot using the DIG-Glykan Detection Kit (Roche Diagnostics) to detect polysaccharides and the core-1-specific antibody Nemod-TF1 to identify the core-1-structure.

any more, whereas in the HexNAcase digested sample the core-1-structure was still identified by immunoblot using Nemod-TF1 antibody.

10.6 Verification of the Core-1-Positive Polysaccharide Structure by Analyses of its separated fragments.

For further verification of core-1-positive polysaccharide structure, the glykan was fragmented by hydrolysis with 1% acidic acid (1.5 h, 100° C.). The glycan fragments were labeled by the fluorophore 2-amino benzamide (2-AB) as already described by J. C. Bigge et al. (1995). For this procedure, samples were rendered particle-free and salt-free by purification at Carbograph SPE column (Alltech Associates Inc.) and lyophilized. The pellet was dissolved in 5 □l 2-AB in DMSO/glacial acetic acid/sodium cyanoborohydride and incubated at 60° C. for 2 h. The 2-AB labeled fragments were separated from free 2-AB by paper chromatography. Finally 2-AB conjugated fragments were eluted by water. After lyophilization the pellet was dissolved in 50% acetonitril. Based on their size, fragments were separated by normal phase HPLC (column: Luna 3□NH2 A100, Phenomenex, eluent A: 15 mM NH4-acetate, eluent B: acetonitril) with fluorescence detection. The sequence of fragments was analysed by ESI mass spectrometry. Finally, for verification of glycosidic bonds and better identification of monosaccharides being components of the fragments, the oligosaccharides were digested with the exoglykosidase beta1-3 galactosidase, alpha1-3,4 fucosidase and HexNAcase as already described before. The success of digestion was controlled by ESI mass spectrometry and the removal of terminal monosaccharides was identified by HPAEC-PAD as already described before.

The already identified structure of repeating units of core-1-positive polysaccharide was confirmed by both analyses getting the expected oligosaccharide fragments and cleaved monosaccharides (table 9).

TABLE 9

| Fragments of oligosaccharides | exoglycosidase | ESI-MS analyses | Monosaccharide analyses |
|---|---|---|---|
| HexNAc-Hex | beta 1-3 galactosidase | HexNAc<br>Hex<br>HexNAc-Hex | GalNAc/GalNH2<br>galactose |
| DesHex-desHex-desHexM | alpha1-3,4 fucosidase | desHexM<br>DesHex-desHexM<br>DesHex-desHex | fucose |
| DesHex-desHex<br>DesHex-desHexM-<br>HexNAcM-HexNAc | alpha1-3,4 fucosidase<br>HexNAcase<br>(alpha1-2,3,4,6<br>GalNAc/GlcNAc) | desHex<br>HexNAc<br>DesHex-desHexM-<br>HexNAc | fucose<br>n.d |

In conclusion, the structure of repeating units of core-1-positive capsular polysaccharide (FIG. 8) was confirmed by a variety of analyses.

Furthermore, the results revealed (please also see FIG. 19, in particular #5), that the glycosidic linkage between the Gal-GalNAc and the backbone GalNAc molecule is alpha-anomeric. This finding was supported by dot blot analyses with mAbs TF1, TF2 and HH8, which are specific for the alpha anomer of TF. The mAbs A68-E/A2 and A68-E/E3 which are specific for TFbeta were also used. Thereby, the tumour-specific Ag TFalpha was identified within the branching structure of capsular polysaccharide of *B. ovatus* AG6.

Example 11

Animal Model 11.1 Intra-Peritoneal Immunization of Mice with Dead Bacteria 11.1.1 Analysis of Mouse Sera by Humoral Immune Response Test 1

Female Balb/c mice (Charles River, 4 per group) were treated with Cyclophosphamid at a doses of 50 mg/kg body weight at day −1. At days 0, 7 and 14 mice were intra peritoneally injected with $5 \times 10^8$ bacteria (core-1 negative strains AG3 (group I), 32 or 53 or core-1 positive strain AG6 (group K)) in PBS or with PBS alone (group L). Serum samples were taken at days −4, 21, 27 and 30.

Mouse sera were analysed for binding to core-1 in ELISA. As Core-1 carrying antigen served asialoglycophorin. As a negative control periodic acid-treated asialoglycophorin was used. Periodate treatment destroys the outer carbohydrate ring of the core-1 thereby destroying the Core-1 epitope.

96-well flat-bottom microtiter plates were coated with asialoglycophorin A (AGP) at a concentration of 2 μg/ml. Plate was washed 3 times with PBS/Tween.

Half the plate was treated with periodate as follows:
Wells were incubated for 5 minutes with 50 mM sodium acetate buffer pH 4.5 followed by a 1 h incubation with 10 mM periodic acid in acetate buffer in the dark. Wells were incubated for 5 minutes with 50 mM sodium acetate buffer pH 4.5. Reaction was stopped by incubation with sodium borohydride (50 mM in PBS, 30 min). Next, plates were washed 5 times with PBS/Tween.

Plates were then blocked by addition of 2% BSA for 30 min.

Incubation with different dilutions of mouse sera were performed for 1.5h. Bound mouse immunoglobulin was detected with a peroxidase-conjugated goat anti-mouse IgM antibody (1:5000 in PBS/1% BSA). Assay was developed with TMB as substrate and reaction was stopped by addition of 2.5 N $H_2SO_4$.

FIG. 9 shows the binding of serum IgM-antibodies to core-1 positive AGP and core-1 negative AGP (AGP+PJ). Only sera of three out of 4 mice immunized with Core-1-positive bacteria (group K) showed strong binding to AGP, whereas the signal is reduced after cleavage of Core-1 with PJ.

Therefore, core-1-positive bacteria are capable of inducing core-1-directed humoral immunity in mice.

11.1.2 Analysis of Mouse Sera by Humoral Immune Response Test 2

Male C3H mice (Charles River, 4 per group) were intra-peritoneally immunized with $5 \times 10^8$ pasteurized bacteria from Core-1 positive and Core-1 negative strains in 200 μl PBS at days 0, 7 and 14. Sera were collected prior to immunization and at days, 13, 21 and 28 and analysed in humoral immune response test 2.

96-well flat-bottom microtiter plates were coated with different carbohydrate-PAA conjugates (GlcNAcβ1-2Galβ1-3GalNAcalpha-PAA, Fucalpha1-2Galβ1-3GalNAc alpha-PAA, GalNAcalpha1-3Galβ3-PAA, Galalpha1-3-GalNAcβ-PAA, Gal beta1-3GalNAc alpha1-PAA) at 5 μg/ml in coating buffer (8.4 g/l $NaHCO_3$, 3.56 g/l $Na_2CO_3$, pH=9.49) and incubated over night at 4° C.

Plate was washed 3 times with PBS/Tween.

Plates were then blocked by addition of 2% BSA for 30 min.

Incubations with different dilutions of mouse sera were performed for 1.5h. Bound mouse immunoglobulin was detected with a peroxidase-conjugated goat anti-mouse IgM antibody (1:5000 in PBS/1% BSA). Assay was developed with TMB as substrate and reaction was stopped by addition of 2.5 N $H_2SO_4$.

FIG. 10 shows the mean value of ELISA signals against the PAA conjugate Gal beta1-3GalNAc alpha1-PAA relative to the ELISA signal against GlcNAcβ1-2Galβ-3GalNAcalpha-PAA, for sera from 4 mice per group at day 0 (pre-immune serum) and day 21 [relative ELISA signal is calculated after the equation: (ELISA signals against Gal beta1-3GalNAc alpha1-PAA)*100/(ELISA signal against GlcNAcβ1-2Galβ1-3GalNAcalpha-PAA)]. Sera were calculated as positive if immune serum showed an increase of at least 50% compared with the pre-immune serum. It could be shown that only the Core-1-positive strains AG6 and MU1 induced a Core-1 specific humoral immune response in mice.

11.1.3 Analysis of Mouse Sera by Humoral Immune Response Test 3

Female Balb/c mice (Charles River, 4 per group) were treated with Cyclophosphamid at a doses of 50 mg/kg body weight at day −1. At days 0, 7 and 14 mice were intra peritoneally injected with $5 \times 10^8$ bacteria (core-1 negative strains AG3 (group I), 32 or 53 or core-1 positive strain AG6

(group K)) in PBS or with PBS alone (group L). Serum samples were taken at days −4, 21, 27 and 30.

Flow cytometric analyses were performed in order to analyze binding of mouse sera to Core-1 positive and core-1 negative human tumour cell lines (NM-wt and NM-D4, respectively; NM-wt is the parental cell of NM-D4 as described in WO2005/017130 A2 and EP1654353, NM-D4 is deposited at the DSMZ under DSM ACC2605). $3 \times 10^5$ cells per tube were pelleted and the pellet was resuspended in 50 µl murine serum (diluted 1:50 in PBS/10% FCS), control antibody or PBS/10% FCS alone. Samples were incubated for 20 min at 4° C., washed with PBS and centrifuged. Next, cells were incubated with Cy3-conjugated goat anti-mouse-IgM antibody (Jackson Immuno Research, 1:200 in PBS/10% FCS) for 20 min at 4° C., washed with PBS and resuspended in 200 µl PBS for flow cytometric analysis.

FIG. 11 a and b shows the binding of IgM antibodies from mouse sera to the human cell lines NM-wt (Core-1 negative) and NM-D4 (core-1 positive). Whereas binding to the Core-1 negative NM-wt line is comparable between mice immunized with Core-1 negative bacteria (group I) and Core-1 positive bacteria (group K), there is a significantly stronger binding of 3 out of 4 mice from group K to the Core-1 positive NM-D4 line. This is indicative of the core-1 specificity of the humoral immune response in mice immunized with Core-1 positive bacteria.

11.1.4 Analysis of Mouse Sera by Humoral Immune Response Tests 1, 2 and 3

C3H mice (Charles River, 4 mice per group) were intraperitoneally immunized with $1 \times 10^9$ pasteurized bacteria from Core-1 positive *Bacteroides ovatus* strain *Bacteroides ovatus* MU-1, A68-BA11-positive *E. coli* strain LH2 and Core-1 negative *E. coli* strains (AG3, *E. coli* 086 DSMZ 8697=32) in 200 µl PBS at days 0, 7 and 14. Sera were collected prior to immunization and at days 13, 21 and 28 and analysed in humoral immune response tests 1, 2 and 3 as described above.

While strain AG3 was negative for all humoral immune response tests, serum collected from mice after immunization with the strains *E. coli* O86 and LH2 showed AGP reactive antibodies in HIRT 1. Nevertheless, only the Core-1 positive strain MU-1 showed strong anti-Core 1 specific humoral immune responses against Core-1 on PAA conjugates (HIRT 2) and on human tumor cells (HIRT 3) in addition to the induction of AGP specific antibodies in HIRT.

Therefore, we could induce a strong Core-1 specific humoral immune response only with a Core-1 positive microorganisms of the *Bacteroides ovatus* (MU-1).

Figure 11D:
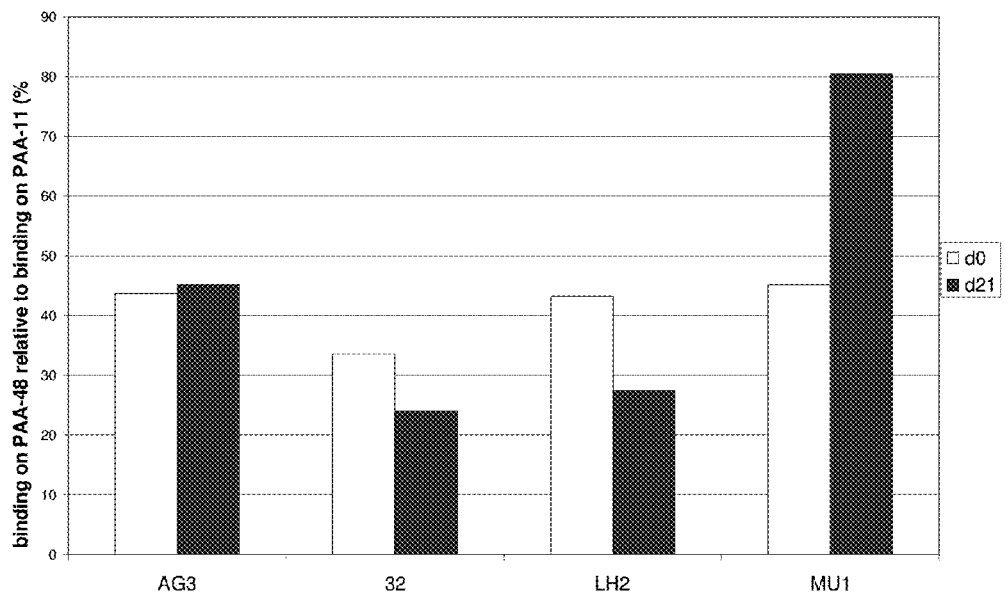
Figure 11E:
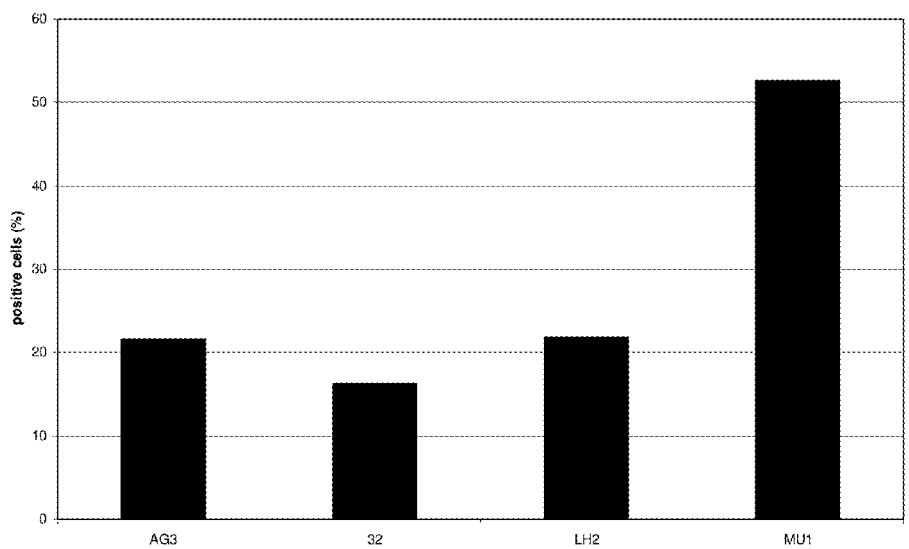

FIG. 11c to e show the results.

11.2. Oral Immunization of Germfree Mice with Live Core-1 Positive Bacteria

Germfree C3H-mice were orally immunized with $2 \times 10^9$ live bacteria of strain AG6 at days 2, 3, 4, 9, 10, 11, 16, 17 and 18. Serum samples were taken at day 0 (pre-immune sera) and at days 14 and 21 and analysed for AGP-specific IgM antibodies in humoral immune response test 1.

Immunized mice showed increased anti-core-1 titers compare to control mice as shown by binding of mouse sera to AGP coated microtiterplates. Detection of bound mouse IgM was performed with peroxidase-coupled anti-mouse-IgM antibodies. Specificity of the signal for core-1 was shown by the decrease of the ELISA signal after treatment with periodic acid (destroying the carbohydrate structure). After 14 or 21 days 3 out of 3 mice had elevated IgM-antibody levels to Core-1 whereas control mice showed no increase of ELISA signals to AGP in comparison to AGP+PJ as shown in FIG. 12.

11.3 Oral Immunization of Conventional Mice with Pasteurised and Living Core-1 Positive Bacteria C3H-mice were orally immunized with $1 \times 10^{11}$ (group A) or $1 \times 10^{10}$ (group B) pasteurized bacteria of strain AG6 daily at days 0 to 28. Serum samples were taken at day −1 (pre-immune sera) and at days 13, 21, 28 and 35 and analysed for AGP-specific IgM antibodies in humoral immune response test 1.

Serum collected from mice after immunization showed increased anti-Core-1 titers as shown by binding of mouse sera to microtiterplates coated with GP or AGP (with and without treatment with periodic acid). Detection of bound mouse IgM was performed with peroxidase-coupled anti-mouse-IgM antibodies. Specificity of the signal for core-1 was shown by the decrease of the ELISA signal after treatment with periodic acid (destroying the carbohydrate structure decrease of at least 30%) and by the lower signal against GP (increase of AGP signal of at least 50%).

It was shown that 5 out of 6 mice from group A and 5 out of 8 mice from group B had developed Core-1 specific antibodies by day 21 (FIG. 13).

In humoral immune response test 3 mouse sera were analysed for binding to the Core-1 positive tumor cell line NM-D4 in comparison to the Core-1 negative cell line NM-wt by flow cytometry. $3 \times 10^5$ cells per tube were pelleted and the pellet was resuspended in 500 murine serum (diluted 1:300 in PBS/1% BSA), control antibody or PBS/1% BSA alone. Samples were incubated for 60 min at 4° C., washed with PBS and centrifuged. Next, cells were incubated with biotin-conjugated goat anti-mouse-IgM antibody (Jackson Immuno Research; 1:200 in PBS/1% BSA) for 60 min at 4° C. and washed with PBS. Following cells were incubated with Cy3-conjugated streptavidin (Jackson Immuno Research, 1:200 in PBS/1% BSA) for 60 min at 4° C. and resuspended in 200 µl PBS for flow cytometric analysis.

Results were calculated after the following formula:

(% positive cells on $NM\text{-}D4_{immune\ serum}$−% positive cells on $NM\text{-}D4_{pre\text{-}immune\ serum}$)/(% positive cells on $NM\text{-}wt_{immune\ serum}$−% positive cells on $NM\text{-}wt_{pre\text{-}immune\ serum}$)=X Mouse sera with a quotient X≧10 were seen as positive (with % positive cells on $NM\text{-}wt_{immune\ serum}$−% positive cells on $NM\text{-}wt_{pre\text{-}immune\ serum}$≧1).

Figure 14:
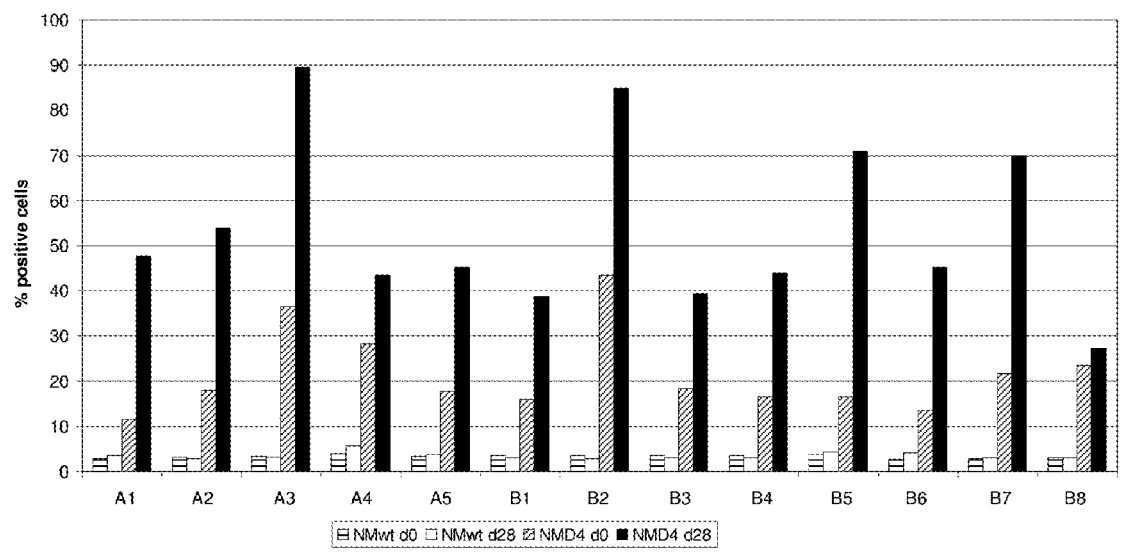

At day 28, 11 of 13 mice had developed a humoral immune response against the Core-1 positive human tumor cell line NM-D4 as shown in FIG. 14.

In humoral immune response test 2 mouse sera from day 28 were analysed for binding to Galβ1-3 GalNAc a-PAA (PAA 48) or Galβ1-3 GlcNAc a-PAA (PAA 43).

96-well flat-bottom microtiter plates were coated with either Galβ1-3 GalNAc a-PAA (PAA 48) or Galβ1-3 GlcNAc a-PAA (PAA 43) at 5 µg/ml in coating buffer (8.4 g/l NaHCO3, 3.56 g/l NA2CO3, pH=9.49) and incubated over night at 4° C. After blocking, incubations with sera were performed for 1.5 hour. Bound mouse immunoglobulin was detected with a peroxidase-conjugated goat anti-mouse IgM antibody (1:5000 in PBS 1% BSA). Assay was developed with TMB as substrate and reaction was stopped by addition of 2.5N H2SOP4.

Figure 21:
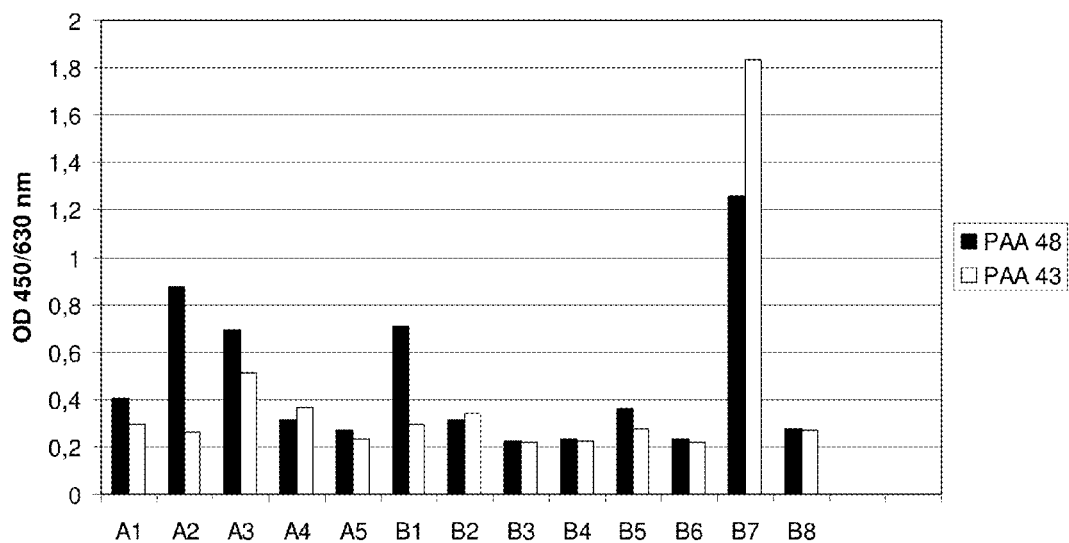

The results are shown in FIG. 21. It was shown that 5 out of 13 mice had developed Core-1 specific antibodies by day 28.

Example 12

Potential of Core-1 Positive Bacteria for the Induction of a Cellular Immune Response (In Vitro)

12.1 Generation of Functional Dendritic Cells

Dendritic cell line NemodDC (pNM-DC) has been used as source for antigen presenting cells (APC). The pNM-DCs were differentiated into iNM-DC, followed by loading with bacterial lysates (BaLy) of following bacteria strains: AG6, MU1, 52 and 53. 50 µg/ml of every BaLy was added together with maturation cytokines to the culture media and iNM-DC were differentiated to their mature status (mNM-DC).

More detailed, in the first step pNM-DC ($1 \times 10^5$/ml) were differentiated into iNM-DC by 7 days incubation in NemodDC medium (70% MEM-alpha, 20% FCS, 10% CM5637) with addition of 1000 U/ml of GM-CSF, 100 U/ml IL-4 and 2.5 ng/ml TNF-alpha. Next, $1 \times 10^6$/ml of immature NM-DC (iNM-DC) were loaded either with bacteria lysates (50 µg/ml), tumor cell lysates ($1 \times 10^6$ lysed tumor cells for loading on $1 \times 10^6$ NM-DC) or AGP- and GP-proteins (20 µg/ml) and maturated for 2 days by addition of 75 ng/ml TNF-alpha.

The maturation phenotype of mNM-DC is very important for successful T-cell activation and was tested by means of flow cytometry for expression of CD1a, CD11c, CD14, CD40, CD35, CD80, CD83, CD86, CD116, HLA-ABC and HLA-DR. Only those DC which had phenotype correspondent to the phenotype of mature DCs were used for T-cell activation.

12.2 Generation of Activated T Cells Against Core-1 and Detection of GM-CSF (Cellular Immune Response Test 1) and TNF-Alpha (Cellular Immune Response Test 2) Production Using ELISA After 7-10 days of priming of T lymphocytes with NM-DC loaded with Core-1-positive bacterial lysates, resulting T cells ($0.7-1 \times 10^6$/ml) were restimulated with mNM-DC ($1 \times 10^5$/ml) loaded with Core-1-positive tumor cell lysates (50 µg/ml). Following 48 hours of incubation supernatants were harvested and assayed using for evaluation of the cytokine production in response to human Core-1-positive tumor cell line NM-D4 the GM-CSF- and TNF-alpha-BD OptEIA™ Kits.

The 96-well plates were pre-coated with 50 µl of appropriate capture anti-human (GM-CSF or TNF-alpha) antibodies diluted 1:250 in coating buffer. After washing and blocking steps, 100 µl of supernatants or standards were added to microwells and incubated for 2 hours at room temperature. For standard curve the recombinant human GM-CSF in concentrations 0; 7.8; 15.6; 31.2; 62.5; 125; 250 pg/ml and the recombinant human TNF-alpha in concentrations 0; 4.7; 9.4; 18.8; 37.5; 75; 150; 300 pg/ml were used. After washing, 100 µl prepared Working Detector solution per well were added, and plate was incubated 1 hour at room temperature. In the next step 100 µl TMB One-Step Substrate Reagent were added per well. After final incubation for 30 minutes and addition of 50 µl of Stop Solution the extensions were read at 450 nm.

The results demonstrated in FIGS. 15 A and B show clear evidence that T cells generated to Corel-positive bacteria lysates are able to recognise DC loaded with Corel-positive cell-lysat from human cell line NM-D4 by production of tumor-inhibitory cytokines such as TNF-alpha and GM-CSF. In contrast, very low level of cytokines was released in response to Corel-negative cell lysates. Moreover, this recognition was specifically inhibited through pre-incubation of lysate-loaded NM-DC with Corel-specific antibody.

12.3 ELISPOT Assay for Evaluation of the Secretion of IFN-Gamma by Activated T Lymphocytes Directed Against Core-1 (Cellular Immune Response Test 2)

ELISpot assay was used for evaluation of IFN-gamma secretion in response to antigen specific stimulation. This assay allows the quantification of functional ability of the pre-sensitised T cells to recognise Corel antigens in an antigen specific manner.

The T lymphocytes were first activated in vitro by being co-cultured with DC loaded with bacterial lysates. After 7 to 10 days of priming, activated T cells were harvested and re-challenged with DC (in ratio T cell to DC 10:1) loaded with Corel-positive (NM-D4) and Corel-negative (NM-wt) human tumor cell lysates.

The wells of the ELISpot plate were pre-coated with mouse-anti-human-IFN-gamma-antibody (Mabtech-Kit) that binds to the nitrocellulose base of the ELISpot plate. The re-challenged T cells were transferred into the wells, and cytokines are released during the incubation period. IFN-gamma that is released locally around each T cell binds to, and is therefore 'captured' by the specific antibody. After 24 hours of incubation the cells were removed. A second anti-human-IFN-gamma antibody in concentration 1 µg/ml is added to the wells; this biotinylated antibody is coupled to an enzyme that is capable of converting a substrate into an insoluble coloured product. The plates are washed once more, and streptavidin conjugated with enzyme-AP in a concentration of 1 µg/ml is added. Finally a precipitating substrate BCIP+NBT is added and the plate is incubated until spots emerge at the side of the responding T cells. The coloured spots are counted and analysed using a digital-imaging system.

The results showed that T cells generated to Corel-positive bacterial lysates (AG6 and MU1) are able to recognise DC loaded with Corel-positive cell-lysat from human tumor cell line NM-D4 by production of tumor-inhibitory cytokine IFN-gamma (FIG. 16). Very low level of cytokines was released in response to Corel-negative cell lysates (R+DC/wt). Furthermore, the specificity of recognition of Corel-positive cell-lysat (R+DC/D4) was proved by blocking of cytokine release with the Core-1 specific antibody Nemod-TF1 (R+DC/D4+Ak).

12.4 Cellular Immune Response Test 3: T-Cell Proliferation Assay

The sensitised and re-stimulated T cells as described above for ELISpot analysis, were transferred after incubation from ELISpot plate into 96-well plate and were assayed using the colorimetric Cell Proliferation Reagent WST-1 (Roche Molecular Biochemicals), whose tetrazolium salt is cleaved by mitochondrial enzymes so that the amount of dye developed (read at 450 nm) directly correlates to the number of metabolically active cells in the culture. Absorbance of culture medium plus wst-1 in the absence of cells was the blank position for the enzyme-linked immunosorbent assay reader. The procedure consists of one-step-adding of 10 µl per well of WST-Proliferation reagent (Roche) and incubation for 3 hours at 37° C. following measurement at 450 nm.

The results demonstrated in FIG. 17, show clear evidence that T cells generated to Corel-positive bacteria lysates, recognise DC loaded with Corel-positive cell-lysat from human tumor cell line NM-D4 as shown by specific proliferation. Moreover, this recognition was specifically inhibited through pre-incubation of lysate-loaded NM-DC with Corel-specific antibody.

12.5 Cellular Immune Response Test 4: Immunofluorescence Test for Core-1 Presentation on DCs Loaded with Bacterial Lysates In order to analyse the processing and presentation of Core-1 by bacterial lysate-loaded NM-DC, immunofluorescence analyses were performed using core-1 specific monoclonal antibodies (Nemod-TF1, NEMOD-TF2). The presentation of the processed Core1-antigen on the surface of the mature DC was demonstrated with help of Immunofluorescence. Immunofluorescence (IF) is a technique allowing the visualization of a specific antigen (Core1) on cells by binding a specific Core-1 antibody following by addition of a secondary antibody labeled with fluorochrome, which is used to recognize a primary antibody.

In the first step pNM-DC ($1\times10^5$/ml) were differentiated into iNM-DC by 7 days incubation in NemodDC medium (70% MEM-alpha, 20% FCS, 10% CM5637) with addition of 1000 U/ml of GM-CSF, 100 U/ml IL-4 and 2.5 ng/ml TNF-alphaNext, $1\times10^6$/ml of immature NM-DC (iNM-DC) were loaded either with bacteria lysates (50 µg/ml), tumor cell lysates ($1\times10^6$ lysed tumor cells for loading on $1\times10^6$ NM-DC) or AGP- and GP-proteins (20 µg/ml) and maturated for 2 days by addition of 75 ng/ml TNF-alpha Matured and antigen loaded DC were washed and $1\times10^6$ cells per 50 µl were placed on the microtiterplate for immunofluorescence staining. 3 µg/ml of Core-1-specific antibody (Nemod-TF1) diluted in culture medium (10% FCS) was incubated with cell suspension for 1 hour at room temperature. After washing steps 50 µl 1:200 diluted secondary goat anti-mouse IgM, Cy3-labeled Ab (Jackson/Dianova) were added and incubated for 30 minutes. Following washing steps, 20 µl of cell suspension were placed into each well of a Multitest slide (10 wells, Roth).

Immunofluorescence stained samples were examined with an Axioplan 2 fluorescence microscope equipped with the digital camera AxioCam (Zeiss).

Figure 18:
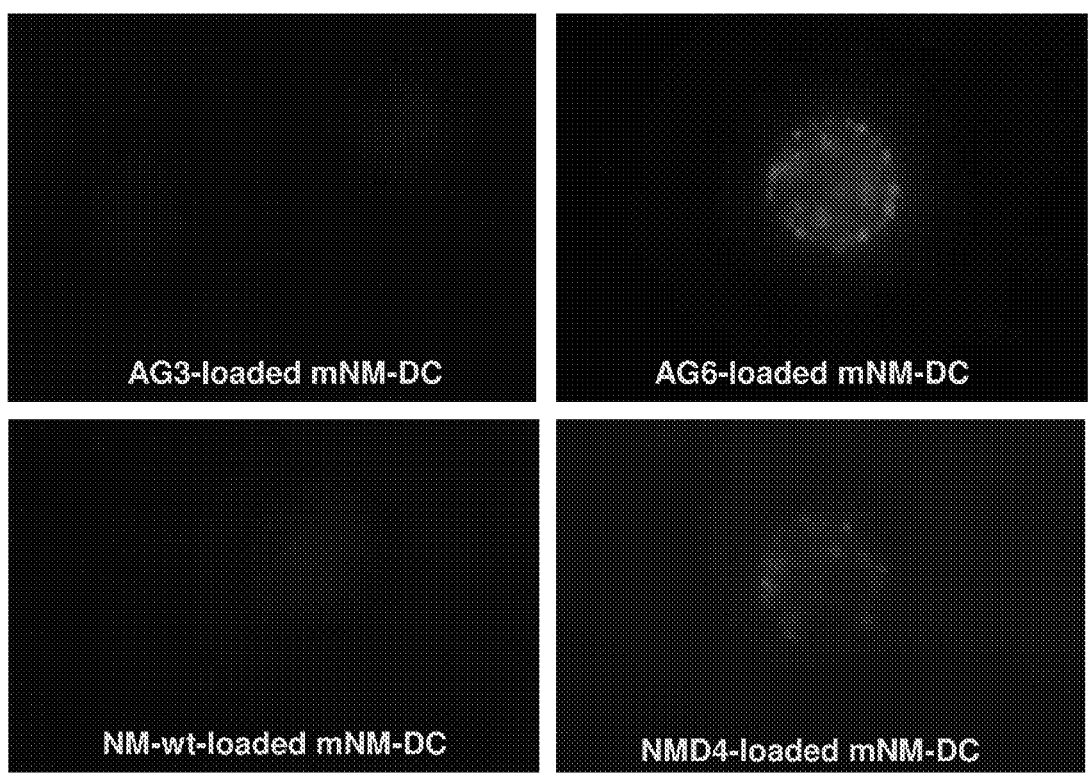

FIG. 18 shows positive Core-1-specific staining of the mature mNM-DC, which have processed AG6- and NM-D4-Core1-positive lysates; and negative immunofluorescence on mNM-DC loaded with Core1-negative lysates (AG3 and NM-wt)

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof. Therefore, as will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples contained in the foregoing description.

It should be understood that various alternatives to the embodiments of the invention described herein may be employed in practicing the invention. It is intended that the following claims define the scope of the invention and that the method and apparatus within the scope of these claims and their equivalents be covered thereby.

The invention claimed is:

1. A formulation selected from the group consisting of a nutraceutical and/or a pharmaceutical composition, wherein the formulation comprises microorganisms and wherein essentially all of the microorganisms are (A) isolated Core-1 positive microorganisms and/or (B) a Core-1 positive fraction or lysate thereof, wherein the Core-1 positive microorganisms and/or the Core-1 positive fraction or lysate thereof carry surface Core-1 in unmasked form and are recognized by at least one Core-1 specific antibody.

2. The formulation according to claim 1, wherein the Core-1 positive microorganisms and/or the Core-1 positive fraction or lysate thereof are recognized by the two Core-1 specific antibodies.

3. The formulation according to claim 1, wherein the recognition of the Core-1 positive microorganisms and/or the Core-1 positive fraction or lysate thereof by the at least one Core-1 specific antibody is periodate sensitive showing reduced binding after periodate treatment.

4. The formulation according to claim 1, wherein the Core-1 positive microorganisms are selected from the group consisting of enterobacterioceae, *Escherichia coli*, *Streptococcus*, *Bacteroides*, *Rhuminococcus*, *Lactobacillus*, *Bifidobacterium*, *Peptostreptococcus*, *Fusobacterium*, *Johnsonella*, *Atopobium*, *Staphylococcus*, *Eubacterium*, *Finegoldia*, *Clostridium*, *Eggerthella*, *Butyribacterium*, *Citrobacter*, *Propionibacterium* and *Corynebacterium*, *Bacteroides ovatus*, *Bacteroides thetaiotaomicron*, *Bacteroides acidophilus*, *Bacteroides caccae*, AG6 (DSM 18726) and/or MU1 (DSM 18728) wherein said microorganisms selected from said group are Core-1 positive and recognized by at least one Core-1 specific antibody.

5. The formulation according to claim 1, wherein said Core-1 positive microorganisms or the fraction of said Core-1 positive microorganism comprise at least one of the carbohydrate structures selected from the group consisting of:

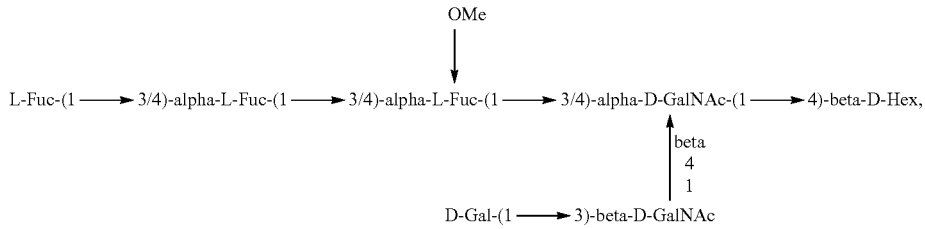

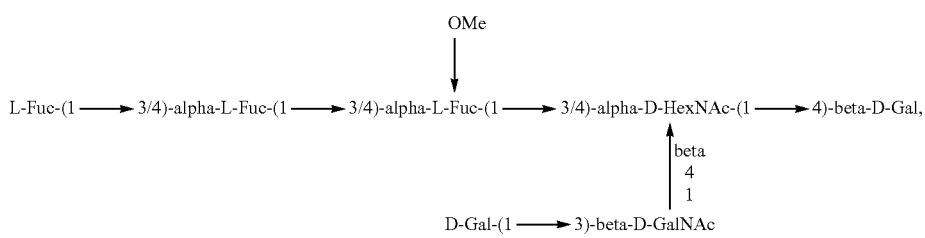

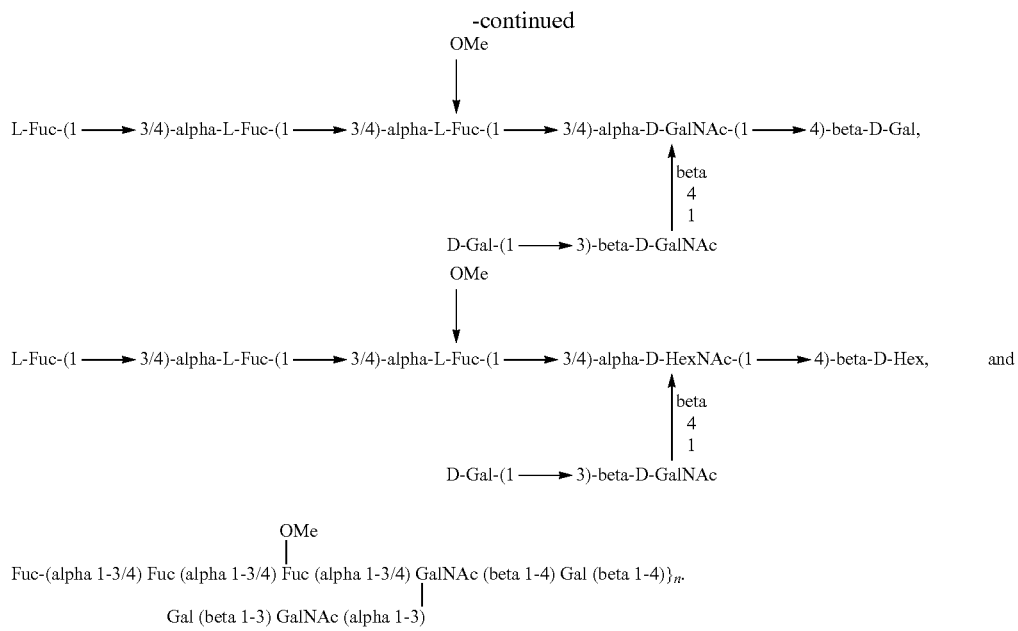

Fuc-(alpha 1-3/4) Fuc (alpha 1-3/4) Fuc (alpha 1-3/4) GalNAc (beta 1-4) Gal (beta 1-4)}$_n$.
|
Gal (beta 1-3) GalNAc (alpha 1-3)

OMe

6. The formulation according to claim 1, wherein said Core-1 positive microorganisms are AG6 (DSM 18726), MU1 (DSM 18728) and/or a AG6 or MU1 homolog, wherein said homolog is characterized in that it is a *Bacteroides*, is recognized by at least two Core-1 specific antibodies, and wherein binding of said antibodies is periodate sensitive showing reduced binding after periodate treatment.

7. The formulation according to claim 1, which induces or enhances a humoral and/or a cellular immune response against Core-1 in a human or animal.

8. The formulation according to claim 7, which induces or enhances a cellular immune response comprising activation of CD4 positive T cells of Th1 cells and/or CD8 positive cytotoxic T cells.

9. An isolated pasteurized or lyophilized Core-1 positive microorganism, which carries surface Core-1 in unmasked form and which is recognized and thus bound by at least one Core-1 specific antibody upon contact.

10. The Core-1 positive microorganism according to claim 9, which is recognized and thus bound by the two Core-1 specific antibodies.

11. The Core-1 positive microorganism according to claim 9, wherein the recognition of the Core-1 positive microorganism by the at least one Core-1 specific antibody is periodate sensitive showing reduced binding after periodate treatment.

12. The Core-1 positive microorganism according to claim 9, wherein said Core-1 positive microorganism comprises at least one of the carbohydrate structures selected from the group consisting of:

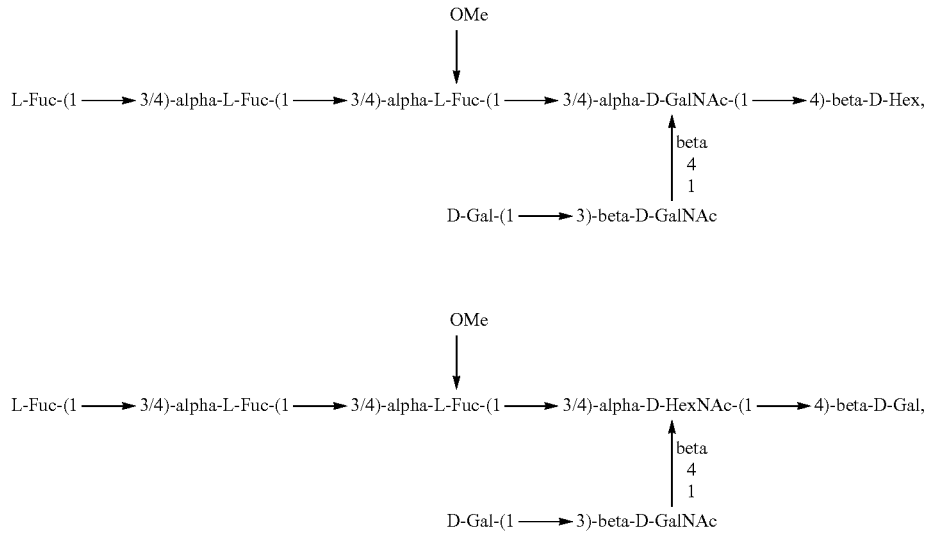

-continued

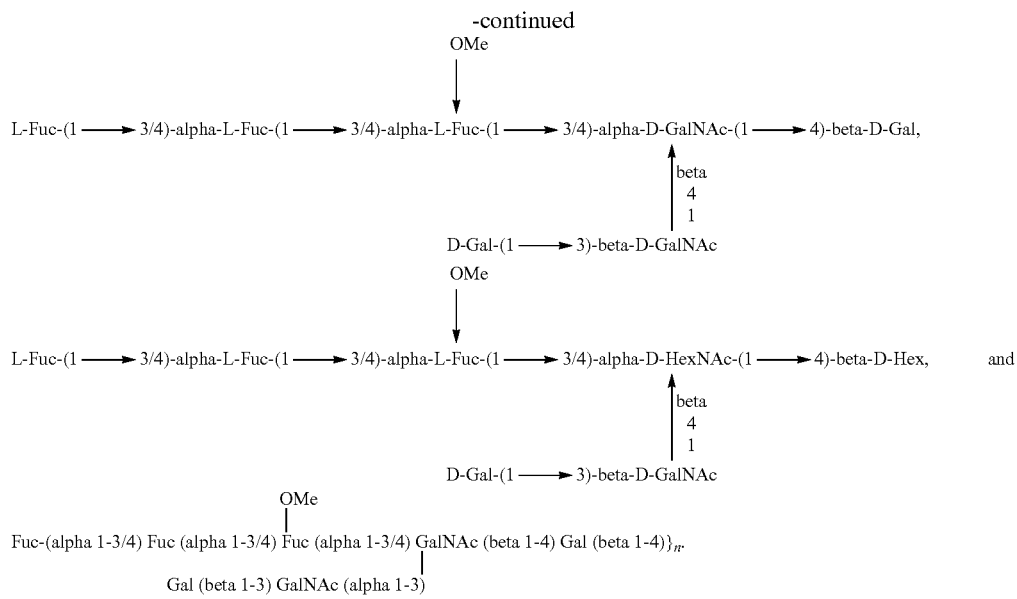

Fuc-(alpha 1-3/4) Fuc (alpha 1-3/4) Fuc (alpha 1-3/4) GalNAc (beta 1-4) Gal (beta 1-4)}$_n$.
|
Gal (beta 1-3) GalNAc (alpha 1-3)

with OMe on the first Fuc.

13. The Core-1 positive microorganism according to claim 9, wherein said Core-1 positive microorganism is AG6 (DSM 18726), MU1 (DSM 18728) and/or a AG6 or MU1 homolog, wherein said homolog is characterized in that it is a *Bacteroides*, is recognized by at least two Core-1 specific antibodies, and wherein binding of said antibodies is periodate sensitive showing reduced binding after periodate treatment.

14. A formulation selected from the group consisting of a nutraceutical and/or a pharmaceutical composition, comprising isolated Core-1 positive microorganisms, wherein the Core-1 positive microorganisms carry surface Core-1 in unmasked form and are recognized by at least one Core-1 specific antibody, and wherein the Core-1 positive microorganisms in the composition are pasteurized or lyophilized.

15. A formulation selected from the group consisting of a nutraceutical and/or a pharmaceutical composition, comprising isolated Core-1 positive microorganisms, wherein the Core-1 positive microorganisms carry surface Core-1 in unmasked form and are recognized by at least one Core-1 specific antibody, and wherein the composition further comprises a *lactobacillus* or a *bifidobacterium*.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Primer 27f for amplifying the bacterial 16S
      ribosomal RNA gene

<400> SEQUENCE: 1
agagtttgat cctggctcag                                                20

<210> SEQ ID NO 2
<211> LENGTH: 16
<212> TYPE: DNA
<213> ORGANISM: Artificial Sequence
<220> FEATURE:
<223> OTHER INFORMATION: Primer 1492r for amplifying bacterial 16S
      ribosomal RNA gene

<400> SEQUENCE: 2
taccttgtta cgactt                                                    16

<210> SEQ ID NO 3
<211> LENGTH: 18
<212> TYPE: DNA
<213> ORGANISM: Artificial Sequence
<220> FEATURE:
<223> OTHER INFORMATION: Sequencing primer 338f

<400> SEQUENCE: 3
```

-continued

```
gctgcctccc gtaggagt                                                18

<210> SEQ ID NO 4
<211> LENGTH: 18
<212> TYPE: DNA
<213> ORGANISM: Artificial Sequence
<220> FEATURE:
<223> OTHER INFORMATION: Sequencing primer 338r

<400> SEQUENCE: 4
actcctacgg gaggcagc                                                18

<210> SEQ ID NO 5
<211> LENGTH: 17
<212> TYPE: DNA
<213> ORGANISM: Artificial Sequence
<220> FEATURE:
<223> OTHER INFORMATION: Sequencing primer 968f

<400> SEQUENCE: 5
aacgcgaaga accttac                                                 17
```